US007303754B2

(12) United States Patent
Moss et al.

(10) Patent No.: US 7,303,754 B2
(45) Date of Patent: Dec. 4, 2007

(54) MVA EXPRESSING MODIFIED HIV ENVELOPE, GAG, AND POL GENES

(75) Inventors: Bernard Moss, Bethesda, MD (US); Patricia L. Earl, Chevy Chase, MD (US); Linda Wyatt, Rockville, MD (US); Leigh Anne Eller, Kampala (UG); Thomas C. VanCott, Brookeville, MD (US); Matthew Edward Harris, Poway, CA (US)

(73) Assignees: The Government of the United States of America, as represented by the Secretary, Department of Health and Human Services, Washington, DC (US); Henry M. Jackson Foundation for the Advancement of Military Medicine, Inc., Rockville, MD (US); The United States of America, as represented by the Secretary, Department of the Army, Washington, DC (US)

( * ) Notice: Subject to any disclaimer, the term of this patent is extended or adjusted under 35 U.S.C. 154(b) by 0 days.

(21) Appl. No.: 11/238,155

(22) Filed: Sep. 28, 2005

(65) Prior Publication Data

US 2006/0134133 A1    Jun. 22, 2006

Related U.S. Application Data

(63) Continuation of application No. PCT/US2004/009906, filed on Mar. 29, 2004.

(60) Provisional application No. 60/459,175, filed on Mar. 28, 2003.

(51) Int. Cl.
*A61K 39/12*    (2006.01)

(52) U.S. Cl. .................. 424/204.1; 424/205.1

(58) Field of Classification Search .................. 424/9.1, 424/199.1
See application file for complete search history.

(56) References Cited

U.S. PATENT DOCUMENTS

2004/0146528 A1    7/2004  Moss et al.

FOREIGN PATENT DOCUMENTS

WO    WO 02/072754 A2    9/2002
WO    WO 2006/026667 A2    3/2006

OTHER PUBLICATIONS

Kusumi et al. Human Immunodeficiency Virus Type 1 Envelope Gene Structure and Diversity In Vivo and after Cocultivation in Vitro. Journal of Virology, Feb. 1992, vol. 66, No. 2, p. 875-885.*
Meyerhans et al. Temporal fluctuations in HIV quasispecies in vivo are not reflected by sequenctial HIV isolations. Cell, Sep. 8 1989, vol. 58, p. 901-910.*

Altman et al. HIV escape: there and back again. Nature Medicine, Mar. 2004, vol. 10, No. 3, p. 229-230.*
Friedrich et al. Reversion of CTL escape—variant immunodeficiency viruses in vivo. Nature Medicine, Mar. 2004, vol. 10, No. 3, p. 275-281.*
Leslie et al. HIV evolution: CTL escape mutation and reversion after transmission. Nature Medicine, Mar. 2004, vol. 10, No. 3, p. 282-289.*
Desrosiers. Prospects for an AIDS vaccine. Nature Medicine, Mar. 2004, vol. 10, No. 3, p. 221-223.*
Voe Laer et al. Gene therapy for HIV infection: what does it need to make it work? The Journal of Gene Medicine 2006, vol. 8, p. 658-667.*
Whitney et al. Live attenuated HIV vaccines: pitfalls and prospects. Current Opinion in Infectious Diseases 2004, vol. 17, p. 17-26.*
Yee et al. Prospects for Gene Therapy Using HIV-Based Vectors. Somatic Cell and Molecular Genetics, Nov. 2001, vol. 26, Nos. 1/6, p. 159-174.*
Pakula et al. Genetic analysis of protein stability and function, Annual Review of Genetics 1989, vol. 23, p. 289-310. Abstract only provided.*
Oestreicher et al. A Single Amino Acid Change in a Pathway-specific Transcription Factor Results in Differing Degrees of Constitutivity, Hyperinducibility and Derepression of Several Structural Genes, Journal of Molecular Biology 1995, vol. 249, p. 693-699.*
Allen, T.M. et al., 2000 "Induction of AIDS virus-specific CTL activity in fresh, unstimulated peripheral blood lymphocytes from rhesus macaques vaccinated with a DNA prime/modified vaccinia virus ankara boost regimen" *J. Immunol.* 164:4968-4978.
Amara, R.R. et al., 2001 "Control of a mucosal challenge and prevention of AIDS by a multiprotein DNA/MVA Vaccine" *Science* 292: 69-74.
Barouch, D.H. et al., 2000 "Control of viremia and prevention of clinical AIDS in rhesus monkeys to cytokine-augmented DNA vaccination" *Science* 290:486-492.
Egan, M.A. et al., 2000 "Simian immunodeficiency virus (SIV) *gag* DNA-vaccinated rhesus monkeys develop secondary cytotoxic T-lymphocyte responses and control viral replication after pathogenic SIV infection" *J. Virol.* 74:7485-7495.

(Continued)

*Primary Examiner*—Bruce R. Campell
*Assistant Examiner*—Louise Humphrey
(74) *Attorney, Agent, or Firm*—Knobbe, Martens, Olson & Bear, LLP

(57) ABSTRACT

The invention provides modified virus Ankara (MVA), a replication-deficient strain of vaccinia virus, expressing human immunodeficiency virus (HIV) env, gag, and pol genes.

14 Claims, 67 Drawing Sheets
(25 of 67 Drawing Sheet(s) Filed in Color)

OTHER PUBLICATIONS

Gorelick, R.J. et al., 1999 "Nucleocapsid protein zinc-finger mutants of simian immunodeficiency virus strain mne produce virions that are replication defective in vitro and in vivo" *Virology* 253:259-270.

Goulder, P.J. et al., 1999 "Anti-HIV cellular immunity: recent advances towards vaccine design" *AIDS (Suppl. A)* 13:S121-S136.

Harris, M.E. et al. 2002 "Among 46 near full-length HIV type 1 genome sequences from rakai district, uganda, subtype D and AD recombinants predominate" *AIDS Res. Hum. Retrovir.* 18:1281-1290.

Hirsch, V.M. et al. 1995 "Limited virus replication following SIV challenge of macaques immunized with attenuated MVA vaccinia expressing SIVsm *env* and *gag-pol*" *Vaccines* 95:195-200.

Hofmann-Lehmann, R. et al., 2000 "Sensitive and robust one-tube real-time reverse transcriptase-polymerase chain reaction to quantify SIV RNA load: comparison of one-versus two-enzyme systems" *AIDS Res. Hum. Retrovir.* 16:1247-1257.

Karacostas, V. et al., 1989 "Human immunodeficiency virus-like particles produced by a vaccinia virus expression vector" *PNAS USA* 86:8964-8967.

Karlsson, G.B. et al., 1997 "Characterization of molecularly cloned simian-human immunodeficiency viruses causing rapid $CD4^+$ lymphocyte depletion in rhesus monkeys" *J. Virol.* 71:4218-4225.

Lechner, F. et al., 2000 "Analysis of successful immune responses in persons infected with hepatitis C virus" *J. Exp. Med.* 191:1499-1512.

Mellors, J.W. et al., 1996 "Prognosis in HIV-1 infection predicted by the quantity of virus in plasma" *Science* 272:1167-1170.

Montefiori, D.C. et al., 1998 "Neutralizing antibodies in sera from macaques infected with chimeric simian-human immunodeficiency virus containing the envelope glycoproteins of either a laboratory-adapted variant or a primary isolate of human immunodeficiency virus type 1" *J. Virol.* 72:3427-3431.

Montefiori, D.C. et al., 1988 "Evaluation of antiviral drugs and neutralizing antibodies to human immunodeficiency virus by a rapid and sensitive microtiter infection assay" *J. Clin. Microbiol.* 26:231-235.

Ourmanov, I. et al., 2000 "Comparative efficacy of recombinant modified vaccinia virus ankara expressing simian immunodeficiency virus (SIV) gag-pol and/or env in macaques challenged with pathogenic SIV" *J. Virol.* 74:2740-2751.

Power, C.A et al., 1999 "A valid ELISPOT assay for enumeration of ex vivo, antigen-specific, IFNγ-producing T cells" *J. Immunol. Methods* 227:99-107.

Quinn, T.C. et al., 2000 "Viral load and heterosexual transmission of human immunodeficiency virus type 1" *N. Engl. J. Med.* 342:921-929.

Robinson, H.L. et al., 2000 "AIDS vaccines: heterologous prime/boost strategies for raising protective T cell responses" *AIDS Rev.* 2:105-110.

Robinson, H.L. et al., 1999 "Neutralizing antibody-independent containment of immunodeficiency virus challenges by DNA priming and recombinant pox virus booster immunizations" *Nature Med.* 5:526-534.

Sauter, M.M. et al., 1996 "An internalization signal in the simian immunodeficiency virus transmembrane protein cytoplasmic domain modulates expression of envelope glycoproteins on the cell surface" *J. Cell Biol.* 132:795-811.

Waldrop, S.L. et al., 1997 "Determination of antigen-specific memory/effector $CD4^+$ T cell frequencies by flow cytometry: evidence for a novel, antigen-specific homeostatic mechanism in HIV-associated immunodeficiency" *J. Clin. Invest.* 99:1739-1750.

* cited by examiner

| Chemokine coreceptor used | PBMC replication | Macrophage replication | T-cell-line replication | REplicative phenotype | Syncytium-inducing phenotype |
|---|---|---|---|---|---|
| X4 | + | – | + | Rapid/high | ++ |
| R5 | + | + | – | Slow/low | – |
| R5/X4 | + | + | + | Rapid/high | + |

FIG. 3

Text File of pLW-48 and the Included Individual HIV Genes and Their Promoters

Entire pLW-48 plasmid sequence:

GAATTCGTTGGTGGTCGCCATGGATGGTGTTATTGTATACTGTCTAAACGCG
TTAGTAAAACATGGCGAGGAAATAAATCATATAAAAAATGATTTCATGATTAA
ACCATGTTGTGAAAAAGTCAAGAACGTTCACATTGGCGGACAATCTAAAAAC
AATACAGTGATTGCAGATTTGCCATATATGGATAATGCGGTATCCGATGTAT
GCAATTCACTGTATAAAAAGAATGTATCAAGAATATCCAGATTTGCTAATTTG
ATAAAGATAGATGACGATGACAAGACTCCTACTGGTGTATATAATTATTTTAA
ACCTAAAGATGCCATTCCTGTTATTATCCATAGGAAAGGATAGAGATGTTT
GTGAACTATTAATCTCATCTGATAAAGCGTGTGCGTGTATAGAGTTAAATTCA
TATAAAGTAGCCATTCTTCCCATGGATGTTTCCTTTTTTACCAAAGGAAATGC
ATCATTGATTATTCTCCTGTTTGATTTCTCTATCGATGCGGCACCTCTCTTAA
GAAGTGTAACCGATAATAATGTTATTATATCTAGACACCAGCGTCTACATGA
CGAGCTTCCGAGTTCCAATTGGTTCAAGTTTTACATAAGTATAAAGTCCGAC
TATTGTTCTATATTATATATGGTTGTTGATGGATCTGTGATGCATGCAATAGC
TGATAATAGAACTTACGCAAATATTAGCAAAATATATTAGACAATACTACAA
TTAACGATGAGTGTAGATGCTGTTATTTTGAACCACAGATTAGGATTCTTGAT
AGAGATGAGATGCTCAATGGATCATCGTGTGATATGAACAGACATTGTATTA
TGATGAATTTACCTGATGTAGGCGAATTTGGATCTAGTATGTTGGGGAAATA
TGAACCTGACATGATTAAGATTGCTCTTTCGGTGGCTGGGTACCAGGCGCG
CCTTTCATTTTGTTTTTTTCTATGCTATAAATGGTACGTCCTGTAGAAACCCC
AACCCGTGAAATCAAAAAACTCGACGGCCTGTGGGCATTCAGTCTGGATCG
CGAAAACTGTGGAATTGATCAGCGTTGGTGGGAAAGCGCGTTACAAGAAAG
CCGGGCAATTGCTGTGCCAGGCAGTTTTAACGATCAGTTCGCCGATGCAGA
TATTCGTAATTATGCGGGCAACGTCTGGTATCAGCGCGAAGTCTTTATACCG
AAAGGTTGGGCAGGCCAGCGTATCGTGCTGCGTTTCGATGCGGTCACTCAT
TACGGCAAAGTGTGGGTCAATAATCAGGAAGTGATGGAGCATCAGGGCGG
CTATACGCCATTTGAAGCCGATGTCACGCCGTATGTTATTGCCGGGAAAAG
TGTACGTATCACCGTTTGTGTGAACAACGAACTGAACTGGCAGACTATCCC
GCCGGGAATGGTGATTACCGACGAAAACGGCAAGAAAAAGCAGTCTTACTT
CCATGATTTCTTTAACTATGCCGGAATCCATCGCAGCGTAATGCTCTACACC
ACGCCGAACACCTGGGTGGACGATATCACCGTGGTGACGCATGTCGCGCA
AGACTGTAACCACGCGTCTGTTGACTGGCAGGTGGTGGCCAATGGTGATGT
CAGCGTTGAACTGCGTGATGCGGATCAACAGGTGGTTGCAACTGGACAAG
GCACTAGCGGGACTTTGCAAGTGGTGAATCCGCACCTCTGGCAACCGGGT
GAAGGTTATCTCTATGAACTGTGCGTCACAGCCAAAAGCCAGACAGAGTGT
GATATCTACCCGCTTCGCGTCGGCATCCGGTCAGTGGCAGTGAAGGGCGA
ACAGTTCCTGATTAACCACAAACCGTTCTACTTTACTGGCTTTGGTCGTCAT
GAAGATGCGGACTTGCGTGGCAAAGGATTCGATAACGTGCTGATGGTGCAC
GACCACGCATTAATGGACTGGATTGGGGCCAACTCCTACCGTACCTCGCAT
TACCCTTACGCTGAAGAGATGCTCGACTGGGCAGATGAACATGGCATCGTG

FIG. 14A

GTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAAC
GGGGAAACTCAGCAAGCGCACTTACAGGCGATTAAAGAGCTGATAGCGCGT
GACAAAAACCACCCAAGCGTGGTGATGTGGAGTATTGCCAACGAACCGGAT
ACCCGTCCGCAAGGTGCACGGGAATATTTCGCGCCACTGGCGGAAGCAAC
GCGTAAACTCGACCCGACGCGTCCGATCACCTGCGTCAATGTAATGTTCTG
CGACGCTCACACCGATACCATCAGCGATCTCTTTGATGTGCTGTGCCTGAA
CCGTTATTACGGATGGTATGTCCAAAGCGGCGATTTGGAAACGGCAGAGAA
GGTACTGGAAAAGAACTTCTGGCCTGGCAGGAGAAACTGCATCAGCCGAT
TATCATCACCGAATACGGCGTGGATACGTTAGCCGGGCTGCACTCAATGTA
CACCGACATGTGGAGTGAAGAGTATCAGTGTGCATGGCTGGATATGTATCA
CCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAA
AGGGATCTTCACTCGCGACCGCAAACCGAAGTCGGCGGCTTTTCTGCTGCA
AAAACGCTGGACTGGCATGAACTTCGGTGAAAAACCGCAGCAGGGAGGCA
AACAATGAGAGCTCGGTTGTTGATGGATCTGTGATGCATGCAATAGCTGATA
ATAGAACTTACGCAAATATTAGCAAAAATATATTAGACAATACTACAATTAAC
GATGAGTGTAGATGCTGTTATTTTGAACCACAGATTAGGATTCTTGATAGAG
ATGAGATGCTCAATGGATCATCGTGTGATATGAACAGACATTGTATTATGAT
GAATTTACCTGATGTAGGCGAATTTGGATCTAGTATGTTGGGGAAATATGAA
CCTGACATGATTAAGATTGCTCTTTCGGTGGCTGGCGGCCCGCTCGAGTAA
AAAATGAAAAAATATTCTAATTTATAGGACGGTTTTGATTTTCTTTTTTTCTAT
GCTATAAATAATAAATAGCGGCCGCACCATGAAAGTGAAGGGGATCAGGAA
GAATTATCAGCACTTGTGGAAATGGGGCATCATGCTCCTTGGGATGTTGATG
ATCTGTAGTGCTGTAGAAAATTTGTGGGTCACAGTTTATTATGGGGTACCTG
TGTGGAAAGAAGCAACCACCACTCTATTTTGTGCATCAGATGCTAAAGCATA
TGATACAGAGGTACATAATGTTTGGGCCACACATGCCTGTGTACCCACAGA
CCCCAACCCACAAGAAGTAGTATTGGAAAATGTGACAGAAAATTTTAACATG
TGGAAAAATAACATGGTAGAACAGATGCATGAGGATATAATCAGTTTATGGG
ATCAAAGCCTAAAGCCATGTGTAAAATTAACCCCACTCTGTGTTACTTTAAAT
TGCACTGATTTGAGGAATGTTACTAATATCAATAATAGTAGTGAGGGAATGA
GAGGAGAAATAAAAAACTGCTCTTTCAATATCACCACAAGCATAAGAGATAA
GGTGAAGAAAGACTATGCACTTTTcTATAGACTTGATGTAGTACCAATAGATA
ATGATAATACTAGCTATAGGTTGATAAATTGTAATACCTCAACCATTACACAG
GCCTGTCCAAAGGTATCCTTTGAGCCAATTCCCATACATTATTGTACCCCGG
CTGGTTTTGCGATTCTAAAGTGTAAAGACAAGAAGTTCAATGGAACAGGGCC
ATGTAAAAATGTCAGCACAGTACAATGTACACATGGAATTAGGCCAGTAGTG
TCAACTCAACTGCTGTTAAATGGCAGTCTAGCAGAAGAAGAGGTAGTAATTA
GATCTAGTAATTTCACAGACAATGCAAAAAACATAATAGTACAGTTGAAAGAA
TCTGTAGAAATTAATTGTACAAGACCCAACAACAATACAAGGAAAAGTATAC
ATATAGGACCAGGAAGAGCATTTTATACAACAGGAGAAATAATAGGAGATAT
AAGACAAGCACATTGCAACATTAGTAGAACAAAATGGAATAACACTTTAAAT
CAAATAGCTACAAAATTAAAAGAACAATTTGGGAATAATAAAACAATAGTCTT
TAATCAATCCTCAGGAGGGGACCCAGAAATTGTAATGCACAGTTTTAATTGT
GGAGGGGAATTCTTCTACTGTAATTCAACACAACTGTTTAATAGTACTTGGA
ATTTTAATGGTACTTGGAATTTAACACAATCGAATGGTACTGAAGGAAATGA

FIG. 14B

```
CACTATCACACTCCCATGTAGAATAAAACAAATTATAAATATGTGGCAGGAA
GTAGGAAAAGCAATGTATGCCCCTCCCATCAGAGGACAAATTAGATGCTCAT
CAAATATTACAGGGCTAATATTAACAAGAGATGGTGGAACTAACAGTAGTGG
GTCCGAGATCTTCAGACCTGGGGGAGGAGATATGAGGGACAATTGGAGAA
GTGAATTATATAAATATAAAGTAGTAAAAATTGAACCATTAGGAGTAGCACCC
ACCAAGGCAAAAGAAGAGTGGTGCAGAGAGAAAAAAGAGCAGTGGGAAC
GATAGGAGCTATGTTCCTTGGGTTCTTGGGAGCAGCAGGAAGCACTATGGG
CGCAGCGTCAATAACGCTGACGGTACAGGCCAGACTATTATTGTCTGGTAT
AGTGCAACAGCAGAACAATTTGCTGAGGGCTATTGAGGCGCAACAGCATCT
GTTGCAACTCACAGTCTGGGGCATCAAGCAGCTCCAGGCAAGAGTCCTGG
CTGTGGAAAGATACCTAAGGGATCAACAGCTCCTAGGGATTTGGGGTTGCT
CTGGAAAACTCATCTGCACCACTGCTGTGCCTTGGAATGCTAGTTGGAGTA
ATAAAACTCTGGATATGATTTGGGATAACATGACCTGGATGGAGTGGGAAA
GAGAAATCGAAAATTACACAGGCTTAATATACACCTTAATTGAGGAATCGCA
GAACCAACAAGAAAAGAATGAACAAGACTTATTAGCATTAGATAAGTGGGCA
AGTTTGTGGAATTGGTTTGACATATCAAATTGGCTGTGGTATGTAAAAATCTT
CATAATGATAGTAGGAGGCTTGATAGGTTTAAGAATAGTTTTTACTGTACTTT
CTATAGTAAATAGAGTTAGGCAGGGATACTCACCATTGTCATTTCAGACCCA
CCTCCCAGCCCCGAGGGGACCCGACAGGCCCGAAGGAATCGAAGAAGAAG
GTGGAGACAGAGACTAATTTTTATGCGGCCGCTGGTACCCAACCTAAAAATT
GAAAATAAATACAAAGGTTCTTGAGGGTTGTGTTAAATTGAAAGCGAGAAAT
AATCATAAATAAGCCCGGGGATCCTCTAGAGTCGACACCATGGGTGCGAGA
GCGTCAGTATTAAGCGGGGGAGAATTAGATCGATGGGAAAAAATTCGGTTA
AGGCCAGGGGGAAAGAAAAAATATAAATTAAAACATATAGTATGGGCAAGCA
GGGAGCTAGAACGATTCGCAGTTAATCCTGGCCTGTTAGAAACATCAGAAG
GCTGTAGACAAATACTGGGACAGCTACAACCATCCCTTCAGACAGGATCAG
AAGAACTTAGATCATTATATAATACAGTAGCAACCCTCTATTGTGTGCATCAA
AGGATAGAGATAAAAGACACCAAGGAAGCTTTAGACAAGATAGAGGAAGAG
CAAAACAAAAGTAAGAAAAAAGCACAGCAAGCAGCAGCTGACACAGGACAC
AGCAATCAGGTCAGCCAAAATTACCCTATAGTGCAGAACATCCAGGGGCAA
ATGGTACATCAGGCCATATCACCTAGAACTTTAAATGCATGGGTAAAAGTAG
TAGAAGAGAAGGCTTTCAGCCCAGAAGTGATACCCATGTTTTCAGCATTATC
AGAAGGAGCCACCCCACAAGATTTAAACACCATGCTAAACACAGTGGGGGG
ACATCAAGCAGCCATGCAAATGTTAAAAGAGACCATCAATGAGGAAGCTGC
AGAATGGGATAGAGTGCATCCAGTGCATGCAGGGCCTATTGCACCAGGCCA
GATGAGAGAACCAAGGGGAAGTGACATAGCAGGAACTACTAGTACCCTTCA
GGAACAAATAGGATGGATGACAAATAATCCACCTATCCCAGTAGGAGAAATT
TATAAAAGATGGATAATCCTGGGATTAAATAAAATAGTAAGAATGTATAGCCC
TACCAGCATTCTGGACATAAGACAAGGACCAAAAGAACCCTTTAGAGACTAT
GTAGACCGGTTCTATAAAACTCTAAGAGCCGAGCAAGCTTCACAGGAGGTA
AAAAATTGGATGACAGAAACCTTGTTGGTCCAAAATGCGAACCCAGATTGTA
AGACTATTTTAAAAGCATTGGGACCAGCGGCTACACTAGAAGAAATGATGAC
AGCATGTCAGGGAGTAGGAGGACCCGGCCATAAGGCAAGAGTTTTGGCTG
AAGCAATGAGCCAAGTAACAAATTCAGCTACCATAATGATGCAGAGAGGCA
ATTTTAGGAACCAAAGAAAGATTGTTAAGTGTTTCAATTGTGGCAAAGAAGG
GCACACAGCCAGAAATTGCAGGGCCCCTAGGAAAAGGGCTGTTGGAAAT
```

FIG. 14C

```
GTGGAAAGGAAGGACACCAAATGAAAGATTGTACTGAGAGACAGGCTAATT
TTTTAGGGAAGATCTGGCCTTCCTACAAGGGAAGGCCAGGGAATTTTCTTCA
GAGCAGACCAGAGCCAACAGCCCCACCAGAAGAGAGCTTCAGGTCTGGGG
TAGAGACAACAACTCCCCCTCAGAAGCAGGAGCCGATAGACAAGGAACTGT
ATCCTTTAACTTCCCTCAGATCACTCTTTGGCAACGACCCCTCGTCACAATA
AAGATAGGGGGGCAACTAAAGGAAGCTCTATTAGATACAGGAGCAGATGAT
ACAGTATTAGAAGAAATGAGTTTGCCAGGAAGATGGAAACCAAAATGATAG
GGGGAATTGGAGGTTTTATCAAAGTAAGACAGTATGATCAGATACTCATAGA
AATCTGTGGACATAAAGCTATAGGTACAGTATTAGTAGGACCTACACCTGTC
AACATAATTGGAAGAAATCTGTTGACTCAGATTGGTTGCACTTTAAATTTTCC
CATTAGCCCTATTGAGACTGTACCAGTAAAATTAAAGCCAGGAATGGATGGC
CCAAAAGTTAAACAATGGCCATTGACAGAAGAAAAAATAAAAGCATTAGTAG
AAATTTGTACAGAAATGGAAAAGGAAGGGAAAATTTCAAAAATTGGGCCTGA
GAATCCATACAATACTCCAGTATTTGCCATAAAGAAAAAAGACAGTACTAAAT
GGAGGAAATTAGTAGATTTCAGAGAACTTAATAAGAGAACTCAAGACTTCTG
GGAAGTTCAATTAGGAATACCACATCCCGCAGGGTTAAAAAAGAAAAAATCA
GTAACAGTACTGGATGTGGGTGATGCATATTTTTCAGTTCCCTTAGATGAAG
ACTTCAGGAAGTATACTGCATTTACCATACCTAGTATAAACAATGAGACACC
AGGGATTAGATATCAGTACAATGTGCTTCCACAGGGATGGAAAGGATCACC
AGCAATATTCCAAAGTAGCATGACAAAAATCTTAGAGCCTTTTAAAAAACAAA
ATCCAGACATAGTTATCTATCAATACATGAACGATTTGTATGTAGGATCTGAC
TTAGAAATAGGGCAGCATAGAACAAAATAGAGGAGCTGAGACAACATCTG
TTGAGGTGGGGACTTACCACACCAGACAAAAACATCAGAAAGAACCTCCA
TTCCTTTGGATGGGTTATGAACTCCATCCTGATAAATGGACAGTACAGCCTA
TAGTGCTGCCAGAAAAAGACAGCTGGACTGTCAATGACATACAGAAGTTAG
TGGGGAAATTGAATACCGCAAGTCAGATTTACCCAGGGATTAAAGTAAGGC
AATTATGTAAACTCCTTAGAGGAACCAAAGCACTAACAGAAGTAATACCACT
AACAGAAGAAGCAGAGCTAGAACTGGCAGAAAACAGAGAGATTCTAAAAGA
ACCAGTACATGGAGTGTATTATGACCCATCAAAAGACTTAATAGCAGAAATA
CAGAAGCAGGGGCAAGGCCAATGGACATATCAAATTTATCAAGAGCCATTT
AAAAATCTGAAAACAGGAAAATATGCAAGAATGAGGGGTGCCCACACTAAT
GATGTAAAACAATTAACAGAGGCAGTGCAAAAAATAACCACAGAAAGCATAG
TAATATGGGGAAAGACTCCTAAATTTAAACTACCCATACAAAAGGAAACATG
GGAAACATGGTGGACAGAGTATTGGCAAGCCACCTGGATTCCTGAGTGGGA
GTTTGTTAATACCCCTCCTTTAGTGAAATTATGGTACCAGTTAGAGAAAGAA
CCCATAGTAGGAGCAGAAACCTTCTATGTAGATGGGGCAGCTAACAGGGAG
ACTAAATTAGGAAAAGCAGGATATGTTACTAACAAAGGAAGACAAAAGGTTG
TCCCCCTAACTAACACAACAAATCAGAAAACTCAGTTACAAGCAATTTATCTA
GCTTTGCAGGATTCAGGATTAGAAGTAAACATAGTAACAGACTCACAATATG
CATTAGGAATCATTCAAGCACAACCAGATAAAAGTGAATCAGAGTTAGTCAA
TCAAATAATAGAGCAGTTAATAAAAAAGGAAAAGGTCTATCTGGCATGGGTA
CCAGCACACAAAGGAATTGGAGGAAATGAACAAGTAGATAAATTAGTCAGT
GCTGGAATCAGGAAAATACTATTTTTAGATGGAATAGATAAGGCCCAAGATG
AACATTAGTTTTTATGTCGACCTGCAGGGAAAGTTTTATAGGTAGTTGATAG
AACAAAATACATAATTTTGTAAAAATAAATCACTTTTTATACTAATATGACACG
ATTACCAATACTTTTGTTACTAATATCATTAGTATACGCTACACCTTTTCCTCA
```

FIG. 14D

```
GACATCTAAAAAAAATAGGTGATGATGCAACTTTATCATGTAATCGAAATAATA
CAAATGACTACGTTGTTATGAGTGCTTGGTATAAGGAGCCCAATTCCATTAT
TCTTTTAGCTGCTAAAAGCGACGTCTTGTATTTTGATAATTATACCAAGGATA
AAATATCTTACGACTCTCCATACGATGATCTAGTTACAACTATCACAATTAAA
TCATTGACTGCTAGAGATGCCGGTACTTATGTATGTCATTCTTTATGACATC
GCCTACAAATGACACTGATAAAGTAGATTATGAAGAATACTCCACAGAGTTG
ATTGTAAATACAGATAGTGAATCGACTATAGACATAATACTATCTGGATCTAC
ACATTCACCAGAAACTAGTTAAGCTTGTCTCCCTATAGTGAGTCGTATTAGA
GCTTGGCGTAATCATGGTCATAGCTGTTTCCTGTGTGAAATTGTTATCCGCT
CACAATTCCACACAACATACGAGCCGGAAGCATAAAGTGTAAAGCCTGGGG
TGCCTAATGAGTGAGCTAACTCACATTAATTGCGTTGCGCTCACTGCCCGCT
TTCGAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCG
TTGCTGGCGTTTTTCGATAGGCTCCGCCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATC
CGGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACA
GTTACCAATGCTTAATCAGTGAGGCACCTATCTCAGCGATCTGTCTATTTCG
TTCATCCATAGTTGCCTGACTCCCCGTCGTGTAGATAACTACGATACGGGAG
GGCTTACCATCTGGCCCCAGTGCTGCAATGATACCGCGAGACCCACGCTCA
CCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTT
GGCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCA
ATACGGGATAATACCGCGCCACATAGCAGAACTTTAAAAGTGCTCATCATTG
GAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTAC
```

*FIG. 14E*

TTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTT
CAATATTATTGAAGCATTTATCAGGGTTATTGTCTCATGAGCGGATACATATT
TGAATGTATTTAGAAAAATAAACAAATAGGGGTTCCGCGCACATTTCCCCGA
AAAGTGCCACCTGACGTCTAAGAAACCATTATTATCATGACATTAACCTATAA
AAATAGGCGTATCACGAGGCCCTTTCGTCTCGCGCGTTTCGGTGATGACGG
TGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACT
GAGAGTGCACCATATGCGGTGTGAAATACCGCACAGATGCGTAAGGAGAAA
ATACCGCATCAGGCGCCATTCGCCATTCAGGCTGCGCAACTGTTGGGAAGG
GCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGAC
GTTGTAAAACGACGGCCAGTGAATTGGATTTAGGTGACACTATA

New Psyn II Promoter which controls ADA envelope expression:

TAAAAAATGAAAAAATATTCTAATTTATAGGACGGTTTTGATTTTCTTTTTTTC
TATGCTATAAATAATAAATA

ADA envelope truncated:

ATGAAAGTGAAGGGGATCAGGAAGAATTATCAGCACTTGTGGAAATGGGGC
ATCATGCTCCTTGGGATGTTGATGATCTGTAGTGCTGTAGAAAATTTGTGGG
TCACAGTTTATTATGGGGTACCTGTGTGGAAAGAAGCAACCACCACTCTATT
TTGTGCATCAGATGCTAAAGCATATGATACAGAGGTACATAATGTTTGGGCC
ACACATGCCTGTGTACCCACAGACCCCAACCCACAAGAAGTAGTATTGGAA
AATGTGACAGAAAATTTTAACATGTGGAAAAATAACATGGTAGAACAGATGC
ATGAGGATATAATCAGTTTATGGGATCAAAGCCTAAAGCCATGTGTAAAATT
AACCCCACTCTGTGTTACTTTAAATTGCACTGATTTGAGGAATGTTACTAATA
TCAATAATAGTAGTGAGGGAATGAGAGGAGAAATAAAAAACTGCTCTTTCAA
TATCACCACAAGCATAAGAGATAAGGTGAAGAAAGACTATGCACTTTTCTAT
AGACTTGATGTAGTACCAATAGATAATGATAATACTAGCTATAGGTTGATAAA
TTGTAATACCTCAACCATTACACAGGCCTGTCCAAAGGTATCCTTTGAGCCA
ATTCCCATACATTATTGTACCCCGGCTGGTTTTGCGATTCTAAAGTGTAAAG
ACAAGAAGTTCAATGGAACAGGGCCATGTAAAAATGTCAGCACAGTACAAT
GTACACATGGAATTAGGCCAGTAGTGTCAACTCAACTGCTGTTAAATGGCAG
TCTAGCAGAAGAAGAGGTAGTAATTAGATCTAGTAATTTCACAGACAATGCA
AAAAACATAATAGTACAGTTGAAAGAATCTGTAGAAATTAATTGTACAAGACC
CAACAACAATACAAGGAAAGTATACATATAGGACCAGGAAGAGCATTTTAT
ACAACAGGAGAAATAATAGGAGATATAAGACAAGCACATTGCAACATTAGTA
GAACAAAATGGAATAACACTTTAAATCAAATAGCTACAAAATTAAAAGAACAA
TTTGGGAATAATAAAACAATAGTCTTTAATCAATCCTCAGGAGGGGACCCAG
AAATTGTAATGCACAGTTTTAATTGTGGAGGGGAATTCTTCTACTGTAATTCA
ACACAACTGTTTAATAGTACTTGGAATTTTAATGGTACTTGGAATTTAACACA

*FIG. 14F*

ATCGAATGGTACTGAAGGAAATGACACTATCACACTCCCATGTAGAATAAAA
CAAATTATAAATATGTGGCAGGAAGTAGGAAAAGCAATGTATGCCCCTCCCA
TCAGAGGACAAATTAGATGCTCATCAAATATTACAGGGCTAATATTAACAAG
AGATGGTGGAACTAACAGTAGTGGGTCCGAGATCTTCAGACCTGGGGGAG
GAGATATGAGGGACAATTGGAGAAGTGAATTATATAAATATAAAGTAGTAAA
AATTGAACCATTAGGAGTAGCACCCACCAAGGCAAAAAGAAGAGTGGTGCA
GAGAGAAAAAGAGCAGTGGGAACGATAGGAGCTATGTTCCTTGGGTTCTT
GGGAGCAGCAGGAAGCACTATGGGCGCAGCGTCAATAACGCTGACGGTAC
AGGCCAGACTATTATTGTCTGGTATAGTGCAACAGCAGAACAATTTGCTGAG
GGCTATTGAGGCGCAACAGCATCTGTTGCAACTCACAGTCTGGGGCATCAA
GCAGCTCCAGGCAAGAGTCCTGGCTGTGGAAAGATACCTAAGGGATCAACA
GCTCCTAGGGATTTGGGGTTGCTCTGGAAAACTCATCTGCACCACTGCTGT
GCCTTGGAATGCTAGTTGGAGTAATAAAACTCTGGATATGATTTGGGATAAC
ATGACCTGGATGGAGTGGGAAAGAGAAATCGAAAATTACACAGGCTTAATAT
ACACCTTAATTGAGGAATCGCAGAACCAACAAGAAAGAATGAACAAGACTT
ATTAGCATTAGATAAGTGGGCAAGTTTGTGGAATTGGTTTGACATATCAAATT
GGCTGTGGTATGTAAAAATCTTCATAATGATAGTAGGAGGCTTGATAGGTTT
AAGAATAGTTTTTACTGTACTTTCTATAGTAAATAGAGTTAGGCAGGGATACT
CACCATTGTCATTTCAGACCCACCTCCCAGCCCCGAGGGGACCCGACAGG
CCCGAAGGAATCGAAGAAGAAGGTGGAGACAGAGAC

PmH5 promoter (which controls HXB2 gag pol expression):

AAAAATTGAAAATAAATACAAAGGTTCTTGAGGGTTGTGTTAAATTGAAAGC
GAGAAATAATCATAAATA

HXB2 gag pol (with safety mutations, Δ integrase):

ATGGGTGCGAGAGCGTCAGTATTAAGCGGGGGAGAATTAGATCGATGGGA
AAAAATTCGGTTAAGGCCAGGGGGAAAGAAAAAATATAAATTAAAACATATA
GTATGGGCAAGCAGGGAGCTAGAACGATTCGCAGTTAATCCTGGCCTGTTA
GAAACATCAGAAGGCTGTAGACAAATACTGGGACAGCTACAACCATCCCTT
CAGACAGGATCAGAAGAACTTAGATCATTATATAATACAGTAGCAACCCTCT
ATTGTGTGCATCAAAGGATAGAGATAAAAGACACCAAGGAAGCTTTAGACAA
GATAGAGGAAGAGCAAAACAAAAGTAAGAAAAAGCACAGCAAGCAGCAGC
TGACACAGGACACAGCAATCAGGTCAGCCAAAATTACCCTATAGTGCAGAA
CATCCAGGGGCAAATGGTACATCAGGCCATATCACCTAGAACTTTAAATGCA
TGGGTAAAAGTAGTAGAAGAGAAGGCTTTCAGCCCAGAAGTGATACCCATG
TTTTCAGCATTATCAGAAGGAGCCACCCCACAAGATTTAAACACCATGCTAA
ACACAGTGGGGGGACATCAAGCAGCCATGCAAATGTTAAAAGAGACCATCA
ATGAGGAAGCTGCAGAATGGGATAGAGTGCATCCAGTGCATGCAGGGCCT
ATTGCACCAGGCCAGATGAGAGAACCAAGGGGAAGTGACATAGCAGGAAC
TACTAGTACCCTTCAGGAACAAATAGGATGGATGACAAATAATCCACCTATC
CCAGTAGGAGAAATTTATAAAAGATGGATAATCCTGGGATTAAATAAAATAG
TAAGAATGTATAGCCCTACCAGCATTCTGGACATAAGACAAGGACCAAAAGA
ACCCTTTAGAGACTATGTAGACCGGTTCTATAAAACTCTAAGAGCCGAGCAA

*FIG. 14G*

```
GCTTCACAGGAGGTAAAAAATTGGATGACAGAAACCTTGTTGGTCCAAAATG
CGAACCCAGATTGTAAGACTATTTTAAAAGCATTGGGACCAGCGGCTACACT
AGAAGAAATGATGACAGCATGTCAGGGAGTAGGAGGACCCGGCCATAAGG
CAAGAGTTTTGGCTGAAGCAATGAGCCAAGTAACAAATTCAGCTACCATAAT
GATGCAGAGAGGCAATTTTAGGAACCAAAGAAAGATTGTTAAGTGTTTCAAT
TGTGGCAAAGAAGGGCACACAGCCAGAAATTGCAGGGCCCCTAGGAAAAA
GGGCTGTTGGAAATGTGGAAGGAAGGACACCAAATGAAAGATTGTACTGA
GAGACAGGCTAATTTTTTAGGGAAGATCTGGCCTTCCTACAAGGGAAGGCC
AGGGAATTTTCTTCAGAGCAGACCAGAGCCAACAGCCCCACCAGAAGAGAG
CTTCAGGTCTGGGGTAGAGACAACAACTCCCCCTCAGAAGCAGGAGCCGAT
AGACAAGGAACTGTATCCTTTAACTTCCCTCAGATCACTCTTTGGCAACGAC
CCCTCGTCACAATAAAGATAGGGGGGCAACTAAAGGAAGCTCTATTAGATA
CAGGAGCAGATGATACAGTATTAGAAGAAATGAGTTTGCCAGGAAGATGGA
AACCAAAAATGATAGGGGGAATTGGAGGTTTTATCAAAGTAAGACAGTATGA
TCAGATACTCATAGAAATCTGTGGACATAAAGCTATAGGTACAGTATTAGTA
GGACCTACACCTGTCAACATAATTGGAAGAAATCTGTTGACTCAGATTGGTT
GCACTTTAAATTTTCCCATTAGCCCTATTGAGACTGTACCAGTAAAATTAAAG
CCAGGAATGGATGGCCCAAAAGTTAAACAATGGCCATTGACAGAAGAAAAA
ATAAAAGCATTAGTAGAAATTTGTACAGAAATGGAAAAGGAAGGGAAAATTT
CAAAAATTGGGCCTGAGAATCCATACAATACTCCAGTATTTGCCATAAAGAA
AAAAGACAGTACTAAATGGAGGAAATTAGTAGATTTCAGAGAACTTAATAAG
AGAACTCAAGACTTCTGGGAAGTTCAATTAGGAATACCACATCCCGCAGGG
TTAAAAAAGAAAAAATCAGTAACAGTACTGGATGTGGGTGATGCATATTTTTC
AGTTCCCTTAGATGAAGACTTCAGGAAGTATACTGCATTTACCATACCTAGT
ATAAACAATGAGACACCAGGGATTAGATATCAGTACAATGTGCTTCCACAGG
GATGGAAAGGATCACCAGCAATATTCCAAAGTAGCATGACAAAAATCTTAGA
GCCTTTTAAAAAACAAAATCCAGACATAGTTATCTATCAATACATGAACGATT
TGTATGTAGGATCTGACTTAGAAATAGGGCAGCATAGAACAAAAATAGAGGA
GCTGAGACAACATCTGTTGAGGTGGGGACTTACCACACCAGACAAAAAACA
TCAGAAAGAACCTCCATTCCTTTGGATGGGTTATGAACTCCATCCTGATAAA
TGGACAGTACAGCCTATAGTGCTGCCAGAAAAAGACAGCTGGACTGTCAAT
GACATACAGAAGTTAGTGGGGAAATTGAATACCGCAAGTCAGATTTACCCA
GGGATTAAAGTAAGGCAATTATGTAAACTCCTTAGAGGAACCAAAGCACTAA
CAGAAGTAATACCACTAACAGAAGAAGCAGAGCTAGAACTGGCAGAAAACA
GAGAGATTCTAAAAGAACCAGTACATGGAGTGTATTATGACCCATCAAAAGA
CTTAATAGCAGAAATACAGAAGCAGGGGCAAGGCCAATGGACATATCAAAT
TTATCAAGAGCCATTTAAAAATCTGAAAACAGGAAAATATGCAAGAATGAGG
GGTGCCCACACTAATGATGTAAAACAATTAACAGAGGCAGTGCAAAAAATAA
CCACAGAAAGCATAGTAATATGGGGAAAGACTCCTAAATTTAAACTACCCAT
ACAAAAGGAAACATGGGAAACATGGTGGACAGAGTATTGGCAAGCCACCTG
GATTCCTGAGTGGGAGTTTGTTAATACCCCTCCTTTAGTGAAATTATGGTAC
CAGTTAGAGAAAGAACCCATAGTAGGAGCAGAAACCTTCTATGTAGATGGG
GCAGCTAACAGGGAGACTAAATTAGGAAAAGCAGGATATGTTACTAACAAA
GGAAGACAAAAGGTTGTCCCCCTAACTAACACAACAAATCAGAAAACTCAGT
TACAAGCAATTTATCTAGCTTTGCAGGATTCAGGATTAGAAGTAAACATAGTA
ACAGACTCACAATATGCATTAGGAATCATTCAAGCACAACCAGATAAAAGTG
```

FIG. 14H

AATCAGAGTTAGTCAATCAAATAATAGAGCAGTTAATAAAAAAGGAAAAGGT
CTATCTGGCATGGGTACCAGCACACAAAGGAATTGGAGGAAATGAACAAGT
AGATAAATTAGTCAGTGCTGGAATCAGGAAAATACTATTTTTAGATGGAATA
GATAAGGCCCAAGATGAACATTAG

FIG. 14I

Sequence of new Psyn II promoter:

Early part of promoter

Critical region    Early start site
TAAAAAATGAAAAAATATTCTAATTTATAGGACGGT

Late part of promoter

TTTGATTTTCTTTTTTCTATGCTATAAATAATAAATA

FIG. 17

Antibodies used: T24 (env); 183-H12-5C (gag); pooled HIV+sera (clade A)

MVA EXPRESSING MODIFIED HIV ENVELOPE, GAG, AND POL GENES

RELATED APPLICATIONS

This application is a continuation of International Patent Application No: PCT/US2004/009906, filed Mar. 29, 2004 designating the U.S. and published in English on Oct. 14, 2004 as WO 2004/087201, which claims the benefit of U.S. Provisional Patent Application No. 60/459,175, filed Mar. 28, 2003, both of with are hereby expressly incorporated by reference in their entireties.

FIELD OF THE INVENTION

The invention provides modified vaccinia Ankara (MVA), a replication-deficient strain of vaccinia virus, expressing human immunodeficiency virus (HIV) env, gag, and pol genes.

BACKGROUND OF THE INVENTION

Cellular immunity plays an important role in the control of immunodeficiency virus infections (P. J. Goulder et al. 1999 *AIDS* 13:S121). Recently, a DNA vaccine designed to enhance cellular immunity by cytokine augmentation successfully contained a highly virulent immunodeficiency virus challenge (D. H. Barouch et al. 2000 *Science* 290:486). Another promising approach to raising cellular immunity is DNA priming followed by recombinant poxvirus boosters (H. L. Robinson et al. 2000 *AIDS Rev* 2:105). This heterologous prime/boost regimen induces 10- to 100-fold higher frequencies of T cells than priming and boosting with DNA or recombinant poxvirus vaccines alone. Previously, investigators showed that boosting a DNA-primed response with a poxvirus was superior to boosting with DNA or protein for the control of a non-pathogenic immunodeficiency virus (H. L. Robinson et al. 1999 *Nat Med* 5:526). There is a need for the control of a pathogenic immunodeficiency virus.

SUMMARY OF THE INVENTION

Here we report that DNA priming followed by a recombinant modified vaccinia Ankara (rMVA) booster has controlled a highly pathogenic immunodeficiency virus challenge in a rhesus macaque model. Both the DNA and rMVA components of the vaccine expressed multiple immunodeficiency virus proteins. Two DNA inoculations at 0 and 8 weeks and a single rMVA booster at 24 weeks effectively controlled an intrarectal challenge administered seven months after the booster. These findings are envisioned as indicating that a relatively simple multiprotein DNA/MVA vaccine can help to control the acquired immune deficiency syndrome (AIDS) epidemic. We also report that inoculations of rMVA induce good immune responses even without DNA priming.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3. Tropic and biologic properties of HIV-1 isolates.

FIG. 14 A-I. Sequences of plasmid transfer vector pLW-48 (SEQ ID NO: 1), Psyn II promoter (which controls ADA envelope expression) (SEQ ID NO: 2), ADA envelope truncated (SEQ ID NO: 3), PmH5 promoter (which controls HXB2 gag pol expression) (SEQ. ID NO: 4), and HXB2 gag pol (with safety mutations, Δ integrase) (SEQ ID NO: 5).

FIG. 17. Sequence of new Psyn II promoter (SEQ ID NO: 2).

BRIEF DESCRIPTION OF THE APPENDICES

Figure 1:
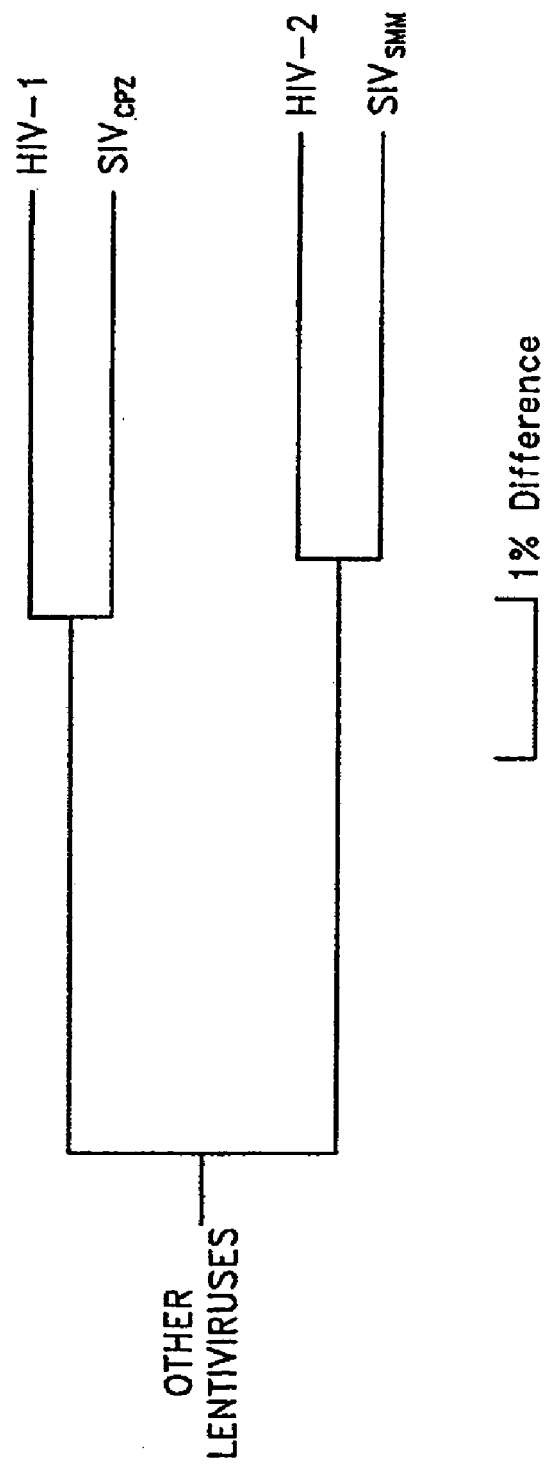
FIG. 1. Phylogenetic relationships of HIV-1 and HIV-2 based on identity of pol gene sequences. $SIV_{cpz}$ and $SIV_{smm}$ are subhuman primate lentiviruses recovered from a chimpanzee and sooty mangabey monkey, respectively.

Appendix 1. DNA sequences of gagpol and env genes from Ugandan HIV-1 clade D isolates (SEQ ID NOs: 51, 52, 53, 54, 55).

Appendix 2. DNA sequences of MVA shuttle plasmids, pLAS-1 and pLAS-2 (SEQ ID NOs: 56, 57).

Appendix 3. DNA sequences of gagpol and env genes from Kenyan HIV-1 clade A isolates (SEQ ID NOs: 58, 59, 60).

Appendix 4. DNA sequences of gagpol and env genes from Tanzanian HIV-1 clade C isolates (SEQ ID NOs: 61, 62).

Appendix 5. American Type Culture Collection, Budapest Treaty Deposit Form BP/1, questions 1-8, regarding MVA 1974/NIH Clone 1.

Appendix 6. American Tissue Type Collection, Additional Information Required When Depositing A Virus for Patent Purposes, regarding MVA 1974/NIH Clone 1.

Deposit of Microorganism

The following microorganism has been deposited in accordance with the terms of the Budapest Treaty with the American Type Culture Collection (ATCC), Manassas, Va., on the date indicated:

| Microorganism | Accession No. | Date |
| --- | --- | --- |
| MVA 1974/NIH Clone 1 | PTA-5095 | Mar. 27, 2003 |

MVA 1974/NIH Clone 1 was deposited as ATCC Accession No. PTA-5095 on Mar. 27, 2003 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

Recombinant MVA Virus

Vaccinia virus, a member of the genus Orthopoxvirus in the family of Poxyiridae, was used as live vaccine to immunize against the human smallpox disease. Successful worldwide vaccination with vaccinia virus culminated in the eradication of variola virus, the causative agent of the smallpox ("The global eradication of smallpox. Final report of the global commission for the certification of smallpox eradication". History of Public Health, No. 4, Geneva: World Health Organization, 1980). Since that WHO declaration, vaccination has been universally discontinued except for people at high risk of poxvirus infections (e.g. laboratory workers).

More recently, vaccinia viruses have also been used to engineer viral vectors for recombinant gene expression and for the potential use as recombinant live vaccines (Mackett, M. et al. 1982 *PNAS USA* 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

For vector applications health risks would be lessened by the use of a highly attenuated vaccinia virus strain. Several such strains of vaccinia virus were especially developed to avoid undesired side effects of smallpox vaccination. Thus, the modified vaccinia Ankara (MVA) has been generated by long-term serial passages of the Ankara strain of vaccinia virus (CVA) on chicken embryo fibroblasts (for review see Mayr, A. et al. 1975 *Infection* 3:6-14; Swiss Patent No. 568,392). The MVA virus is publicly available from American Type Culture Collection as ATCC No. VR-1508. MVA is distinguished by its great attenuation, that is to say by diminished virulence and ability to replicate in primate cells while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 *J Gen Virol* 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 *PNAS USA* 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

The recombinant MVA vaccinia viruses can be prepared as set out hereinafter. A DNA-construct which contains a DNA-sequence which codes for a foreign polypeptide flanked by MVA DNA sequences adjacent to a naturally occurring deletion, e.g. deletion III, or other non-essential sites, within the MVA genome, is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. The DNA-construct contains sequences flanking the left and the right side of a naturally occurring deletion, e.g. deletion III, within the MVA genome. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the UVA infected cells by transfection, for example by means of calcium phosphate precipitation (Graham et al. 1973 *Virol* 52:456-467; Wigler et al. 1979 *Cell* 16:777-785), by means of electroporation (Neumann et al. 1982 *EMBO J.* 1:841-845), by microinjection (Graessmann et al. 1983 *Meth Enzymol* 101:482-492), by means of liposomes (Straubinger et al. 1983 *Meth Enzymol* 101:512-527), by means of spheroplasts (Schaffner 1980 *PNAS USA* 77:2163-2167) or by other methods known to those skilled in the art.

HIVs and Their Replication

The etiological agent of acquired immune deficiency syndrome (AIDS) is recognized to be a retrovirus exhibiting characteristics typical of the lentivirus genus, referred to as human immunodeficiency virus (HIV). The phylogenetic relationships of the human lentiviruses are shown in FIG. 1. HIV-2 is more closely related to $SIV_{smm}$, a virus isolated from sooty mangabey monkeys in the wild, than to HIV-1. It is currently believed that HIV-2 represents a zoonotic transmission of $SIV_{smm}$ to man. A series of lentiviral isolates from captive chimpanzees, designated $SIV_{cpz}$, are close genetic relatives of HIV-1.

Figure 2:
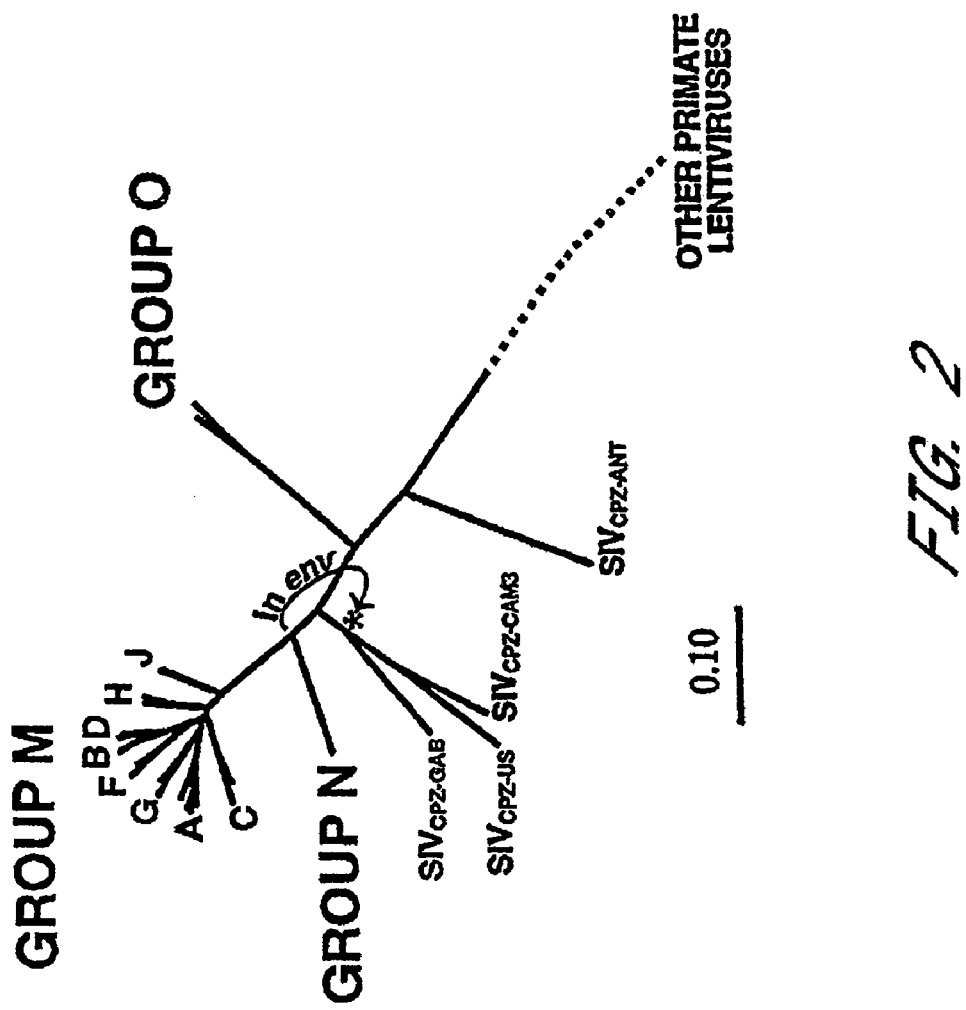
FIG. 2. Phylogenetic relationships of HIV-1 groups M, N and O with four different $SIV_{cpz}$ isolates based on full-length pol gene sequences. The bar indicates a genetic distance of 0.1 (10% nucleotide divergence) and the asterisk positions group N HIV-1 isolates based on env sequences.

The earliest phylogenetic analyses of HIV-1 isolates focused on samples from Europe/North America and Africa; discrete clusters of viruses were identified from these two areas of the world. Distinct genetic subtypes or clades of HIV-1 were subsequently defined and classified into three groups: M (major); O (outlier); and N (non-M or O) (FIG. 2). The M group of HIV-1, which includes over 95% of the global virus isolates, consists of at least eight discrete clades (A, B, C, D, F, G, H, and J), based on the sequence of complete viral genomes. Members of HIV-1 group O have been recovered from individuals living in Cameroon, Gabon, and Equatorial Guinea; their genomes share less than 50% identity in nucleotide sequence with group M viruses. The more recently discovered group N HIV-I strains have been identified in infected Cameroonians, fail to react serologically in standard whole-virus enzyme-linked immunosorbent assay (ELISA), yet are readily detectable by conventional Western blot analysis.

Most current knowledge about HIV-1 genetic variation comes from studies of group M viruses of diverse geographic origin. Data collected during the past decade indicate that the HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

All of the HIV-1 group M subtypes can be found in Africa. Clade A viruses are genetically the most divergent and were the most common HIV-1 subtype in Africa early in the epidemic. With the rapid spread of HIV-1 to southern Africa during the mid to late 1990s, clade C viruses have become the dominant subtype and now account for 48% of HIV-1 infections worldwide. Clade B viruses, the most intensively studied HIV-1 subtype, remain the most prevalent isolates in Europe and North America.

High rates of genetic recombination are a hallmark of retroviruses. It was initially believed that simultaneous infections by genetically diverse virus strains were not likely to be established in individuals at risk for HIV-1. By 1995, however, it became apparent that a significant fraction of the HIV-1 group M global diversity included interclade viral recombinants. It is now appreciated that HIV-1 recombinants will be found in geographic areas such as Africa, South America, and Southeast Asia, where multiple HIV-1 subtypes coexist and may account for more than 10% of circulating HIV-1 strains. Molecularly, the genomes of these recombinant viruses resemble patchwork mosaics, with juxtaposed diverse HIV-1 subtype segments, reflecting the multiple crossover events contributing to their generation. Most HIV-1 recombinants have arisen in Africa and a majority contains segments originally derived from lade A viruses. In Thailand, for example, the composition of the predominant circulating strain consists of a clade A gag plus pol gene segment and a lade E env gene. Because the clade E env gene in Thai HIV-1 strains is closely related to the clade E env present in virus isolates from the Central African Republic, it is believed that the original recombination event occurred in Africa, with the subsequent introduction of a descendent virus into Thailand. Interestingly, no full-length HIV-1 subtype E isolate (i.e., with subtype E gag, pol, and env genes) has been reported to date.

The discovery that α and β chemokine receptors function as coreceptors for virus fusion and entry into susceptible $CD4^+$ cells has led to a revised classification scheme for HIV-1 (FIG. 3). Isolates can now be grouped on the basis of chemokine receptor utilization in fusion assays in which HIV-1 gp120 and $CD4^+$ coreceptor proteins are expressed in separate cells. As indicated in FIG. 3, HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

Figure 4:
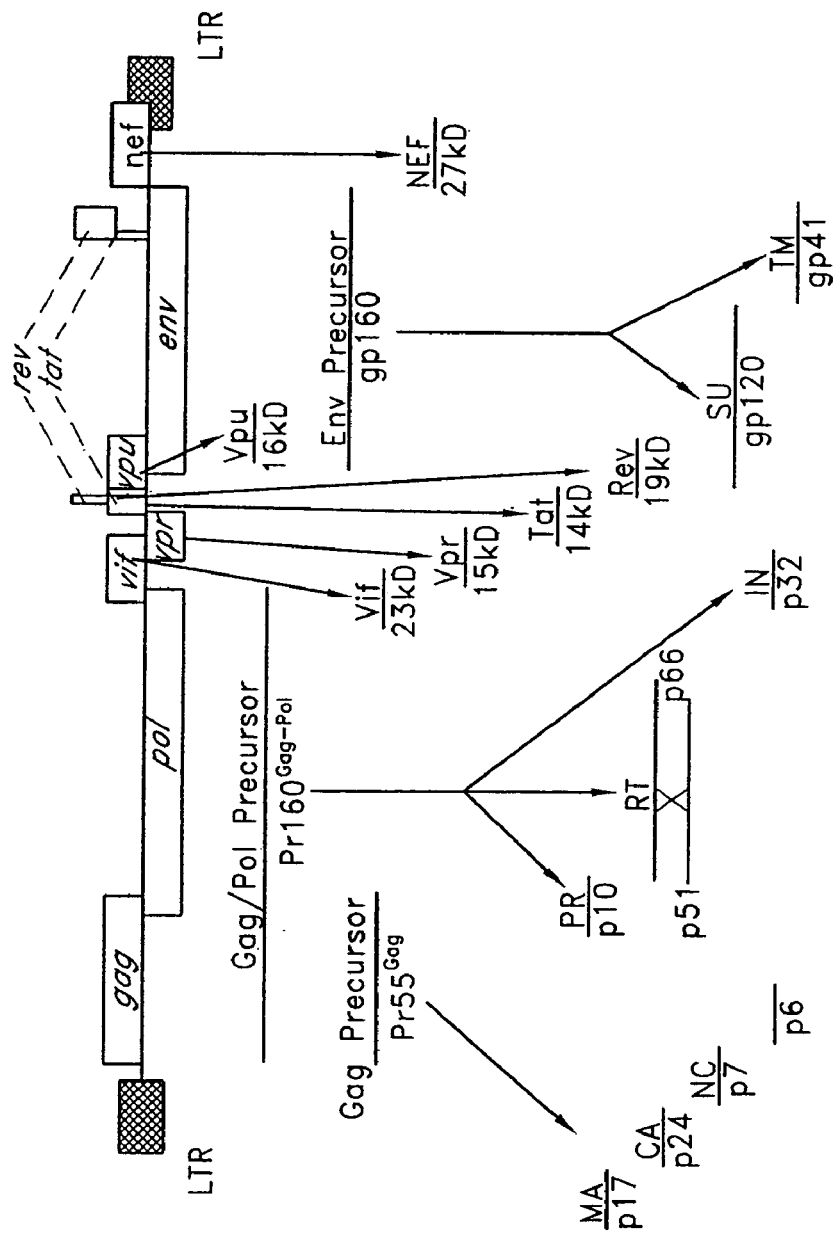
FIG. 4. HIV-encoded proteins. The location of the HIV genes, the sizes of primary translation products (in some cases polyproteins), and the processed mature viral proteins are indicated.

As is the case for all replication-competent retroviruses, the three primary HIV-1 translation products, all encoding structural proteins, are initially synthesized as polyprotein precursors, which are subsequently processed by viral or cellular proteases into mature particle-associated proteins (FIG. 4). The 55-kd Gag precursor $Pr55^{Gag}$ is cleaved into the matrix (MA), capsid (CA), nucleocapsid (NC), and p6 proteins. Autocatalysis of the 160-kd Gag-Pol polyprotein, $Pr160^{Gag-Pol}$, gives rise to the protease (PR), the heterodimeric reverse transcriptase (RT), and the integrase (IN) proteins, whereas proteolytic digestion by a cellular enzyme(s) converts the glycosylated 160-kd Env precursor gp160 to the gp120 surface (SU) and gp41 transmembrane (TM) cleavage products. The remaining six HIV-1-encoded proteins (Vif, Vpr, Tat, Rev, Vpu, and Nef) are the primary translation products of spliced mRNAs.

Gag

Figure 5:
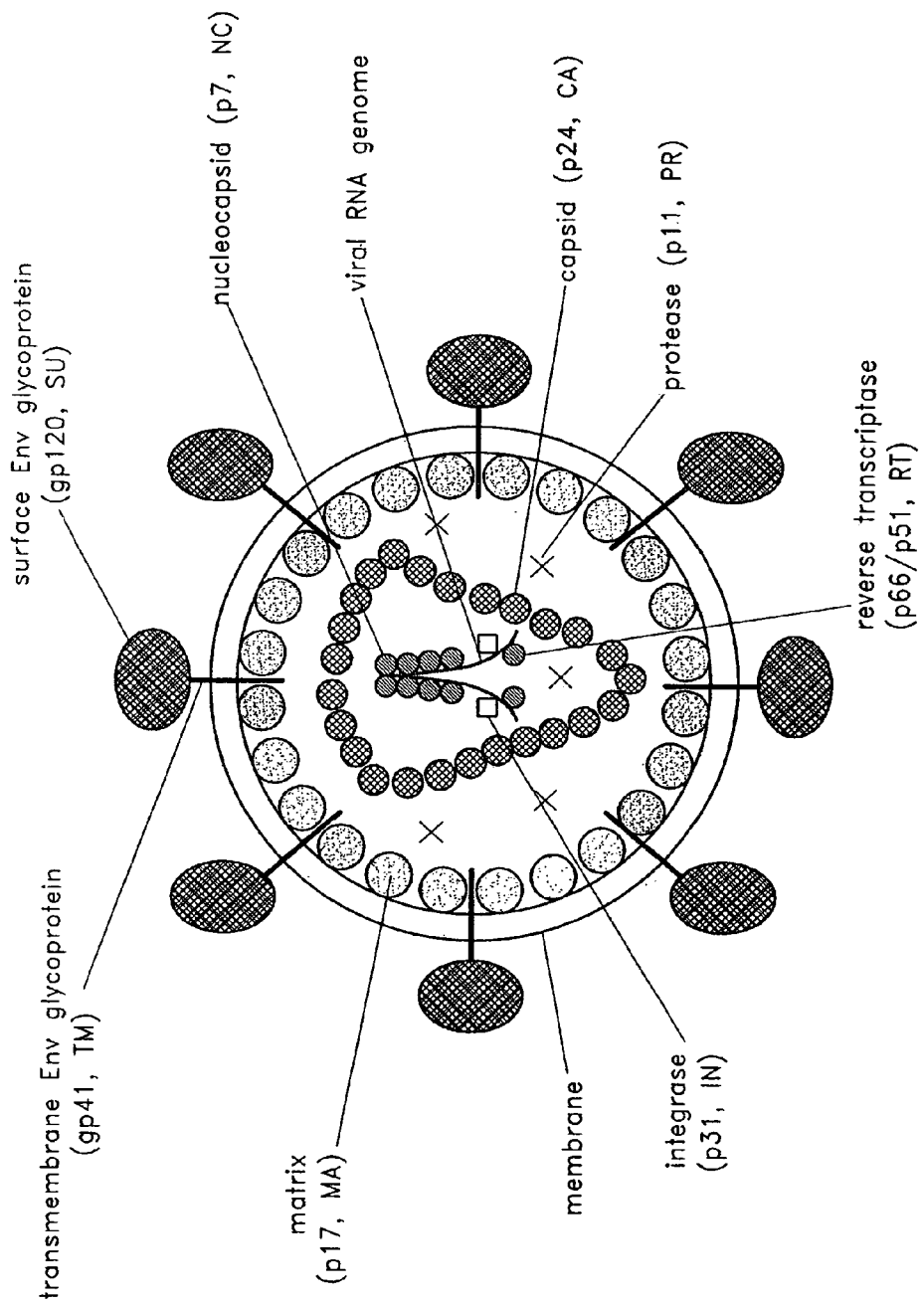
FIG. 5. Schematic representation of a mature HIV-1 virion.

The Gag proteins of HIV, like those of other retroviruses, are necessary and sufficient for the formation of noninfectious, virus-like particles. Retroviral Gag proteins are generally synthesized as polyprotein precursors; the HIV-1 Gag precursor has been named, based on its apparent molecular mass, $Pr55^{Gag}$. As noted previously, the mRNA for $Pr55^{Gag}$ is the unspliced 9.2-kb transcript (FIG. 4) that requires Rev for its expression in the cytoplasm. When the pol ORF is present, the viral protease (PR) cleaves $Pr55^{Gag}$ during or shortly after budding from the cell to generate the mature Gag proteins p17 (MA), p24 (CA), p7 (NC), and p6 (see FIG. 4). In the virion, MA is localized immediately inside the lipid bilayer of the viral envelope, CA forms the outer portion of the cone-shaped core structure in the center of the particle, and NC is present in the core in a ribonucleoprotein complex with the viral RNA genome (FIG. 5).

The HIV $Pr55^{Gag}$ precursor oligomerizes following its translation and is targeted to the plasma membrane, where particles of sufficient size and density to be visible by EM are assembled. Formation of virus-like particles by $Pr55^{Gag}$ is a self-assembly process, with critical Gag-Gag interactions taking place between multiple domains along the Gag precursor. The assembly of virus-like particles does not require the participation of genomic RNA (although the presence of nucleic acid appears to be essential), pol-encoded enzymes, or Env glycoproteins, but the production of infectious virions requires the encapsidation of the viral RNA genome and the incorporation of the Env glycoproteins and the Gag-Pol polyprotein precursor $Pr160^{Gag-Pol}$.

Pol

Downstream of gag lies the most highly conserved region of the HIV genome, the pol gene, which encodes three enzymes: PR, RT, and IN (see FIG. 4). RT and IN are required, respectively, for reverse transcription of the viral RNA genome to a double-stranded DNA copy, and for the integration of the viral DNA into the host cell chromosome. PR plays a critical role late in the life cycle by mediating the production of mature, infectious virions. The pol gene products are derived by enzymatic cleavage of a 160-kd Gag-Pol fusion protein, referred to as Pr160$^{Gag-Pol}$. This fusion protein is produced by ribosomal frameshifting during translation of Pr55$^{Gag}$ (see FIG. 4). The frame-shifting mechanism for Gag-Pol expression, also utilized by many other retroviruses, ensures that the pol-derived proteins are expressed at a low level, approximately 5% to 10% that of Gag. Like Pr55$^{Gag}$, the N-terminus of Pr160$^{Gag-Pol}$ is myristylated and targeted to the plasma membrane.

Protease

Early pulse-chase studies performed with avian retroviruses clearly indicated that retroviral Gag proteins are initially synthesized as polyprotein precursors that are cleaved to generate smaller products. Subsequent studies demonstrated that the processing function is provided by a viral rather than a cellular enzyme, and that proteolytic digestion of the Gag and Gag-Pol precursors is essential for virus infectivity. Sequence analysis of retroviral PRs indicated that they are related to cellular "aspartic" proteases such as pepsin and renin. Like these cellular enzymes, retroviral PRs use two apposed Asp residues at the active site to coordinate a water molecule that catalyzes the hydrolysis of a peptide bond in the target protein. Unlike the cellular aspartic proteases, which function as pseudodimers (using two folds within the same molecule to generate the active site), retroviral PRs function as true dimers. X-ray crystallographic data from HIV-1 PR indicate that the two monomers are held together in part by a four-stranded antiparallel β-sheet derived from both N- and C-terminal ends of each monomer. The substrate-binding site is located within a cleft formed between the two monomers. Like their cellular homologs, the HIV PR dimer contains flexible "flaps" that overhang the binding site and may stabilize the substrate within the cleft; the active-site Asp residues lie in the center of the dimer. Interestingly, although some limited amino acid homology is observed surrounding active-site residues, the primary sequences of retroviral PRs are highly divergent, yet their structures are remarkably similar.

Reverse Transcriptase

By definition, retroviruses possess the ability to convert their single-stranded RNA genomes into double-stranded DNA during the early stages of the infection process. The enzyme that catalyzes this reaction is RT, in conjunction with its associated RNaseH activity. Retroviral RTs have three enzymatic activities: (a) RNA-directed DNA polymerization (for minus-strand DNA synthesis), (b) RNaseH activity (for the degradation of the tRNA primer and genomic RNA present in DNA-RNA hybrid intermediates), and (c) DNA-directed DNA polymerization (for second- or plus-strand DNA synthesis).

The mature HIV-1 RT holoenzyme is a heterodimer of 66 and 51 kd subunits. The 51-kd subunit (p51) is derived from the 66-kd (p66) subunit by proteolytic removal of the C-terminal 15-kd RNaseH domain of p66 by PR (see FIG. 4). The crystal structure of HIV-1 RT reveals a highly asymmetric folding in which the orientations of the p66 and p51 subunits differ substantially. The p66 subunit can be visualized as a right hand, with the polymerase active site within the palm, and a deep template-binding cleft formed by the palm, fingers, and thumb subdomains. The polymerase domain is linked to RNaseH by the connection subdomain. The active site, located in the palm, contains three critical Asp residues (110, 185, and 186) in close proximity, and two coordinated Mg$^{2+}$ ions. Mutation of these Asp residues abolishes RT polymerizing activity. The orientation of the three active-site Asp residues is similar to that observed in other DNA polymerases (e.g., the Klenow fragment of E. coli DNA poII). The p51 subunit appears to be rigid and does not form a polymerizing cleft; Asp 110, 185, and 186 of this subunit are buried within the molecule. Approximately 18 base pairs of the primer-template duplex lie in the nucleic acid binding cleft, stretching from the polymerase active site to the RNaseH domain.

In the RT-primer-template-dNTP structure, the presence of a dideoxynucleotide at the 3' end of the primer allows visualization of the catalytic complex trapped just prior to attack on the incoming dNTP. Comparison with previously obtained structures suggests a model whereby the fingers close in to trap the template and dNTP prior to nucleophilic attack of the 3'-OH of the primer on the incoming dNTP. After the addition of the incoming dNTP to the growing chain, it has been proposed that the fingers adopt a more open configuration, thereby releasing the pyrophosphate and enabling RT to bind the next dNTP. The structure of the HIV-1 RNaseH has also been determined by x-ray crystallography; this domain displays a global folding similar to that of E. coli RNaseH.

Integrase

A distinguishing feature of retrovirus replication is the insertion of a DNA copy of the viral genome into the host cell chromosome following reverse transcription. The integrated viral DNA (the provirus) serves as the template for the synthesis of viral RNAs and is maintained as part of the host cell genome for the lifetime of the infected cell. Retroviral mutants deficient in the ability to integrate generally fail to establish a productive infection.

The integration of viral DNA is catalyzed by integrase, a 32-kd protein generated by PR-mediated cleavage of the C-terminal portion of the HIV-1 Gag-Pol polyprotein (see FIG. 4).

Retroviral IN proteins are composed of three structurally and functionally distinct domains: an N-terminal, zinc-finger-containing domain, a core domain, and a relatively nonconserved C-terminal domain. Because of its low solubility, it has not yet been possible to crystallize the entire 288-amino-acid HIV-1 IN protein. However, the structure of all three domains has been solved independently by x-ray crystallography or NMR methods. The crystal structure of the core domain of the avian sarcoma virus IN has also been determined. The N-terminal domain (residues 1 to 55), whose structure was solved by NMR spectroscopy, is composed of four helices with a zinc coordinated by amino acids His-12, His-16, Cys-40, and Cys-43. The structure of the N-terminal domain is reminiscent of helical DNA binding proteins that contain a so-called helix-turn-helix motif, however, in the HIV-1 structure this motif contributes to dimer formation. Initially, poor solubility hampered efforts to solve the structure of the core domain. However, attempts at crystallography were successful when it was observed that a Phe-to-Lys change at IN residue 185 greatly increased solubility without disrupting in vitro catalytic activity. Each monomer of the HIV-1 IN core domain (IN residues 50 to 212) is composed of a five-stranded β-sheet flanked by helices; this structure bears striking resemblance to other polynucleotidyl transferases including RNaseH and the bacteriophage MuA transposase. Three highly conserved residues are found in analogous positions in other polynucleotidyl transferases; in HIV-1 IN these are Asp-64, Asp-116 and Glu-152, the so-called D,D-35-E motif. Mutations at these positions block HIV IN function both in vivo and in vitro. The close proximity of these three amino acids in the crystal structure of both avian sarcoma virus and HIV-1 core domains supports the hypothesis that these residues play a central role in catalysis of the polynucleotidyl transfer reaction that is at the heart of the integration process. The C-terminal domain, whose structure has been solved by NMR methods, adopts a five-stranded β-barrel folding topology reminiscent of a Src homology 3 (SH3) domain. Recently, the x-ray structures of SIV and Rous sarcoma virus IN protein fragments encompassing both the core and C-terminal domains have been solved.

Env

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

Figure 6:
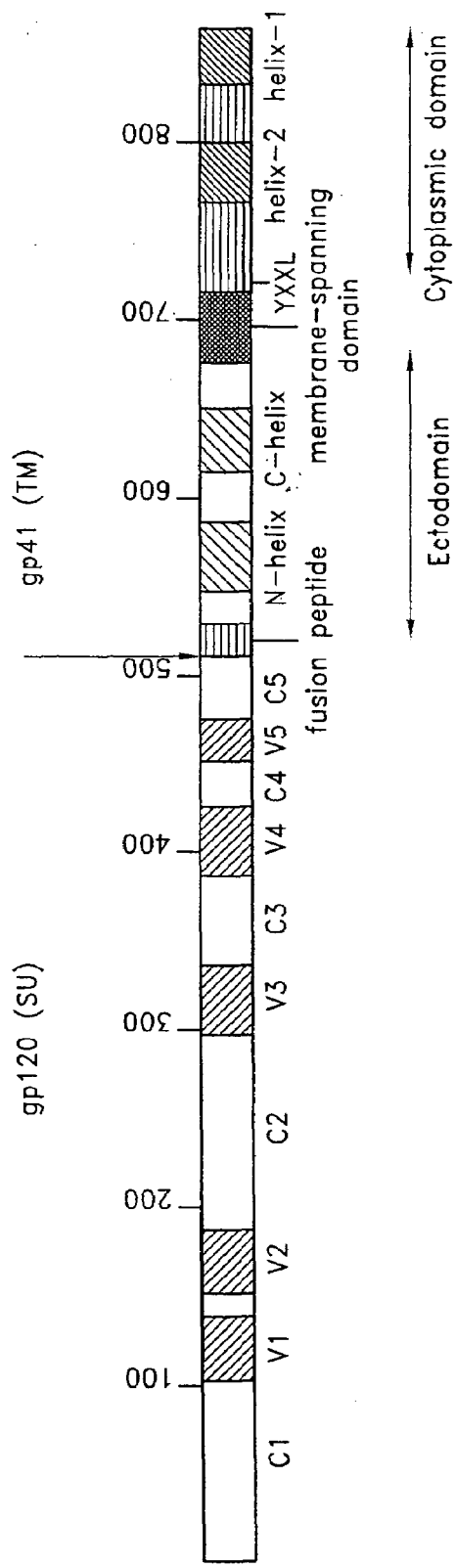
FIG. 6. Linear representation of the HIV-1 Env glycoprotein. The arrow indicates the site of gp160 cleavage to gp120 and gp41. In gp120, cross-hatched areas represent variable domains ($V_1$ to $V_5$) and open boxes depict conserved sequences ($C_1$ to $C_5$). In the gp41 ectodomain, several domains are indicated: the N-terminal fusion peptide, and the two ectodomain helices (N-and C-helix). The membrane-spanning domain is represented by a black box. In the gp41 cytoplasmic domain, the Tyr-X-X-Leu (YXXL) endocytosis motif (SEQ ID NO: 9) and two predicted helical domains (helix-1 and -2) are shown. Amino acid numbers are indicated.

The HIV Env glycoprotein is synthesized from the singly spliced 4.3-kb Vpu/Env bicistronic mRNA (see FIG. 4); translation occurs on ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41 (FIG. 6). The gp160 is cotranslationally glycosylated, forms disulfide bonds, and undergoes oligomerization in the ER. The predominant oligomeric form appears to be a trimer, although dimers and tetramers are also observed. The gp160 is transported to the Golgi, where, like other retroviral envelope precursor proteins, it is proteolytically cleaved by cellular enzymes to the mature SU glycoprotein gp120 and TM glycoprotein gp41 (see FIG. 6). The cellular enzyme responsible for cleavage of retroviral Env precursors following a highly conserved Lys/Arg-X-Lys/Arg-Arg motif is furin or a furin-like protease, although other enzymes may also catalyze gp160 processing. Cleavage of gp160 is required for Env-induced fusion activity and virus infectivity. Subsequent to gp160 cleavage, gp120 and gp41 form a noncovalent association that is critical for transport of the Env complex from the Golgi to the cell surface. The gp120-gp41 interaction is fairly weak, and a substantial amount of gp120 is shed from the surface of Env-expressing cells.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. As shown in FIG. 6, gp120 contains interspersed conserved ($C_1$ to $C_5$) and variable ($V_1$ to $V_5$) domains. The Cys residues present in the gp120s of different isolates are highly conserved and form disulfide bonds that link the first four variable regions in large loops.

A primary function of viral Env glycoproteins is to promote a membrane fusion reaction between the lipid bilayers of the viral envelope and host cell membranes. This membrane fusion event enables the viral core to gain entry into the host cell cytoplasm. A number of regions in both gp120 and gp41 have been implicated, directly or indirectly, in Env-mediated membrane fusion. Studies of the $HA_2$ hemagglutinin protein of the orthomyxoviruses and the F protein of the paramyxoviruses indicated that a highly hydrophobic domain at the N-terminus of these proteins, referred to as the fusion peptide, plays a critical role in membrane fusion. Mutational analyses demonstrated that an analogous domain was located at the N-terminus of the HIV-1, HIV-2, and SIV TM glycoproteins (see FIG. 6). Nonhydrophobic substitutions within this region of gp41 greatly reduced or blocked syncytium formation and resulted in the production of noninfectious progeny virions.

C-terminal to the gp41 fusion peptide are two amphipathic helical domains (see FIG. 6) which play a central role in membrane fusion. Mutations in the N-terminal helix (referred to as the N-helix), which contains a Leu zipper-like heptad repeat motif, impair infectivity and membrane fusion activity, and peptides derived from these sequences exhibit potent antiviral activity in culture. The structure of the ectodomain of HIV-1 and SIV gp41, the two helical motifs in particular, has been the focus of structural analyses in recent years. Structures were determined by x-ray crystallography or NMR spectroscopy either for fusion proteins containing the helical domains, a mixture of peptides derived from the N- and C-helices, or in the case of the SIV structure, the intact gp41 ectodomain sequence from residue 27 to 149. These studies obtained fundamentally similar trimeric structures, in which the two helical domains pack in an antiparallel fashion to generate a six-helix bundle. The N-helices form a coiled-coil in the center of the bundle, with the C-helices packing into hydrophobic grooves on the outside.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Use of Recombinant MVA Virus to Boost CD+8 Cell Immune Response

The present invention relates to generation of a $CD8^+$ T cell immune response against an antigen and also eliciting an antibody response. More particularly, the present invention relates to "prime and boost" immunization regimes in which the immune response induced by administration of a priming composition is boosted by administration of a boosting composition. The present invention is based on inventors' experimental demonstration that effective boosting can be achieved using modified vaccinia Ankara (MVA) vectors, following priming with any of a variety of different types of priming compositions including recombinant MVA itself.

A major protective component of the immune response against a number of pathogens is mediated by T lymphocytes of the $CD8^+$ type, also known as cytotoxic T lymphocytes (CTL). An important function of $CD8^+$ cells is secretion of gamma interferon (IFNγ), and this provides a measure of $CD8^+$ T cell immune response. A second component of the immune response is antibody directed to the proteins of the pathogen.

The present invention employs MVA which, as the experiments described below show, has been found to be an effective means for providing a boost to a $CD8^+$ T cell immune response primed to antigen using any of a variety of different priming compositions and also eliciting an antibody response.

Remarkably, the experimental work described below demonstrates that use of embodiments of the present invention allows for recombinant MVA virus expressing an HIV antigen to boost a CD8+ T cell immune response primed by a DNA vaccine and also eliciting an antibody response. The MVA was found to induce a CD8+ T cell response after intradermal, intramuscular or mucosal immunization. Recombinant MVA has also been shown to prime an immune response that is boosted by one or more inoculations of recombinant MVA.

Non-human primates immunized with plasmid DNA and boosted with the MVA were effectively protected against intramucosal challenge with live virus. Advantageously, the inventors found that a vaccination regime used intradermal, intramuscular or mucosal immunization for both prime and boost can be employed, constituting a general immunization regime suitable for inducing CD8+ T cells and also eliciting an antibody response, e.g. in humans.

The present invention in various aspects and embodiments employs an MVA vector encoding an HIV antigen for boosting a CD8+ T cell immune response to the antigen primed by previous administration of nucleic acid encoding the antigen and also eliciting an antibody response.

A general aspect of the present invention provides for the use of an MVA vector for boosting a CD8+ T cell immune response to an HIV antigen and also eliciting an antibody response.

One aspect of the present invention provides a method of boosting a CD8+ T cell immune response to an HIV antigen in an individual, and also eliciting an antibody response, the method including provision in the individual of an MVA vector including nucleic acid encoding the antigen operably linked to regulatory sequences for production of antigen in the individual by expression from the nucleic acid, whereby a CD8+ T cell immune response to the antigen previously primed in the individual is boosted.

An immune response to an HIV antigen may be primed by immunization with plasmid DNA or by infection with an infectious agent.

A further aspect of the invention provides a method of inducing a CD8+ T cell immune response to an HIV antigen in an individual, and also eliciting an antibody response, the method comprising administering to the individual a priming composition comprising nucleic acid encoding the antigen and then administering a boosting composition which comprises an MVA vector including nucleic acid encoding the antigen operably linked to regulatory sequences for production of antigen in the individual by expression from the nucleic acid.

A further aspect provides for use of an MVA vector, as disclosed, in the manufacture of a medicament for administration to a mammal to boost a CD8+ T cell immune response to an HIV antigen, and also eliciting an antibody response. Such a medicament is generally for administration following prior administration of a priming composition comprising nucleic acid encoding the antigen.

The priming composition may comprise any viral vector, such as a vaccinia virus vector such as a replication-deficient strain such as modified vaccinia Ankara (MVA) or NYVAC (Tartaglia et al. 1992 *Virology* 118:217-232), an avipox vector such as fowlpox or canarypox, e.g. the strain known as ALVAC (Paoletti et al. 1994 *Dev Biol Stand* 82:65-69), or an adenovirus vector or a vesicular stomatitis virus vector or an alphavirus vector.

The priming composition may comprise DNA encoding the antigen, such DNA preferably being in the form of a circular plasmid that is not capable of replicating in mammalian cells. Any selectable marker should not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with a boosting composition, or first and second boosting compositions, the first and second boosting compositions being the same or different from one another. Still further boosting compositions may be employed without departing from the present invention. In one embodiment, a triple immunization regime employs DNA, then adenovirus as a first boosting composition, then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be encoded in respective priming and boosting compositions (however many boosting compositions are employed) need not be identical, but should share at least one CD8+ T cell epitope. The antigen may correspond to a complete antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

An HIV antigen of the invention to be encoded by a recombinant MVA virus includes polypeptides having immunogenic activity elicited by an amino acid sequence of an HIV Env, Gag, Pol, Vif, Vpr, Tat, Rev, Vpu, or Nef amino acid sequence as at least one CD8+ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full length Env precursor sequence is presented for use in the present invention, Env is optionally deleted of subsequences. For example, regions of the gp120 surface and gp41 transmembrane cleavage products can be deleted.

Although a full length Gag precursor sequence is presented for use in the present invention, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full length Pol precursor sequence is presented for use in the present invention, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Percent identify can be determined, for example, by comparing sequence information using the GAP computer program, version 6.0, available from the University of Wisconsin Genetics Computer Group (UWGCG). The GAP program utilizes the alignment method of Needleman and Wunsch (*J Mol Biol* 1970 48:443), as revised by Smith and Waterman (*Adv Appl Math* 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (*Nucl Acids Res* 1986 14:6745), as described by Schwartz and Dayhoff (eds., *Atlas of Protein Sequence and Structure*, National Biomedical Research Foundation, Washington, D.C. 1979, pp. 353-358); (2) a penalty of 3.0 for each gap and an additional 0.10 penalty for each symbol in each gap; and (3) no penalty for end gaps.

In a preferred embodiment, an Env of the present invention is a variant form of at least one HIV envelope protein. Preferably, the Env is composed of gp120 and the membrane-spanning and ectodomain of gp41 but lacks part or all of the cytoplasmic domain of gp41.

Known HIV sequences are readily available from commercial and institutional HIV sequence databases, such as GENBANK, or as published compilations, such as Myers et al. eds., Human Retroviruses and *AIDS, A Compilation and Analysis of Nucleic Acid and Amino Acid Sequences*, Vol. I and II, Theoretical Biology and Biophysics, Los Alamos, N. Mex. (1993), or using for hiv-web.lanl.gov/.

Substitutions or insertions of an HIV Env, Gag, or Pol to obtain an additional HIV Env, Gag, or Pol, encoded by a nucleic acid for use in a recombinant MVA virus of the present invention, can include substitutions or insertions of at least one amino acid residue (e.g., 1-25 amino acids). Alternatively, at least one amino acid (e.g., 1-25 amino acids) can be deleted from an HIV Env, Gag, or Pol sequence. Preferably, such substitutions, insertions or deletions are identified based on safety features, expression levels, immunogenicity and compatibility with high replication rates of MVA.

Amino acid sequence variations in an HIV Env, Gag, or Pol of the present invention can be prepared e.g., by mutations in the DNA. Such HIV Env, Gag, or Pol include, for example, deletions, insertions or substitutions of nucleotides coding for different amino acid residues within the amino acid sequence. Obviously, mutations that will be made in nucleic acid encoding an HIV Env, Gag, or Pol must not place the sequence out of reading frame and preferably will not create complementary domains that could produce secondary mRNA structures.

HIV Env, Gag, or Pol-encoding nucleic acid of the present invention can also be prepared by amplification or site-directed mutagenesis of nucleotides in DNA or RNA encoding an HIV Env, Gag, or Pol and thereafter synthesizing or reverse transcribing the encoding DNA to produce DNA or RNA encoding an HIV Env, Gag, or Pol, based on the teaching and guidance presented herein.

Recombinant MVA viruses expressing HIV Env, Gag, or Pol of the present invention, include a finite set of HIV Env, Gag, or Pol-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., 1978 *Principles of Protein Structure*, Springer-Verlag, New York, N.Y., and Creighton, T. E., 1983 *Proteins: Structure and Molecular Properties*, W. H. Freeman & Co., San Francisco, Calif. For a presentation of nucleotide sequence substitutions, such as codon preferences, see Ausubel et al. eds. *Current Protocols in Molecular Biology*, Greene Publishing Assoc., New York, N.Y. 1994 at §§ A.1.1-A.1.24, and Sambrook, J. et al. 1989 *Molecular Cloning: A Laboratory Manual*, Second Edition, Cold Spring Harbor Laboratory Press, Cold Spring Harbor, N.Y. at Appendices C and D.

Thus, one of ordinary skill in the art, given the teachings and guidance presented herein, will know how to substitute other amino acid residues in other positions of an HIV env, gag, or pol DNA or RNA to obtain alternative HIV Env, Gag, or Pol, including substitutional, deletional or insertional variants.

Within the MVA vector, regulatory sequences for expression of the encoded antigen will include a natural, modified or synthetic poxvirus promoter. By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, marker genes and other sequences may be included as appropriate, in accordance with the knowledge and practice of the ordinary person skilled in the art: see, for example, Moss, B. (2001). Poxyiridae: the viruses and their replication. In Fields Virology, D. M. Knipe, and P. M. Howley, eds. (Philadelphia, Lippincott Williams & Wilkins), pp. 2849-2883. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, 1998 Ausubel et al. eds., John Wiley & Sons.

Promoters for use in aspects and embodiments of the present invention must be compatible with poxvirus expression systems and include natural, modified and synthetic sequences.

Either or both of the priming and boosting compositions may include an adjuvant, such as granulocyte macrophage-colony stimulating factor (GM-CSF) or encoding nucleic acid therefor.

Administration of the boosting composition is generally about 1 to 6 months after administration of the priming composition, preferably about 1 to 3 months.

Preferably, administration of priming composition, boosting composition, or both priming and boosting compositions, is intradermal, intramuscular or mucosal immunization.

Administration of MVA vaccines may be achieved by using a needle to inject a suspension of the virus. An alternative is the use of a needleless injection device to administer a virus suspension (using, e.g., BIOJECTOR™ needleless injector) or a resuspended freeze-dried powder containing the vaccine, providing for manufacturing individually prepared doses that do not need cold storage. This would be a great advantage for a vaccine that is needed in rural areas of Africa.

MVA is a virus with an excellent safety record in human immunizations. The generation of recombinant viruses can be accomplished simply, and they can be manufactured reproducibly in large quantities. Intradermal, intramuscular or mucosal administration of recombinant MVA virus is therefore highly suitable for prophylactic or therapeutic vaccination of humans against AIDS which can be controlled by a $CD8^+$ T cell response.

The individual may have AIDS such that delivery of the antigen and generation of a $CD8^+$ T cell immune response to the antigen is of benefit or has a therapeutically beneficial effect.

Most likely, administration will have prophylactic aim to generate an immune response against HIV or AIDS before infection or development of symptoms.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. intravenous, cutaneous or subcutaneous, nasal, intramuscular, intraperitoneal routes.

As noted, administration is preferably intradermal, intramuscular or mucosal.

Physiological saline solution, dextrose or other saccharide solution or glycols such as ethylene glycol, propylene glycol or polyethylene glycol may be included.

For intravenous, cutaneous, subcutaneous, intramuscular or mucosal injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included as required.

A slow-release formulation may be employed.

Following production of MVA particles and optional formulation of such particles into compositions, the particles may be administered to an individual, particularly human or other primate. Administration may be to another mammal, e.g. rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16th edition, 1980, Osol, A. (ed.).

In one preferred regimen, DNA is administered at a dose of 250 µg to 2.5 mg/injection, followed by MVA at a dose of $10^6$ to $10^9$ infectious virus particles/injection.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g. protection against HIV or AIDS.

Further aspects and embodiments of the present invention will be apparent to those of ordinary skill in the art, in view of the above disclosure and following experimental exemplification, included by way of illustration and not limitation, and with reference to the attached figures.

EXAMPLE 1

Control of a Mucosal Challenge and Prevention of AIDS by a Multiprotein DNA/MVA Vaccine Here we tested DNA priming and poxvirus boosting for the ability to protect against a highly pathogenic mucosal challenge. The 89.6 chimera of simian and human immunodeficiency viruses (SHIV-89.6) was used for the construction of immunogens and its highly pathogenic derivative, SHIV-89.6P, for challenge (G. B. Karlsson et al. 1997 *J Virol* 71:4218). SHIV-89.6 and SHIV-89.6P do not generate cross-neutralizing antibody (D. C. Montefiori et al 1998 *J Virol* 72:3427) and allowed us to address the ability of vaccine-raised T cells and non-neutralizing antibodies to control an immunodeficiency virus challenge. Modified vaccinia Ankara (MVA) was used for the construction of the recombinant poxvirus. MVA has been highly effective at boosting DNA-primed CD8 T cells and enjoys the safety feature of not replicating efficiently in human or monkey cells (H. L. Robinson et al. 2000 *AIDS Reviews* 2:105).

To ensure a broad immune response both the DNA and recombinant MVA (rMVA) components of the vaccine expressed multiple immunodeficiency virus proteins. The DNA prime (DNA/89.6) expressed simian immunodeficiency virus (SIV) Gag, Pol, Vif, Vpx, and Vpr and human immunodeficiency virus-1 (HIV-1) Env, Tat, and Rev from a single transcript (R. J. Gorelick et al. 1999 *Virology* 253:259; M. M. Sauter et al. 1996 *J Cell Biol* 132:795).

Molecularly cloned SHIV-89.6 sequences were cloned into the vector pGA2 using ClaI and RsrII sites. This cloning deleted both long terminal repeats (LTRs) and nef. The SHIV-89.6 sequences also were internally mutated for a 12-base pair region encoding the first four amino acids of the second zinc finger in nucleocapsid. This mutation renders SHIV viruses noninfectious (R. J. Gorelick et al 1999 *Virology* 253:259). A mutation in gp41 converted the tyrosine at position 710 to cysteine to achieve better expression of Env on the plasma membrane of DNA-expressing cells (M. M. Sauter et al. 1996 *J Cell Biol* 132:795). pGA2 uses the CMV immediate early promoter without intron A and the bovine growth hormone polyadenylation sequence to express vaccine inserts. Vaccine DNA was produced by Althea (San Diego, Calif.). In transient transfections of 293T cells, DNA/89.6 produced about 300 ng of Gag and 85 ng of Env per $1\times10^6$ cells.

The rMVA booster (MVA/89.6) expressed SIV Gag, Pol, and HIV-1 Env under the control of vaccinia virus early/late promoters.

The MVA double recombinant virus expressed both the HIV 89.6 Env and the SIV 239 Gag-Pol, which were inserted into deletion II and deletion III of MVA, respectively. The 89.6 Env protein was truncated for the COOH-terminal 115 amino acids of gp41. The modified H5 promoter controlled the expression of both foreign genes.

Figure 7A:
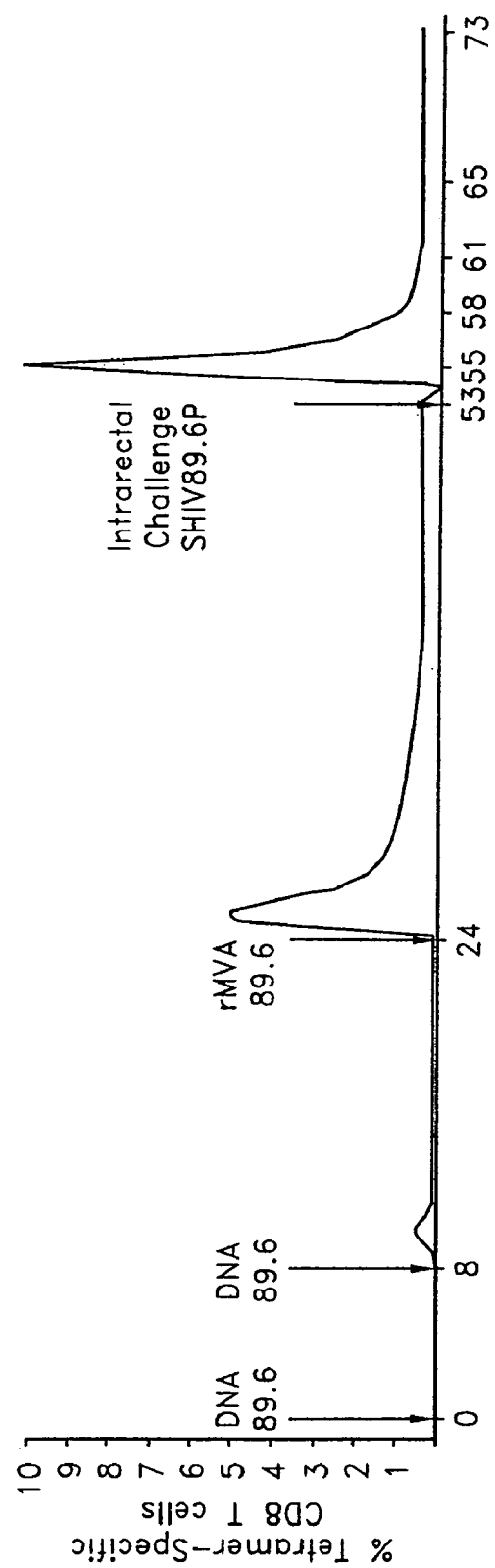
FIG. 7. Temporal frequencies of Gag-specific T cells. (A) Gag-specific CD8 T cell responses raised by DNA priming and rMVA booster immunizations. The schematic presents mean Gag-CM9-tetramer data generated in the high-dose i.d. DNA-immunized animals. (B) Gag-specific IFN-γ ELISPOTs in A*01 (open bars) and non-A*01 (filled bars) macaques at various times before challenge and at two weeks after challenge. Three pools of 10 to 13 Gag peptides (22-mers overlapping by 12) were used for the analyses. The numbers above data bars represent the arithmetic mean±SD for the ELISPOTs within each group. The numbers at the top of the graphs designate individual animals. *, data not available; #, <20 ELISPOTs per $1 \times 10^6$ peripheral blood mononuclear cells (PBMC). Temporal data for Gag-CM9-Mamu-A*01 tetramer-specific T cells can be found in FIG. 12.

Vaccination was accomplished by priming with DNA at 0 and 8 weeks and boosting with rMVA at 24 weeks (FIG. 7A).

I.d. and i.m. DNA immunizations were delivered in phosphate-buffered saline (PBS) with a needleless jet injector (Bioject, Portland, Oreg.) to deliver five i.d. 100-μl injections to each outer thigh for the 2.5-mg dose of DNA or one i.d. 100-μl injection to the right outer thigh for the 250-μg dose of plasmid. I.m. deliveries of DNA were done with one 0.5-ml injection of DNA in PBS to each outer thigh for the 2.5-mg dose and one 100-μl injection to the right outer thigh for the 250-μg dose. $1 \times 10^8$ pfu of MVA/89.6 was administered both i.d. and i.m. with a needle. One 100-μl dose was delivered to each outer thigh for the i.d. dose and one 500-μl dose to each outer thigh for the i.m dose. Control animals received 2.5 mg of the pGA2 vector without vaccine insert with the Bioject device to deliver five 100-μl doses i.d. to each outer thigh. The control MVA booster immunization consisted of $2 \times 10^8$ pfu of MVA without an insert delivered i.d. and i.m. as described for MVA/89.6.

Four groups of six rhesus macaques each were primed with either 2.5 mg (high-dose) or 250 μg (low-dose) of DNA by intradermal (i.d.) or intramuscular (i.m.) routes using a needleless jet injection device (Bioject, Portland, Oreg.) (T. M. Allen et al. 2000 *J Immunol* 164:4968).

Young adult rhesus macaques from the Yerkes breeding colony were cared for under guidelines established by the Animal Welfare Act and the NIH "Guide for the Care and Use of Laboratory Animals" with protocols approved by the Emory University Institutional Animal Care and Use Committee. Macaques were typed for the *Mamu-A*01* allele with polymerase chain reaction (PCR) analyses (M. A. Egan et al. 2000 *J Virol* 74:7485; I. Ourmanov et al. 2000 *J Virol* 74:2740). Two or more animals containing at least one *Mamu-A*01* allele were assigned to each group. Animal numbers are as follows: 1, RBr-5*; 2, RIm-5*; 3, RQf-5*; 4, RZe-5; 5, ROm-5; 6, RDm-5; 7, RAj-5*; 8, RJi-5*; 9, RAl-5*; 10, RDe-5*; 11, RAi-5; 12, RPr-5; 13, RKw-4*; 14, RWz-5*; 15, RGo-5; 16, RLp-4; 17, RWd-6; 18, RAt-5; 19, RPb-5*; 20, RIi-5*; 21, RIq-5; 22, RSp-4; 23, RSn-5; 24, RGd-6; 25, RMb-5*; 26, RGy-5*; 27, RUs-4; and 28, RPm-5. Animals with the A*01 allele are indicated with asterisks.

Gene gun deliveries of DNA were not used because these had primed non-protective immune responses in a 1996-98 trial (H. L. Robinson et al. 1999 *Nat Med* 5:526). The MVA/89.6 booster immunization ($2 \times 10^8$ plaque-forming units, pfu) was injected with a needle both i.d. and i.m. A control group included two mock immunized animals and two naive animals. The challenge was given at 7 months after the rMVA booster to test for the generation of long-term immunity. Because most HIV-1 infections are transmitted across mucosal surfaces, an intrarectal challenge was administered.

DNA priming followed by rMVA boosting generated high frequencies of virus-specific T cells that peaked at one week following the rMVA booster (FIG. 7). The frequencies of T cells recognizing the Gag-CM9 epitope were assessed by means of Mamu-A*01 tetramers, and the frequencies of T cells recognizing epitopes throughout Gag were assessed with pools of overlapping peptides and an enzyme-linked immunospot (ELISPOT) assay (C. A. Power et al. 1999 *J Immunol Methods* 227:99).

For tetramer analyses, about $1 \times 10^6$ peripheral blood mononuclear cells (PBMC) were surface-stained with antibodies to CD3 conjugated to fluorescein isothiocyanate (FITC) (FN-18; Biosource International, Camarillo, Calif.), CD8 conjugated to peridinin chlorophyl protein (PerCP) (SK1; Becton Dickinson, San Jose, Calif.), and Gag-CM9 (CTPYDINQM)-*Mamu-A*01* tetramer (SEQ ID NO: 6) conjugated to allophycocyanin (APC), in a volume of 100 μl at 8° to 10° C. for 30 min. Cells were washed twice with cold PBS containing 2% fetal bovine serum (FBS), fixed with 1% paraformaldehyde in PBS, and analyzed within 24 hrs on a FACScaliber (Becton Dickinson, San Jose, Calif.). Cells were initially gated on lymphocyte populations with forward scatter and side scatter and then on CD3 cells. The CD3 cells were then analyzed for CD8 and tetramer-binding cells. About 150,000 lymphocytes were acquired for each sample. Data were analyzed using FloJo software (Tree Star, San Carlos, Calif.).

For interferon-γ (IFN-γ) ELISPOTs, MULTISCREEN 96 well filtration plates (Millipore Inc. Bedford, Mass.) were coated overnight with antibody to human IFN-γ (Clone B27, Pharmingen, San Diego, Calif.) at a concentration of 2 μg/ml in sodium bicarbonate buffer (pH 9.6) at 8° to 10° C. Plates were washed two times with RPMI medium and then blocked for 1 hour with complete medium (RPMI containing 10% FBS) at 37° C. Plates were washed five more times with plain RPMI medium, and cells were seeded in duplicate in 100 μl complete medium at numbers ranging from $2 \times 10^4$ to $5 \times 10^5$ cells per well. Peptide pools were added to each well to a final concentration of 2 μg/ml of each peptide in a volume of 100 μl in complete medium. Cells were cultured at 37° C. for about 36 hrs under 5% $CO_2$. Plates were washed six times with wash buffer (PBS with 0.05% Tween-20) and then incubated with 1 μg of biotinylated antibody to human IFN-γ per milliliter (clone 7-86-1; Diapharma Group, West Chester, Ohio) diluted in wash buffer containing 2% FBS. Plates were incubated for 2 hrs at 37° C. and washed six times with wash buffer. Avidin-horseradish peroxidase (Vector Laboratories, Burlingame, Calif.) was added to each well and incubated for 30 to 60 min at 37° C. Plates were washed six times with wash buffer and spots were developed using stable DAB as substrate (Research Genetics, Huntsville, Ala.). Spots were counted with a stereo dissecting microscope. An ovalbumin peptide (SIINFEKL) (SEQ ID NO: 7) was included as a control in each analysis. Background spots for the ovalbumin peptide were generally <5 for $5 \times 10^5$ PBMCs. This background when normalized for $1 \times 10^6$ PBMC was <10. Only ELISPOT counts of twice the background ($\geq 20$) were considered significant. The frequencies of ELISPOTs are approximate because different dilutions of cells have different efficiencies of spot formation in the absence of feeder cells (C. A. Power et al. 1999 *J Immunol Methods* 227: 99). The same dilution of cells was used for all animals at a given time point, but different dilutions were used to detect memory and acute responses.

Figure 7B:
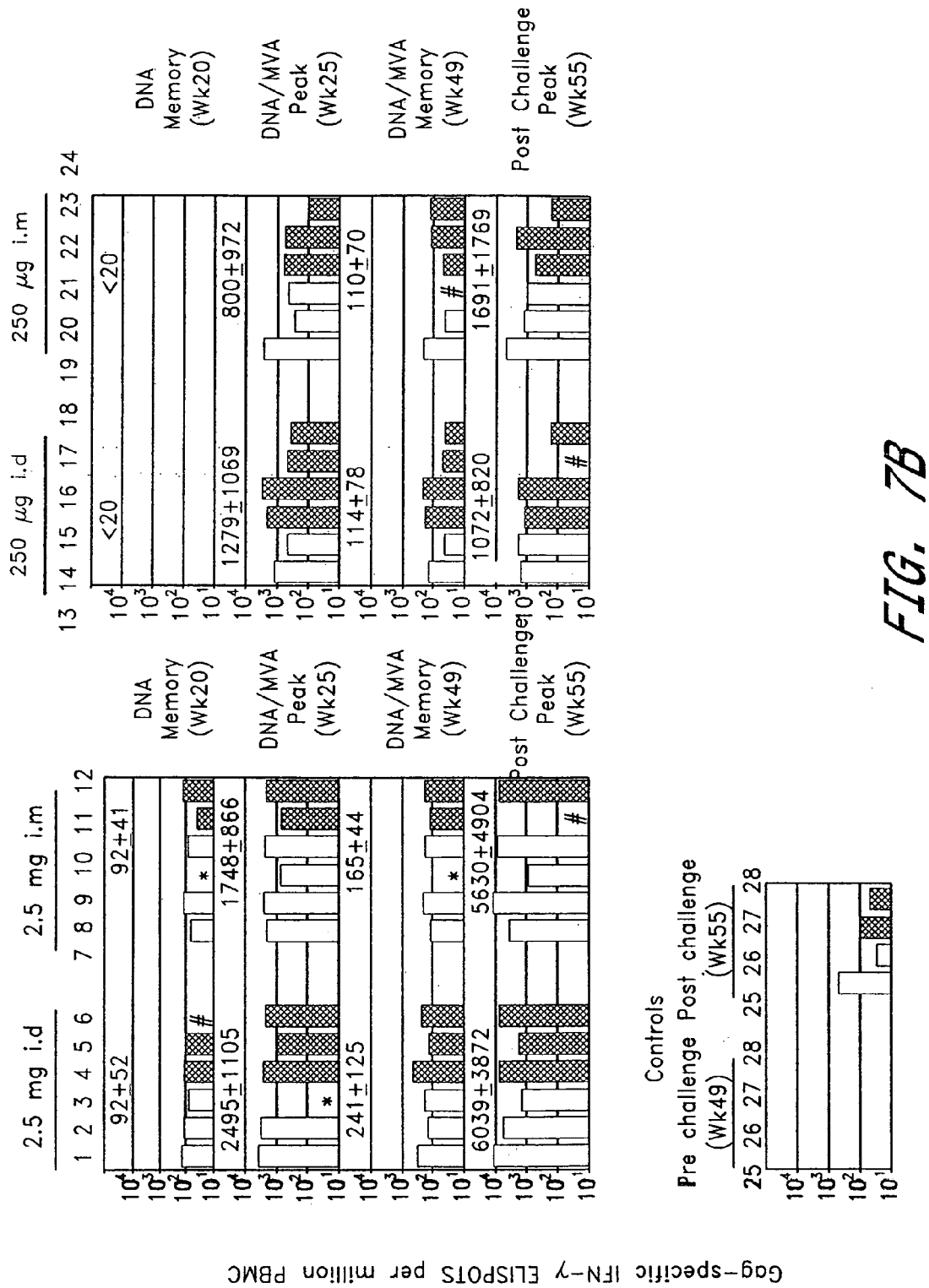
Figure 12:
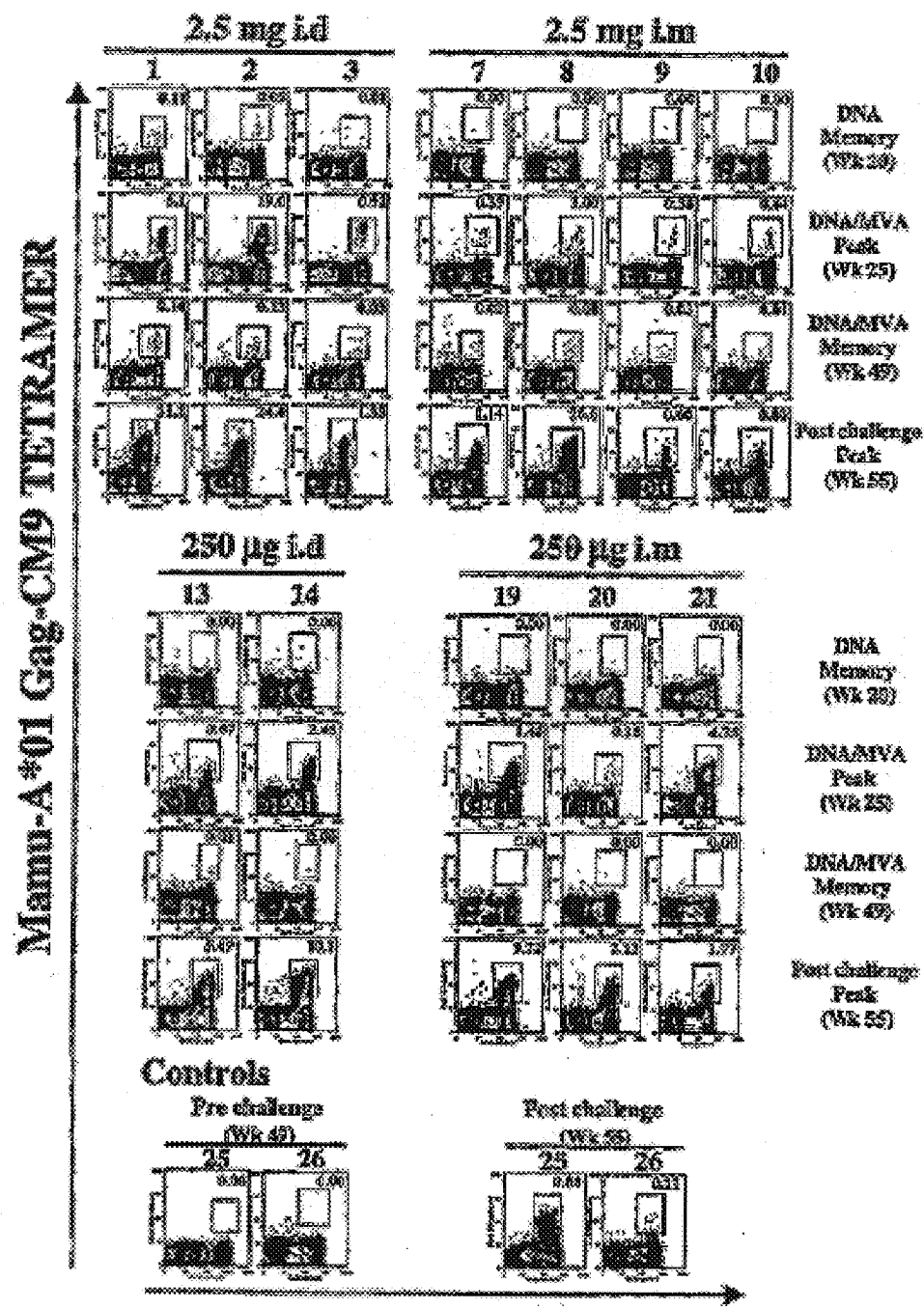
FIG. 12. Gag-CM9-Mamu-A*01 tetramer-specific T cells in *Mamu-A*01 vaccinated and control macaques at various times before challenge and at two weeks after challenge. The number at the upper right corner of each plot represents the frequency of tetramer-specific CD8 T cells as a % of total CD8 T cells. The numbers above each column of FACS data designate individual animals.
Figure 13:
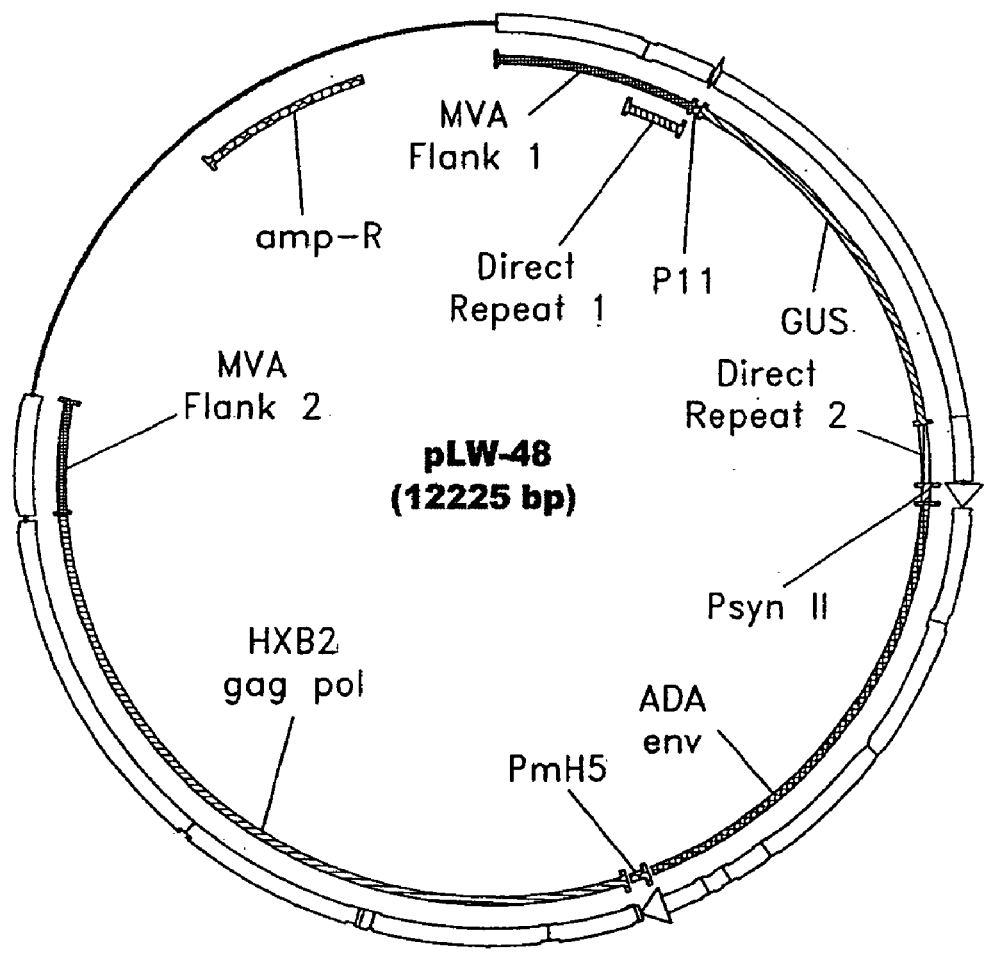
FIG. 13. Map of plasmid transfer vector pLW-48.

Gag-CM9 tetramer analyses were restricted to macaques that expressed the *Mamu-A*01* histocompatibility type, whereas ELISPOT responses did not depend on a specific histocompatibility type. As expected, the DNA immunizations raised low levels of memory cells that expanded to high frequencies within 1 week of the rMVA booster (FIGS. 7 and 12). In *Mamu-A*01* macaques, CD8 cells specific to the Gag-CM9 epitope expanded to frequencies as high as 19% of total CD8 T cells (FIG. 12). This peak of specific cells underwent a 10- to 100-fold contraction into the DNA/MVA memory pool (FIGS. 7A and 12). ELISPOTs for three pools of Gag peptides also underwent a major expansion (frequencies up to 4000 spots for $1\times10^6$ PBMC) before contracting from 5- to 20-fold into the DNA/MVA memory response (FIG. 7B). The frequencies of ELISPOTs were the same in macaques with and without the A*01 histocompatibility type (P>0.2).

Simple linear regression was used to estimate correlations between postbooster and postchallenge ELISPOT responses, between memory and postchallenge ELISPOT responses, and between logarithmically transformed viral loads and ELISPOT frequencies. Comparisons between vaccine and control groups and A*01 and non A*01 macaques were performed by means of two-sample t tests with logarithmically transformed viral load and ELISPOT responses. Two-way analyses of variance were used to examine the effects of dose and route of administration on peak DNA/MVA ELISPOTs, on memory DNA/MVA ELISPOTs, and on logarithmically transformed Gag antibody data.

At both peak and memory phases of the vaccine response, the rank order for the height of the ELISPOTs in the vaccine groups was 2.5 mg i.d.>2.5 mg i.m.>250 µg i.d.>250 µg i.m. (FIG. 7B). The IFN-γ ELISPOTs included both CD4 and CD8 cells. Gag-CM9-specific CD8 cells had good lytic activity after restimulation with peptide.

The highly pathogenic SHIV-89.6P challenge was administered intrarectally at 7 months after the rMVA booster, when vaccine-raised T cells were in memory (FIG. 7).

The challenge stock ($5.7\times10^9$ copies of viral RNA per milliliter) was produced by one intravenous followed by one intrarectal passage in rhesus macaques of the original SHIV-89.6P stock (G. B. Karlsson et al. 1997 *J Virol* 71:4218). Lymphoid cells were harvested from the intrarectally infected animal at peak viremia, CD8-depleted, and mitogen-stimulated for stock production. Before intrarectal challenge, fasted animals were anesthetized (ketamine, 10 mg/kg) and placed on their stomach with the pelvic region slightly elevated. A feeding tube (8Fr (2.7 mm)×16 inches (41 cm); Sherwood Medical, St. Louis, Mo.) was inserted into the rectum for a distance of 15 to 20 cm. Following insertion of the feeding tube, a syringe containing 20 intrarectal infectious doses in 2 ml of RPMI-1640 plus 10% FBS was attached to the tube and the inoculum was slowly injected into the rectum. After delivery of the inoculum, the feeding tube was flushed with 3.0 ml of RPMI without FBS and then slowly withdrawn. Animals were left in place, with pelvic regions slightly elevated, for a period of ten minutes after the challenge.

The challenge infected all of the vaccinated and control animals (FIG. 8). However, by 2 weeks after challenge, titers of plasma viral RNA were at least 10-fold lower in the vaccine groups (geometric means of $1\times10^7$ to $5\times10^7$) than in the control animals (geometric mean of $4\times10^8$) (FIG. 8A) (S. Staprans et al. in: *Viral Genome Methods* K. Adolph, ed. CRC Press, Boca Raton, Fla., 1996 pp. 167-184; R. Hofmann-Lehmann et al. 2000 *AIDS Res Hum Retroviruses* 16:1247).

For the determination of SHIV copy number, viral RNA from 150 µl of ACD anticoagulated plasma was directly extracted with the QIAamp Viral RNA kit (Qiagen), eluted in 60 µl of AVE buffer, and frozen at −80° C. until SHIV RNA quantitation was performed. Five microliters of purified plasma RNA was reverse-transcribed in a final 20-µl volume containing 50 mM KCl, 10 mM Tris-HCl (pH 8.3), 4 mM $MgCl_2$, 1 mM each deoxynucleotide triphosphate (dNTP), 2.5 µM random hexamers, 20 units MultiScribe RT, and 8 units ribonuclease inhibitor. Reactions were incubated at 25° C. for 10 min, followed by incubation at 42° C. for 20 min, and inactivation of reverse transcriptase at 99° C. for 5 min. The reaction mix was adjusted to a final volume of 50 µl containing 50 mM KCl, 10 mM Tris-HCl (pH 8.3), 4 mM $MgCl_2$, 0.4 mM each dNTP, 0.2 µM forward primer, 0.2 µM reverse primer, 0.1 µM probe, and 5 units AmpliTaq Gold DNA polymerase (all reagents from PerkinElmer Applied Biosystems, Foster City, Calif.). The primer sequences within a conserved portion of the SIV gag gene are the same as those described previously (S. Staprans et al. in: *Viral Genome Methods* K. Adolph, ed. CRC Press, Boca Raton, Fla., 1996 pp. 167-184). A PerkinElmer Applied Biosystems 7700 Sequence Detection System was used with the PCR profile: 95° C. for 10 min, followed by 40 cycles at 93° C. for 30 s, and 59.5° C. for 1 min. PCR product accumulation was monitored with the 7700 sequence detector and a probe to an internal conserved gag gene sequence: 6FAM-CT-GTCTGCGTCATTTGGTGC-Tamra (SEQ ID NO: 8), where FAM and Tamra denote the reporter and quencher dyes. SHIV RNA copy number was determined by comparison with an external standard curve consisting of virion-derived SIVmac239 RNA quantified by the SIV bDNA method (Bayer Diagnostics, Emeryville, Calif.). All specimens were extracted and amplified in duplicate, with the mean result reported. With a 0.15-ml plasma input, the assay has a sensitivity of $10^3$ RNA copies per milliliter of plasma and a linear dynamic range of $10^3$ to $10^8$ RNA copies (R2=0.995). The intraassay coefficient of variation was <20% for samples containing >$10^4$ SHIV RNA copies per milliliter, and <25% for samples containing $10^3$ to $10^4$ SHIV RNA copies per milliliter. To more accurately quantitate low SHIV RNA copy number in vaccinated animals at weeks 16 and 20, we made the following modifications to increase the sensitivity of the SHIV RNA assay: (i) Virions from ≦1 ml of plasma were concentrated by centrifugation at 23,000 g at 10° C. for 150 min before viral RNA extraction, and (ii) a one-step reverse transcriptase PCR method was used (R. Hofmann-Lehmann et al. 2000 *AIDS Res Hum Retroviruses* 16:1247). These changes provided a reliable quantification limit of 300 SHIV RNA copies per milliliter, and gave SHIV RNA values that were highly correlated to those obtained by the first method used (r=0.91, P<0.0001).

Figure 8C:
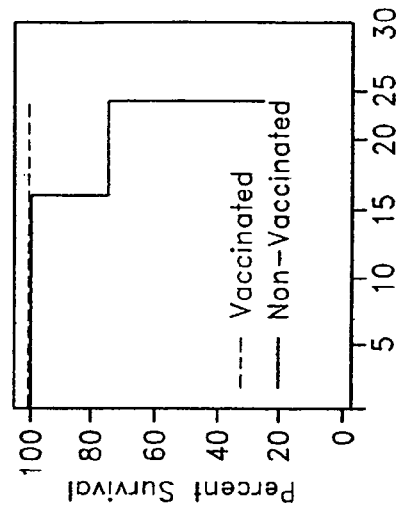
FIG. 8. Temporal viral loads, CD4 counts, and survival after challenge of vaccinated and control animals. (A) Geometric mean viral loads and (B) geometric mean CD4 counts. (C) Survival curve for vaccinated and control animals. The dotted line represents all 24 vaccinated animals. (D) Viral loads and (E) CD4 counts for individual animals in the vaccine and control groups. The key to animal numbers is presented in (E). Assays for the first 12 weeks after challenge had a detection level of 1000 copies of RNA per milliliter of plasma. Animals with loads below 1000 were scored with a load of 500. For weeks 16 and 20, the detection level was 300 copies of RNA per milliliter. Animals with levels of virus below 300 were scored at 300.

By 8 weeks after challenge, both high-dose DNA-primed groups and the low-dose i.d. DNA-primed group had reduced their geometric mean loads to about 1000 copies of viral RNA per milliliter. At this time, the low-dose i.m. DNA-primed group had a geometric mean of $6\times10^3$ copies of viral RNA and the nonvaccinated controls had a geometric mean of $2\times10^6$. By 20 weeks after challenge, even the low-dose i.m. group had reduced its geometric mean copies of viral RNA to 1000. Among the 24 vaccinated animals, only one animal, animal number 22 in the low-dose i.m. group, had intermittent viral loads above $1\times10^4$ copies per milliliter (FIG. 8D).

Figure 8B:
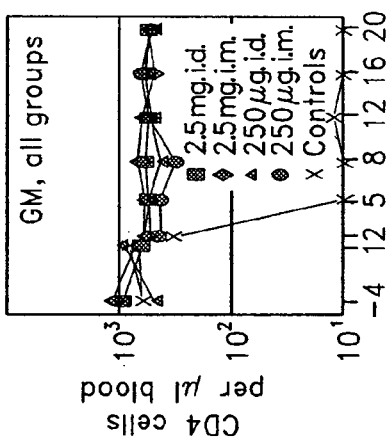
Figure 8A:
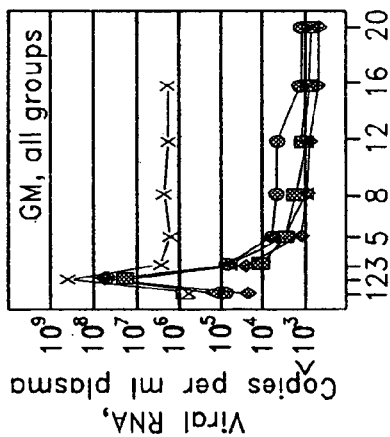
Figure 8D:
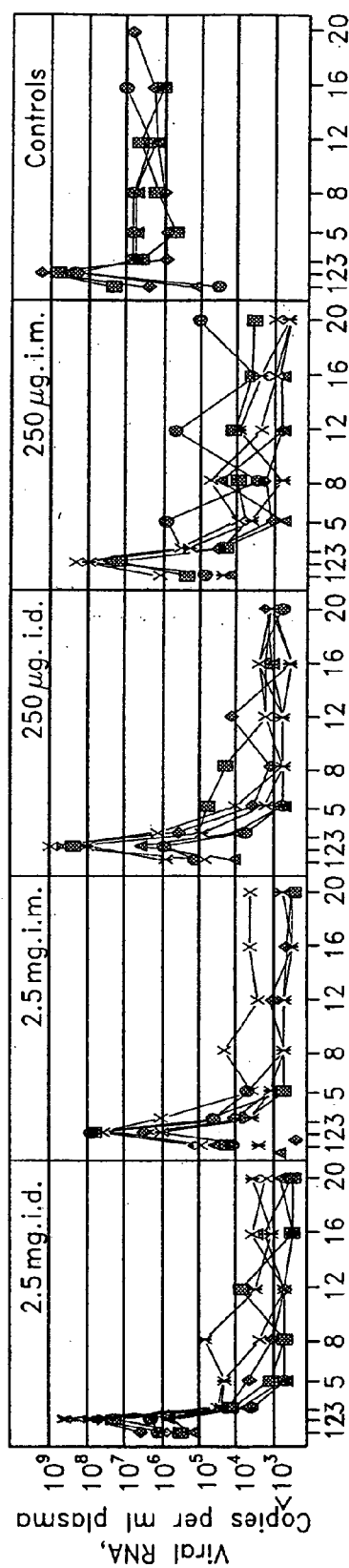
Figure 8E:
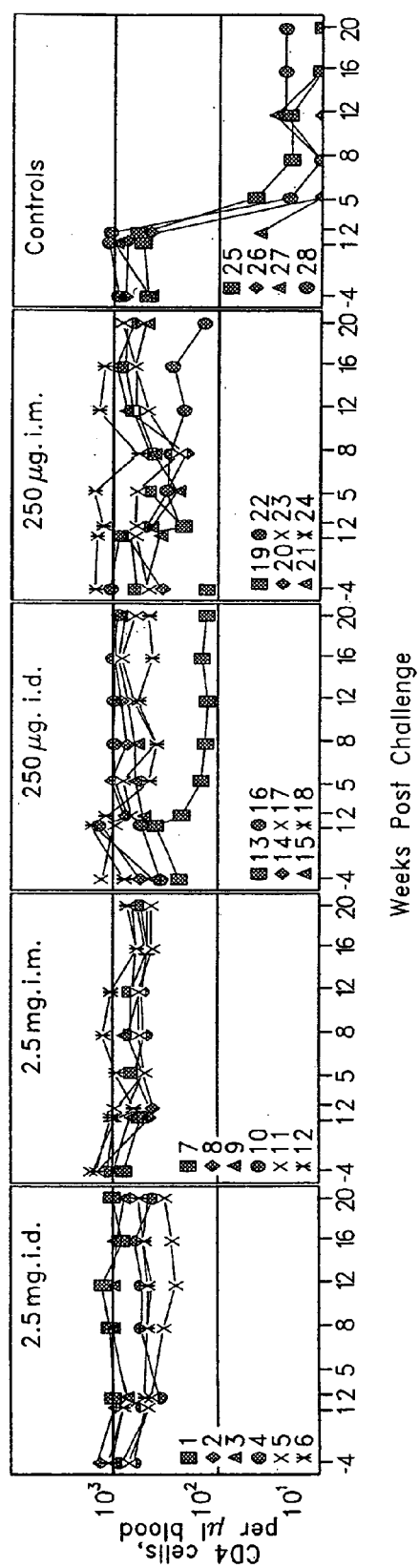

By 5 weeks after challenge, all of the nonvaccinated controls had undergone a profound depletion of CD4 cells (FIG. 8B). All of the vaccinated animals maintained their CD4 cells, with the exception of animal 22 in the low dose i.m. group (see above), which underwent a slow CD4 decline (FIG. 8E). By 23 weeks after challenge, three of the four control animals had succumbed to AIDS (FIG. 8C). These animals had variable degrees of enterocolitis with diarrhea, cryptosporidiosis, colicystitis, enteric *campylobacter* infection, splenomegaly, lymphadenopathy, and SIV-associated giant cell pneumonia. In contrast, all 24 vaccinated animals maintained their health.

Figure 9A:
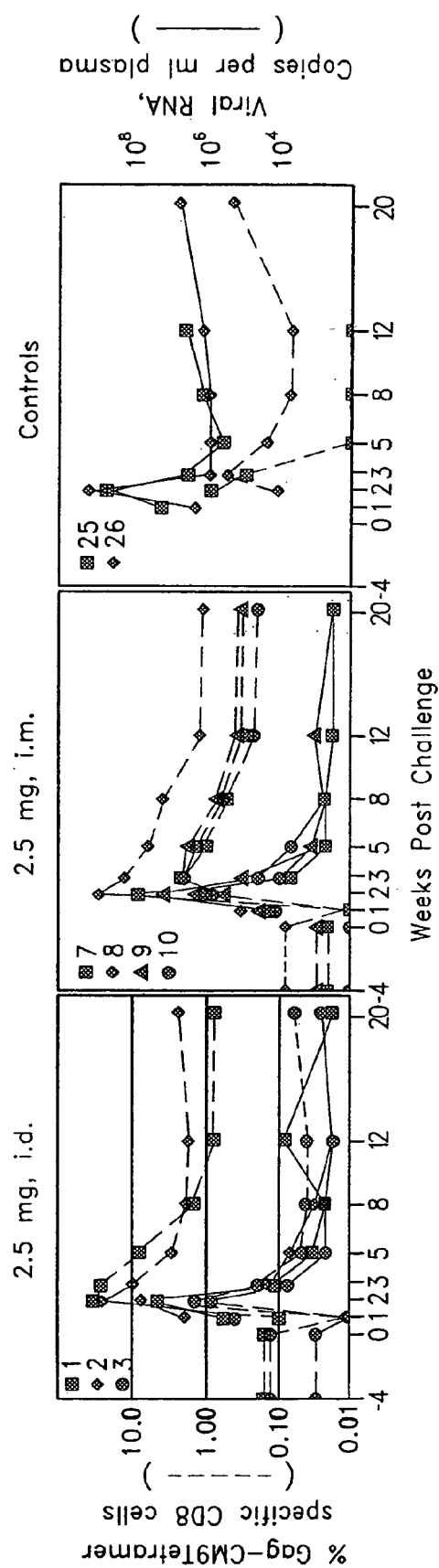
FIG. 9. Postchallenge T cell responses in vaccine and control groups. (A) Temporal tetramer+ cells (dashed line) and viral loads (solid line). (B) Intracellular cytokine assays for IFN-γ production in response to stimulation with the Gag-CM9 peptide at two weeks after challenge. This ex vivo assay allows evaluation of the functional status of the peak postchallenge tetramer+ cells displayed in FIG. 7A. (C) Proliferation assay at 12 weeks after challenge. Gag-Pol-Env (open bars) and Gag-Pol (hatched bars) produced by transient transfections were used for stimulation. Supernatants from mock-transfected cultures served as control antigen. Stimulation indices are the growth of cultures in the presence of viral antigens divided by the growth of cultures in the presence of mock antigen.

Containment of the viral challenge was associated with a burst of antiviral T cells (FIGS. 7 and 9A). At one week after challenge, the frequency of tetramer+ cells in the peripheral blood had decreased, potentially reflecting the recruitment of specific T cells to the site of infection (FIG. 9A). However, by two weeks after challenge, tetramer+ cells in the peripheral blood had expanded to frequencies as high as, or higher than, after the rMVA booster (FIGS. 7 and 9A). The majority of the tetramer+ cells produced IFN-γ in response to a 6-hour peptide stimulation (FIG. 9B) (S. L. Waldrop et al. 1997 *J Clin Invest* 99:1739) and did not have the "stunned" IFN-γ negative phenotype sometimes observed in viral infections (F. Lechner et al. 2000 *J Exp Med* 191:1499).

For intracellular cytokine assays, about 1×10$^6$ PBMC were stimulated for 1 hour at 37° C. in 5 ml polypropylene tubes with 100 μg of Gag-CM9 peptide (CTPYDINQM) (SEQ ID NO: 6) per milliliter in a volume of 100 μl RPMI containing 0.1% bovine serum albumin (BSA) and 1 μg of antibody to human CD28 and 1 μg of antibody to human CD49d (Pharmingen, San Diego, Calif.) per milliliter. Then, 900 μl of RPMI containing 10% FBS and monensin (10 μg/ml) was added, and the cells were cultured for an additional 5 hrs at 37° C. at an angle of 5° under 5% $CO_2$. Cells were surface stained with antibodies to CD8 conjugated to PerCP (clone SK1, Becton Dickinson) at 8° to 10° C. for 30 min, washed twice with cold PBS containing 2% FBS, and fixed and permeabilized with CYTOFIX/CYTOPERMυ solution (Pharmingen). Cells were then incubated with antibodies to human CD3 (clone FN-18; Biosource International, Camarillo, Calif.) and IFN-γ (Clone B27; Pharmingen) conjugated to FITC and phycoerythrin, respectively, in Perm wash solution (Pharmingen) for 30 min at 4° C. Cells were washed twice with Perm wash, once with plain PBS, and resuspended in 1% paraformaldehyde in PBS. About 150,000 lymphocytes were acquired on the FACS-caliber and analyzed with FloJo software.

The postchallenge burst of T cells contracted concomitant with the decline of the viral load. By 12 weeks after challenge, virus-specific T cells were present at about one-tenth of their peak height (FIGS. 7A and 9A). In contrast to the vigorous secondary response in the vaccinated animals, the naive animals mounted a modest primary response (FIGS. 7B and 9A). Tetramer+ cells peaked at less than 1% of total CD8 cells (FIG. 9A), and IFN-γ-producing ELISPOTs were present at a mean frequency of about 300 as opposed to the much higher frequencies of 1000 to 6000 in the vaccine groups (FIG. 7B) (P<0.05).

Figure 9B:
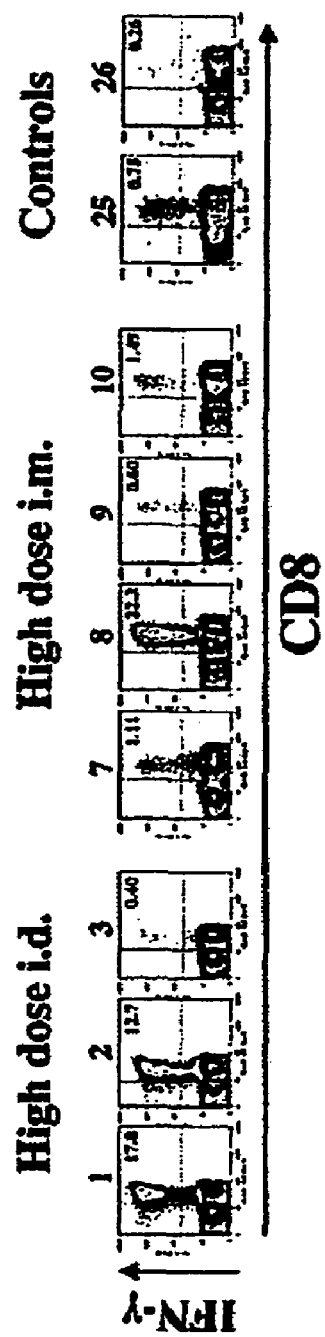

The tetramer+ cells in the control group, like those in the vaccine group, produced IFN-γ after peptide stimulation (FIG. 9B). By 12 weeks after challenge, three of the four controls had undetectable levels of IFN-γ-producing ELISPOTs. This rapid loss of antiviral T cells in the presence of high viral loads may reflect the lack of CD4 help.

Figure 9C:
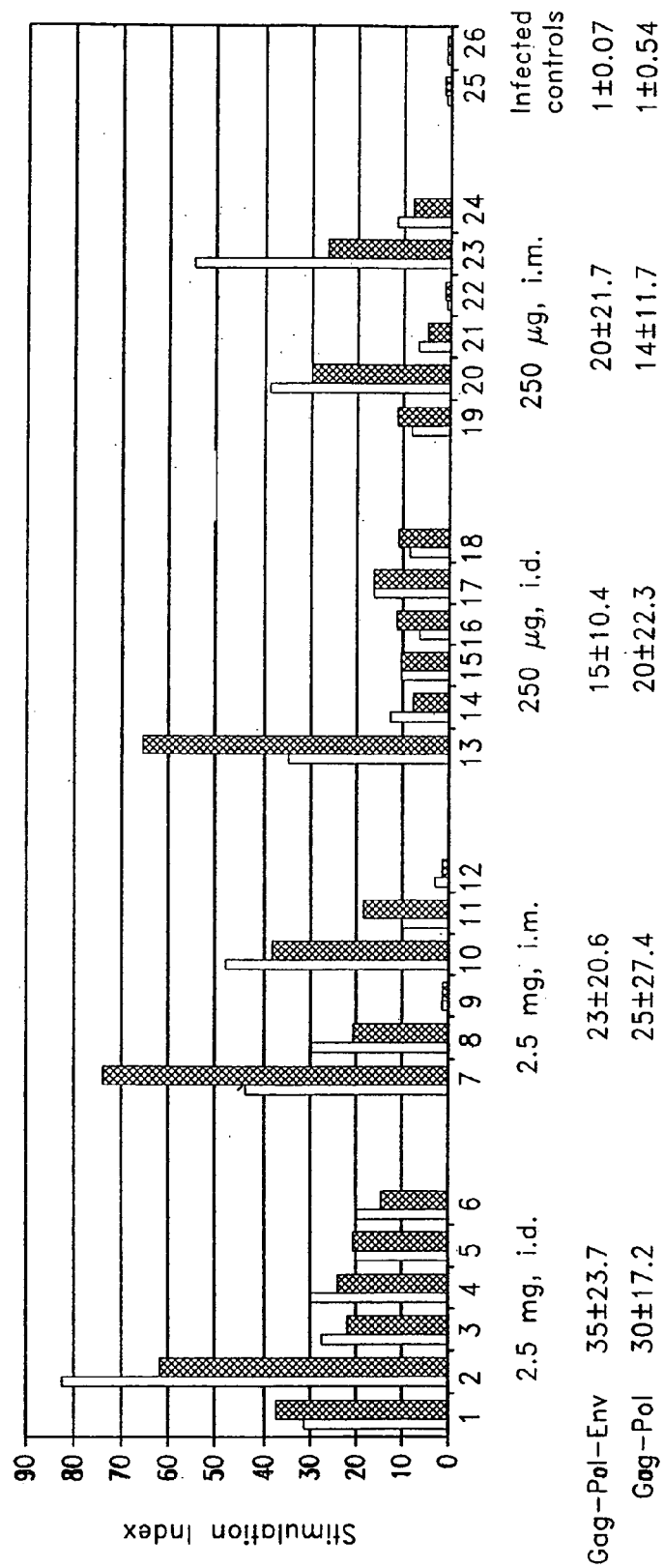

T cell proliferative responses demonstrated that virus-specific CD4 cells had survived the challenge and were available to support the antiviral immune response (FIG. 9C).

About 0.2 million PBMC were stimulated in triplicate for 5 days with the indicated antigen in 200 μl of RPMI at 37° C. under 5% $CO_2$. Supernatants from 293T cells transfected with DNA expressing either SHIV-89.6 Gag and Pol or SHIV-89.6 Gag, Pol and Env were used directly as antigens (final concentration of ~0.5 μg of p27 Gag per milliliter). Supernatants from mock DNA (vector alone)-transfected cells served as negative controls. On day six, cells were pulsed with 1 μCi of tritiated thymidine per well for 16 to 20 hours. Cells were harvested with an automated cell harvester (TOMTEC, Harvester 96, Model 1010, Hamden, Conn.) and counted with a Wallac 1450 MICROBETA Scintillation counter (Gaithersburg, Md.). Stimulation indices are the counts of tritiated thymidine incorporated in PBMC stimulated with 89.6 antigens divided by the counts of tritiated thymidine incorporated by the same PBMC stimulated with mock antigen.

At 12 weeks after challenge, mean stimulation indices for Gag-Pol-Env or Gag-Pol proteins ranged from 35 to 14 in the vaccine groups but were undetectable in the control group. Consistent with the proliferation assays, intracellular cytokine assays demonstrated the presence of virus-specific CD4 cells in vaccinated but not control animals. The overall rank order of the vaccine groups for the magnitude of the proliferative response was 2.5 mg i.d.>2.5 mg i.m.>250 μg i.d.>250 μg i.m.

Figures 10A, 10B, 10C:
FIG. 10. Lymph node histomorphology at 12 weeks after challenge. (A) Typical lymph node from a vaccinated macaque showing evidence of follicular hyperplasia characterized by the presence of numerous secondary follicles with expanded germinal centers and discrete dark and light zones. (B) Typical lymph node from an infected control animal showing follicular depletion and paracortical lymphocellular atrophy. (C) A representative lymph node from an age-matched, uninfected macaque displaying nonreactive germinal centers. (D) The percentage of the total lymph node area occupied by germinal centers was measured to give a non-specific indicator of follicular hyperplasia. Data for uninfected controls are for four age-matched rhesus macaques.
Figure 10D:
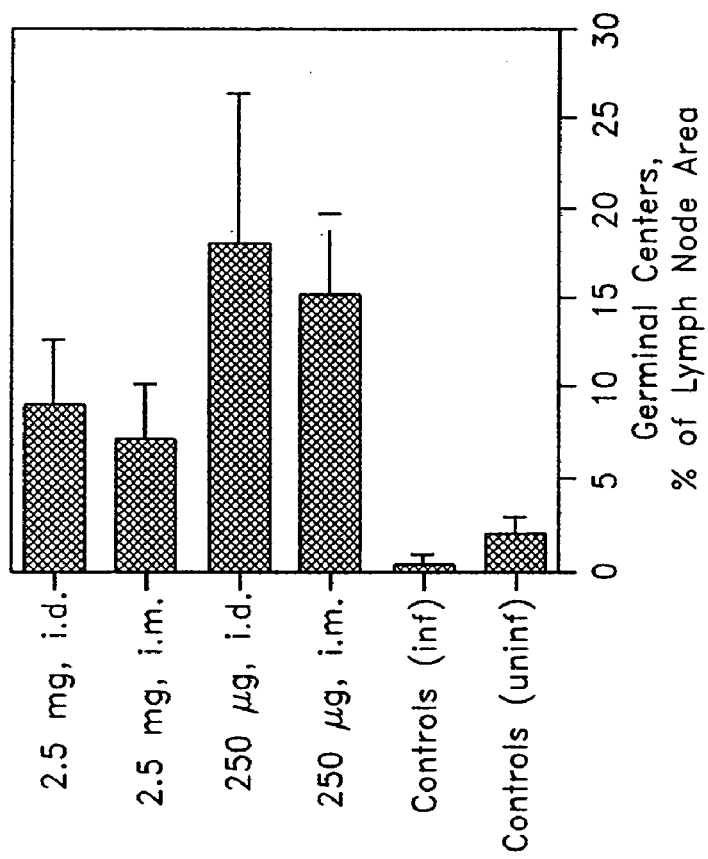
Figure 11A:
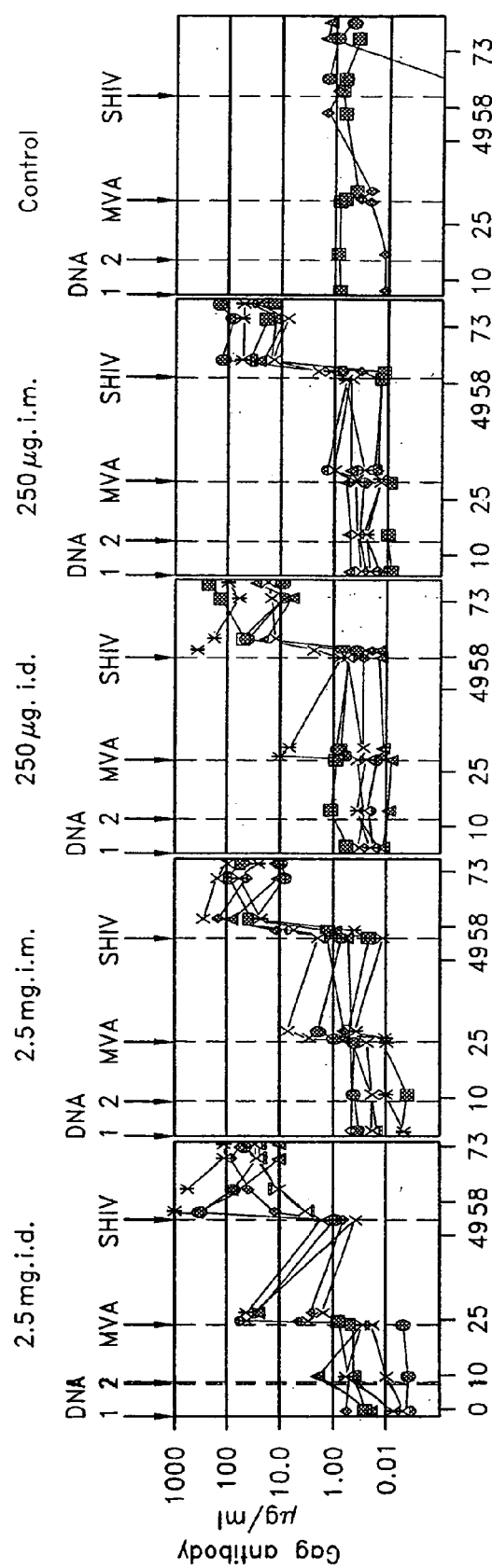
FIG. 11. Temporal antibody responses. Micrograms of total Gag (A) or Env (B) antibody were determined with ELISAs. The titers of neutralizing antibody for SHIV-89.6 (C) and SHIV-89.6P (D) were determined with MT-2 cell killing and neutral red staining (D. C. Montefiori et al. 1988 *J Clin Microbiol* 26:231). Titers are the reciprocal of the serum dilution giving 50% neutralization of the indicated viruses grown in human PBMC. Symbols for animals are the same as in FIG. 8.
Figure 11B:
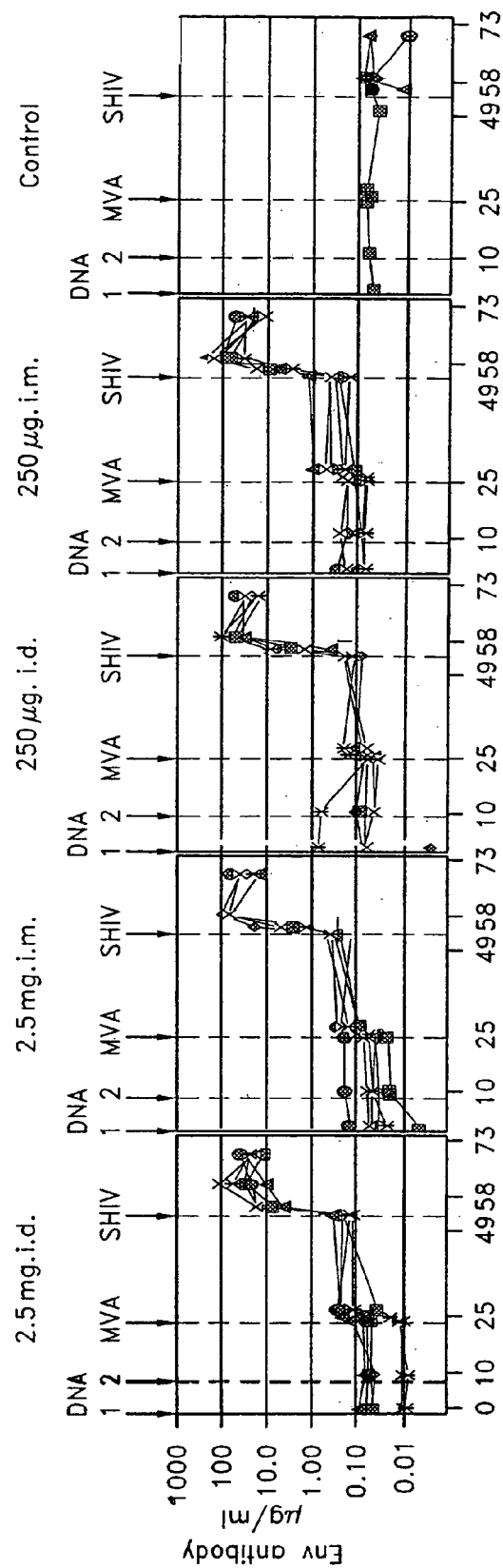
Figure 11C:
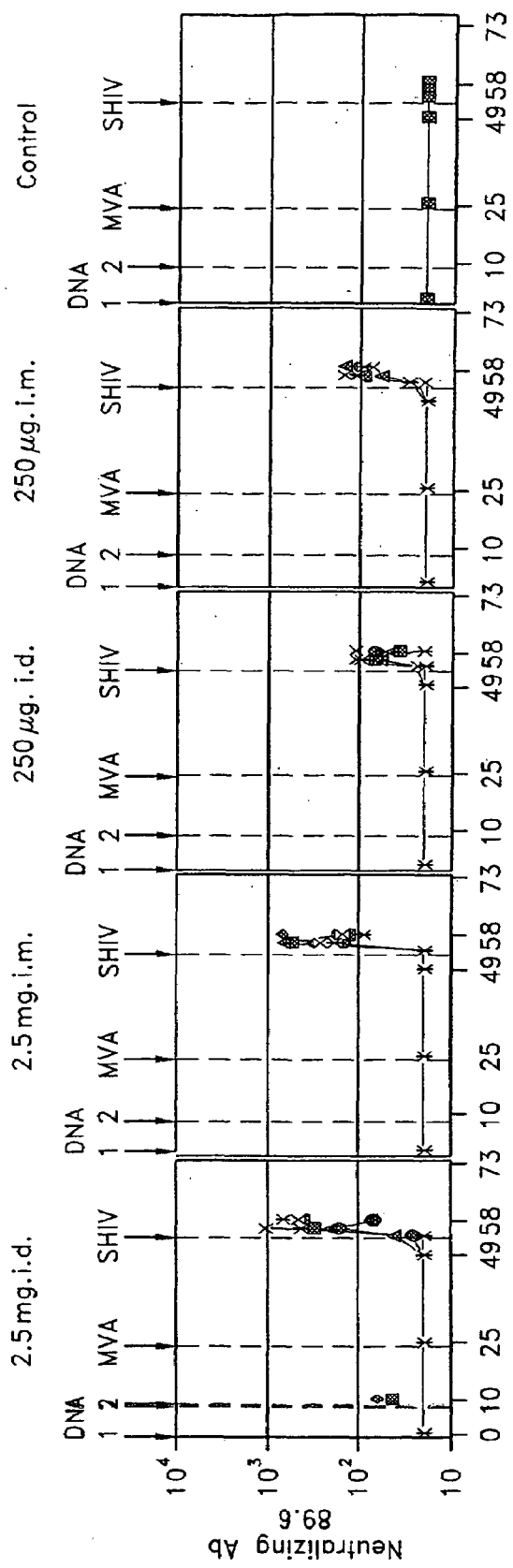
Figure 11D:
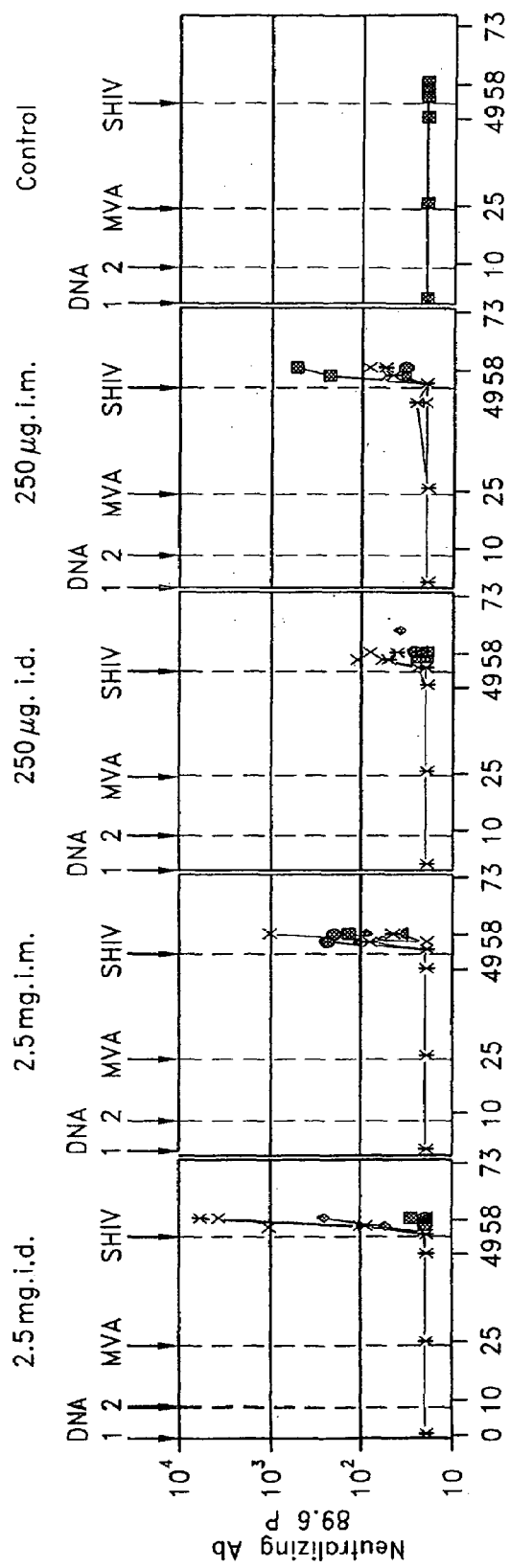

At 12 weeks after challenge, lymph nodes from the vaccinated animals were morphologically intact and responding to the infection, whereas those from the infected controls had been functionally destroyed (FIG. 10). Nodes from vaccinated animals contained large numbers of reactive secondary follicles with expanded germinal centers and discrete dark and light zones (FIG. 10A). By contrast, lymph nodes from the non-vaccinated control animals showed follicular and paracortical depletion (FIG. 10B), while those from unvaccinated and unchallenged animals displayed normal numbers of minimally reactive germinal centers (FIG. 10C). Germinal centers occupied <0.05% of total lymph node area in the infected controls, 2% of the lymph node area in the uninfected controls, and up to 18% of the lymph node area in the vaccinated groups (FIG. 10D). More vigorous immune reactivity in the low-dose than the high-dose DNA-primed animals was suggested by more extensive germinal centers in the low dose group (FIG. 10D). At 12 weeks after challenge, in situ hybridization for viral RNA revealed rare virus-expressing cells in lymph nodes from 3 of the 24 vaccinated macaques, whereas virus-expressing cells were readily detected in lymph nodes from each of the infected control animals. In the controls, which had undergone a profound depletion in CD4 T cells, the cytomorphology of infected lymph node cells was consistent with a macrophage phenotype.

The prime/boost strategy raised low levels of antibody to Gag and undetectable levels of antibody to Env (FIG. 11). Postchallenge, antibodies to both Env and Gag underwent anamnestic responses with total Gag antibody reaching heights approaching 1 mg/ml and total Env antibody reaching heights of up to 100 μg/ml.

Enzyme-linked immunosorbent assays (ELISAs) for total antibody to Gag used bacterially produced SIV gag p27 to coat wells (2 μg per milliliter in bicarbonate buffer). ELISAs for antibody to Env antibody used 89.6 Env produced in transiently transfected 293T cells and captured with sheep antibody against Env (catalog number 6205; International Enzymes, Fairbrook Calif.). Standard curves for Gag and Env ELISAs were produced with serum from a SHIV-89.6-infected macaque with known amounts of immunoglobulin G (IgG) specific for Gag or Env. Bound antibody was detected with peroxidase-conjugated goat antibody to macaque IgG (catalog # YNGMOIGGFCP; Accurate Chemical, Westbury, N.Y.) and TMB substrate (Catalog # T3405; Sigma, St. Louis, Mo.). Sera were assayed at three-fold dilutions in duplicate wells. Dilutions of test sera were performed in whey buffer (4% whey and 0.1% tween 20 in 1×PBS). Blocking buffer consisted of whey buffer plus 0.5% nonfat dry milk. Reactions were stopped with 2M $H_2SO_4$ and the optical density read at 450 nm. Standard curves were fitted and sample concentrations were interpolated as µg of antibody per ml of serum using SOFTmax 2.3 software (Molecular Devices, Sunnyvale, Calif.).

By 2 weeks after challenge, neutralizing antibodies for the 89.6 immunogen, but not the SHIV-89.6P challenge, were present in the high-dose DNA-primed groups (geometric mean titers of 352 in the i.d. and 303 in the i.m. groups) (FIG. 11C) (D.C. Montefiori et al. 1988 *J Clin* Microbiol 26:231). By 5 weeks after challenge, neutralizing antibody to 89.6P had been generated (geometric mean titers of 200 in the high-dose i.d. and 126 in the high-dose i.m. group) (FIG. 11D) and neutralizing antibody to 89.6 had started to decline. By 16 to 20 weeks after challenge, antibodies to Gag and Env had fallen in most animals.

Our results demonstrate that a multiprotein DNA/MVA vaccine can raise a memory immune response capable of controlling a highly virulent mucosal immunodeficiency virus challenge. Our levels of viral control were more favorable than have been achieved using only DNA (M. A. Egan et al. 2000 *J Virol* 74:7485) or rMVA vaccines (I. Ourmanov et al. 2000 *J Virol* 74:2740) and were comparable to those obtained for DNA immunizations adjuvanted with interleukin-2 (D. H. Barouch et al. 2000 *Science* 290:486). All of these previous studies have used more than three vaccine inoculations, none have used mucosal challenges, and most have challenged at peak effector responses and not allowed a prolonged post vaccination period to test for "long term" efficacy.

The dose of DNA had statistically significant effects on both cellular and humoral responses (P<0.05), whereas the route of DNA administration affected only humoral responses. Intradermal DNA delivery was about 10 times more effective than i.m. inoculations for generating antibody to Gag (P=0.02). Neither route nor dose of DNA appeared to have a significant effect on protection. At 20 weeks after challenge, the high-dose DNA-primed animals had slightly lower geometric mean levels of viral RNA ($7\times10^2$ and $5\times10^2$) than the low-dose DNA-primed animals ($9\times10^2$ and $1\times10^3$).

The DNA/MVA vaccine controlled the infection, rapidly reducing viral loads to near or below 1000 copies of viral RNA per milliliter of blood. Containment, rather than prevention of infection, affords the opportunity to establish a chronic infection (H. L. Robinson et al. 1999 *Nat Med* 5:526). By rapidly reducing viral loads, a multiprotein DNA/MVA vaccine will extend the prospect for long-term non-progression and limit HIV transmission (J. W. Mellors et al. 1996 *Science* 272:1167; T. C. Quinn et al. 2000 N Engl J Med 342:921).

EXAMPLE 2

MVA Expressing Modified HIV Env, Gag, and Pol Genes

This disclosure describes the construction of a modified vaccinia Ankara (MVA) recombinant virus, MVA/HIV clade B recombinant virus expressing the HIV strain ADA env and the HXB2 gag pol (MVA/HIV ADA env+HXB2 gag pol). For amplification, the lab name of MVA/HIV 48 will be used, which denotes the plasmid from which the construct comes.

The HIV gag-pol genes were derived from the Clade B infectious HXB2 virus. The gag-pol gene was truncated so that most of the integrase coding sequences were removed and amino acids 185, 266, and 478 were mutated to inactivate reverse transcriptase, inhibit strand transfer activity, and inhibit the RNaseH activity, respectively. The Clade B CCR5 tropic envelope gene was derived from the primary ADA isolate; TTTTTNT (SEQ ID NO: 14) sequences were mutated without changing coding capacity to prevent premature transcription termination and the cytoplasmic tail was truncated in order to improve surface expression, immunogenicity, and stability of the MVA vector. The HIV genes were inserted into a plasmid transfer vector so that gag-pol gene was regulated by the modified H5 early/late vaccinia virus promoter and the env gene was regulated by the newly designed early/late Psyn II promoter to provide similar high levels of expression. A self-deleting GUS reporter gene was included to allow detection and isolation of the recombinant virus. The HIV genes were flanked by MVA sequences to allow homologous recombination into the deletion 3 site so that the recombinant MVA would remain TK positive for stability and high expression in resting cells. The recombinant MVA was isolated and shown to express abundant amounts of gag-pol-env and to process gag. Production of HIV-like particles was demonstrated by centrifugation and by electron microscopy. The presence of env in the HIV-like particles was demonstrated by immunoelectron microscopy.

Table of Sequences

| Description | SEQ ID NO | FIG. NO |
|---|---|---|
| pLW-48 map | N/A | 13 |
| pLW-48 sequence | 1 | 14 |
| Psyn II promoter | 2 | 14 |
| ADA envelope truncated | 3 | 14 |
| PmH5 promoter | 4 | 14 |
| HXB2 gag pol | 5 | 14 |

Plasmid Transfer Vector

Figure 15:
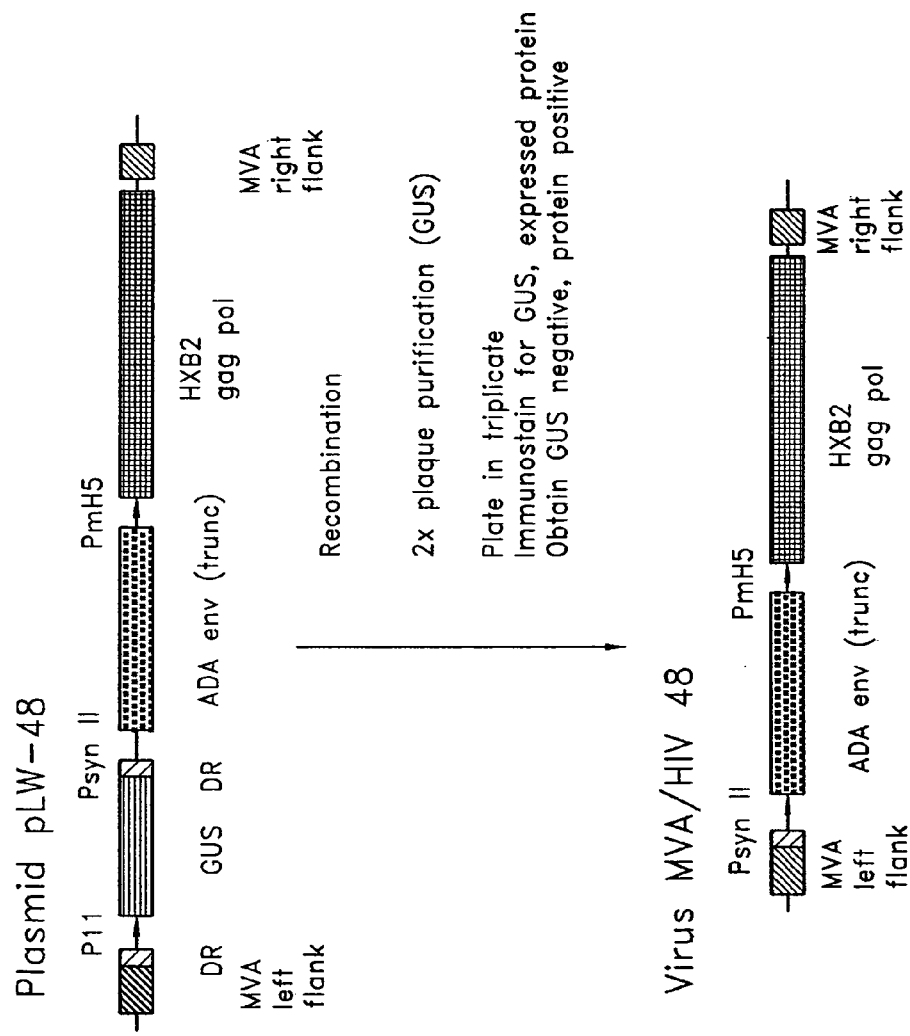
FIG. 15. Plasmid transfer vector pLW-48 and making MVA recombinant virus MVA/HIV 48.

The plasmid transfer vector used to make the MVA recombinant virus, pLW-48, (FIG. 15) by homologous recombination was constructed as follows:

1. From the commercially obtained plasmid, pGem-4Z (Promega), flanking areas on either side of deletion III, designated flank 1 and flank 2, containing 926 and 520 base pairs respectively, were amplified by PCR from the MVA stains of vaccinia virus. Within these flanks, a promoter, the mH5, which had been modified from the originally published sequence by changing two bases that had been shown by previously published work to increase the expression of the cloned gene, was added.

Figure 16:
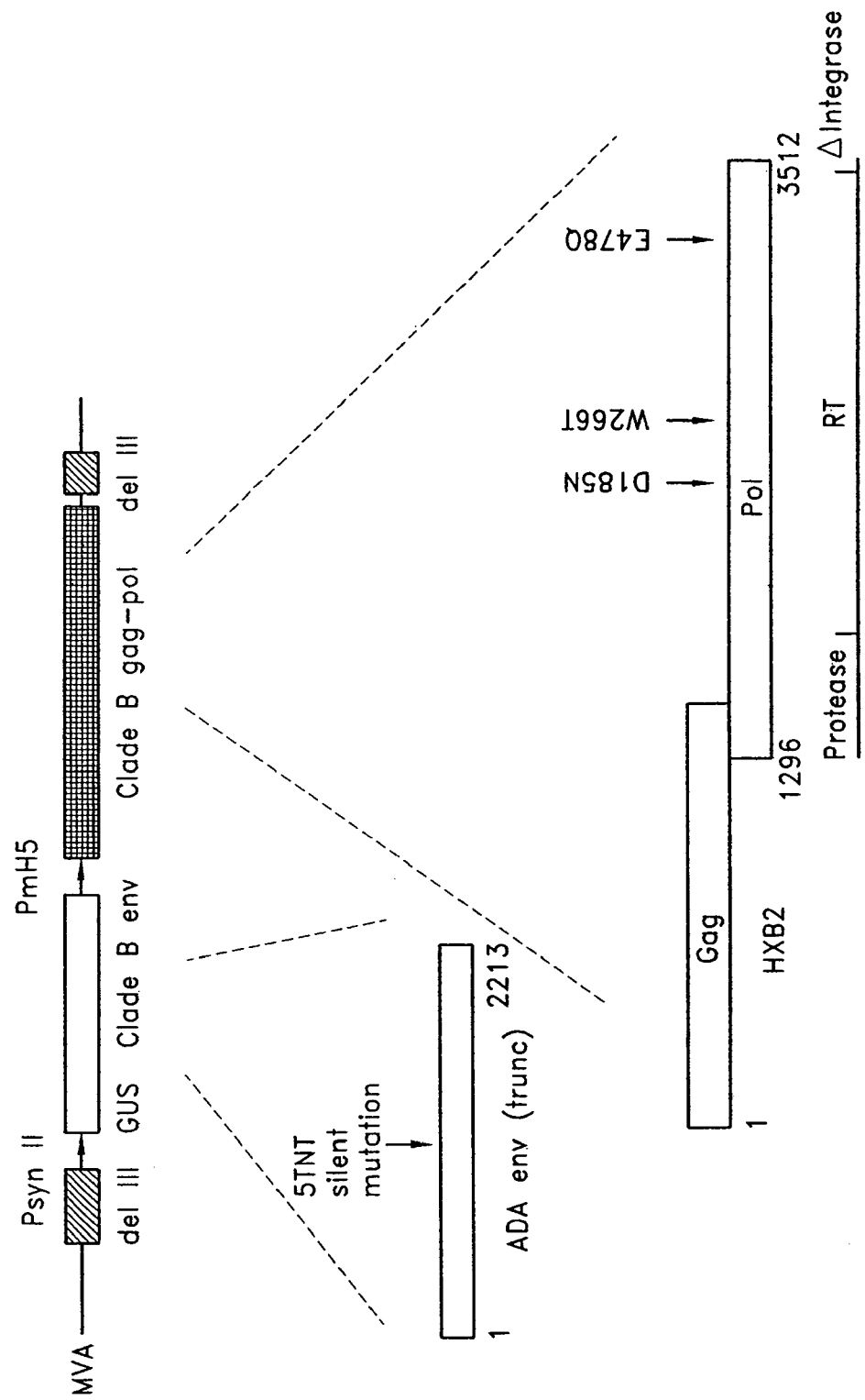
FIG. 16. A clade B gag pol.

2. A clade B gag pol (FIG. 16) was truncated so that the integrase was removed and was cloned into the plasmid so that it was controlled by the mH5 promoter. This gene contained the complete HXB2 sequence of the gag. The pol gene has reverse transcriptase safety mutations in amino acid 185 within the active site of RT, in amino acid 266 which inhibits strand transfer activity, and at amino acid 478 which inhibits the RNaseH activity. In addition, the integrase gene was deleted past EcoRI site.

3. A direct repeat of 280 basepairs, corresponding to the last 280 base pairs of MVA flank 1, was added after flank 1.

4. The p11 promoter and GUS reporter gene were added between the two direct repeats of flank 1 so that this screening marker could initially be used for obtaining the recombinant virus, yet deleted out in the final recombinant virus (Scheiflinger, F. et al. 1998 *Arch Virol* 143:467-474; Carroll, M. W. and B. Moss 1995 *BioTechniques* 19:352-355).

5. A new promoter, Psyn II, was designed to allow for increased expression of the ADA env. The sequence of this new early/late promoter is given in FIG. 17.

6. A truncated version of the ADA envelope with a silent 5TNT mutation was obtained by PCR and inserted in the plasmid under the control of the Psyn II promoter. The envelope was truncated in the cytoplasmic tail of the gp41 gene, deleting 115 amino acids of the cytoplasmic tail. This truncation was shown to increase the amount of envelope protein on the surface of infected cells and enhance immunogenicity of the envelope protein in mice, and stability of the recombinant virus in tissue culture.

Recombinant MVA Construction

1. MVA virus, which may be obtained from ATCC Number VR-1508, was plaque purified three times by terminal dilutions in chicken embryo fibroblasts (CEF), which were made from 9 day old SPF Premium SPAFAS fertile chicken eggs, distributed by B and E Eggs, Stevens, Pa.

2. Secondary CEF cells were infected at an MOI of 0.05 of MVA and transfected with 2 μg of pLW-48, the plasmid described above. Following a two-day incubation at 37° C., the virus was harvested, frozen and thawed 3×, and plated out on CEF plates.

3. At 4 days, those foci of infection that stained blue after addition of X-gluc substrate, indicating that recombination had occurred between the plasmid and the infecting virus, were picked and inoculated on CEF plates. Again, those foci that stained blue were picked.

4. These GUS containing foci were plated out in triplicate and analyzed for GUS staining (which we wanted to now delete) and ADA envelope expression. Individual foci were picked from the 3rd replicate plates of those samples that had about equal numbers of mixed populations of GUS staining and nonstaining foci as well as mostly envelope staining foci.

5. These foci were again plated out in triplicate, and analyzed the same way. After 5 passages, a virus was derived which expressed the envelope protein but which had deleted the GUS gene because of the double repeat. By immunostaining, this virus also expressed the gag pol protein.

Characterization of MVA Recombinant Virus MVA/HIV 48

1. Aliquots of MVA/HIV 48 infected cell lysates were analyzed by radioimmunoprecipitation and immunostaining with monoclonal antibodies for expression of both the envelope and gag pol protein. In both of these tests, each of these proteins was detected.

2. The recombinant virus was shown to produce gag particles in the supernatant of infected cells by pelleting the $^{35}$S-labeled particles on a 20% sucrose cushion.

3. Gag particles were also visualized both outside and budding from cells as well as within vacuoles of cells in the electron microscope in thin sections. These gag particles had envelope protein on their surface.

Unless otherwise indicated, all nucleotide sequences determined by sequencing a DNA molecule herein were determined using an automated DNA sequencer, and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Summary

In summary, we have made a recombinant MVA virus, MVA/HIV 48, which has high expression of the ADA truncated envelope and the HXB2 gag pol. The MVA recombinant virus is made using a transiently expressed GUS marker that is deleted in the final virus. High expression of the ADA envelope is possible because of a new hybrid early/late promoter, Psyn II. In addition, the envelope has been truncated because we have shown truncation of the envelope enhances the amount of protein on the surface of the infected cells, and hence enhances immunogenicity; stability of the recombinant is also enhanced. The MVA recombinant makes gag particles which have been shown by pelleting the particles through sucrose and analyzing by PAGE. Gag particles with envelope protein on the surface have also been visualized in the electron microscope.

EXAMPLE 3

Additional Modified or Synthetic Promoters Designed for Gene Expression in MVA or Other Poxviruses Additional modified or synthetic promoters were designed for gene expression in MVA or other poxviruses. Promoters were modified to allow expression at early and late times after infection and to reduce possibility of homologous recombination between identical sequences when multiple promoters are used in same MVA vector. Promoters are placed upstream of protein coding sequence.

```
m7.5 promoter:
                                         (SEQ ID NO: 10)
CGCTTTTTATAGTAAGTTTTTCACCCATAAATAATAAATACAATAATTAA
TTTCTCGTAAAAATTGAAAAACTATTCTAATTTATTGCACGGT Psyn II promoter:
                                         (SEQ ID NO: 2)
TAAAAAATGAAAAAATATTCTAATTTATAGGACGGTTTTGATTTTCTTTT
TTTCTATGCTATAAATAATAAATA Psyn III promoter:
                                         (SEQ ID NO: 11)
TAAAAATTGAAAAAATATTCTAATTTATAGGACGGTTTTGATTTTCTTTT
TTTCTATACTATAAATAATAAATA Psyn IV promoter:
                                         (SEQ ID NO: 12)
TAAAAATTGAAAACTATTCTAATTTATAGGACGGTTTTGATTTTCTTTT
TTTCTATACTATAAATAATAAATA Psyn V promoter:
                                         (SEQ ID NO: 13)
AAAAAATGATAAAGTAGGTTCAGTTTTATTGCTGGTTTAAAATCACGCTT
TCGAGTAAAAACTACGAATATAAAT
```

EXAMPLE 4

Tables A-F

Table A: MVA/48 immunization—guinea pigs.

Groups of guinea pigs were immunized at days 0 and 30 with 1×10⁸ infectious units of MVA/48 by either the intramuscular (IM) or intradermal (ID) route. As a control another group was immunized IM with the same dose of non-recombinant MVA. Sera taken before as well as after each immunization were analyzed for neutralizing activity against HIV-1-MN. Titers are the reciprocal serum dilution at which 50% of MT-2 cells were protected from virus-induced killing. Significant neutralizing activity was observed in all animals after the second immunization with MVA/48 (day 49).

Table B: Frequencies of HIV-1 gag-specific T cells following immunization of mice with MVA/48.

Groups of BalbC mice were immunized at days 0 and 21 with 1×10⁷ infectious units of MVA/48 by one of three routes: intraperitoneal (IP), intradermal (ID), or intramuscular (IM). A control group was immunized with non-recombinant MVA. At 5 weeks after the last immunization, splenocytes were prepared and stimulated in vitro with an immunodominant peptide from HIV-1 p24 for 7 days. The cells were then mixed either with peptide-pulsed P815 cells or with soluble peptide. Gamma interferon-producing cells were enumerated in an ELISPOT assay. A value of >500 was assigned to wells containing too many spots to count. Strong T cell responses have been reported in mice immunized IP with other viruses. In this experiment, IP immunization of mice with MVA/48 elicited very strong HIV-1 gag-specific T cell responses.

Table C: DNA prime and MVA/48 boost—total ELISPOTS per animal.

Ten rhesus macaques were primed (weeks 0 and 8) with a DNA vaccine expressing HIV-1 antigens including Ada envelope and HXB2 gagpol. At week 24 the animals were boosted intramuscularly with 1×10⁸ infectious units of MVA/48. Fresh peripheral blood mononuclear cells (PBMC) were analyzed for production of gamma interferon in an ELISPOT assay as follows: PBMC were incubated for 30-36 hours in the presence of pools of overlapping peptides corresponding to the individual HIV-1 antigens in the vaccines. The total number of gamma interferon-producing cells from each animal is shown in the table. T cell responses to DNA vaccination were limited (weeks 2-20). However, boosting with MVA/48 resulted in very strong HIV-1-specific T cell responses in all animals (week 25).

Table D: Antibody response following immunization of macaques with MVA/SHIV KB9.

Groups of rhesus macaques were immunized with 2×10⁸ infectious units of MVA/SHIV-KB9 at weeks 0 and 4 by one of several routes: Tonsilar, intradermal (ID), or intramuscular (IM). Another group was immunized with non-recombinant MVA using the same routes. Serum samples from 2 weeks after the second immunization were analyzed for binding to KB9 envelope protein by ELISA and for neutralization of SHIV-89.6P and SHIV-89.6. In the ELISA assay, soluble KB9 envelope protein was captured in 96 well plates using an antibody to the C-terminus of gp120. Serial dilutions of sera were analyzed and used to determine the endpoint titers. Neutralization of SHIV-89.6P and SHIV-89.6 was determined in an MT-2 cell assay. Titers are the reciprocal serum dilution at which 50% of the cells were protected from virus-induced killing. In in vitro neutralization assays, SHIV-89.6P and SHIV-89.6 are heterologous, i.e. sera from animals infected with one of the viruses do not neutralize the other virus. Thus, two immunizations with MVA/SHIV-KB9 elicited good ELISA binding antibodies in all animals and neutralizing antibodies to the homologous virus (SHIV-89.6P) in some animals. In addition, heterologous neutralizing antibodies were observed in a subset of animals.

Table E: Frequencies of gag CM-9-specific CD3/CD8 T cells following immunization of macaques with MVA/SHIV-KB9.

Groups of MamuA*01 positive rhesus macaques were immunized with 2×10⁸ infectious units of MVA/SHIV-KB9 at weeks 0 and 4 by one of several routes: tonsilar, intradermal (ID), or intramuscular IM). Another group was immunized with non-recombinant MVA. The frequencies of CD3+/CD8+ T cells that bound tetrameric complex containing the SIV gag-specific peptide CM9 were determined by flow cytometry at various times after each immunization. Time intervals were as follows: 1a, 1b, and 1d were one, two, and four weeks after the first immunization, respectively; 2a, 2b, 2c, and 2d were one, two, three, and twelve weeks after the second immunization, respectively. Values above background are shown in bold face. Strong SIV gag-specific responses were observed after a single immunization with MVA/SHIV-KB9 in all immunized animals. Boosting was observed in most animals following the second immunization. In addition, measurable tetramer binding was still found twelve weeks after the second immunization.

Table F: Frequencies of specific T cells following immunization of macaques with MVA/SHIV KB9.

Groups of macaques were immunized with MVA/SHIV-KB9 as described above. MVA/SHIV-KB9 expresses 5 genes from the chimeric virus, SHIV-89.6P: envelope, gag, polymerase, tat, and nef. Thus, the frequencies of T cells specific for each of the 5 antigens were analyzed using pools of peptides corresponding to each individual protein. Fresh PBMC were stimulated with pools of peptides for 30-36 hours in vitro. Gamma interferon-producing cells were enumerated in an ELISPOT assay. The total number of cells specific for each antigen is given as "total # spots". In addition, the number of responding animals and average # of spots per group is shown. PBMC were analyzed at one week after the first immunization (1a) and one week after the second immunization (2a). Another group of 7 animals was immunized with non-recombinant MVA. In these animals, no spots above background levels were detected. Thus, a single immunization with MVA/SHIV-KB9 elicited strong SHIV-specific T cell responses in all animals. Gag and envelope responses were the strongest; most animals had responses to gag, all animals had responses to envelope. The Elispot responses were also observed after the second immunization with MVA/SHIV-KB9, albeit at lower levels. At both times, the rank order of responses was: tonsilar>ID>IM. We show good immune response to nef and some immune response to tat.

TABLE A

MVA/48 immunization - guinea pigs HIV-MN neutralizing antibody - reciprocal titer

| Animal # | Group | Route | day 0 | Day 4 MVA #1 | day 30 | day 3 MVA#2 | day 49 |
|---|---|---|---|---|---|---|---|
| 885 | MVA | I.M. | <20 | I.M. | 31 | I.M. | 24 |
| 891 | " | " | <20 | " | 85 | " | <20 |
| 882 | MVA/48 | I.M. | <20 | I.M. | <20 | I.M. | 5,524 |
| 883 | " | " | <20 | " | 68 | " | 691 |

TABLE A-continued

MVA/48 immunization - guinea pigs HIV-MN neutralizing antibody - reciprocal titer

| Animal # | Group | Route | day 0 | Day 4 MVA #1 | day 30 | day 3 MVA#2 | day 49 |
|---|---|---|---|---|---|---|---|
| 886 | " | " | <20 | " | <20 | " | 4,249 |
| 890 | " | " | <20 | " | 180 | " | 89 |
| 879 | MVA/48 | I.D. | <20 | I.D. | <20 | I.D. | 817 |
| 881 | " | " | <20 | " | <20 | " | 234 |
| 888 | " | " | <20 | " | 24 | " | 112 |
| 889 | " | " | <20 | " | 22 | " | 376 |

TABLE B

Frequencies of HIV-gag-specific T cells following immunization of mice with MVA/48

| Group | P815 cells + gag peptide | | gag peptide | | no stimulation | |
|---|---|---|---|---|---|---|
| MVA control | 0 | 2 | 0 | 4 | 1 | 2 |
| MVA/48 (IP) | >500 | >500 | >500 | >500 | 8 | 8 |
| MVA/48 (ID) | 12 | 5 | 49 | 33 | 4 | 2 |
| MVA/48 (IM) | 22 | 18 | 66 | 49 | 12 | 8 |

TABLE C

DNA prime and MVA/48 boost. Total ELISPOTS per Animal

| | WEEKS | | | | | | |
|---|---|---|---|---|---|---|---|
| Animal # | −2 | 2 | 6 | $10^2$ | $14^2$ | $20^2$ | $25^2$ |
| I. RLW | 4 | 731* | < | 47 | 43 | 50 | 3905 |
| RVI | 5 | 997* | < | < | < | 8 | 205 |
| Roa | $<^1$ | < | 1 | < | < | < | 245 |
| RHc | < | < | < | < | < | < | 535 |
| Ryl | < | < | < | < | < | < | 4130 |
| RQk | < | 46 | < | < | < | < | 630 |
| RDr | < | < | < | 14 | < | < | 1965 |
| RZc | < | 5 | < | 58 | < | < | 925 |
| RSf | < | 118 | < | < | < | 20 | 5570 |
| Ras | < | 69 | < | < | < | < | 1435 |
| Total | 9 | 1966 | 1 | 119 | 43 | 78 | 19545 |
| Geo Mean | 4.5 | 105.3 | 1.0 | 33.7 | 43.0 | 20.0 | 1147.7 |

DNA primes were at 0 and 8 weeks and MVA/48 boost was at 24 weeks
[1] < = Background (2 × the number of ELISPOTs in the unstimulated control + 10)
[2] Costimulatory antibodies were added to the ELISPOT incubations
*Animals from this bleed date exhibited higher than usual ELISPOTs.

TABLE D

Antibody response following immunization of macaques with MVA/SHIV KB9

| Animal # | Route | KB9 env ELISA titer | KB9 env elisa average | KB9 env elisa std dev. | SHIV-89.6 Nab titer | SHIV-89.6P Nab titer | SHIV-89.6 # pos animals | SHIV-89.6P # pos animals |
|---|---|---|---|---|---|---|---|---|
| 598 | tonsil | 25,600 | 31,086 | 20,383 | <20 | <20 | 3 | 2 |
| 601 | " | 51,200 | | | <20 | <20 | | |
| 606 | " | 25,600 | | | <20 | <20 | | |
| 642 | " | 51,200 | | | 75 | 31 | | |
| 646 | " | 51,200 | | | 61 | 48 | | |
| 653 | " | 6,400 | | | <20 | <20 | | |
| 654 | " | 6,400 | | | 22 | <20 | | |
| 602 | i.d. | 25,600 | 18,800 | 15,341 | 38 | <20 | 2 | 4 |
| 604 | " | 12,800 | | | <20 | 262 | | |
| 608 | " | 3,200 | | | 20 | 66 | | |
| 637 | " | 12,800 | | | <20 | 35 | | |
| 638 | " | 51,200 | | | <20 | <20 | | |
| 645 | " | 25,600 | | | <20 | <20 | | |
| 647 | " | 12,800 | | | 32 | 162 | | |
| 650 | " | 6,400 | | | <20 | <20 | | |
| 599 | i.m. | 6,400 | 17,000 | 16,516 | <20 | <20 | 0 | 3 |
| 600 | " | 6,400 | | | <20 | 29 | | |
| 609 | " | 6,400 | | | <20 | <20 | | |
| 639 | " | 51,200 | | | <20 | 85 | | |
| 640 | " | 12,800 | | | <20 | <20 | | |
| 641 | " | 25,600 | | | <20 | 41 | | |
| 649 | " | 1,600 | | | <20 | <20 | | |
| 651 | " | 25,600 | | | 20 | <20 | | |
| 603 | Control | <100 | <100 | | <20 | <20 | 0 | 0 |
| 605 | " | <100 | | | <20 | <20 | | |
| 607 | " | <100 | | | <20 | <20 | | |
| 643 | " | <100 | | | <20 | <20 | | |
| 644 | " | <100 | | | <20 | <20 | | |
| 648 | " | <100 | | | <20 | <20 | | |
| 652 | " | <100 | | | <20 | <20 | | |

TABLE E

Frequencies of gag CM9-specific CD3/CD8 T cells following immunization of macaques with MVA/SHIV KB9

| Animal # | Route | Virus | pre-bleed | 1a | 1b | 1d | 2a | 2b | 2c | 2d |
|---|---|---|---|---|---|---|---|---|---|---|
| 598 | Tonsil | MVA/KB9 | 0.018 | 0.41 | 0.79 | 0.25 | 2.64 | 1.13 | 0.51 | 0.21 |
| 601 | " | " | 0.071 | 0.34 | 0.38 | 0.27 | 0.83 | 0.7 | 0.36 | 0.039 |
| 646 | " | " | 0.022 | 0.68 | 0.76 | 0.43 | 1.12 | 0.91 | 0.53 | 0.15 |
| 653 | " | " | 0.041 | 0.69 | 0.85 | 0.53 | 0.68 | 0.49 | 0.47 | 0.3 |
| 648 | " | MVA | | 0.033 | 0.039 | | 0.022 | 0.058 | 0.033 | 0.013 |
| 602 | i.d. | MVA/KB9 | 0.019 | 0.17 | 0.92 | 0.5 | 0.95 | 0.59 | 0.5 | 0.2 |
| 604 | " | " | 0.013 | 0.11 | 0.38 | 0.32 | 0.44 | 0.38 | 0.19 | 0.25 |
| 650 | " | " | 0.095 | 0.17 | 0.6 | 0.23 | 2.87 | 1.12 | 0.9 | 0.16 |
| 647 | " | " | 0.032 | 0.22 | 0.38 | 0.14 | 0.84 | 0.91 | 0.34 | 0.17 |
| 652 | " | MVA | | 0.041 | 0.038 | 0.059 | 0.025 | 0.022 | 0.026 | 0.055 |
| 599 | i.m. | MVA/KB9 | | 0.081 | 0.31 | 0.082 | | 0.12 | 0.054 | 0.11 |
| 600 | " | " | 0.034 | 0.15 | 0.41 | 0.17 | 0.29 | 0.27 | 0.16 | 0.049 |
| 649 | " | " | 0.00486 | 0.35 | 1.34 | 0.56 | 2.42 | 0.77 | 0.69 | 0.22 |
| 651 | " | " | 0.049 | 0.12 | 0.69 | 0.25 | 1.01 | 0.32 | 0.24 | 0.22 |
| 603 | " | MVA | | 0.024 | 0.087 | 0.073 | | 0.082 | 0.027 | 0.17 |

TABLE F

Frequencies of specific T cells following immunization of macaques with MVA/SHIV KB9

| Study groups | Gag specific | | | Tat specific | | | Nef specific | | | Env specific | | | Total |
|---|---|---|---|---|---|---|---|---|---|---|---|---|---|
| | # responding animals | Total # spots | average # spots | # responding animals | total # spots | average # spots | # responding animals | total # spots | average # spots | # Responding animals | Total # spots | Average # spots | # Responding animals |
| tonsil 1a | 4/6 | 1325 | 221 | 0/6 | 0 | 0 | 3/6 | 195 | 33 | 6/6 | 8760 | 1460 | 6/6 |
| tonsil 2a | 5/6 | 1405 | 234 | 0/6 | 0 | 0 | 1/6 | 560 | 93 | 6/6 | 4485 | 748 | 6/6 |
| i.d. 1a | 7/7 | 1335 | 191 | 0/7 | 0 | 0 | 2/7 | 215 | 31 | 7/7 | 7320 | 1046 | 7/7 |
| i.d. 2a | 4/7 | 755 | 108 | 0/7 | 0 | 0 | 1/7 | 55 | 8 | 7/7 | 2700 | 386 | 7/7 |
| i.m. 1a | 7/7 | 925 | 132 | 1/7 | 60 | 9 | 3/7 | 180 | 26 | 7/7 | 5490 | 784 | 7/7 |
| i.m. 2a | 4/7 | 250 | 36 | 0/7 | 0 | 0 | 0/7 | 0 | 0 | 6/7 | 2205 | 315 | 6/7 |

EXAMPLE 5

Construction and Pre-Clinical Immunogenicity of a Recombinant MVA Vaccine Expressing Subtype D HIV-1 Env, Gag and Pol for Use in Uganda Recombinant MVA vaccines have been successful in generating SIV and SHIV specific humoral and CD8 T cell responses in non-human primates and, alone or in combination with DNA vaccines, have provided protection in rhesus macaques from disease after pathogenic SHIV challenge. An overall program goal is to conduct clinical vaccine trials in Africa using vaccines that induce both neutralizing antibody and CD8 T cell specific responses and that are based upon representative full-length HIV-1 sequences isolated from the target vaccine cohorts. The predominant incident and prevalent HIV-1 subtype in Uganda is subtype D. Several R5 subtype D HIV-1 strains were selected and used to prepare recombinant MVA vaccines expressing env, gag, protease and RT. Initially, multiple env and gag/pol clones from 3 pure Ugandan subtype D isolates were selected. These sequences were separately cloned into pCR2.1 and tested for expression levels in-vitro by immunoprecipitation, and for envelope function as assessed by envelope-mediated fusion with CD4 and CCR5 or CXCR4 expressing cells. Based on these in-vitro analyses, several R5 subtype D env and gag/pol sequences were selected and cloned into MVA shuttle plasmids containing GFP and the modified H5 promoter for sequential cloning into deletions II and III, respectively, of MVA. The parent MVA used was a 1974 stock chosen to eliminate FDA concerns regarding potential BSE contamination. Several recombinant MVA (rMVA-UGD) expressing subtype D env and gag/pol were prepared in primary CEF cells using gamma-irradiated FBS from a USDA approved source and selected using GFP expression. These rMVA-UGD were further plaque-purified and amplified to titers sufficient for in-vivo immunogenicity studies. Pre-clinical humoral and cellular immunogenicity of the various rMVA-UGD were then assessed in BALB/c mice.

MVA Expressing Altered HIV-1 Envelope, Gag, and Polymerase Genes from Ugandan Clade D This example describes the construction of 5 recombinant Modified Vaccinia Virus Ankara (MVA) viruses expressing envelope (env) and gagpol genes from HIV-1 clade D isolates from Uganda.

Sequences from Ugandan Clade D

Env and gagpol genes from three Ugandan clade D HIV-1 isolates were used:

| HIV-1 Isolate name | GenBank Accession # | Lab designation (LVD) |
|---|---|---|
| 99UGA03349 | AF484518 | B |
| 99UGA07412 | AF484477 | C |
| 98UG57128 | AF484502 | D |

Env and gagpol genes were PCR amplified from Ugandan HIV-1 clade D isolates by short term co-cultures on normal human PBMC (Harris et al. 2002 *AIDS Research and Human Retroviruses* 18:1281) using the oligonucleotides shown in Table G and cloned into pCR2.1-TOPO (Invitrogen). (HIV-1 infected individuals contain a population or quasi-species of related but distinct viruses. Upon co-culture, multiple viruses can emerge such that the sequences of individual amplified genes from the co-culture may differ from the sequence of the full genome.) The resulting amplified env genes have a C-terminal deletion of 115 amino acids that was previously shown to enhance expression and yield a more stable recombinant virus. The resulting gagpol genes have a deletion of the entire integrase and Rnase H portions of the genes. Within both the env and gagpol genes, several mutations were made by site-directed mutagenesis (Quik Change from Stratagene). In the env genes, silent mutations were made to eliminate two naturally occurring vaccinia virus early transcription termination signals (TTTTTNT, SEQ ID NO: 14) (Earl et. al 1990 *J Virol* 64:2451). In the pol genes, two mutations were made in separate locations in the active site of reverse transcriptase to abolish enzymatic activity (Larder et. al 1987 *Nature* 327:716)(see Tables H(i) & (ii) for details on changes made to env and gagpol genes).

PCR2.1-TOPO plasmids containing the amplified genes were first characterized with respect to the orientation of the gene. Clones in which the gene was oriented properly with respect to the T7 promoter were chosen and protein expression was analyzed as previously described (Earl et al. 1997 *J Virol* 71:2674). Briefly, BS-C-1 cells were infected with vTF7-3 (Fuerst et al. 1986 *PNAS USA* 83:8122), a recombinant vaccinia virus expressing T7 RNA polymerase, transfected with a plasmid, and metabolically labeled. Cell lysates were subjected to immunoprecipitation with serum pooled from several HIV-1 clade D-infected individuals. Proteins were analyzed by SDS-polyacrylamide gel electrophoresis and visualized by autoradiography. One env and one gagpol DNA clone from each clade D isolate was chosen for construction of recombinant MVA viruses. DNA sequencing was performed to confirm the integrity of each gene. Sequences are presented in Appendix 1.

Cloning into Shuttle Plasmids

Figure 18:
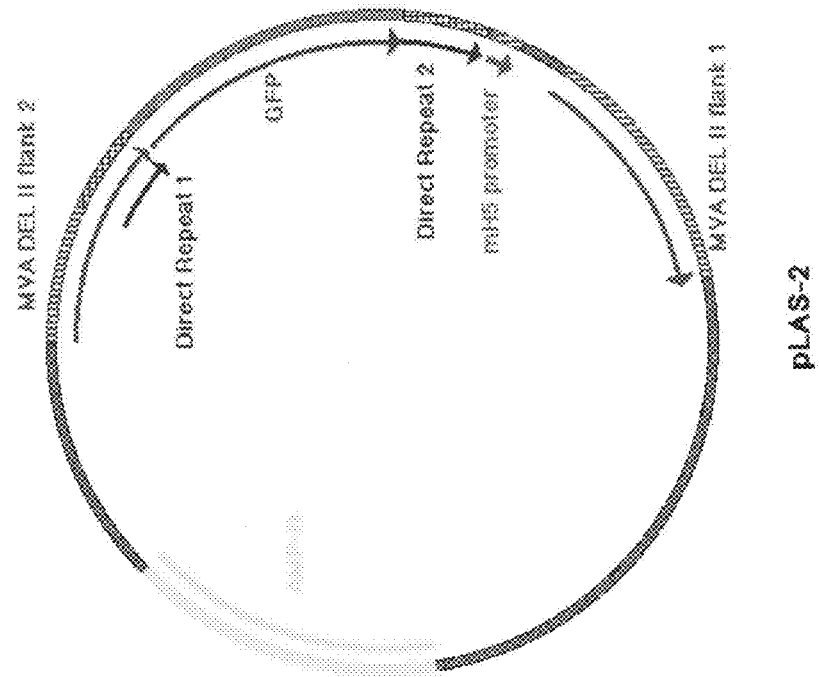
FIG. 18. pLAS-1 and pLAS-2.
Figure 18:
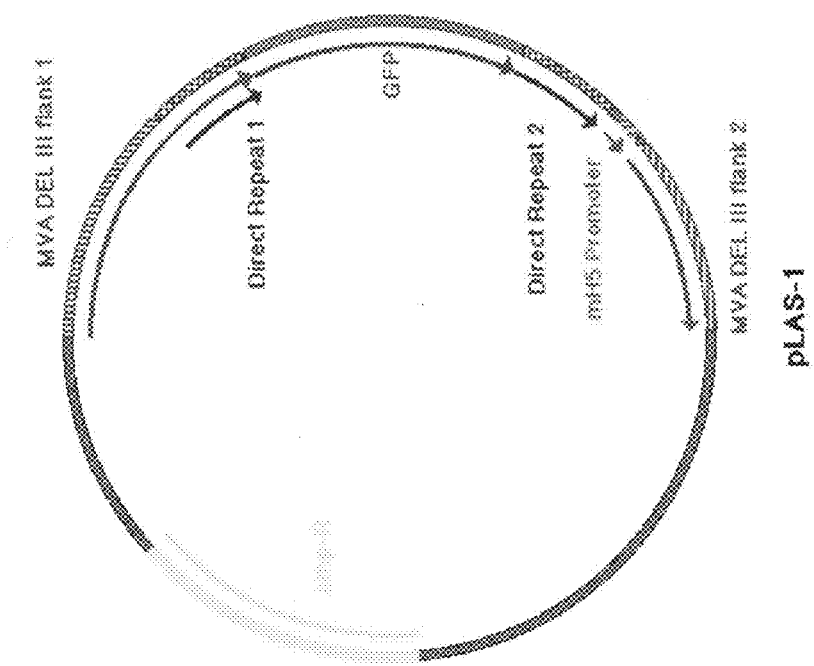
Figure 22:
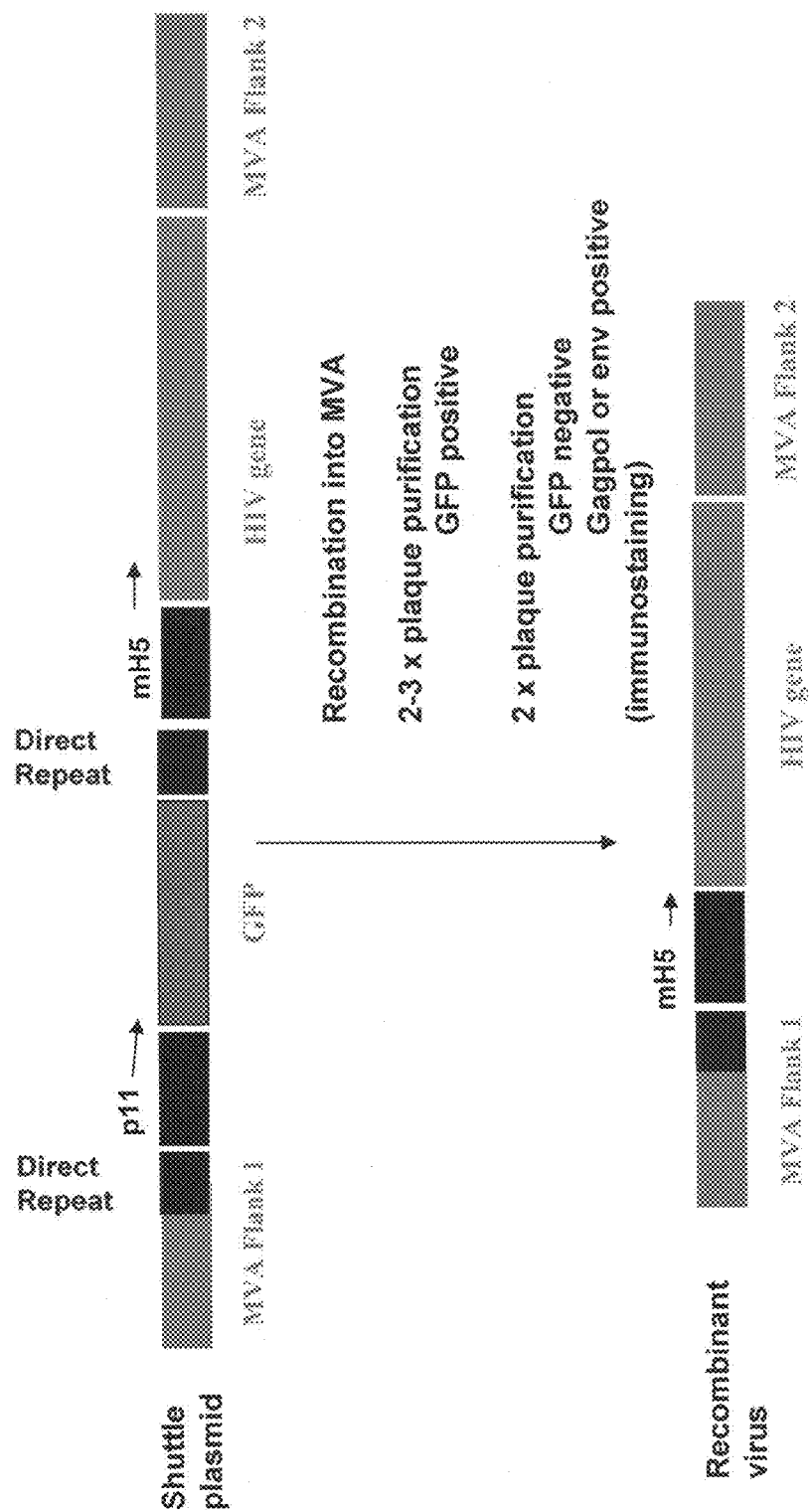
FIG. 22. Schematic for recombinant MVA production.
Figure 23:
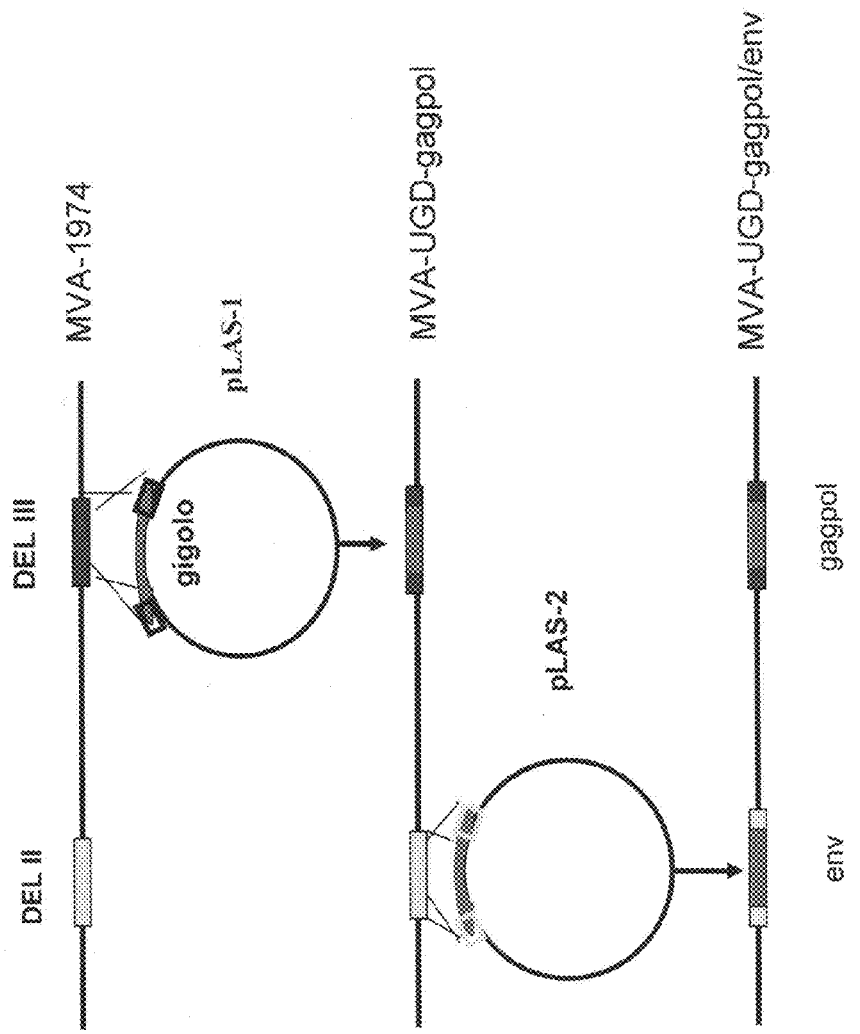
FIG. 23. Overview of making recombinant MVA/UGD viruses.

Two MVA shuttle plasmids, pLAS-1 and pLAS-2 (FIG. 18), were used for construction of recombinant MVA viruses. DNA sequences of both plasmids are presented in Appendix 2. In both plasmids, the foreign gene is driven by the modified H5 promoter. In addition, both plasmids contain a cassette with the gene for green fluorescent protein (GFP) driven by the vaccinia p11 promoter. This cassette is flanked by direct repeats that will readily recombine to eliminate GFP during virus propagation. Thus, GFP is used as a positive screening marker in early rounds of plaque purification, and as a negative screening marker in final recombinant virus selection (FIG. 22). MVA flanking sequences in pLAS-1 and pLAS-2 direct recombination into deletion III (Del III) and deletion II (Del II) of MVA, respectively.

Figure 19:
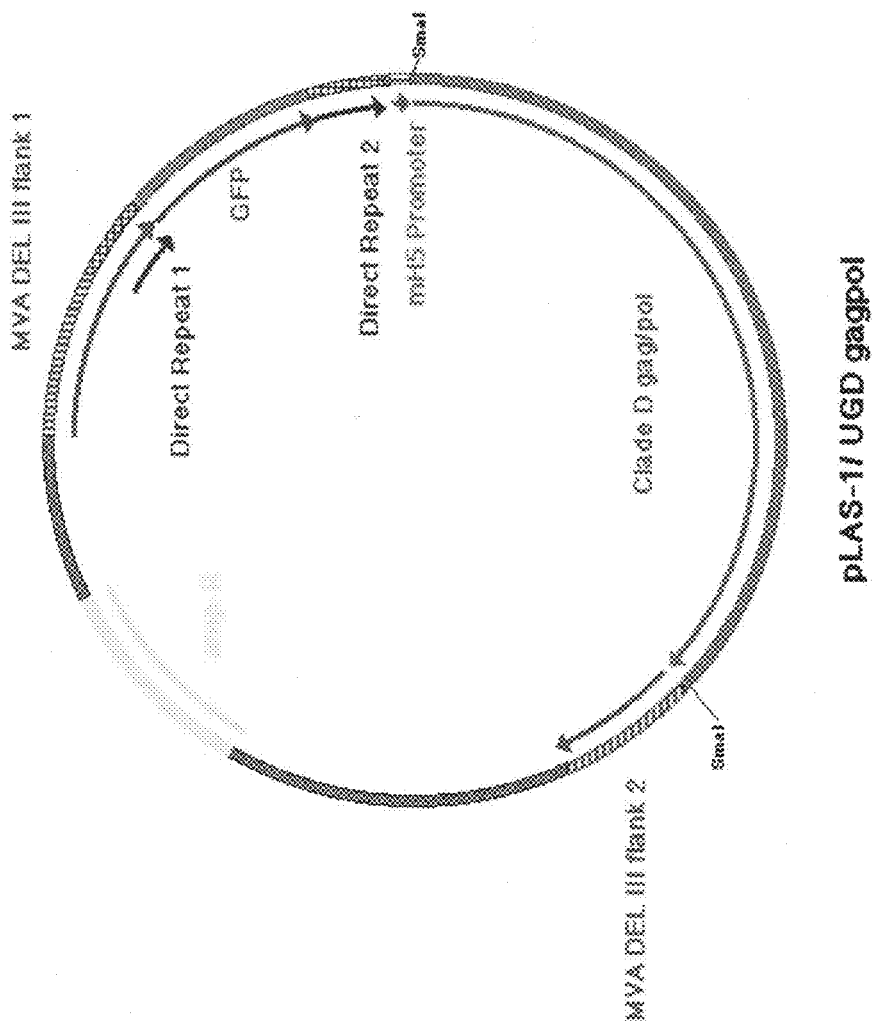
FIG. 19. pLAS-1/UGDgag.

Gagpol genes from 2 isolates (99UGA03349 and 99UGA07412) were cloned separately into pLAS-1 for insertion into Del III of MVA. The plasmids were named pLAS-1/UGD/Bgag and pLAS-1/UGD/Cgag (FIG. 19 & Table I). When the env gene is cloned into the NotI restriction site, a short open reading frame precedes the env open reading frame. This open reading frame is out of frame with env and terminates at approximately nucleotide 75 in the env gene.

Figure 20:
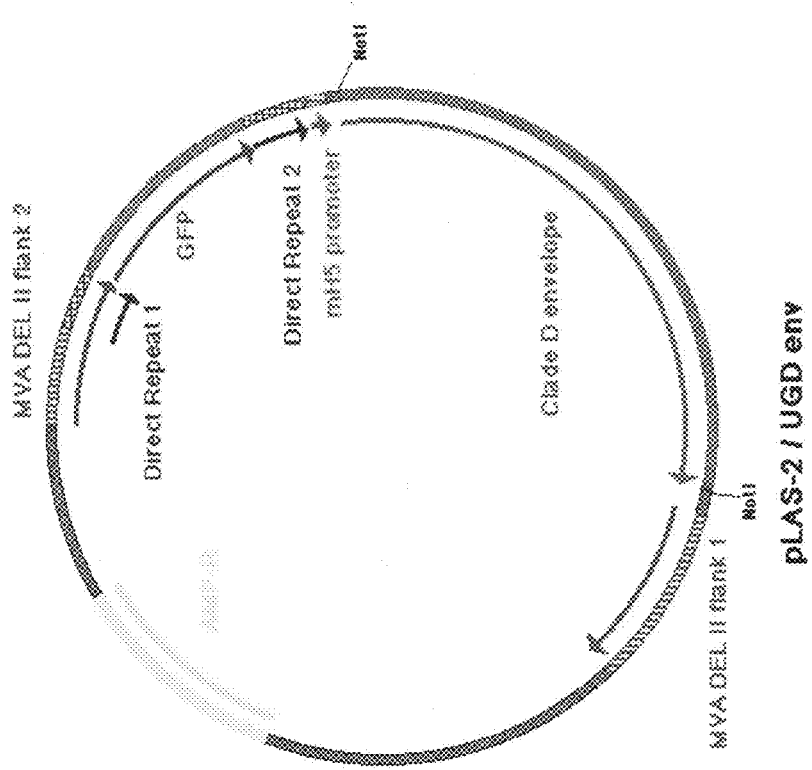
FIG. 20. pLAS-2/UGDenv.

Env genes from three isolates (99UGA03349, 99UGA07412, 98UG57128) were cloned separately into MVA shuttle plasmid pLAS-2, for insertion into Del II of MVA. Plasmids were named pLAS-2/UGD/Benv, pLAS-2/UGD/Cenv, and pLAS-2/UGD/Denv (FIG. 20 & Table I). When the env gene is cloned into the NotI restriction site, a short open reading frame precedes the env open reading frame. This open reading frame is out of frame with env and terminates at approximately nucleotide 75 in the env gene.

Figure 21:
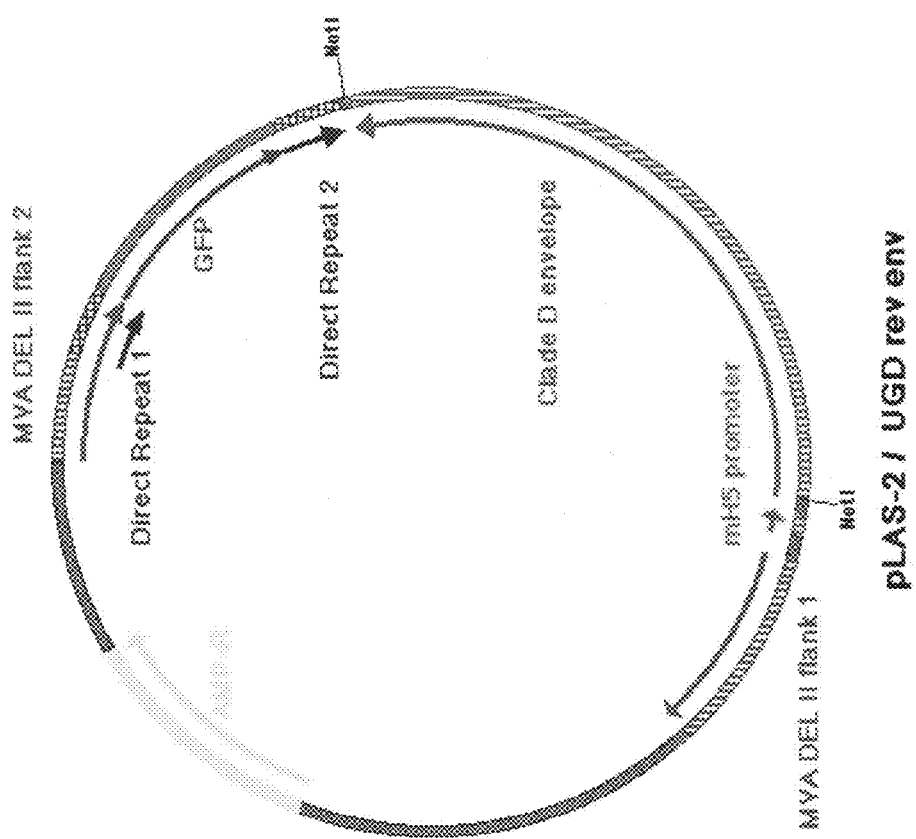
FIG. 21. pLAS-2/UGDrev env.

Foreign genes in pLAS-1 and pLAS-2 recombine into the vaccinia genome in the same orientation as the surrounding vaccinia genes. To test the effect of reversing the orientation of the env gene on the level of gene expression and stability of viruses, two of the env genes and their promoters were excised from pLAS-2 with restriction endonucleases BspE1 and EcoRV; sticky ends were filled in with Klenow enzyme; and the fragments were then reinserted into pLAS-2 the opposite orientation (FIG. 21). Plasmids were named pLAS-2/UGD/revCenv and pLAS-2/UGD/revDenv (Table I).

Recombinant MVA Construction

Parent MVA: MVA 1974/NIH Clone 1 was used as the parent for all recombinant viruses. It was derived from a stock of MVA at passage 572, prepared on Feb. 22, 1974 in the laboratory of A. Mayr in Germany. After receipt in the Laboratory of Viral Diseases, this stock was passaged a total of 6 times in chicken embryo fibroblast (CEF) cells, including 3 clonal purifications. Amplification was performed on the final, clonally purified virus. All CEF cells were derived from specific pathogen-free (SPAFAS) eggs.

Recombinant viruses expressing gagpol: CEF cells were infected with MVA 1974/NIH Clone 1 and transfected with either pLAS-1/UGD/Bgag or pLAS-1/UGD/Cgag for insertion into Del III. Two to three rounds of plaque purification were performed based on GFP expression. Further rounds of plaque purification were performed by picking plaques based on lack of GFP expression and concomitant positive gag expression as measured by immunostaining using a monoclonal antibody to HIV-1 p24 (183-H12-5C; obtained from the NIH AIDS Research and Reference Reagent Program) (FIG. 22). Recombinant gagpol-expressing viruses were amplified and characterized for gag expression by immunoprecipitation as described above. The two viruses were named MVA/UGD/Bgag and MVA/UGD/Cgag. These viruses were then used as the parent in making gagpol/env recombinant viruses (see below).

Recombinant viruses expressing gagpol and env: Recombinant viruses, MVA/UGD/Bgag and MVA/UGD/Cgag were used as parent viruses for insertion of env genes. Thus, CEF cells were infected with either MVA/UGD/Bgag or MVA/UGD/Cgag and subsequently transfected with one of the pLAS-2-env-containing plasmids described above (FIG.

Figure 24:
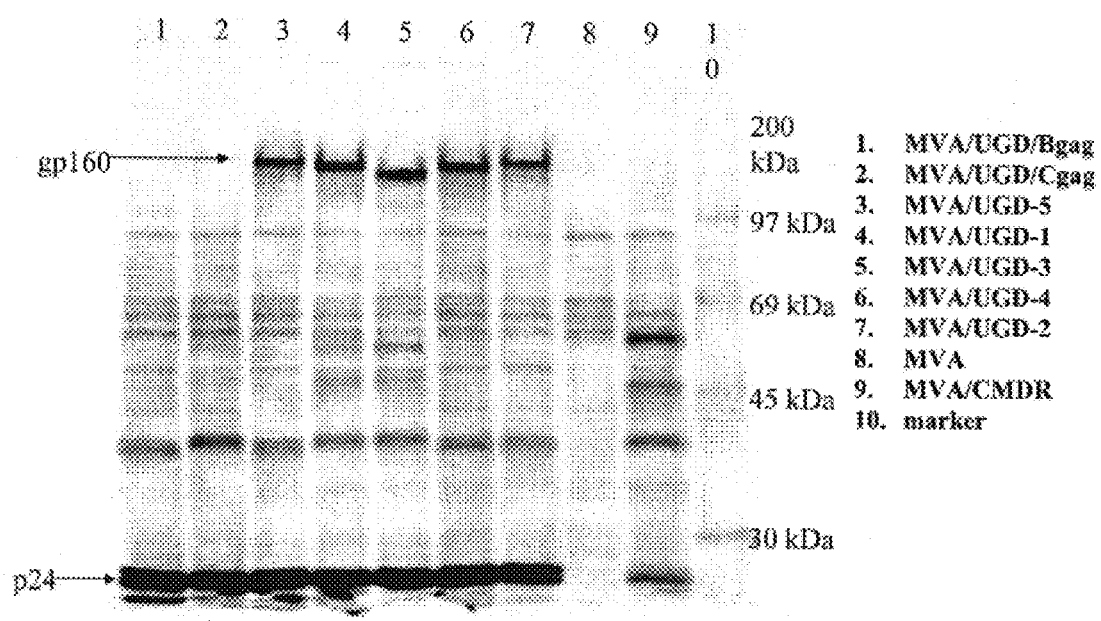
FIG. 24. Immunoprecipitation analysis.

23 & Table I). As above, the first two rounds of plaque purification were performed based on GFP expression. In subsequent rounds of purification, plaques were selected based on loss of GFP expression and positive gag and env expression as measured by immunostaining in duplicate cultures (FIG. 22). A total of 5 gagpol/env-expressing viruses (MVA/UGD-1 through -5) were amplified and characterized (Table J). Characterization of recombinant MVA/UGD viruses:

The 5 MVA/UGD viruses have been characterized for gene expression and function. Immunoprecipitation of env and gag proteins is shown in FIG. 24. BS-C-1 cells were infected with individual recombinant viruses at a multiplicity of infection of 10, metabolically labeled, and lysates were subjected to immunoprecipitation with a pool of sera from HIV-1 clade D infected individuals. Viruses expressing gagpol only (MVA/UGD/Bgag and Cgag) were included, as was non-recombinant MVA as a negative control and MVA/CMDR as a positive control. The latter virus expresses gagpol/env from a Clade E HIV-1 isolate. All viruses produced high levels of gag protein and efficient processing into p24 was observed. In addition, all env-expressing viruses produced high levels of env protein (gp160).

Figure 25A:
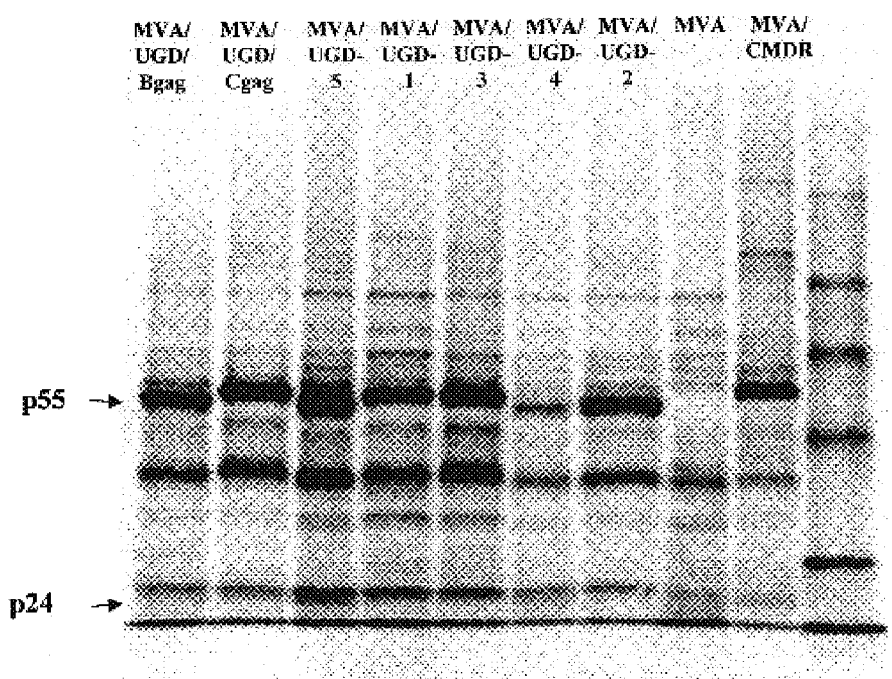
FIG. 25. Functional analysis of expressed proteins. A, Virus-like partikle assay. B. Env fusion assay.
Figure 25B:
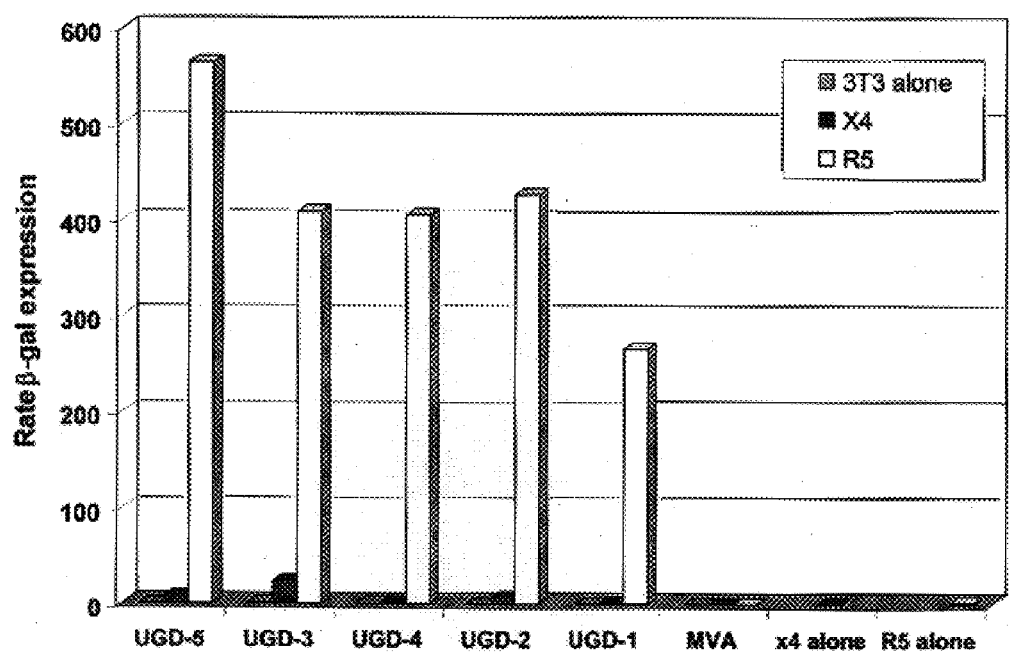

FIG. 25 demonstrates that the gag and env proteins produced by the MVA/UGD viruses are functional. Virus-like particles were obtained by centrifugation of the supernatant of infected cells through a sucrose cushion (Karacostas et al. 1993 *Virology* 193:661). Pelleted material was then separated by SDS-polyacrylamide gel electrophoresis and analyzed by autoradiography (Panel A). As seen, p55 and p24 gag proteins were found in the pellet indicating that virus-like particles were formed. Panel B shows results of an assay in which env-expressing cells (infected with MVA/UGD virus) were mixed with cells expressing CD4 and co-receptor (X4 or R5) (Nussbaum, Broder, & Berger 1994 *J Virol* 68:5411). Fusion was measured by beta-galactosidase activity in cell lysates. As shown, all five MVA/UGD viruses induced fusion with CD4/R5-expressing cells.

Immunogenicity of Recombinant MVA/UGD Viruses (study 1)

Figure 27:
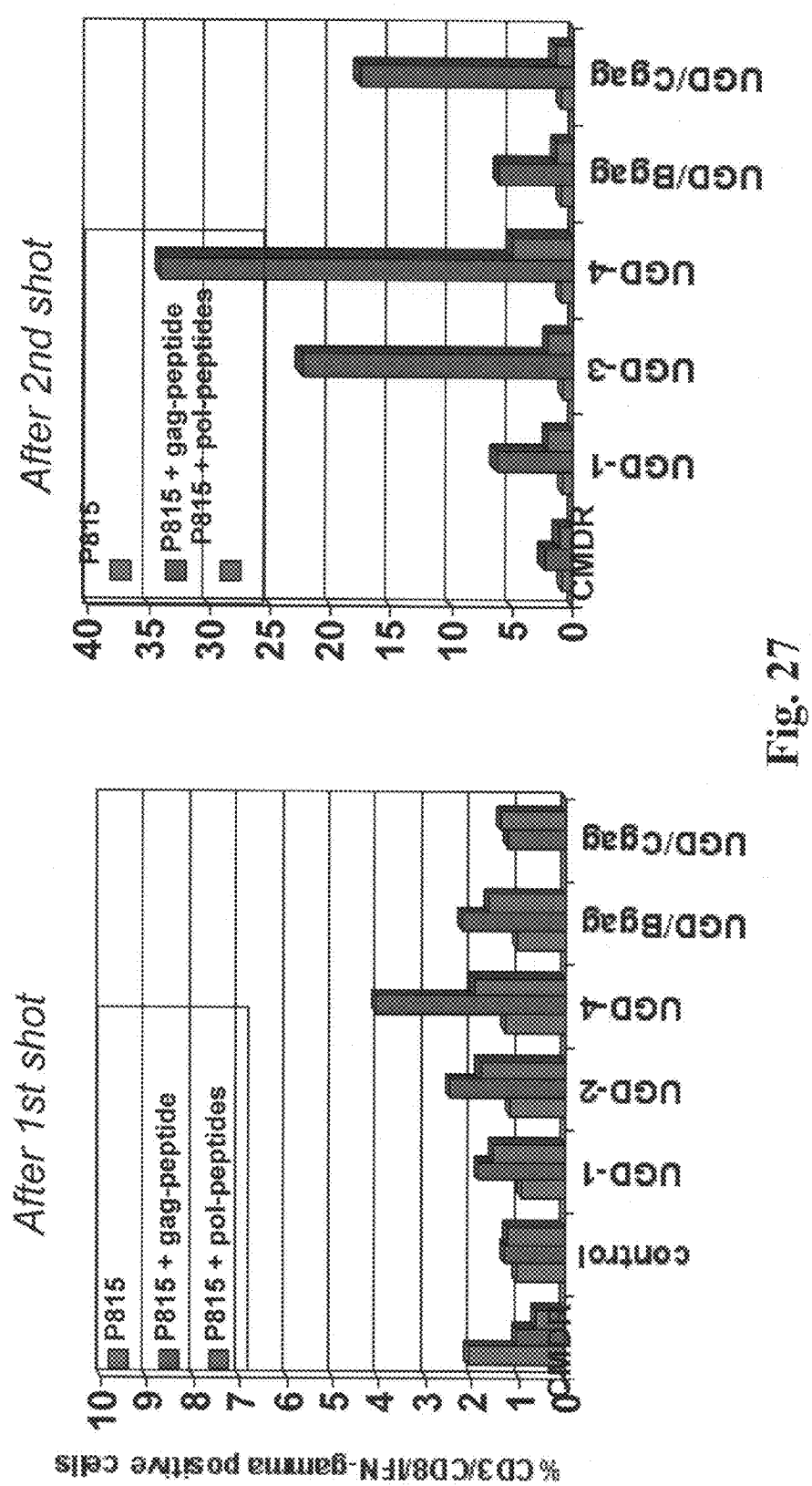
FIG. 27. MVA/UGD induced gag-specific intracellular IFN-γ production.
Figure 28A:
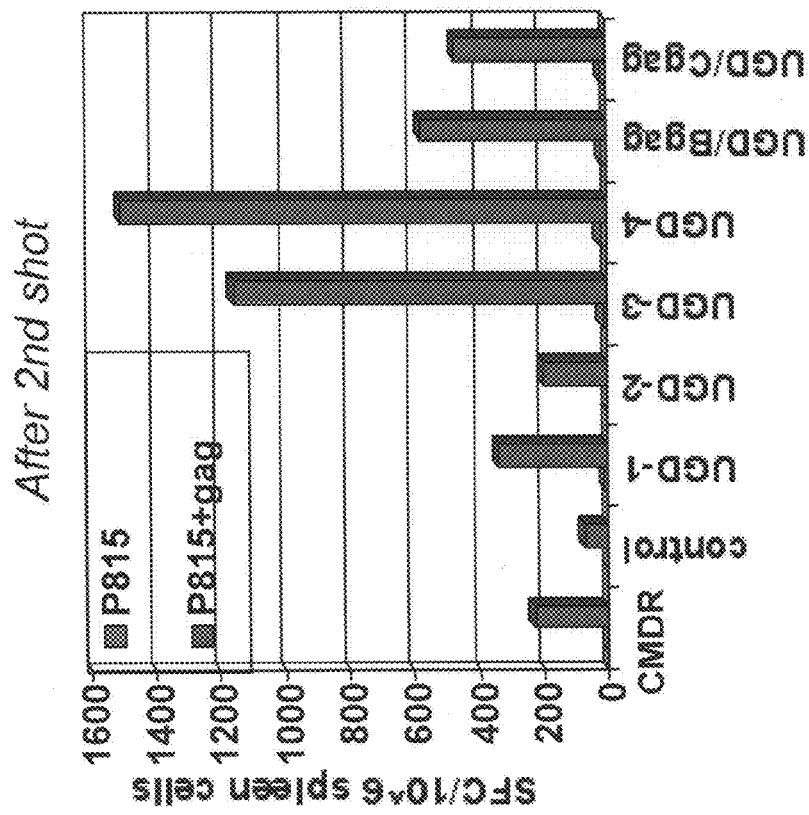
FIG. 28A. MVA/UGD induced gag-specific IFN-γ ELISPOT.
Figure 28A:
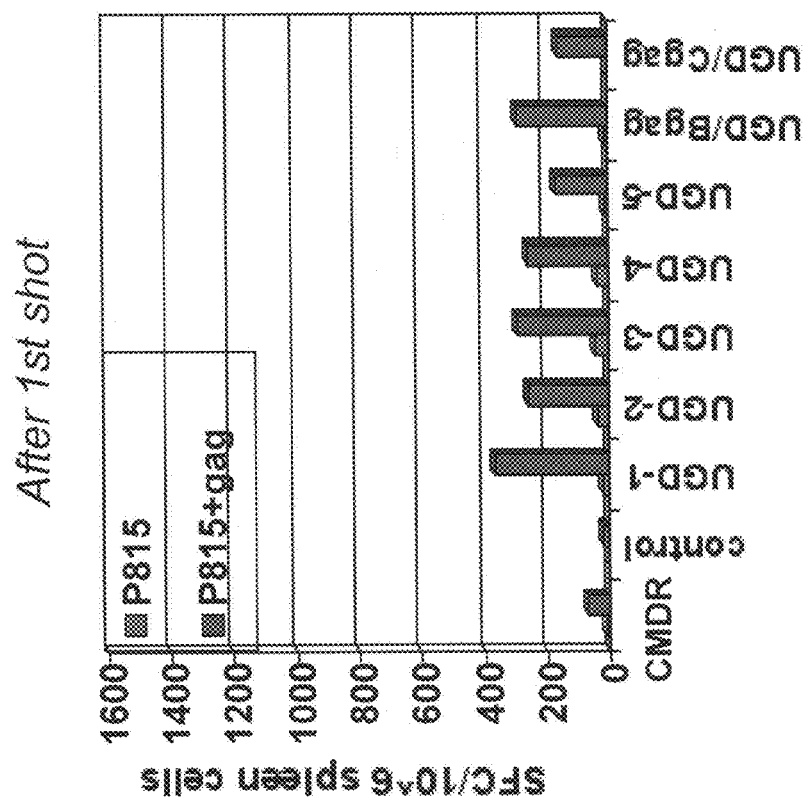
Figure 28B:
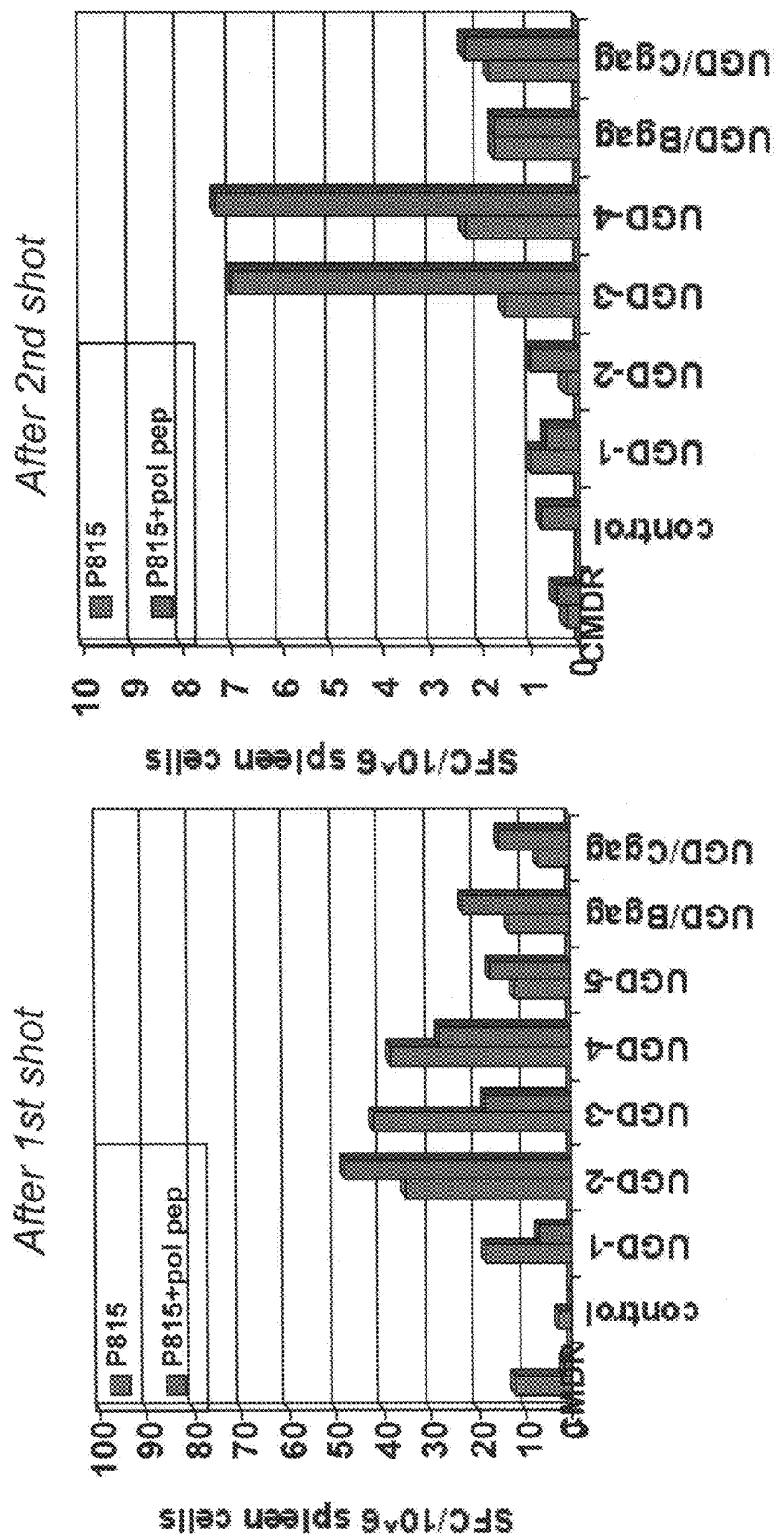
FIG. 28B. MVA/UGD induced pol-specific IFN-γ ELISPOT.

Groups of Balb/c mice were immunized with individual MVA/UGD viruses, non-recombinant MVA (negative control), or MVA/CMDR (positive control—expressing clade E gagpol/env) at weeks 0 and 3. The dose was $10^7$ infectious units per immunization and the route was intraperitoneal. Humoral and cell mediated responses were measured and are shown in FIGS. 26-28.

Figure 26A:
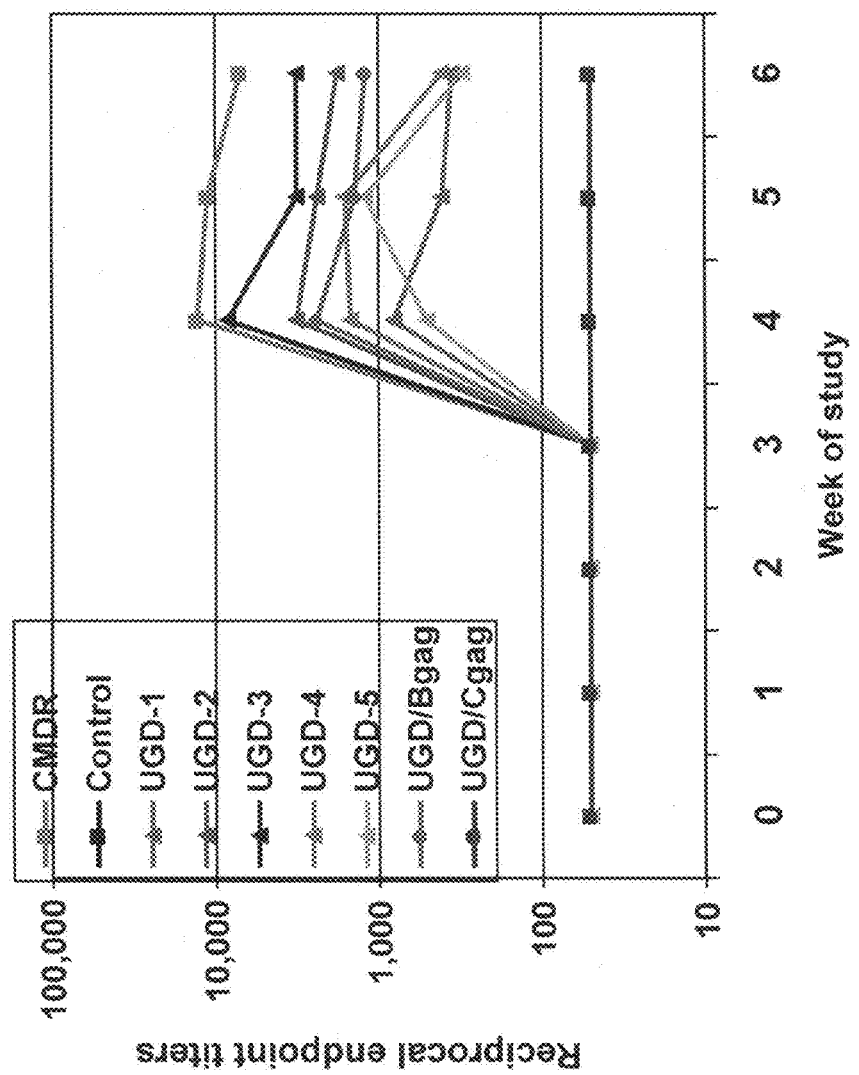
FIG. 26. MVA/UGD induced HIV env-and gag-specific antibody responses. A. HIV p24-specofoc serum IgG responses. B. HIV env-specific serum IgG responses. C. MVA/UGD induced HIV env- and gag-specific antibody responses (study 1).
Figure 26B:
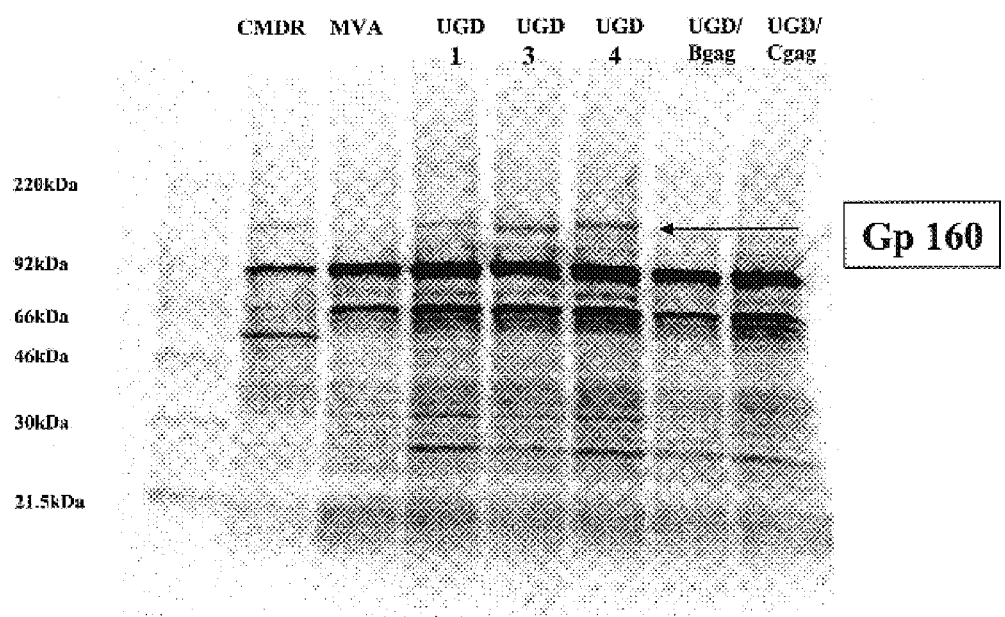
Figure 26C:
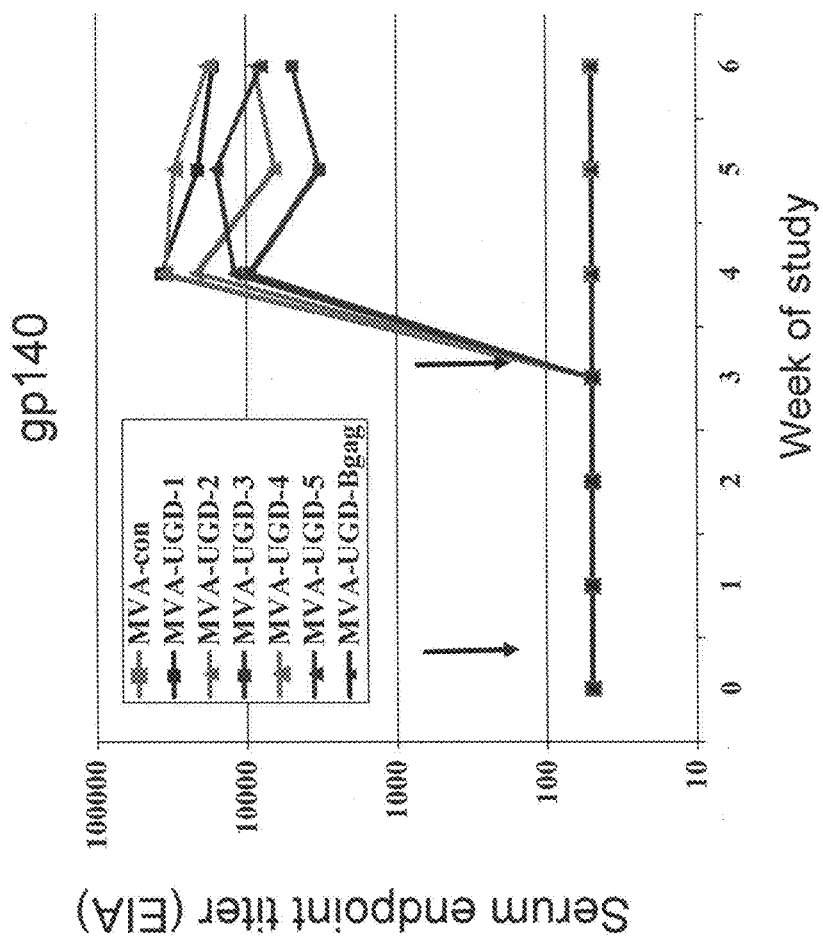

Antibody responses after 2 immunizations are shown in FIG. 26. Reciprocal endpoint ELISA titers to p24 at various times after immunization are shown in Panel A. All UGD viruses elicited gag-specific antibodies after 2 immunizations. Env-specific responses are shown in Panel B. In this experiment, pooled sera from groups of mice were used to immunoprecipitate metabolically labeled, autologous gp160 proteins. As seen, sera from mice immunized with MVA/UGD-1, -3, and -4 reacted with gp160 (the other viruses were not tested in this assay). Reciprocal endpoint titers to gp140 env at various times after immunization are shown in Panel C. All UGD viruses elicited env-specific antibodies after 2 immunizations.

Figure 29:
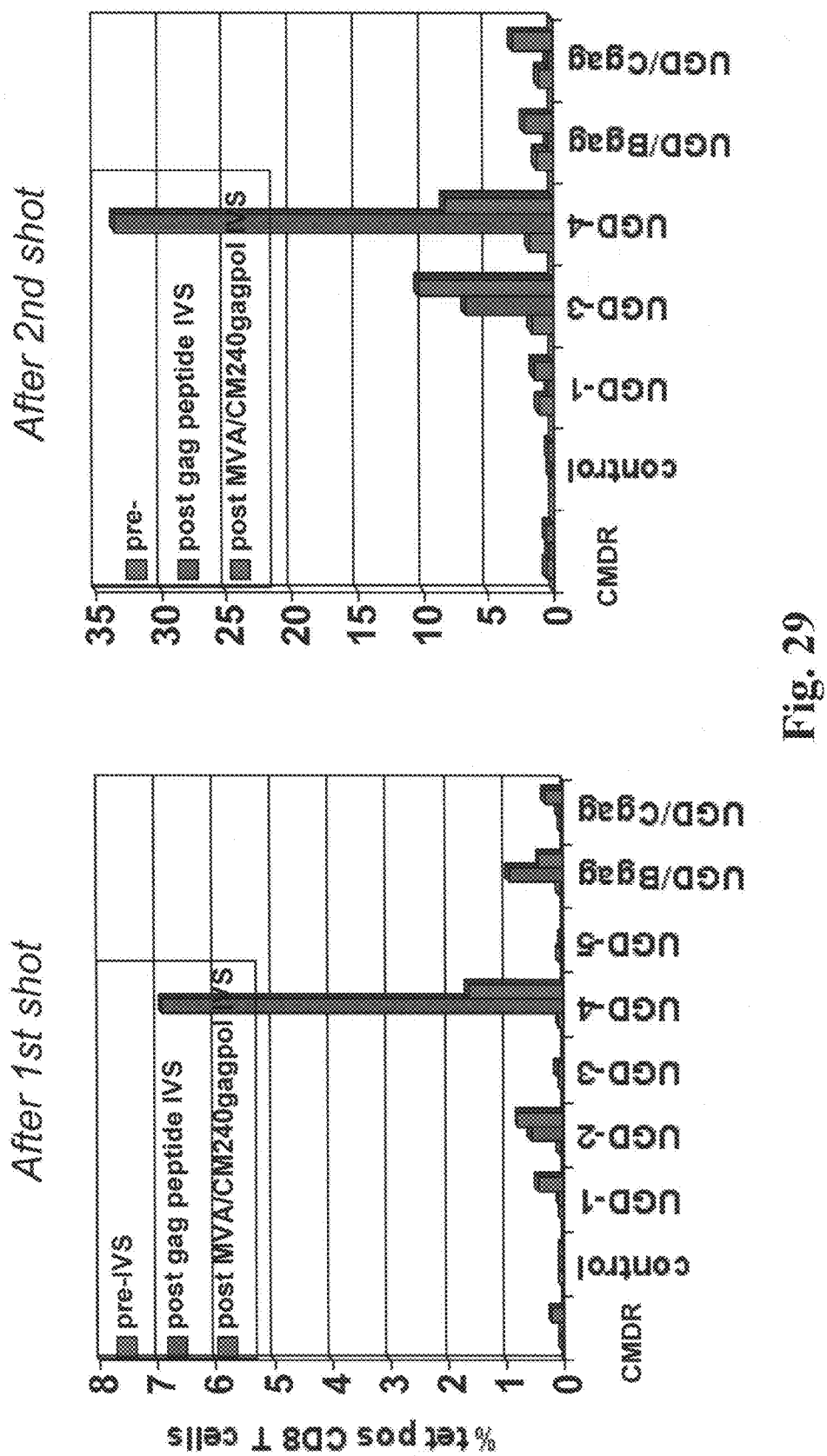
FIG. 29. MVA/UGD induced gag-specific tetramer staining.

T cell responses were measured with several assays. First, gag and pol peptide-specific intracellular interferon gamma (IFN-γ) responses were measured by intracellular cytokine staining. Splenocytes were collected 3 weeks after immunization, stimulated in-vitro for 7 days, and then cultured overnight with peptide-pulsed P815 cells. Brefeldin A was added to prevent secretion of INF-γ. CD3 positive, CD8 positive, IFN-γ positive cells were enumerated by flow cytometry. Analyses were performed after one and two immunizations. Both gag- and pol-specific responses were observed after two immunizations (FIG. 27) (samples from animals immunized with MVA/UGD-2, and 5 were not assayed). Second, gag- and pol-specific INF-γ responses were measured by ELISPOT (FIGS. 28 A & B). Briefly, splenocytes from immunized mice were mixed with gag or pol peptide-pulsed P815 cells in 96-well nitrocellulose plates coated with anti-IFN-γ antibody. After overnight incubation, spots were visualized by sequential incubation with anti-IFN-γ biotin antibody, straptavidin-HRP, and AEC substrate. Spots were enumerated using a Zeiss ELISPOT reader. Gag peptide-specific responses were found after one immunization and were boosted in most groups after the second immunization. Pol peptide-specific responses were found in several groups after two immunizations. Third, gag peptide-specific responses were measured by tetramer staining (H-2 Kd gag LAI tetramer: AMQMLKETI, SEQ ID NO: 63) (FIG. 29). Splenocytes were stimulated in vitro with either gag peptide or MVA/CM240gagpol, a recombinant virus expressing a clade E gagpol. CD3 positive, CD8 positive, tetramer positive cells were enumerated by flow cytometry. Positive tetramer staining was observed with cells from several groups of mice.

Immunogenicity of Recombinant MVA/UGD Viruses (Study 2)

Figure 30:
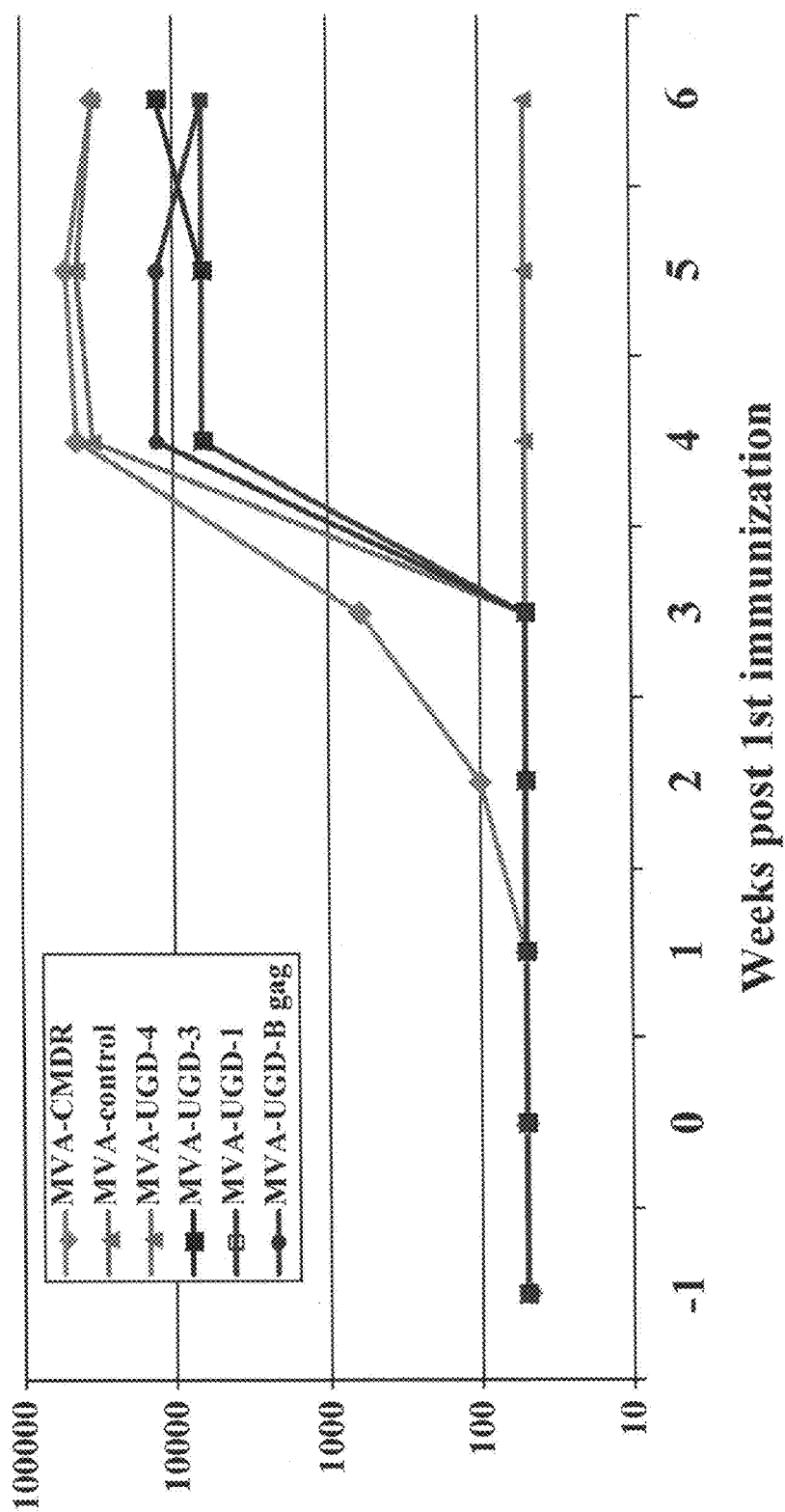
FIG. 30. MVA/UGD induced gag-specific antibody responses (study 2).

A second mouse immunogenicity study was performed to confirm the humoral and cellular immunogenicity of MVA/UGD-3 and MVA/UGD-4. BALB/c mice (10 per group) were administered intraperitoneal immunizations of $10^7$ infectious units of MVA at weeks 0 and 3. Five mice per group were sacrificed two weeks after the $1^{st}$ and $2^{nd}$ immunizations and spleens were removed for assessment of cellular immunogenicity. Sera were collected from each mouse at weeks-1, 0, 1, 2, 3, 4 and 5. Splenocytes and sera were pooled together by group. HIV gag-specific serum IgG responses were detected from all MVA/UGD-immunized groups after the $2^{nd}$ immunization (FIG. 30). These gag-specific responses were predominantly of subclass IgG2a for both MVA/UGD-3 and MVA/UGD-4 demonstrating a Th1-type response (Table Q).

Figure 31A:
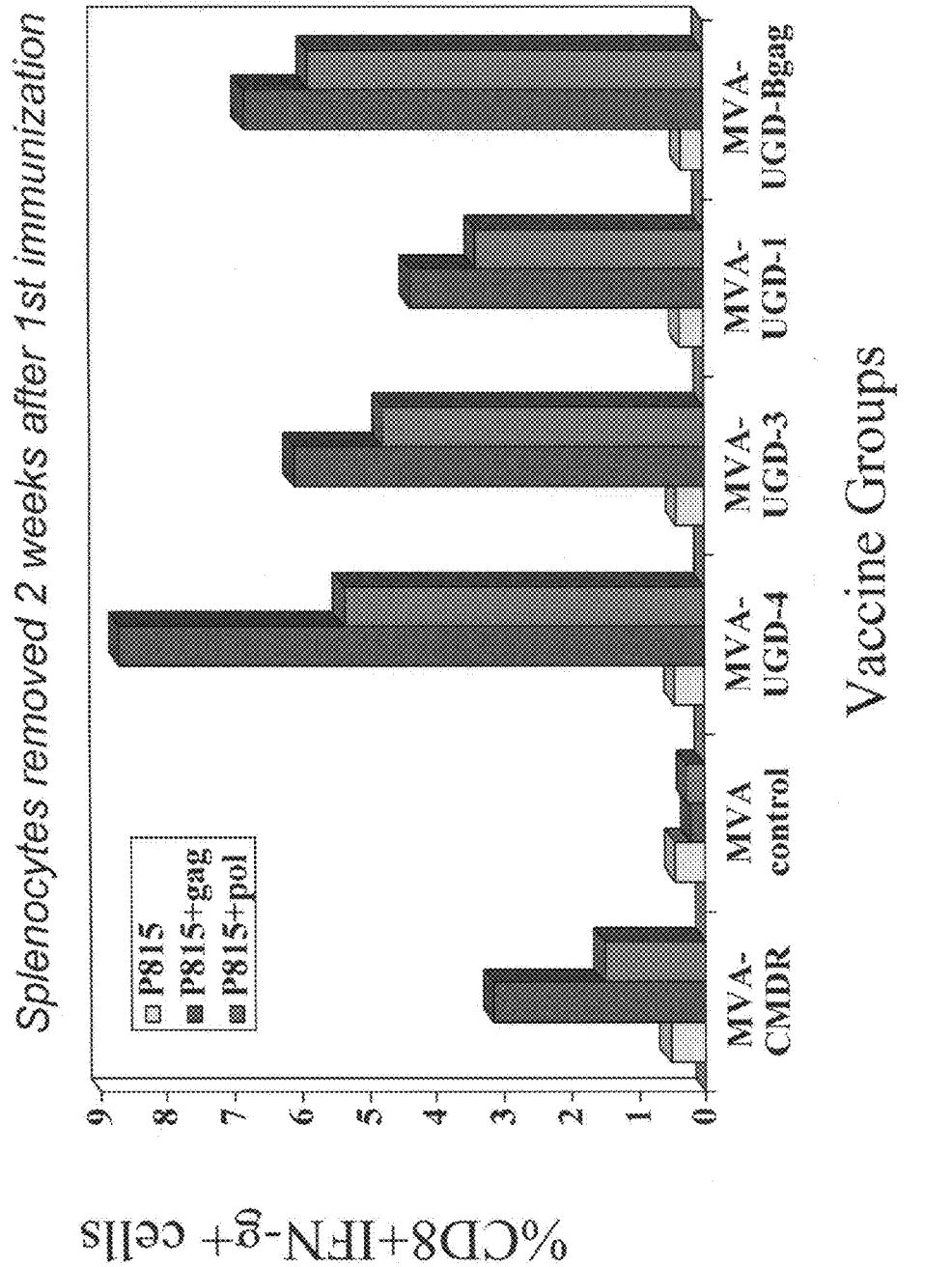
FIGS. 31A & B. MVA/UGD induced gag-and pol-specific intracellular IFN-γ production (study 2).
Figure 31B:
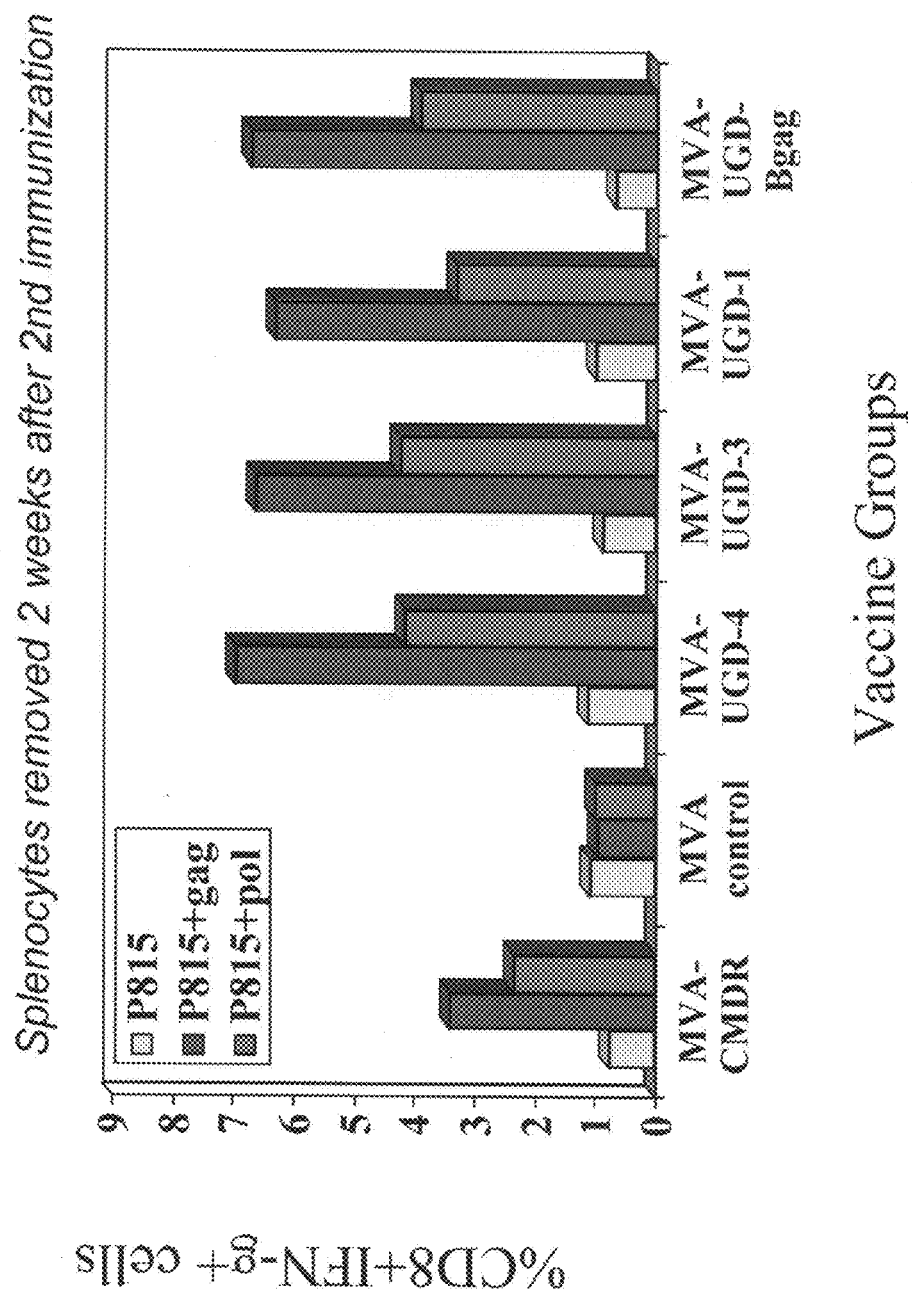
Figure 32A:
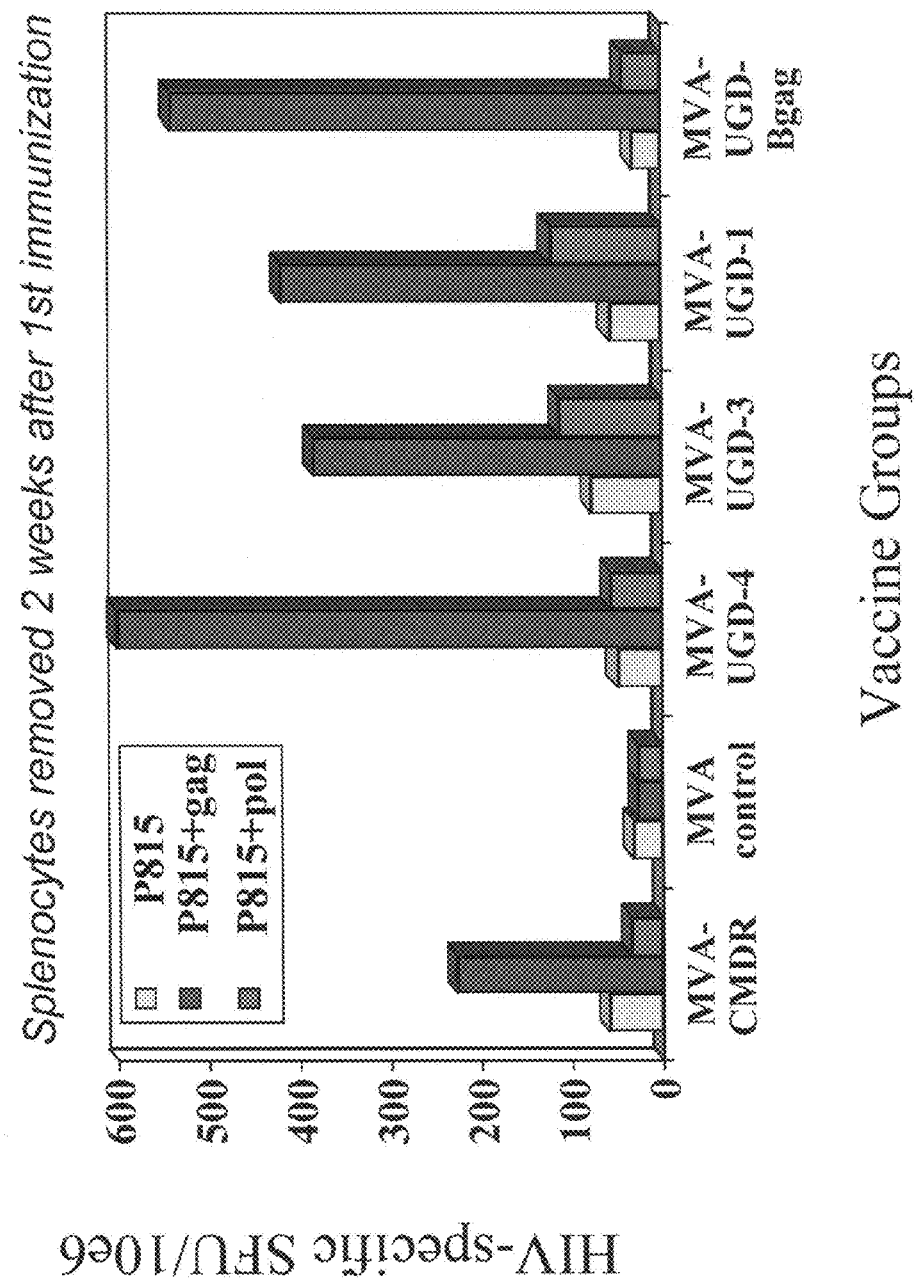
FIGS. 32 A, B, & C. MVA/UGD induced gag-and pol-specific IFN-γ ELISPOT (study 2).
Figure 32B:
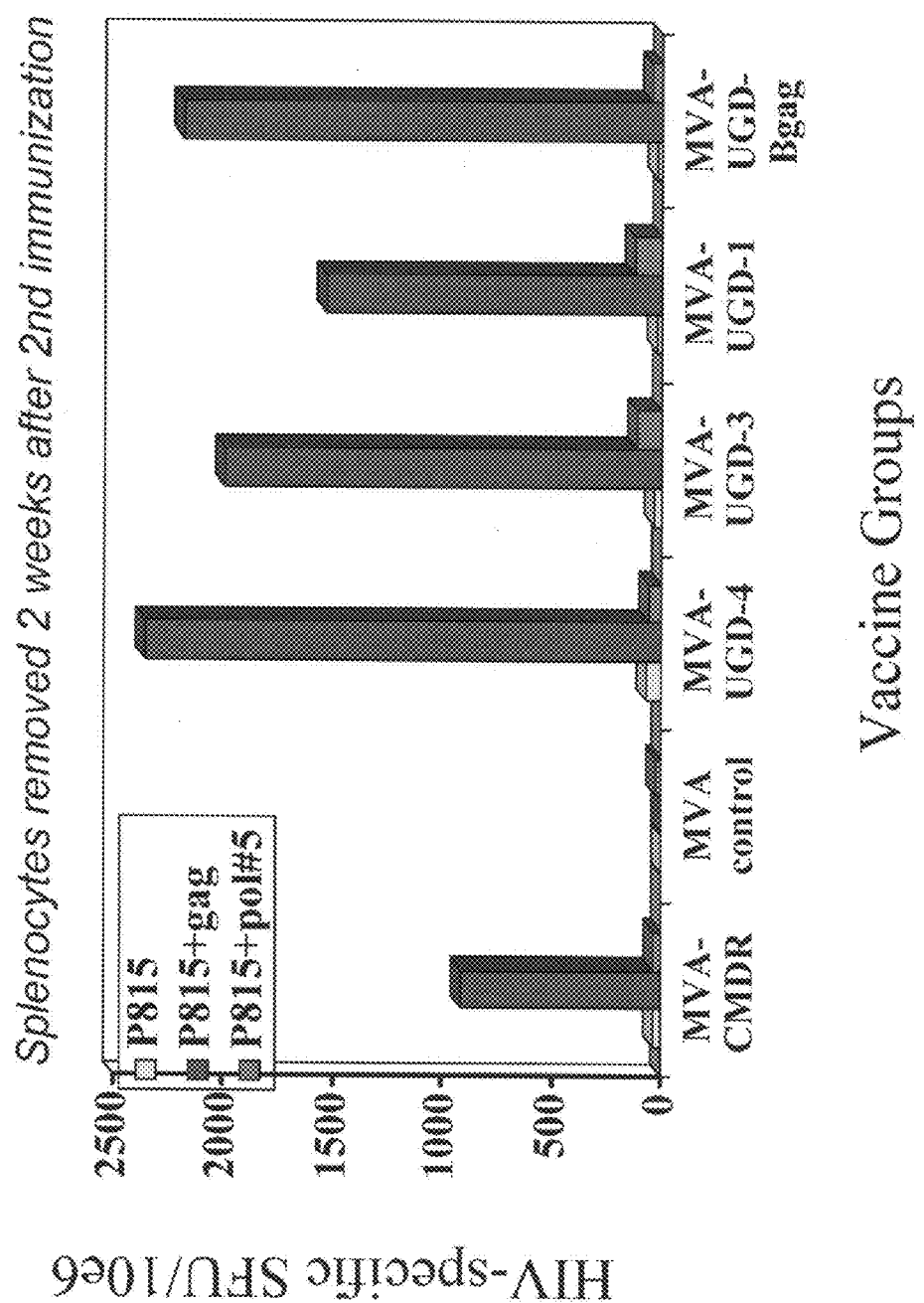
Figure 32C:
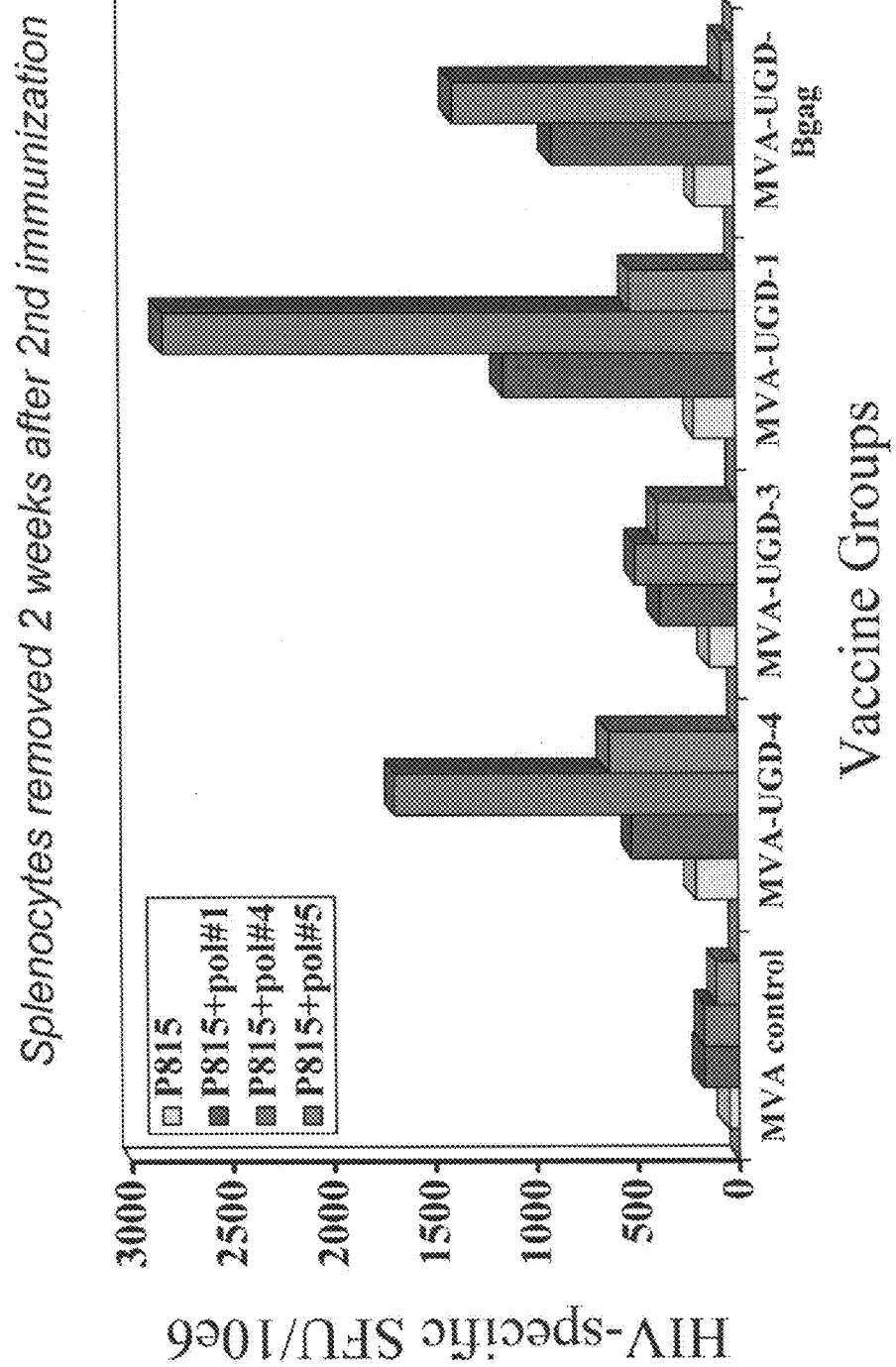
Figure 33:
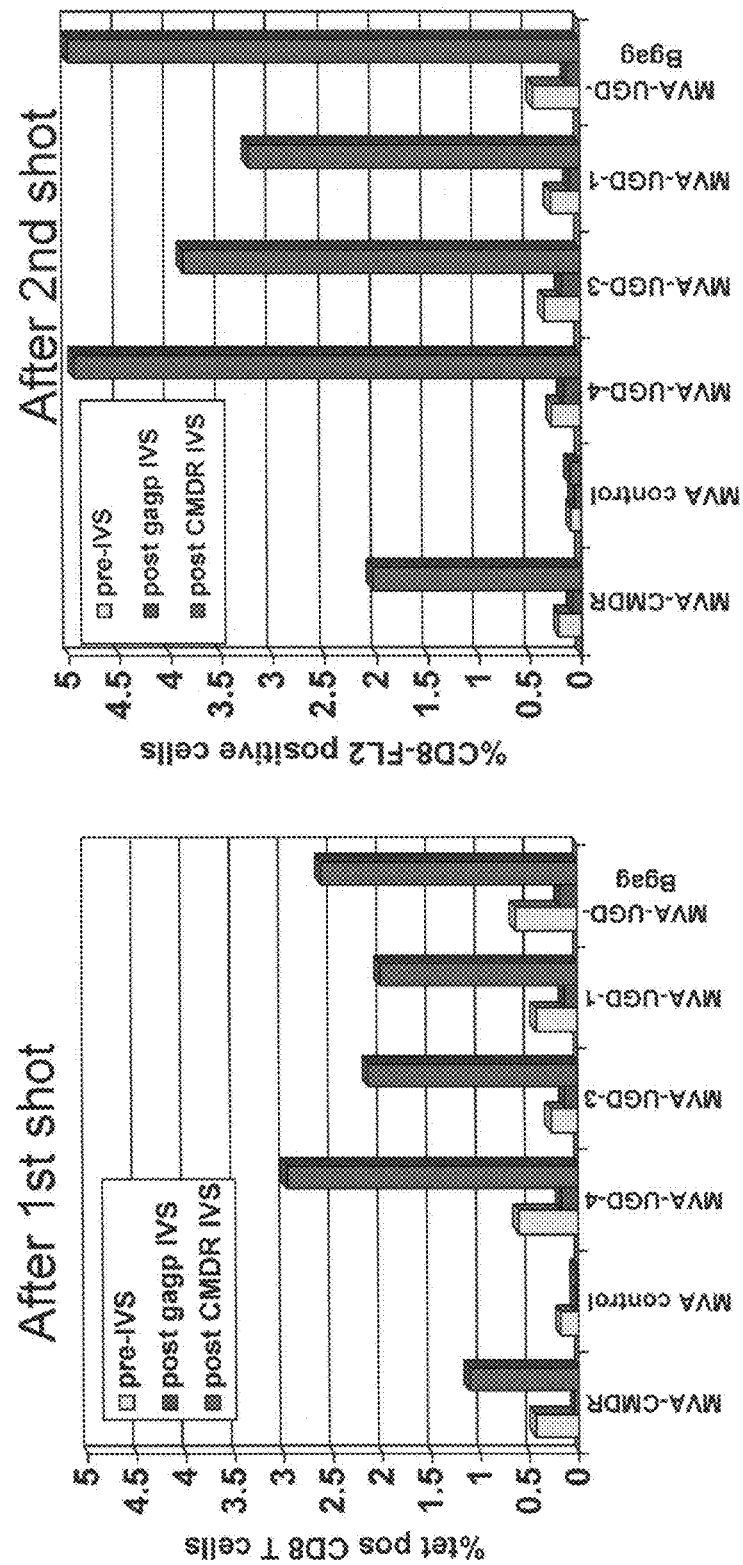
FIG. 33. MVA/UGD induced gag-specific tetramer staining (study 2).
Figure 34:
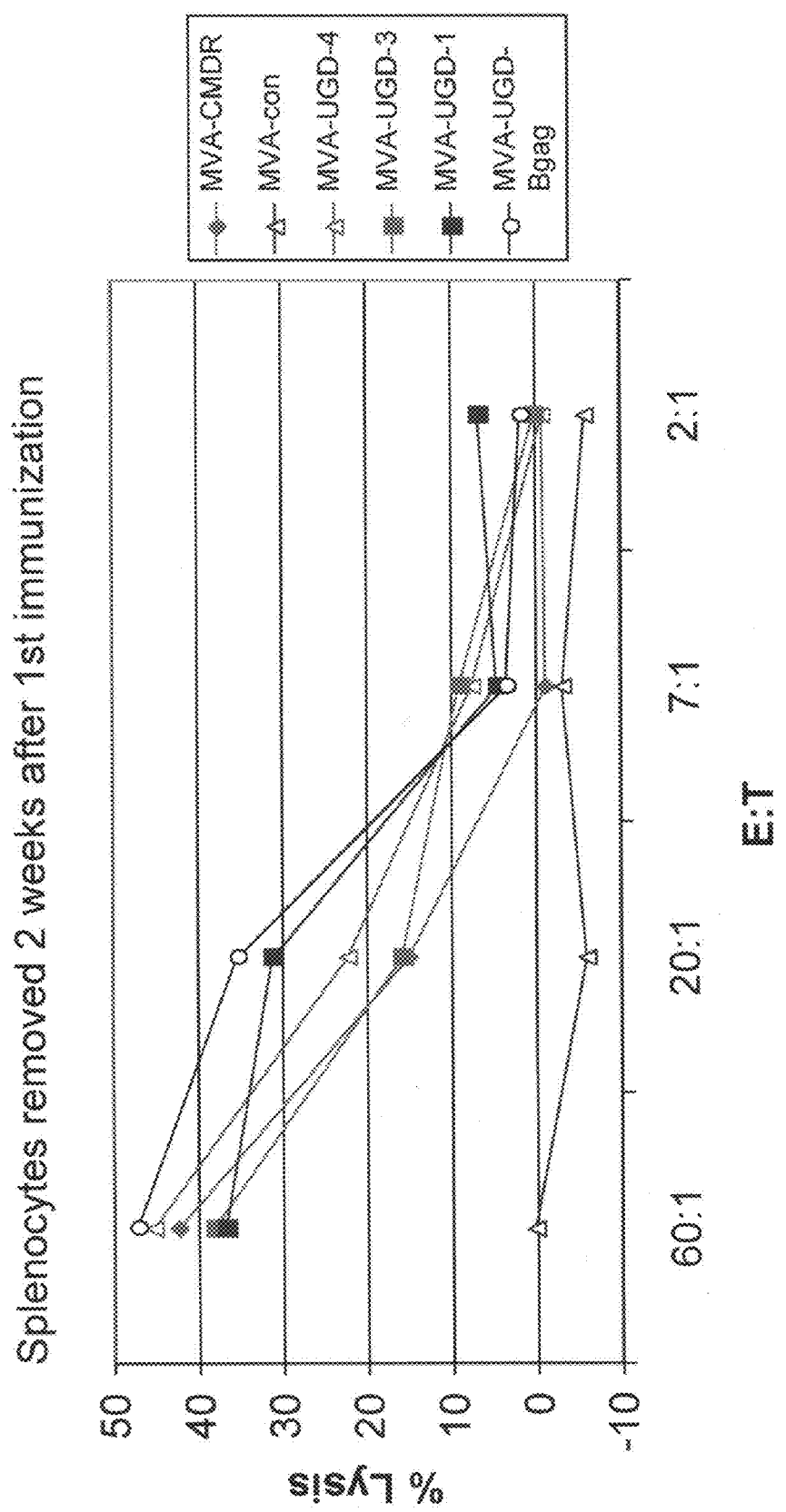
FIG. 34. MVA/UGD induced gag-specific cytotoxic T cell killing.
Figure 35:
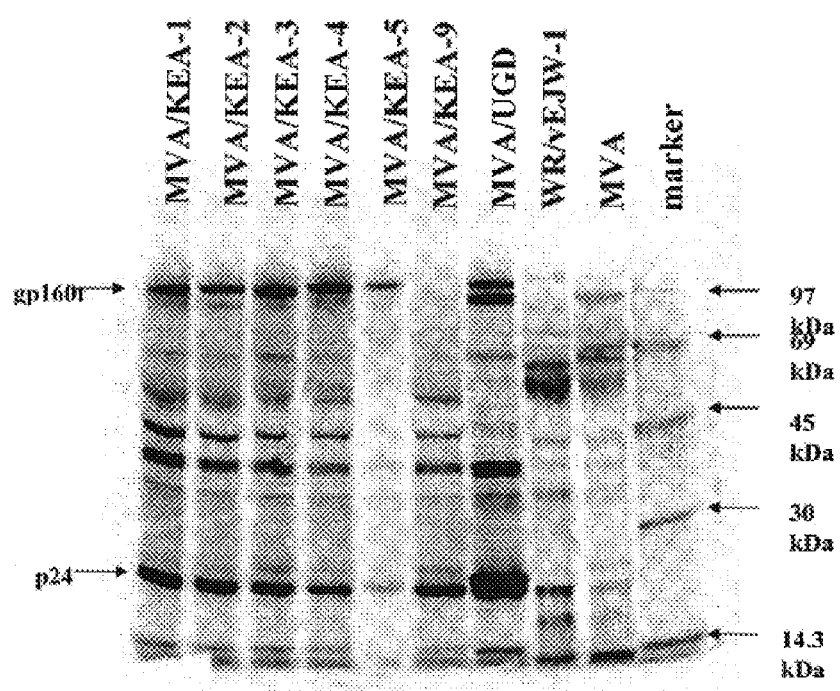
FIG. 35. Immunoprecipitation analysis of cell lysates (MVA/KEA).
Figure 36:
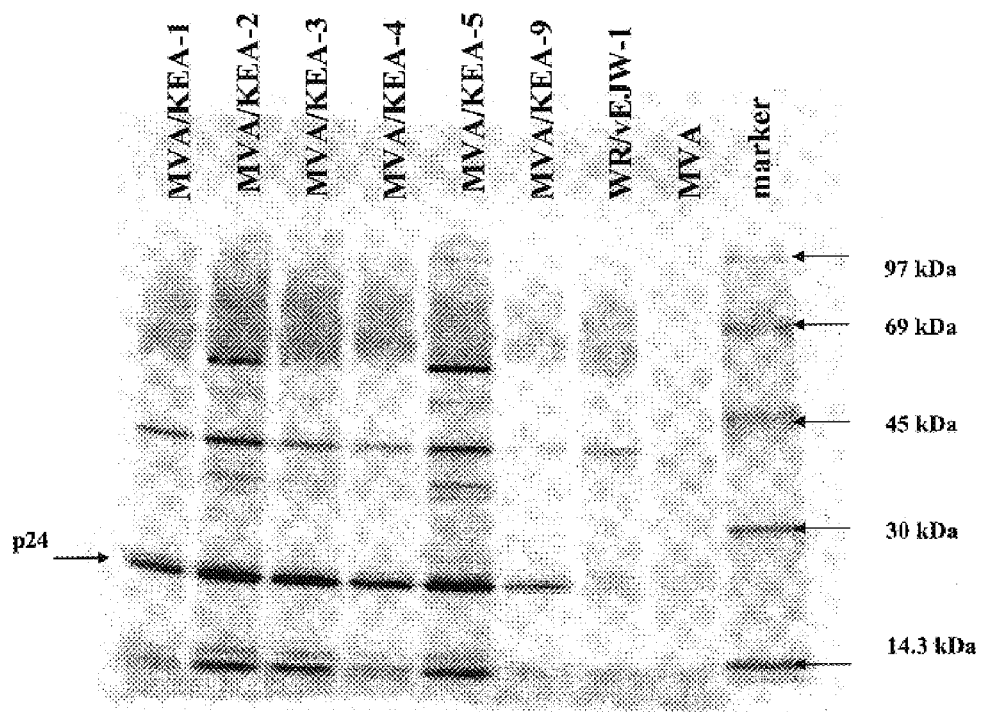
FIG. 36. Gag particle assay (MVA/KEA).
Figure 37:
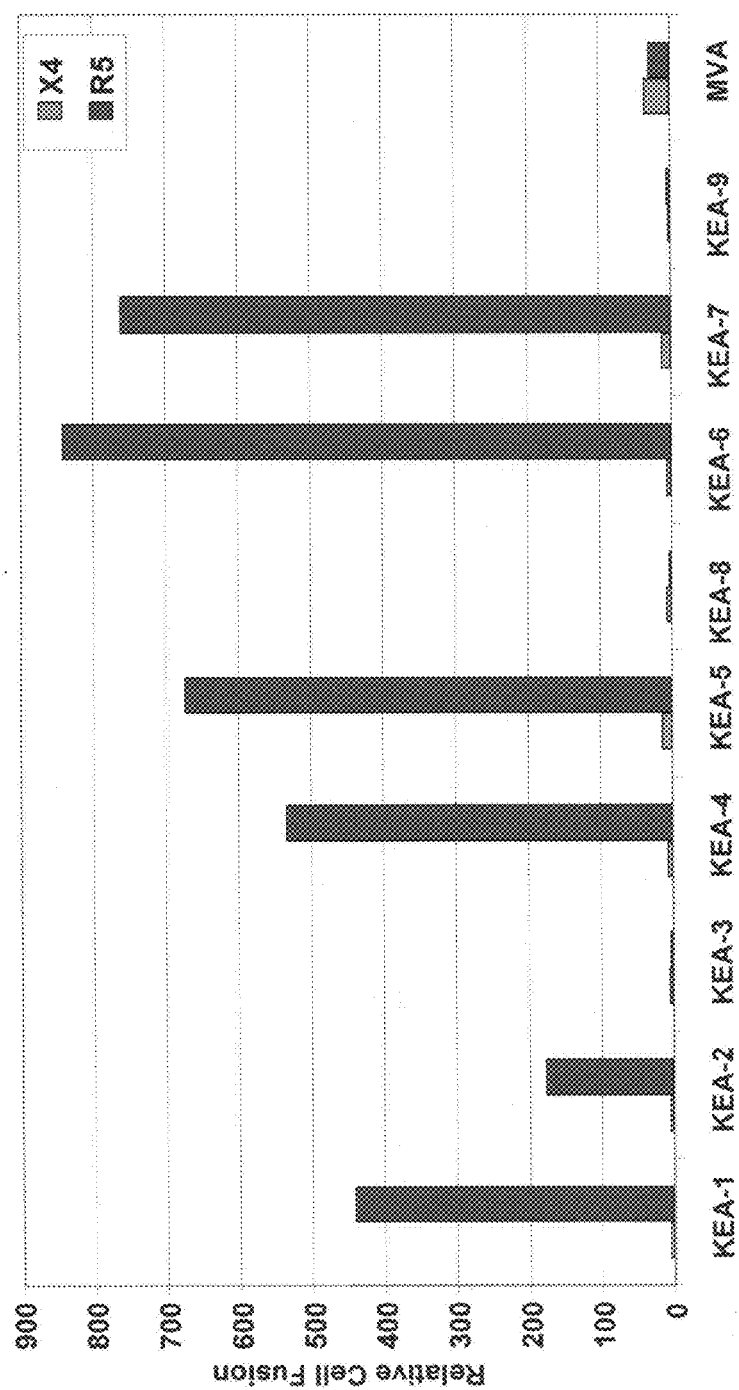
FIG. 37. Fusion assay (MVA/KEA).

HIV-specific cell-mediated immunity was assessed by four separate assays: (1) intracellular IFN-γ staining by flow cytometry (ICS), (2) IFN-γ secretion by ELISPOT, (3) gag-peptide specific tetramer staining and (4) cytotoxic T lymphocyte (CTL) killing. (1) ICS: Splenocytes were collected two weeks after the $1^{st}$ immunization, stimulated for 7 days with MVA-infected P815 cells and then incubated overnight with P815 cells pulsed with a gag or pol peptide previously shown to be target of CD8 T cells in BALB/c mice (Casimiro et al. 2002 *J Virol* 76:185). Brefeldin A was included in the overnight incubation to prevent cytokine secretion. Both HIV gag- and pol-specific responses were detected for the MVA/UGD-immunized, but not control immunized, mice as evidenced by the production of intracellular INF-γ after peptide stimulation (FIG. 31A). For example, 8.5% and 5% of splenocyte lymphocytes from MVA/UGD-4-immunized mice were positive for gag and pol, respectively. Similar results were obtained for the MVA/UGD immunized mice after the $2^{nd}$ immunization (FIG. 31B). (2) IFN-γ ELISPOT: HIV gag-specific IFN-γ responses were detected by ELISPOT without prior in-vitro stimulation after both the 1st (FIG. 32A) and 2nd immunization (FIG. 32B) with a boost detected after the 2nd immunization. HIV gag-specific responses were stronger than the pol-specific responses. HIV pol-specific responses were detectable after a 7-day in-vitro stimulation with P815 cells pulsed with pol peptide (FIG. 32C). (3) Tetramer staining: HIV gag peptide-specific responses were measured by tetramer staining (H-2 Kd gag LAI tetramer: AMQMLKETI, SEQ ID NO: 63) (FIG. 33). Splenocytes were stained pre or post a 7-day in-vitro stimulation with P815 cells either pulsed with gag peptide or infected with MVA/CM240gag/pol, a recombinant virus expressing a subtype E gagpol. CD3 positive/CD8 positive/tetramer positive cells were enumerated by flow cytometry. Positive tetramer staining was observed for all of the MVA/UGD immunized groups both pre-IVS and post-IVS with MVA-infected P815 cells. (4) CTL: Splenocytes removed 2 weeks after the 1st immunization were stimulated in-vitro with MVA/CME (a recombinant MVA expressing env and gagpol from a subtype E HIV-1 isolate) infected P815 cells for 7 days and tested for the ability to lyse P815 cells pulsed with gag peptide. Splenocytes from all MVA/UGD, but not MVA control, immunized mice efficiently lysed peptide-pulsed P815 cells at E:T ratios of 20:1 (FIG. 34).

EXAMPLE 6

Construction and Pre-Clinical Immunogenicity of a Recombinant MVA Vaccine Expressing Subtype A HIV-1 Env, Gag and Pol for Use in Kenya As part of the overall program goal to conduct clinical vaccine trials in Africa, HIV-1 sequences from Kenya were selected. The predominant incident and prevalent HIV-1 subtype in Kenya is subtype A. Several R5 subtype A HIV-1 strains were selected and used to prepare recombinant MVA vaccines expressing env and gagpol (gag, protease and RT). One gagpol and two env clones from pure Kenyan subtype A isolates were selected.

| HIV-1 Isolate name | GenRank Accession # | Publication |
|---|---|---|
| 00KE-KER2008 | AF457052 | AIDS 16: 1809 (2002) |
| 00KE-KNH1144 | AF457066 | " |
| 00KE-KNH1207 | AF457068 | " |

All the steps described in EXAMPLE 5 for construction of subtype D recombinant MVA viruses were followed for the selected subtype A clones. These include:

PCR amplification of truncated genes and cloning into pCR2.1.

Testing for in vitro expression.

Testing for env and gag function.

Site directed mutagenesis in env to eliminate vaccinia virus early transcription termination sites.

Site directed mutagenesis in pol to inactivate enzymatic activity.

Cloning into MVA shuttle plasmids pLAS-1 (gagpol) and pLAS-2 (env).

Recombination of gagpol into MVA 1974/NIH Clone 1 using primary CEF cells.

Figure 38:
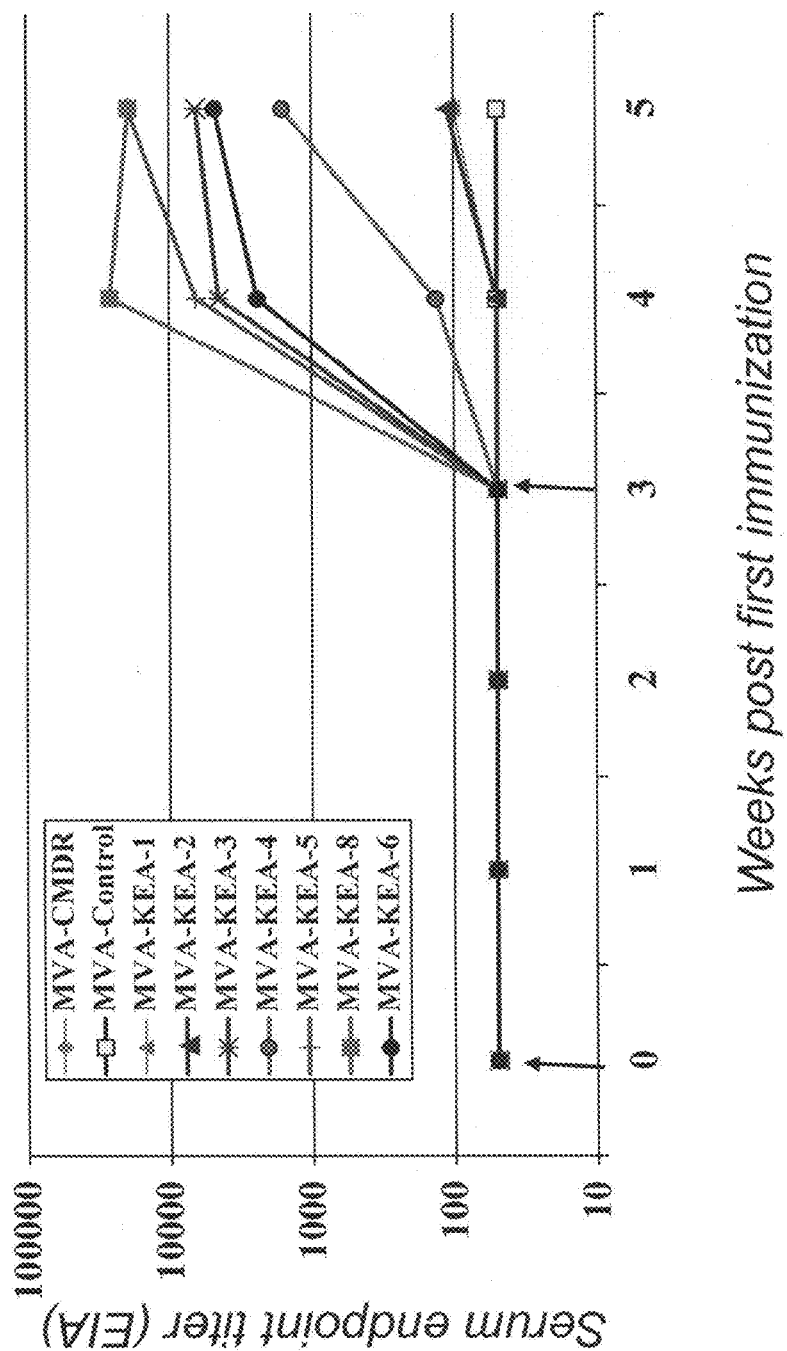
FIG. 38. MVA/KEA induced HIV-1 env-specific antibody responses.

Recombination of env into the recombinant virus expressing gag to produce a single virus expressing both gagpol and env.

Recombination of env into MVA 1974/NIH Clone 1 to produce a virus expressing env only.

In addition to the mutations described in EXAMPLE 5 and utilized with the Ugandan subtype D env genes, two other mutations were introduced into one of the Kenyan clade A env genes (KNH1144). First, the tyr at position 717 was mutated using site directed mutagenesis to either ala or ser. This mutation has been shown to increase cell surface expression of env proteins (Rowell et. al. 1995 *J Immunol* 155:473; LaBranche et al. 1995 *J Virol* 69:5217). Second, the env protein was further truncated at the C-terminus just prior to the transmembrane domain yielding a soluble, secreted form of the protein. Published studies have shown that immunization with this form of the env protein results in enhanced antibody production as compared to membrane bound env.

The specifics of deletions and mutations in env and gagpol genes for KEA isolates are given in Table K. Plasmids and viruses expressing KEA env and gagpol genes are given in Table L and M.

Characterization of Recombinant MVA/KEA Viruses

The MVA/KEA viruses were characterized for gene expression and function. Immunoprecipitation of env and gag protiens is shown in FIG. 35. BSC-1 cells were infected with individual recombinant viruses at a multiplicity of infection of 10, metabolically labeled, and lysates were subjected to imunoprecipitation with a pool of antibodies including: monoclonal antibody T24 (env), monoclonal antibody 183-H12-5C (gag), and pooled HIV-1+sera. MVA/UGD and WR/vEJW-1 were included as positive controls for env and gag expression, respectively. All MVA/KEA viruses express high levels of env and/or gag, as expected.

Virus-like particles were obtained by centrifugation of the supernatant of infected cells through a sucrose cushion (Karacostas et al. 1993 *Virology* 193:661). Gag p24 protein was found in the pelleted material indicating the formation of virus-like particles (FIG. 36).

A cell-cell fusion assay was used to assess the function of expressed, membrane bound env. In this assay env-expressing cells (infected with MVA/KEA virus) were mixed with cells expressing CD4 and co-receptor (X4 or R5) (Nussbaum, et al. 1994 *J Virol* 68:5411). Fusion was measured by beta-galactosidase activity in cell lysates. All viruses expressing membrane bound env induced fusion with CD4/R5-expressing cells (FIG. 37).

Immunogenicity of env and gag in Mice

The 5 recombinant MVA viruses expressing env, gag and pol from Kenyan subtype A HIV-1 isolates (MVA/KEA-1 through MVA/KEA-5), the 3 viruses expressing subtype A env alone (MVA/KEA-6 through MVA/KEA-8) and the MVA expressing subtype A gag/pol (MVA/KEA-9) were evaluated in an in-vivo mouse immunogenicity study designed to measure the humoral and cellular immunogenicity of these vaccines. BALB/c mice (10 per group) were administered intraperitoneal immunizations of $10^7$ infectious units of individual MVA/KEA viruses at weeks 0 and 3. Five mice per group were sacrificed two weeks after the 1st and 2nd immunizations and spleens were removed for assessment of cellular immunogenicity. Sera were collected from each mouse at weeks-1, 0, 1, 2, 3, 4 and 5. Splenocytes and sera were pooled together by group. HIV env-specific serum IgG responses were detected from all MVA/KEA-immunized groups after the $2^{nd}$ immunization (FIG. 38). While env-specific responses were detected in all groups except for the control group, they were strongest in MVA/KEA-3, 4, 5, 6 and 8.

Figure 39:
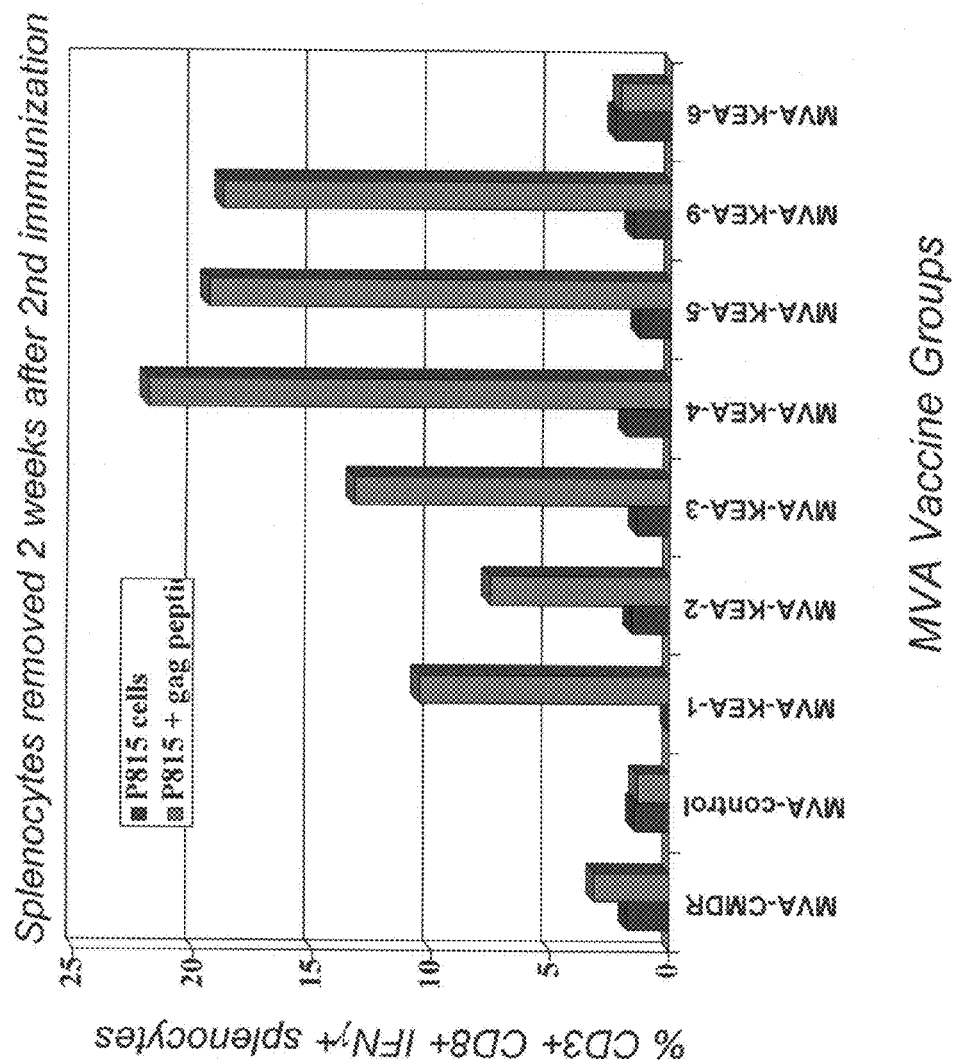
FIG. 39. MVA/KEA induced gag-specific intracellular IFN-γ production.
Figure 40:
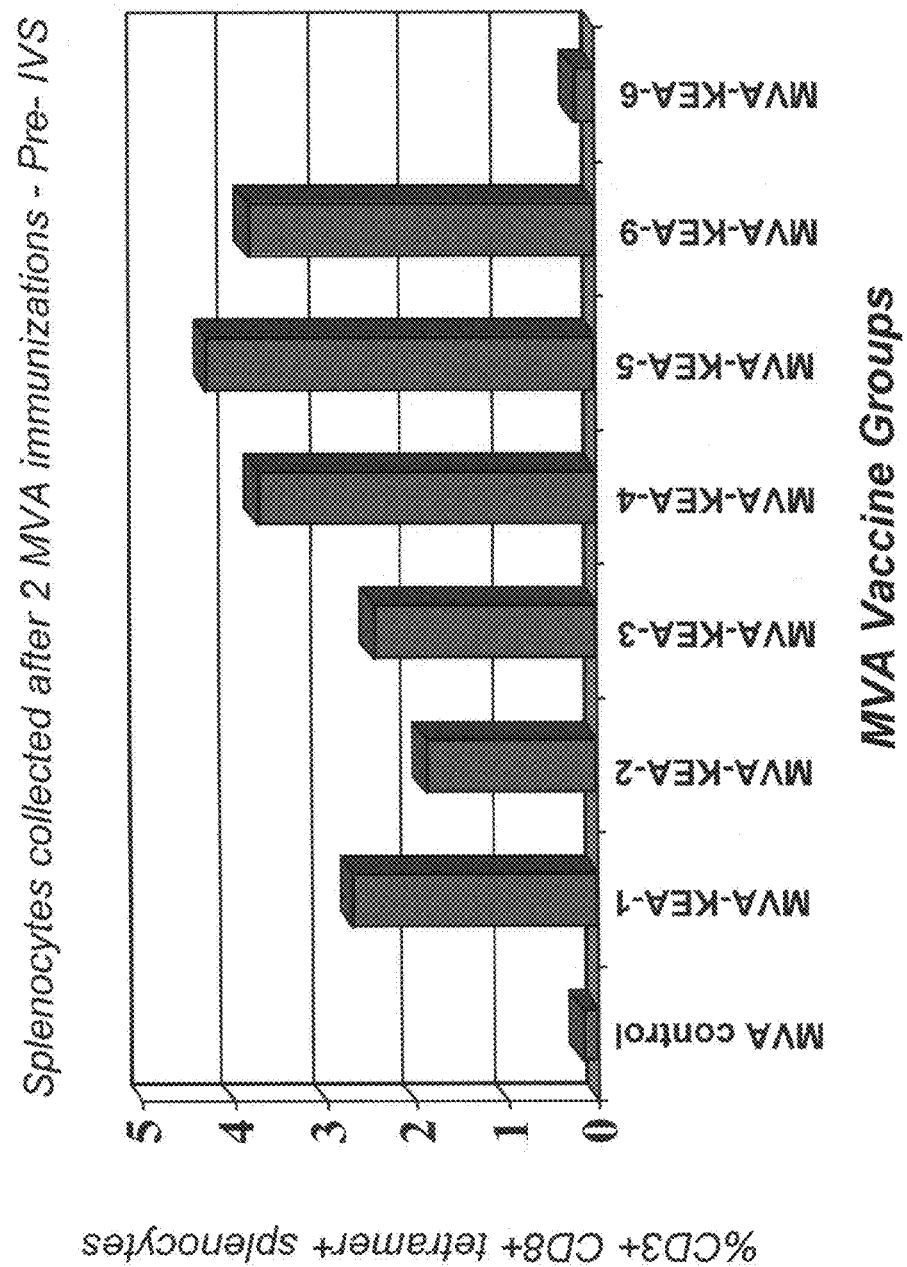
FIG. 40. MVA/KEA induced gag-specific tetramer staining.
Figure 41:
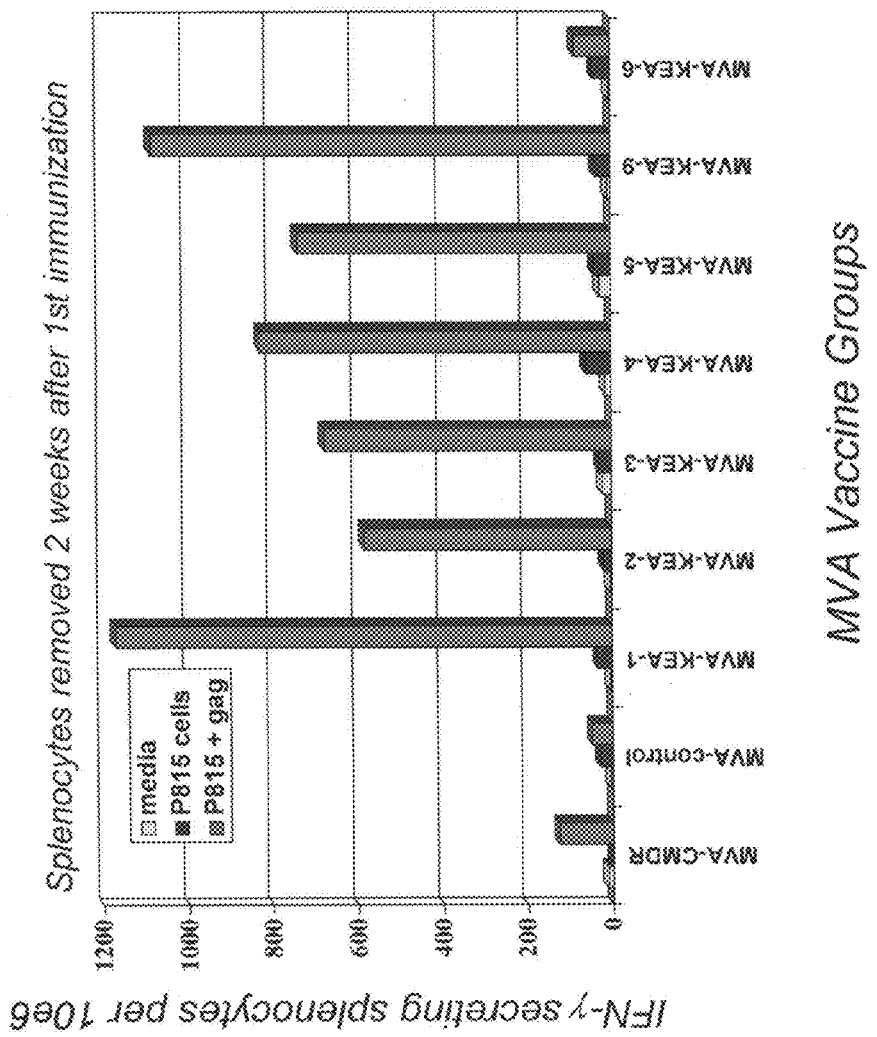
FIG. 41. MVA/KEA induced gag-specific IFN-γ ELISPOT.

HIV-specific cell-mediated immunity was assessed by three assays: (1) intracellular IFN-γ staining by flow cytometry (ICS), (2) IFN-γ secretion by ELISPOT, and (3) gag-peptide specific tetramer staining. (1) ICS: Splenocytes were collected two weeks after the $2^{nd}$ immunization, stimulated for 7 days with MVA-infected P815 cells and then incubated overnight with P815 cells pulsed with a gag or pol peptide previously shown to be target of CD8 T cells in BALB/c mice (Casimiro et al. 2002 J Virol 76:185). Brefeldin A was included during the overnight incubation to prevent cytokine secretion. HIV gag-specific responses were detected for each of the groups immunized with MVA/KEA viruses expressing env, gag and pol or gag and pol, but not control immunized, mice as evidenced by the production of intracellular IFN-γ after peptide stimulation (FIG. 39). Splenocytes positive for HIV gag ranged from 7% to 22% for the MVA/KEA-immunized mice. (2) IFN-γ ELISPOT: HIV gag-specific IFN-γ responses from splenocytes without prior in-vitro stimulation were detected in all groups receiving MVA/KEA viruses expressing gag after the $1^{st}$ immunization (FIG. 40). (3) Tetramer staining: HIV gag peptide-specific responses were measured by tetramer staining (H-2 Kd gag LAI tetramer: AMQMLKETI, SEQ ID NO: 63) (FIG. 41). Splenocytes were stained pre-IVS. CD3 positive CD8 positive, tetramer positive cells were enumerated by flow cytometry. Similar to the above ICS and IFN-γ ELISPOT results, positive tetramer staining was observed for all of the groups immunized with MVA-KEA expressing gag.

II. EXAMPLE 7

Construction of a Recombinant MVA Vaccine Expressing Subtype C HIV-1 Env, Gag, and Pol for Use in Tanzania As part of the overall program goal to conduct clinical vaccine trials in Africa, HIV-1 sequences from Tanzania were selected. The predominant incident and prevalent HIV-1 subtype in Tanzania is subtype C. Several R5 subtype C HIV-1 strains were selected and used to prepare recombinant MVA vaccines expressing env, gag, protease and RT. One gagpol and one env clone from pure Tanzanian subtype C isolates were selected.

| HIV-1 Isolate name | GenBank Accession # | Publication |
| --- | --- | --- |
| 00TZA-125 | AY253304 | AIDS Res & Hum Retrov, in press |
| 00TZA-246 | AY253308 | AIDS Res & Hum Retrov, in press |

Steps described in EXAMPLE 5 were followed for the selected subtype C clones. These include:

PCR amplification of truncated genes and cloning into pCR2.1.

Testing for in vitro expression.

Testing for env and gag function.

Site directed mutagenesis in env to eliminate vaccinia virus early transcription termination sites.

Site directed mutagenesis in pol to inactivate enzymatic activity.

Cloning into MVA shuttle plasmids pLAS-1 (gagpol) and pLAS-2 (env).

Recombination of gagpol into MVA 1974/NIH Clone 1 using primary CEF cells.

Recombination of env into the recombinant virus expressing gag to produce a single virus expressing both gagpol and env.

Recombination of env into MVA 1974/NIH Clone 1 to produce a virus expressing env only. The specifics of deletions and mutations in env and gagpol genes for TZC isolates is given in Table N. Plasmids and viruses expressing TZC env and gagpol genes are given in Table O and P.

Characterization of Recombinant MVA/TZA Viruses

Figure 42:
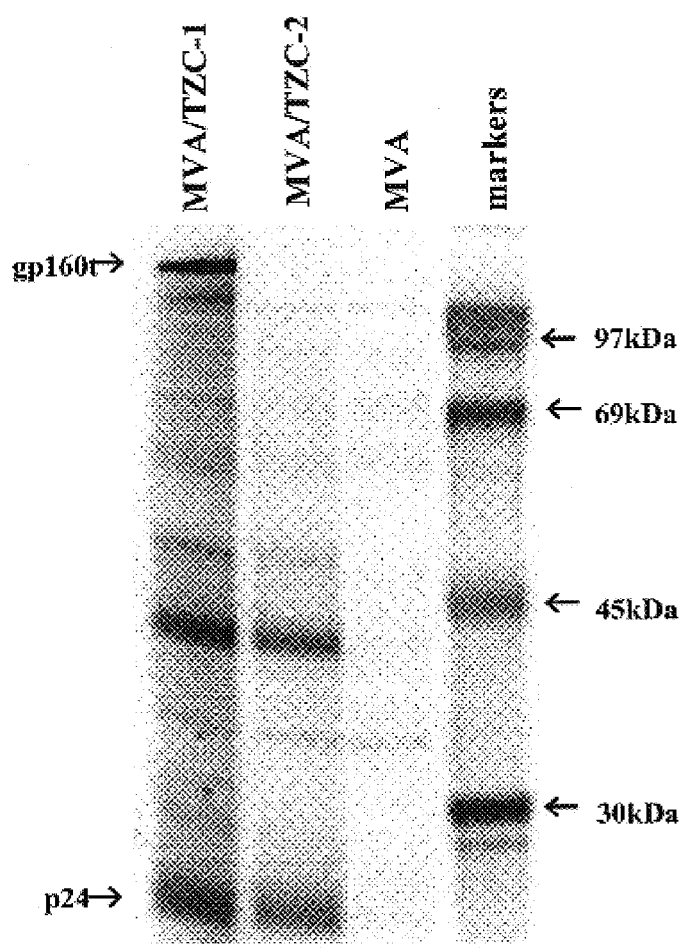
FIG. 42. Immunoprecipitation analysis of cell lysates (MVA/TZC).
Figure 43:
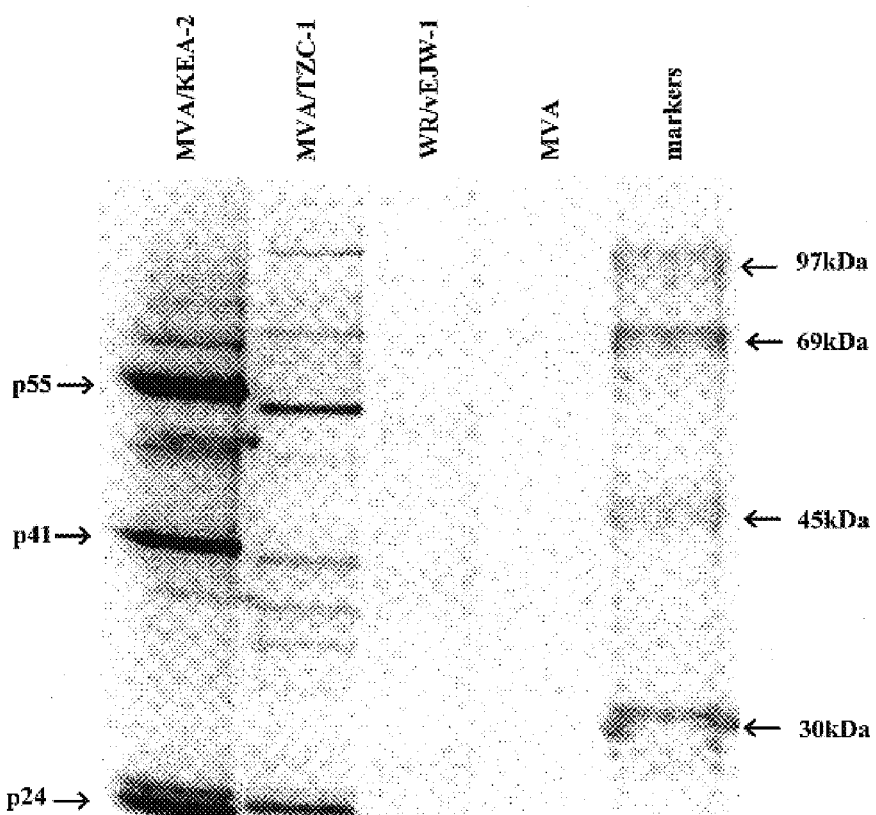
FIG. 43. Fusion assay (MVA/TZC).

The KEA viruses were characterized for gene expression. Immunoprecipitation of env and gag proteins is shown in FIG. 42. BSC-1 cells were infected with individual recombinant viruses at a multiplicity of infection of 10, metabolically labeled, and lysates were subjected to immunoprecipitation with a pool of sera from HIV-1 infected individuals. MVA/CMDR and MVA were included as positive and negative controls, respectively. The MVA/KEA virus expresses high levels of env and gag. Virus-like particles were obtained by centrifugation of the supernatant of infected cells through a sucrose cushion (Karacostas et al. 1993 Virology 193:661). Gag p24 protein was found in the pelleted material indicating the formation of virus-like particles (FIG. 43).

EXAMPLE 8

Stability of Expression of HIV-1 genes in Recombinant MVA Viruses

The stability of the inserted env and gagpol genes in recombinant viruses from each of the subtypes was tested after serial passage in CEF cells. Viruses were grown in CEF cells using a procedure that mimics that used for expansion of virus for large scale vaccine production, i.e. infection at low multiplicity, growth for 3 days at 37C, harvesting of virus from cell lysates. After repeated passage, the virus stocks were tested for stability of the inserts using a 3-day immunostaining protocol. In this protocol, CEF cell monolayers were infected at a low multiplicity allowing for visualization of individual viral foci. After 3 days, the monolayers were fixed and then stained with monoclonal antibodies specific for either env or gag. Staining and non-staining foci were enumerated and results are shown in Table R. Very few non-staining foci were detected after 10-11 passages of each virus indicating that the inserted genes are stable after repeated passage in culture.

TABLE G

Oligonucleotides used for PCR amplification of env and gagpol genes

| Clade D Ugandan HIV-1 isolates | envelope | |
|---|---|---|
| | 5' primer | 3' primer |
| 99UGA03349 | GCGCCCCGGGTCGACGCGGCCGCGCCATGAG AGTGAGGGGGATACAGAGGAAC (SEQ ID NO: 15) | GCGCCCCGGGCGGCCGCAGAAAAATTAGCCTTG CTCTCCACCTTCTTCTTCTATTCC (SEQ ID NO: 16) |
| 99UGA07412 | GCGCCCCGGGTCGACGCGGCCGCGCCATGAG AGTGAGGGAGACAGTGAGGAATTAT (SEQ ID NO: 17) | GCGCCCCGGGCGGCCGCAGAAAAATTAGCCTTG CTCTCCACCTTCTTCTTCTATTCC (SEQ ID NO: 18) |
| 98UG57128 | GCGCCCCGGGTCGACGCGGCCGCGCCATGAG AGTGAGGGGGATAGAGAGGAATTAT (SEQ ID NO: 19) | GCGCCCCGGGCGGCCGCAGAAAAATTAGCCTTG CTCTCCACCTTCTCCTTC (SEQ ID NO: 20) |

| Clade D Ugandan HIV-1 isolates | gagpol | |
|---|---|---|
| | 5' primer | 3' primer |
| 99UGA03349 | GCGCCCCGGGGCCATGGGTGCGAGAGCGTCA GTATTAAGC (SEQ ID NO: 21) | GCGCCCCGGGAGAAAAATTAGAAGGTTTCTGCT CCTACTATGGGTTCCT (SEQ ID NO: 22) |
| 99UGA07412 | GCGCCCCGGGGCCATGGGTGCGAGAGCGTCA GTGTTAAGT (SEQ ID NO: 23) | GCGCCCCGGGAGAAAAATTAGAAAGTTTCTGCT CCTACTATGGGTTCCT (SEQ ID NO: 24) |

TABLE H

Deletions/mutations in env genes envelope

| | C-terminal truncation | | | | TTTTTNT silent mutations | | | |
|---|---|---|---|---|---|---|---|---|
| Clade D Ugandan HIV-1 isolates | DNA sequence at C-terminus | # of last nucleotide | amino acid sequence at C-terminus | # of last amino acid | amino acid nucleotide | # | amino acid nucleotide | # |
| 99UGA0334 | GGAATAGAAGAAGAAG GTGGAGAGCAAGGC (SEQ ID NO: 25) | 2178 | GIEEEGGEQG (SEQ ID NO: 26) | 726 | phe to phe T to C | 168 | phe to phe T to C | 374 |
| | | | | | | 504 | | 1122 |
| 99UGA07412 | GGAATAGAAGAAGAAG GTGGAGAGCAAGGC (SEQ ID NO: 27) | 2211 | GIEEEGGEQG (SEQ ID NO: 28) | 737 | phe to phe T to C | 173 | phe to phe T to C | 384 |
| | | | | | | 519 | | 1152 |
| 98UG57128 | GGAACAGAAGGAGAA GGTGGAGAGCAAGGC (SEQ ID NO: 29) | 2262 | GTEGEGGEQG (SEQ ID NO: 30) | 754 | phe to phe T to C | 182 | phe to phe T to C | 391 |
| | | | | | | 546 | | 1173 |

Deletions/mutations in gagpol genes

| | gagpol C-terminal truncation | | | | pol RT active site mutations | | | |
|---|---|---|---|---|---|---|---|---|
| Clade D Ugandan HIV-1 isolates | DNA sequence at C-terminus | # of last nucleotide | amino acid sequence at C-terminus | # of last amino acid | amino acid nucleotide | # | amino acid nucleotide | # |
| 99UGA03349 | AAGGAACCCATAG TAGGAGCAGAAAC CTTC (SEQ ID NO: 31) | 3065 | KEPIVGAETF (SEQ ID NO: 32) | 1022 | asp to glu T to G | 692 2075 | asp to his GAT to CAC | 767 2298 & 2300 |
| 99UGA07412 | AAGGAACCCATAG TAGGAGCAGAAAC TTTC (SEQ ID NO: 33) | 3077 | KEPIVGAETF (SEQ ID NO: 34) | 1026 | asp to glu T to G | 696 2087 | asp to his GAT to CAC | 771 2310 & 2312 |

TABLE I

UGD Plasmids

| Plasmid | parent plasmid | HIV isolate | Insertion site in MVA | Direction in relation to vaccinia |
|---|---|---|---|---|
| pLAS-1/UGD/Bgag | pLAS-1 | 99UGA03349 | Del III | same |
| pLAS-1/UGD/Cgag | pLAS-1 | 99UGA07412 | Del III | same |
| pLAS-2/UGD/Benv | pLAS-2 | 99UGA03349 | Del II | same |
| pLAS-2/UGD/Cenv | pLAS-2 | 99UGA07412 | Del II | same |
| pLAS-2/UGD/Denv | pLAS-2 | 98UG57128 | Del II | same |

TABLE I-continued

UGD Plasmids

| Plasmid | parent plasmid | HIV isolate | Insertion site in MVA | Direction in relation to vaccinia |
|---|---|---|---|---|
| pLAS-2/UGD/revCenv | pLAS-2 | 99UGA07412 | Del II | reverse |
| pLAS-2/UGD/revDenv | pLAS-2 | 98UG57128 | Del II | reverse |

TABLE J

UGD Viruses

| Virus | gag/pol HIV isolate | gagpol Direction in relation to vaccinia | env HIV isolate | Env Direction in relation to vaccinia |
|---|---|---|---|---|
| MVA/UGD-1 | 99UGA07412 | same | 99UGA07412 | Same |
| MVA/UGD-2 | 99UGA03349 | same | 98UG57128 | Reverse |
| MVA/UGD-3 | 99UGA07412 | same | 99UGA03349 | Same |
| MVA/UGD-4 | 99UGA03349 | same | 99UGA07412 | Reverse |
| MVA/UGD-5 | 99UGA03349 | same | 98UG57128 | Same |
| MVA/UGD-Bgag | 99UGA03349 | same | — | — |
| MVA/UGD-Cgag | 99UGA07412 | same | — | — |

TABLE K

Deletions/mutations in env genes (KEA)

envelope

| Clade A Kenyan HIV-1 isolates | C-terminal truncation | | | | TTTTTNT mutations | | Tyrosine mutations | |
|---|---|---|---|---|---|---|---|---|
| | DNA sequence at C-terminus | # of last nucleotide | amino acid sequence at C-terminus | # of last amino acid | amino acid nucleotide | # | amino acid nucleotide | # |
| 00KE-KNH1207 | AGAATCGAAGG AGAAGGTGGAG AGCAAGAC (SEQ ID NO: 35) | 2209 | GRIEGEGGEQD (SEQ ID NO: 36) | 736 | phe to phe T to C | 378 1134 | | |
| 00KE-KNH1144 | AGAATCGAAGG AGAAGGTGGAG AGCAAGAC (SEQ ID NO: 37) | 2239 | GRIEGEGGEQD (SEQ ID NO: 38) | 746 | phe to phe T to C | 389 1167 | | |
| 00KE-KNH1144 | AGAATCGAAGG AGAAGGTGGAG AGCAAGAC (SEQ ID NO: 39) | 2239 | GRIEGEGGEQD (SEQ ID NO: 40) | 746 | | | tyr to ala TAC to GCG | 717 2149 to 2151 |
| 00KE-KNH1144 | AGAATCGAAGG AGAAGGTGGAG AGCAAGAC (SEQ ID NO: 41) | 2239 | GRIEGEGGEQD (SEQ ID NO: 42) | 746 | | | tyr to ser TAC to AGC | 717 2149 to 2151 |
| 00KE-KNH1144 | GACATATCAAAT TGGCTGTGGTAT ATAAGA (SEQ ID NO: 43) | 2064 | DISNWLWYIR (SEQ ID NO: 44) | 688 | | | | |

Mutations/deletions in gagpol genes (KEA)

| Clade A Kenyan HIV-1 isolates | gagpol C-terminal truncation | | | | pol RT active site mutations | | | |
|---|---|---|---|---|---|---|---|---|
| | DNA sequence at C-terminus | # of last nucleotide in gagpol | amino acid sequence at C-terminus | # of last amino acid in pol | amino acid nucleotide | #amino acid # in pol nucleotide # in gagpol | amino acid nucleotide | #amino acid # in pol nucleotide # in gagpol# |
| 00KE-KER2008 | GACCCCATAG CAGGAGCAGA | 3074 | KDPIAGAETF (SEQ | 595 | asp to glu T to G | 265 2084 | asp to his GAT to CAC | 340 2307 to 2309 |

TABLE K-continued

GACTTTC (SEQ ID NO: 46)
ID NO: 45)

TABLE L

KEA Plasmids

| Plasmid | parent plasmid | HIV isolate | Insertion site in MVA | Direction in relation to vaccinia |
|---|---|---|---|---|
| pLAS-1/KER2008gag | pLAS-1 | 00KE-KER2008 | Del III | same |
| pLAS-2/KNH1144env | pLAS-2 | 00KE-KNH1144 | Del II | same |
| pLAS-2/KNH1207env | pLAS-2 | 00KE-KNH1207 | Del II | same |
| pLAS-2/KNH1144gp140 | pLAS-2 | 00KE-KNH1144 | Del II | same |
| pLAS-2/KNH1144(Y/A) | pLAS-2 | 00KE-KNH1144 | Del II | same |
| pLAS-2/KNH1144(Y/S) | pLAS-2 | 00KE-KNH1144 | Del II | same |

TABLE M

KEA Viruses

| Virus | gag/pol HIV isolate | gag/pol Direction in relation to vaccinia | env HIV isolate | env Direction in relation to vaccinia |
|---|---|---|---|---|
| MVA/KEA-1 | 00KE-KER2008 | same | 00KE-KNH1144 | same |
| MVA/KEA-2 | 00KE-KER2008 | same | 00KE-KNH1207 | same |
| MVA/KEA-3 | 00KE-KER2008 | same | 00KE-KNH1144 (gp140) | same |
| MVA/KEA-4 | 00KE-KER2008 | same | 00KE-KNH1144 (Y/A) | same |
| MVA/KEA-5 | 00KE-KER2008 | same | 00KE-KNH1144 (Y/S) | same |
| MVA/KEA-6 | — | | 00KE-KNH1144 | same |
| MVA/KEA-7 | — | | 00KE-KNH1207 | same |
| MVA/KEA-8 | — | | 00KE-KNH1144 (gp140) | same |
| MVA/KEA-9 | 00KE-KER2008 | same | — | |

TABLE N

Mutations/deletions in env genes (TZC)

| | envelope | | | | TTTTTNT silent mutations | |
|---|---|---|---|---|---|---|
| Clade C Tanzanian | C-terminal truncation | | | | | |
| HIV-1 isolates | DNA sequence at C-terminus | # of last nucleotide | amino acid sequence at C-terminus | # of last amino acid | amino acid nucleotide | # |
| 00TZA-125 | GGAATCGAAGAAGAAGGTGGA GAGCAAGAC (SEQ ID NO: 47) | 2223 | GIEEEGGEQD (SEQ ID NO: 48) | 741 | phe to phe T to C | 396 1161 |

Mutations/deletions in gagpol (TZC)

| | gagpol C-terminal truncation | | | | pol RT active site mutations | | | |
|---|---|---|---|---|---|---|---|---|
| Clade C Tanzanian HIV-1 isolates | DNA sequence at C-terminus | # of last nucleotide of gagpol | amino acid sequence at C-terminus of pol | # of last amino acid in pol | amino acid | amino acid # in pol nucleotide # in gagpol | amino acid | amino acid # in pol nucleotide # in gagpol |
| 00TZA-246 | AAAGAACCCATA GTAGGAGCAGAA ACTTTCT (SEQ ID NO: 49) | 3083 | KEPIVGAETF (SEQ ID NO: 50) | 601 | asp to glu T to G | 271 2093 | asp to his GAT to CAC | 346 2316 & 2318 |

TABLE O

TZC Plasmids

| Plasmid | parent plasmid | HIV isolate | Insertion site in MVA | Direction in relation to vaccinia |
|---|---|---|---|---|
| pLAS-1/TZC246gag | pLAS-1 | 00TZA-246 | Del III | same |
| pLAS-2/TZC125env | pLAS-2 | 00TZA-125 | Del II | same |

TABLE P

TZC Viruses

| Virus | gag/pol HIV isolate | gag/pol Direction in relation to vaccinia | env HIV isolate | env Direction in relation to vaccinia |
|---|---|---|---|---|
| MVA/TZC-1 | 00TZA-246 | same | 00TZA-125 | same |
| MVA/TZC-2 | 00TZA-246 | same | — | |
| MVA/TZC-3 | — | | 00TZA-125 | same |

TABLE Q

HIV-1 gag IgG2a/IgG1 ratios

| Group | | Week 1 | Ratio G2a/G1 | Week 2 | Ratio G2a/G1 | Week 3 | Ratio G2a/G1 |
|---|---|---|---|---|---|---|---|
| MVA/CMDR | G1 | 34,100 | 2.5 | 34,100 | 2.5 | 29,900 | 2 |
| | G2a | 85,300 | | 85,300 | | 59,700 | |
| MVA control | G1 | <100 | — | <100 | — | <100 | — |
| | G2a | <100 | | <100 | | <100 | |
| MVA/UGD-4 | G1 | 34,100 | 1.6 | 25,600 | 1.6 | 19,200 | 1.8 |
| | G2a | 55,500 | | 41,600 | | 35,200 | |

TABLE Q-continued

HIV-1 gag IgG2a/IgG1 ratios

| Group | | Week 1 | Ratio G2a/G1 | Week 2 | Ratio G2a/G1 | Week 3 | Ratio G2a/G1 |
|---|---|---|---|---|---|---|---|
| MVA/UGD-3 | G1 | 3,200 | 3.3 | 3,200 | 5.3 | 3,200 | 5.3 |
| | G2a | 10,600 | | 17,100 | | 17,100 | |
| MVA/UGD-1 | G1 | 9,600 | 0.7 | 4,800 | 1.3 | 4,800 | 1.3 |
| | G2a | 6,400 | | 6,400 | | 6,400 | |
| MVA/UGD gag | G1 | 4,800 | 6.2 | 3,200 | 9.3 | 2,400 | 12.4 |
| | G2a | 29,900 | | 29,900 | | 29,900 | |

TABLE R

Stability of inserts in rMVA viruses

| | Gag | | | Env | | |
|---|---|---|---|---|---|---|
| Virus | total foci # | non-staining foci # | % | total foci # | non-staining foci # | % |
| After 10 passages MVA/UGD-4 | 270 | 3 | 1.1 | 270 | 3 | 1.1 |
| After 11 passages | | | | | | |
| MVA/KEA-1 | 360 | 2 | 0.56 | 310 | 0 | 0 |
| MVA/KEA-2 | 230 | 3 | 1.3 | 280 | 0 | 0 |
| MVA/KEA-3 | 340 | 0 | 0 | 340 | 0 | 0 |
| MVA/KEA-4 | 210 | 0 | 0 | 210 | 0 | 0 |
| MVA/KEA-5 | 220 | 1 | 0.45 | 210 | 0 | 0 |
| After 11 passages MVA/TZC | 600 | 5 | 0.83 | 800 | 1 | 0.13 |

Appendix 1—DNA sequences of gagpol and env genes from Ugandan HIV-1 clade D isolates:

```
99UGA03349 gagpol (SEQ ID NO: 51):
ATGGGTGCGAGAGCGTCAGTATTAAGCGGGGGAAAATTAGATGAATGGGAAAAAATTCGGTTACG
GCCAGGGGGAAACAAAAAATATAGATTAAAACATTTAGTATGGGCAAGCAGGGAGCTAGAACGAT
TTGCACTTAATCCTGGTCTTTTAGAAACATCAGAAGGCTGTAGACAAATAATAGAACAGCTACAA
CCATCTATTCAGACAGGATCAGAGGAACTTAAATCATTACATAATACAGTAGTAACCCTCTATTG
TGTACATGAAAGGATAAAGGTAGCAGATACCAAGGAAGCTTTAGATAAGATAAAGGAAGAACAAA
CCAAAAGTAAGAAAAAAGCACAGCAAGCAACAGCTGACAGCAGCCAGGTCAGCCAAAATTATCCT
ATAGTACAAAACCTACAGGGGCAAATGGTACACCAGTCCTTATCACCTAGGACTTTGAATGCATG
GGTAAAAGTAATAGAAGAGAAGGCTTTCAGCCCAGAAGTAATACCCATGTTTTCAGCATTATCAG
AAGGAGCCACCCCAACAGATTTAAACACCATGCTAAACACAGTGGGGGGACATCAAGCAGCCATG
CAAATGTTAAAAGAGACTATCAATGAGGAAGCTGCAGAATGGGATAGGCTACATCCAGTGCCTGC
AGGGCCTGTTGCACCAGGCCAAATGAGAGAACCAAGGGGAAGTGATATAGCAGGAACTACCAGTA
CCCTTCAGGAACAAATAGGATGGATGACAAGCAATCCACCTATCCCAGTAGGAGAAATCTATAAA
AGATGGATAATCCTAGGATTAAATAAAATAGTAAGAATGTATAGCCCTGTCAGCATTTTGGACAT
AAGACAAGGACCAAAGGAACCCTTTAGAGACTATGTAGATCGGTTCTATAAAACTCTACGAGCCG
AGCAAGCTTCACAGGATGTAAAAAATTGGATGACTGAAACCTTGTTAGTCCAAAATGCGAATCCA
GATTGTAAAACTATCTTAAAAGCATTGGGACCAGCGGCTACATTAGAAGAAATGATGACAGCATG
TCAGGGAGTGGGGGGACCCAGTCATAAAGCAAGAGTTTTGGCTGAGGCAATGAGCCAAGCATCAA
ACACAAATGCTGTTATAATGATGCAGAGGGGCAATTTCAAGGGCAAGAAAATCATTAAGTGTTTC
AACTGTGGCAAAGAAGGACACCTAGCAAAAAATTGTAGGGCTCCTAGGAAAAGAGGCTGTTGGAA
ATGTGGAAAGGAAGGGCACCAAATGAAAGATTGTAATGAAAGACAGGCTAATTTTTTAGGGAGAA
TTTGGCCTTCCCACAAGGGGAGGCCAGGGAATTTCCTTCAGAGCAGACCAGAGCCAACAGCCCCA
CCAGCAGAGAGCTTCGGGTTTGGGGAAGAGATAACACCGTCCCAGAAACAGGAGGGGAAAGAGGA
GCTGTATCCTTCAGCCTCCCTCAAATCACTCTTTGGCAACGACCCCTAGTCACAATAAAAATAGG
GGGACAGCTAAAGGAAGCTCTATTAGATACAGGAGCAGATGATACAGTAGTAGAAGAAATGAATT
TGCCAGGAAAATGGAAACCAAAAATGATAGGGGGAATTGGGGGCTTTATCAAAGTAAGACAGTAT
GATCAAATACTCGTAGAAATCTATGGATATAAGGCTACAGGTACAGTATTAGTAGGACCTACACC
TGTCAACATAATTGGAAGAAATTTGTTGACTCAGATTGGTTGCACTTTAAATTTTCCAATTAGTC
CTATTGAAACTGTACCAGTAAAATTAAAGTCAGGGATGGATGGTCCAAGAGTTAAACAATGGCCA
TTGACAGAAGAGAAAATAAAAGCACTAATAGAAATTTGTACAGAAATGGAAAAGGAAGGAAAACT
TTCAAGAATTGGACCTGAAAATCCATACAATACTCCAATATTTGCCATAAAGAAAAAGACAGTA
CTAAGTGGAGAAAATTAGTAGATTTCAGAGAACTTAATAAGAGAACTCAAGATTTCTGGGAAGTT
```

-continued

CAACTAGGAATACCACATCCTGCAGGGTAAAAAAGAAAAAATCAGTAACAGTACTGGAGGTGGG
TGATGCATATTTTTCAGTTCCCTTATATGAAGACTTTAGAAAATACACTGCATTCACCATACCTA
GTATAAACAATGAGACACCAGGAATTAGATATCAGTACAATGTGCTTCCACAAGGATGGAAAGGA
TCACCGGCAATATTCCAAAGTAGCATGACAAAAATTTTAGAACCTTTTAGAAAACAAAATCCAGA
AGTGGTTATCTACCAATACATGCACGATTTGTATGTAGGATCTGACTTAGAAATAGGGCAGCATA
GAATAAAAATAGAGGAATTAAGGGGACACCTATTGAAGTGGGGATTTACCACACCAGACAAAAAT
CATCAGAAGGAACCTCCATTTCTTTGGATGGGTTATGAACTCCATCCTGATAAATGGACAGTACA
GCCTATAAAACTGCCAGAAAAAGAAAGCTGGACTGTCAATGATCTGCAGAAGTTAGTGGGGAAAT
TAAATTGGGCAAGTCAAATTTATTCAGGAATTAAAGTAAGACAATTATGCAAATGCCCTTAGGGGA
ACCAAAGCACTGACAGAAGTAGTACCACTGACAGAAGAAGCAGAATTAGAACTGGCAGAAAACAG
GGAACTTCTAAAAGAAACAGTACATGGAGTGTATTATGACCCATCAAAAGACTTAATAGCAGAAA
TACAGAAACAAGGGCAAGACCAATGGACATATCAAATTTATCAAGAACAATATAAAAATTTGAAA
ACAGGAAAGTATGCAAAGAGGAGGAGTACCCACACTAATGATGTAAAACAATTAACAGAGGCAGT
GCAAAAAATAGCCCAAGAATGTATAGTGATATGGGGAAAGACTCCTAAATTCAGACTACCCATAC
AAAAGGAAACATGGGAAACATGGTGGACAGAGTATTGGCAGGCCACCTGGATTCCTGAGTGGGAG
TTTGTCAATACCCCTCCCTTGGTTAAATTATGGTACCAGTTAGAGAAGGAACCCATAGTAGGAGC
AGAAACCTTCTAA

99UGA07412 gagpol (SEQ ID NO: 52):
ATGGGTGCGAGAGCGTCAGTGTTAAGTGGGGGAAAATTAGATGAATGGGAAAGAATTCGGTTACG
GCCAGGGGGAAACAAAAGATATAAACTAAAACATATAGTATGGGCAAGCAGGGAGCTAGAGCGAT
TTGCACTTAATCCTGGCCTTTTAGAAACATCAGAAGGCTGTAAACAAATATTGGGACAGCTACAA
CCAGCTATTCAGACAGGATCAGAAGAACTTAAATCATTATATAATACAGTAGCAACCCTCTATTG
TGTACATGAGAGGCTAAAGGTAACAGACACCAAGGAAGCTTTAGACAAAATAGAGGAAGAACAAA
CCAAAAGTAAGAAAAAAGCACAGCAAGCAACAGCTGACACAAAAAACAGCAGCCAGGTCAGCCAA
AATTATCCTATAGTACAAAACCTACAGGGGCAAATGGTACACCAGGCTATATCACCTAGAACGTT
GAACGCATGGGTAAAAGTAATAGAGGAGAAGGCTTTCAGCCCAGAAGTAATACCCATGTTTTCAG
CATTATCAGAAGGAGCCACCCCACAAGATTTAAACACCATGCTAAACACAGTGGGGGACATCAG
GCAGCCATGCAGATGTTAAAAGAGACCATCAATGAGGAAGCTGCAGAATGGGATAGGTTACATCC
AGTACATGCAGGGCCTATTGCACCAGGACAAATGAGAGAACCAACAGGAAGTGATATAGCAGGAA
CTACTAGTACCCTTCAGGAACAAATAGGATGGATGACCAGCAATCCACCTATCCCAGTAGGAGAA
ATCTATAAAAGATGGATAATCCTAGGATTAAATAAAATAGTAAGGATGTATAGCCCTGTCAGTAT
TTTGGACATAAAACAAGGGCCAAAGGAACCCTTTAGAGACTATGTAGATCGGTTCTATAAAACTC
TAAGGGCCGAGCAAGCTTCACAGGAGGTAAAAGGTTGGATGACCGAAACCTTGTTGGTCCAAAAT
GCAAACCCAGATTGTAAAACCATCTTAAAAGCATTGGGACCAGCGGCTACATTAGAAGAAATGAT
GACAGCATGTCAGGGAGTGGGGGGACCCGGTCATAAAGCAAGAGTTTTGGCTGAGGCAATGAGTC
AAGTCTCAACAAATACTGCTATAATGATGCAGAGAGGCAATTTTAAGGGCCCAAAGAAAAGCATT
AAGTGTTTTAACTGTGGCAAAGAAGGTCACACAGCAAAAAACTGTAGGCTCCTAGGAAAAGGGG
CTGTTGGAAATGTGGAAGGGAAGGACATCAAATGAAAGATTGCACTGAAAGACAGGCTAATTTTT
TAGGGAAAATTTGGCCTTCCCACAAGGGAAGGCCAGGGAATTTCCTTCAGAACAGACCAGAGCCA
ACAGCCCCACCAGAAGAAAGCTTCGGGTTTGGGAAGAGATAACACCCTCTCAGAAACAGGAGAA
GAAGGACAAGGAGCTGTATCCTGTAGCTTCCCTCAAATCACTCTTTGGCAACGACCCCTTGTCAC
AATAAAGATAGGGGGACAGCTAAAGGAAGCTCTACTAGATACAGGAGCAGATGATACAGTATTAG
AAGAAATAAATTTGCCAGGAAAATGGAAACCAAAAATGATAGGGGGGAATTGGAGGCTTTATCAAA
GTAAGACAGTATGAGCAAATACTTGTAGAAATCTGTGGACAGAAAGCTATAGGTACAGTATTAGT
AGGGCCTACACCTGTCAACATAATTGGAAGAAATTTGTTGACTCAGATTGGTTGCACTTTAAATT
TTCCAATTAGCCCTATTGAAACTGTACCAGTAAAATTAAAGCCAGGGATGGACGGTCCAAAAGTT
AAACAATGGCCATTGACAGAAGAAAAGGTAAAAGCACTAATAGAAATTTGTACAGAAATGGAAAA
GGAAGGAAAAATTTCAAGAATTGGACCTGAAAATCCATACAATACTCCAATATTTGCCATAAAGA
AAAAGGACAGTACTAAGTGGAGAAAATTAGTAGATTTCAGGGAACTTAATAAGAGAACTCAAGAC
TTCTGGGAAGTTCAACTAGGAATACCACATCCTGCGGGGTAAAAAAGAAAAAATCAGTAACAGT
ACTGGAGGTGGGTGATGCATATTTTTCAGTTCCCTTATATGAAGATTTTAGAAAATATACTGCAT
TCACCATACCTAGTATAAACAATGAAACACCAGGAATTAGATATCAGTACAATGTGCTTCCACAA
GGGTGGAAAGGATCACCAGCAATATTCCAAAGTAGCATGACAAAAATCTTAGAACCTTTTAGAAA
ACAAAATCCAGAAATGGTTATCTATCAATACATGCACGATTTGTATGTAGGATCTGACTTAGAAA
TAGGGCAGCATAGAATAAAAATAGAAGAATTAAGGGGACACCTGTTGAAGTGGGGATTTACCACA
CCAGACAAAAAGCATCAGAAAGAACCTCCATTTCTTTGGATGGGTTATGAACTCCATCCTGATAA
ATGGACAGTACAGTCTATAAAACTGCCAGAACAAGAAAGCTGGACTGTCAATGATATACAGAAGT
TAGTGGGAAATTAAATTGGGCAAGTCAGATTTATCCAGGAATTAAAGTAAGACAATTATGCAAA
TGCATTAGGGGTACCAAAGCACTGACAGAAGTAGTACCACTGACAGAAGAAGCAGAATTAGAACT
GGCAGAAAACAGGGAAATTCTAAGAGAACCAGTACATGGAGTGTATTATGACCCATCAAAAGACT
TAATAGCAGAGATACAGAAACAAGGGCAAGACCAGTGGACATACCAAATTTATCAAGAACAATAT
AAAAATCTGAAAACAGGAAAGTATGCAAAAGTGAGGGGTACCCACACTAATGATGTAAAACAATT
AACAGAGGCAGTACAAAAAATAACCCAAGAATGTATAGTGATATGGGGAAAGCCTCCTAAATTTA
GACTACCCATACAAAAAGAAACATGGGAAATATGGTGGACAGAGTATTGGCAGGCCACCTGGATT
CCTGAGTGGGAGTTTGTCAATACCCCTCCTTTAGTTAAATTATGGTACCAATTAGAGAAGGAACC
CATAGTAGGAGCAGAAACTTTCTAA 99UGA03349 envelope (SEQ ID NO: 53):
ATGAGAGTGAGGGGGATACAGAGGAACTATCAAAACTTGTGGAGATGGGCACCTTGCTCCTTGG
GATGTTGATGATATGTAAGGCTACAGAACAGTTGTGGGTCACAGTTTACTATGGGGTACCTGTGT
GGAAAGAAGCAACCACTACTCTATTTTGTGCATCAGATGCTAAATCATATAAAGAAGAAGCACAT
AATATCTGGGGTACACATGCCTGTGTACCAACAGACCCCAACCCACGAGAATTAATAATAGAAAA
TGTCACAGAAAACTTTAACATGTGGAAAAATAACATGGTGGAGCAGATGCATGAGGATATAATCA
GTTTATGGGATCAAAGCCTAAAACCATGTGTAAAATTAACCCCACTCTGTGTCACTTTAAACTGC
ACTGAATGGAGGAAGAATAACACTATCAATGCCACCAGAATAGAAATGAAAACTGCTCTTTTCAA
TCTAACCACAGAATAAGAGATAGGAAAAAGCAAGTGCATGCACTTTTCTATAAACTTGATGTGG
TACCAATAGATGATAATAATAGTACTAATACCAGCTATAGGTTAATAAATTGTAATACCTCAGCC
ATTACACAGGCGTGTCCAAAGGTAACCTTTGAGCCAATTCCCATACATTATTGTGCCCCAGCTGG
ATATGCGATTCTAAAATGTAACAATAAGAAGTTCAATGGGACAGGTCCATGCGATAATGTCAGTA -continued CAGTACAGTGTACACATGGAATTAGGCCAGTAGTATCCACTCAATTGTTGTTGAATGGCAGTCTA
GCAGAAGAAGACATAATAATTAGATCTGAGAATCTCACAAATAATGCTAAAATCATAATAGTACA
GCTTAATGAGTCTGTAACAATTAATTGCACAAGGCCCTACAACAATACAAGAAGAGGTGTACATA
TAGGACCAGGGCGAGCATACTATACAACAGACATAATAGGAGATATAAGACAAGCACATTGTAAC
ATTAGTGGAGCAGAATGGAATAAGACTTTACATCGGGTAGCTAAAAAATTAAGAGACCTATTTAA
AAAGACAACAATAATTTTTAAACCGTCCTCCGGAGGGGACCCAGAAATTACAACACACAGCTTTA
ATTGTAGAGGGGAATTCTTCTACTGCAATACAACAAGACTGTTTAATAGCATATGGGGAAATAAT
AGTACAGGAGTTGATGAGAGTATAACACTCCCATGCAGAATAAAACAAATTATAAACATGTGGCA
GGGAGTAGGAAAAGCAATGTATGCCCCTCCCATTGAAGGACTAATCAGCTGCTCATCAAATATTA
CAGGATTACTGTTGACAAGAGATGGTGGTGGAAGTAACAGTAGTCAGAATGAGACCTTCAGACCT
GGAGGGGAGATATGAGAGACAATTGGAGAAGTGAATTATATAAATATAAAGTAGTAAGAATTGA
ACCATTAGGTCTAGCACCCTCCAAGGCAAAAAGAAGAGTAGTAGAAAGAGAGAAAAGAGCAATAG
GACTAGGAGCTATGTTCCTTGGGTTCTTGGGAGCAGCAGGAAGCACGATGGGCGCAGCGTCACTG
ACGCTGACGGTACAGGCCAGACAGCTATTGTCTGGTATAGTGCAACAGCAAAACAATTTGCTGAA
GGCTATAGAGGCGCAACAGCACCTGTTGCAACTCACAGTCTGGGCGTTAAACAGCTCCAGGCAA
GAGTCCTGGCTGTGAAAGCTACCTAAGGGATCAACAGCTCCTAGGAATTTGGGGTTGCTCTGGA
AAACACATTTGCACCACCAATGTGCCCTGGAACTCTAGCTGGAGTAATAAAACTCTAAAATCAAT
TTGGGATAACATGACCTGGATGGAGTGGGAAAGAGAAATTGACAATTACACAGGGATAATATACA
ATTTACTTGAAGAATCGCAAACCCAGCAAGAAAGAAATGAACAAGACCTATTGAAATTGGACCAA
TGGGCAAGTTTGTGGAATTGGTTTAGCATAACAAAATGGCTGTGGTATATAAAAATATTTATAAT
GATAGTAGGAGGCTTGATAGGCTTAAGGATAGTTTTTGCTGTGCTTTCTATAGTAAATAGAGTTA
GGCAGGGATATTCACCTCTGTCGTTTCAGACCCTCCTCCCAGCCCCGCGGGGACCCGACAGGCCC
GAAGGAATAGAAGAAGAAGGTGGAGAGCAAGGCTAA 99UGA07412 envelope (SEQ IS NO: 54):
ATGAGAGTGAGGGAGACAGTGAGGAATTATCAGCACTTGTGGAGATGGGGCATCATGCTCCTTGG
GATGTTAATGATATGTAGTGCTGCAGACCAGCTGTGGGTCACAGTGTATTATGGGGTACCTGTGT
GGAAAGAAGCAACCACTACTCTATTTTGTGCATCAGATGCTAAAGCACATAAAGCAGAGGCACAT
AATATCTGGGCTACACATGCCTGTGTACCAACAGACCCCAATCCACGAGAAATAATACTAGGAAA
TGTCACAGAAAACTTTAACATGTGGAATAACATGGTAGAGCAGATGCATGAGGATATAATCA
GTTTATGGGATCAAAGTCTAAAACCATGTGTAAAATTAACCCCACTCTGTGTTACTTTAAACTGC
ACTACATATTGGAATGGAACTTTACAGGGGAATGAAACTAAAGGGAAGAATAGAAGTGACATAAT
GACATGCTCTTTCAATATAACCACAGAAATAAGAGGTAGAAAGAAGCAAGAAACTGCACTTTTCT
ATAAACTTGATGTGGTACCACTAGAGGATAAGGATAGTAATAAGCATACCAACTATAGCAGCTAT
AGATTAATAAAATTGCAATACCTCAGTCGTGACACAGGCGTGTCCAAAAGTAACCTTTGAGCCAAT
TCCCATACATTATTGTGCCCCAGCTGGATTTGCGATTCTGAAATGTAATAATAAGACGTTCAATG
GAACGGGTCCATGCAAAAATGTCAGCACAGTACAGTGTACACATGGAATTAGGCCAGTAGTGTCA
ACTCAACTGTTGTTGAATGGCAGTCTAGCAGAAGAAGAGATAATAATTAGATCTGAAAATATCAC
AAATAATGCAAAAACCATAATAGTACAGCTTAATGAGTCTGTAACAATTGATTGCATAAGGCCCA
ACAACAATACAAGAAAAAGTATACGCATAGGACCAGGGCAAGCACTCTATACAACAGACATAATA
GGGAATATAAGACAAGCACATTGTAATGTTAGTAAAGTAAAATGGGGAAGAATGTTAAAAAGGGT
AGCTGAAAAATTAAAAGACCTTCTTAACCAGACAAAGAACATAACTTTTGAACATCCTCAGGAG
GGGACCCAGAAATTACAACACACAGCTTTAATTGTGGAGGGGAATTCTTCTACTGCAATACATCA
GGACTATTTAATGGGAGTCTGCTTAATGAGCAGTTTAATGAGACATCAAATGATACTCTCACACT
CCAATGCAGAATAAAACAAATTATAAACATGTGGCAAGGAGTAGGAAAAGCAATGTATGCCCCTC
CCATTGCAGGACCAATCAGCTGTTCATCAAATATTACAGGACTATTGTTGACAAGAGATGGTGGT
AATACTGGTAATGATTCAGAGATCTTCAGACCTGGAGGGGAGATATGAGAGACAATTGGAGAAG
TGAATTATACAAATATAAGTAGTAAGAATTGAACCAATGGGTCTAGCACCCACCAGGGCAAAAA
GAAGAGTGGTGGAAAGAGAAAAAAGAGCAATAGGACTGGGAGCTATGTTCCTTGGGTTCTTGGGA
GCGGCAGGAAGCACGATGGGCGCAGCGTCACTGACGCTGACGGTACAGGCCAGACAGTTATTGTC
TGGTATAGTGCAACAGCAAAACAATTTGCTGAGAGCTATAGAGGCGCAACAGCATCTGTTGCAAC
TCACAGTCTGGGGCATTAAACAGCTCCAGGCAAGAGTCCTGGCTATGGAAAGCTACCTAAAGGAT
CAACAGCTCCTAGGAATTTGGGGTTGCTCTGGAAAACACATTTGCACCACTACTGTGCCCTGGAA
CTCTACCTGGAGTAATAGATCTGTAGAGGAGATTTGGAATAATATGACCTGGATGCAGTGGGAAA
GAGAAATTGAGAATTACACAGGTTTAATATACACCTTAATTGAAGAATCGCAAACCCAGCAAGAA
AAGAATGAACAAGAACTATTGCAATTGGATAAATGGGCAAGTTTGTGGAATTGGTTTAGTATAAC
AAAATGGCTGTGGTATATAAAAATATTCATAATGATAGTAGGAGGCTTAATAGGTTTAAGAATAG
TTTTTGCTGTGCTTTCTTTAGTAAATAGAGTTAGGCAGGGATATTCACCTCTGTCTTTTCAGACC
CTCCTCCCAGCCCCGAGGGGACCCGACAGGCCCGAAGGAATAGAAGAAGAAGGTGGAGAGCAAGG
CTAA 98UG57128 envelope (SEQ ID NO: 55):
ATGAGAGTGAGGGGGATAGAGAGGAATTATCAGCACTTATGGTGGAGATGGGGCACCATGCTCCT
TGGGATATTGATGATATGTAGTGCTGCAGAACAATTGTGGGTCACAGTTTATTATGGGGTACCTG
TGTGGAAAGAAGCAACCACTACTCTATTTTGTGCATCAGATGCTAAAGCATATAAAGCAGAGGCA
CACAATATCTGGGCTACACATGCCTGTGTACCAACAGACCCCAACCCACAAGAAATAGTACTAGA
AAATGTCACAGAAAACTTTAACATGTGGAAAATAGCATGGTGGAGCAGATGCATGAGGATGTA
ATCAGTTTATGGGATCAAAGCCTAAAACCATGTGTAAAATTAACCCCACTCTGTGTCACTTTAAA
CTGCACTAATGCCACTGCCACTAATGCCACTGCCACTAGTCAAAATAGCACTGATGGTAGTAATA
AAACTGTTAACACAGACACAGGAATGAAAAACTGCTCTTTCAATGTAACCACAGATCTAAAAGAT
AAGAAGAGGCAAGACTATGCACTTTTCTATAAACTTGATGTGGTACGAATAGATGATAAGAATAC
CAATGGTACTAATACCAACTATAGATTAATAAATTGTAATACCTCAGCCATTACACAAGCGTGTC
CAAAGATAACCTTTGAGCCAATTCCCATACATTATTGTGCCCCAGCTGGATATGCGATTCTAAAA
TGTAATAATAAGACATTCAATGGGACGGGTCCATGCAAAAACGTCAGCACAGTACAGTGTACACA
TGGGATTAGGCCAGTAGTGTCAACTCAACTGTTGTTGAATGGCAGTCTAGCAGAGGAAGAGATAG
TAATTAGATCTGAAAACCTCACAAATAATGCTAAAATTATAATAGTACAGCTTAATGAAGCTGTA
ACAATTAATTGCACAAGACCCTCCAACAATACAAGACGAAGTGTACATATAGGACCAGGGCAAGC
AATCTATTCAACAGGACAAATAATAGGAGATATAAGAAAAGCACATTGTAATATTAGTAGAAAAG
AATGGAATAGCACCTTACAACAGGTAACTAAAAAATTAGGAAGCCTGTTTAACACAACAAAAATA
ATTTTTAATGCATCCTCGGGAGGGGACCCAGAAATTACAACACACAGCTTTAATTGTAACGGGGA -continued
ATTCTTCTACTGCAATACAGCAGGACTGTTTAATAGTACATGGAACAGGACAAATAGTGAATGGA
TAAATAGTAAATGGACAAATAAGACAGAAGATGTAAATATCACACTTCAATGCAGAATAAAACAA
ATTATAAACATGTGGCAGGGAGTAGGAAAAGCAATGTATGCCCCTCCCGTTAGTGGAATAATCCG
ATGTTCATCAAATATTACAGGACTGTTGCTGACAAGAGATGGTGGTGGTGCAGATAATAATAGGC
AGAATGAGACCTTCAGACCTGGGGGAGGAGATATGAGAGACAATTGGAGAAGTGAATTATACAAA
TATAAAGTAGTAAGAATTGAACCACTAGGTATAGCACCCACCAAGGCAAGGAGAAGAGTGGTGGA
AAGAGAAAAAAGAGCAATAGGACTGGGAGCCTTGTTCCTTGGGTTCTTGGGAACAGCAGGAAGCA
CGATGGGCGCAGTGTCAATGACGCTGACGGTACAGGCCAGACAAGTATTGTCTGGTATAGTGCAA
CAGCAAAACAATCTGCTGAGGGCTATAGAGGCGCAACAGCATCTGTTGCAACTCACAGTCTGGGG
CATTAAACAGCTCCAGGCAAGAATCCTGGCTGTGGAAAGCTACCTAAAGGATCAACAGCTCCTAG
GAATTTGGGGTTGCTCTGGAAAACACATTTGCACCACTAATGTGCCCTGGAACTCTAGCTGGAGT
AATAAATCTCTAAATTATATTTGGAATAACATGACCTGGATGGAGTGGGAAAAGGAAATTGACAA
TTACACAGAATTAATATACAGCTTAATTGAAGTATCGCAAATCCAGCAAGAAAAGAATGAACAAG
AACTATTGAAATTGGACAGTTGGGCAAGTTTGTGGAATTGGTTTAGCATAACAAAATGGCTGTGG
TATATAAAAATATTCATAATGATAGTAGGAGGCTTGATAGGCTTAAGAATAGTTTTTGCTGTGCT
TTCTTTAGTAAATAGAGTTAGGCAGGGATACTCACCTCTGTCGTTTCAGACCCTTATCCCAGCCT
CGAGGGGACCCGACAGGCCCGAAGGAACAGAAGGAGAAGGTGGAGAGCAAGGCTAA Appendix 2—DNA sequences of MVA shuttle plasmids:

pLAS-1 (SEQ ID NO: 56):
GAATTCGTTGGTGGTCGCCATGGATGGTGTTATTGTATACTGTCTAAACGCGTTAGTAAAACATG
GCGAGGAAATAAATCATATAAAAAATGATTTCATGATTAAACCATGTTGTGAAAAAGTCAAGAAC
GTTCACATTGGCGGACAATCTAAAAACAATACAGTGATTGCAGATTTGCCATATATGGATAATGC
GGTATCCGATGTATGCAATTCACTGTATAAAAAGAATGTATCAAGAATATCCAGATTTGCTAATT
TGATAAAGATAGATGACGATGACAAGACTCCTACTGGTGTATATAATTATTTTAAACCTAAAGAT
GCCATTCCTGTTATTATATCCATAGGAAAGGATAGAGATGTTTGTGAACTATTAATCTCATCTGA
TAAAGCGTGTGCGTGTATAGAGTTAAATTCATATAAAGTAGCCATTCTTCCCATGGATGTTTCCT
TTTTTACCAAAGGAAATGCATCATTGATTATTCTCCTGTTTGATTTCTCTATCGATGCGGCACCT
CTCTTAAGAAGTGTAACCGATAATAATGTTATTATATCTAGACACCAGCGTCTACATGACGAGCT
TCCGAGTTCCAATTGGTTCAAGTTTTACATAAGTATAAAGTCCGACTATTGTTCTATATTATATA
TGGTTGTTGATGGATCTGTGATGCATGCAATAGCTGATAATAGAACTTACGCAAATATTAGCAAA
AATATATTAGACAATACTACAATTAACGATGAGTGTAGATGCTGTTATTTTGAACCACAGATTAG
GATTCTTGATAGAGATGAGATGCTCAATGGATCATCGTGTGATATGAACAGACATTGTATTATGA
TGAATTTACCTGATGTAGGCGAATTTGGATCTAGTATGTTGGGAAATATGAACCTGACATGATT
AAGATTGCTCTTTCGGTGGCTGGGTACCAGGCGCGCCTTTCATTTTGTTTTTTTCTATGCTATAA
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAGGGCATCGAC
TTCAAGGAGGACGGCAACATCCTGGGGCACAAGCTGGAGTACAACTACAACAGCCACAACGTCTA
TATCATGGCCGACAAGCAGAAGAACGGCATCAAGGTGAACTTCAAGATCCGCCACAACATCGAGG
ACGGCAGCGTGCAGCTCGCCGACCACTACCAGCAGAACACCCCCATCGGCGACGGCCCCGTGCTG
CTGCCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGCACGAGCTGTACA
AGTAAGAGCTCGGTTGTTGATGGATCTGTGATGCATGCAATAGCTGATAATAGAACTTACGCAAA
TATTAGCAAAAATATATTAGACAATACTACAATTAACGATGAGTGTAGATGCTGTTATTTTGAAC
CACAGATTAGGATTCTTGATAGAGATGAGATGCTCAATGGATCATCGTGTGATATGAACAGACAT
TGTATTATGATGAATTTACCTGATGTAGGCGAATTTGGATCTAGTATGTTGGGAAATATGAACC
TGACATGATTAAGATTGCTCTTTCGGTGGCTGGCGGCCCGCTCGAGGCCGCGGTGGTACCCAACCTA
AAAATTGAAAATAAATACAAAGGTTCTTGAGGGTTGTGTTAAATTGAAAGCGAGAAATAATCATA
AATAAGCCCGGGGATCCTCTAGAGTCGACCTGCAGGGAAAGTTTTATAGGTAGTTGATAGAACAA
AATACATAATTTTGTAAAAATAAATCACTTTTTATACTAATATGACACGATTACCAATACTTTTG
TTACTAATATCATTAGTATACGCTACACCTTTTCCTCAGCATCTAAAAAAATAGGTGATGATGC
AACTTTATCATGTAATCGAAATAATACAAATGACTACGTTGTTATGAGTGCTTGGTATAAGGAGC
CCAATTCCATTATTCTTTTAGCTGCTAAAAGCGACGTCTTGTATTTTGATAATTATACCAAGGAT
AAAAATATCTTACGACTCTCCATACGATGATCTAGTTACAACTATCACAATTAAATCATTGACTGC
TAGAGATGCCGGTACTTATGTATGTGCATTCTTTATGACATCGCCTACAAATGACACTGATAAAG
TAGATTATGAAGAATACTCCACAGAGTTGATTGTAAATACAGATAGTGAATCGACTATAGACATA
ATACTATCTGGATCTACACATTCACCAGAAACTAGTTAAGCTTGTCTCCCTATAGTGAGTCGTAT
TAGAGCTTGGCGTAATCATGGTCATAGCTGTTTCCTGTGTGAAATTGTTATCCGCTCACAATTCC
ACACAACATACGAGCCGGAAGCATAAAGTGTAAAGCCTGGGGTGCCTAATGAGTGAGCTAACTCA
CATTAATTGCGTTGCGCTCACTGCCCGCTTTCGAGTCGGGAAACCTGTCGTGCCAGCTGCATTAA
TGAATCGGCCAACGCGCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAA

-continued

AAAGAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCT
TCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCAACGTTGTTGGCATTG
CTACAGGCATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGCACTGCATAATTCTC
TTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTT
ACTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCG
CGCACATTTCCCCGAAAAGTGCCACCTGACGTCTAAGAAACCATTATTATCATGACATTAACCTA
TAAAAATAGGCGTATCACGAGGCCCTTTCGTCTCGCGCGTTTCGGTGATGACGGTGAAAACCTCT
GACACATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACTATGCGGCATCAGAGCA
GATTGTACTGAGAGTGCACCATATGCGGTGTGAAATACCGCACAGATGCGTAAGGAGAAAATACC
GCATCAGGCGCCATTCGCCATTCAGGCTGCGCAACTGTTGGGAAGGGCGATCGGTGCGGGCCTCT
TCGCTATTACGCCAGCTGGCGAAAGGGGGATGTGCTGCAAGGCGATTAAGTTGGGTAACGCCAGG
GTTTTCCCAGTCACGACGTTGTAAAACGACGGCCAGTGAATTGGATTAGGTGACACTATA pLAS-2 (SEQ ID NO: 57):
CCTCCTGAAAAACTGGAATTTAATACACCATTTGTGTTCATCATCAGACATGATATTACTGGATT
TATATTGTTTATGGGTAAGGTAGAATCTCCTTAATATGGGTACGGTGTAAGGAATCATTATTTTA
TTTATATTGATGGGTACGTGAAATCTGAATTTTCTTAATAAATATTATTTTTATTAAATGTGTAT
ATGTTGTTTTGCGATAGCCATGTATCTACTAATCAGATCTATTAGAGATATTATTAATTCTGGTG
CAATATGACAAAAATTATACACTAATTAGCGTCTCGTTTCAGACATGGATCTGTCACGAATTAAT
ACTTGGAAGTCTAAGCAGCTGAAAAGCTTTCTCTCTAGCAAAGATGCATTTAAGGCGGATGTCCA
TGGACATAGTGCCTTGTATTATGCAATAGCTGATAATAACGTGCGTCTAGTATGTACGTTGTTGA
ACGCTGGAGCATTGAAAAATCTTCTAGAGAATGAATTTCCATTACATCAGGCAGCCACATTGGAA
GATACCAAAATAGTAAAGATTTTGCTATTCAGTGGACTGGATGATTCGAGGTACCAGGCGCGCCC
TTTCATTTTGTTTTTTTCTATGCTATAAATGGTGAGCAAGGGCGAGGAGCTGTTCACCGGGGTGG
TGCCCATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTGCCCGT
GCCCTGGCCCACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACACCCTGGT
GAACCGCATCGAGCTGAAGGGCATCGACTTCAAGGAGGACGGCAACATCCTGGGGCACAAGCTGG
AGTACAACTACAACAGCCACAACGTCTATATCATGGCCGACAAGCAGAAGAACGGCATCAAGGTG
AACTTCAAGATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCAGTCCGCCC
TGAGCAAAGACCCCAACGAGAAGCGCGATCACATGGTCCTGCTGGAGTTCGTGACCGCCGCCGGG
ATCACTCTCGGCATGCACGAGCTGTACAAGTAAGAGCTCGCTTTCTCTCTAGCAAAGATGCATTT
AAGGCGGATGTCCATGGACATAGTGCCTTGTATTATGCAATAGCTGATAATAACGTGCGTCTAGT
ATGTACGTTGTTGAACGCTGGAGCATTGAAAAATCTTCTAGAGAATGAATTTCCATTACATCAGG
CAGCCACATTGGAAGATACCAAAATAGTAAAGATTTTGCTATTCAGTGGACTGGATGATTCTCCG
GATGGTACCCAACCTAAAAATTGAAAATAAATACAAAGGTTCTTGAGGGTTGTGTTAAATTGAAA
GCGAGAAATAATCATAAATAAGCCCGGGGATCCTCTAGAGTCGACCTGCAGGCATGCTCGAGCGG
CCGCCAGTGTGATGGATATCTGCAGAATTCGGCTTGGGGGGCTGCAGGTGGATGCGATCATGACG
TCCTCTGCAATGGATAACAATGAACCTAAAGTACTAGAAATGGTATATGATGCTACAATTTTACC
CGAAGGTAGTAGCATGGATTGTATAAACAGACACATCAATATGTGTATACAACGCACCTATAGTT
CTAGTATAATTGCCATATTGGATAGATTCCTAATGATGAACAAGGATGAACTAAATAATACACAG
TGTCATATAATTAAAGAATTTATGACATACGAACAAATGGCGATTGACCATTATGGAGAATATGT
AAACGCTATTCTATATCAAATTCGTAAAAGACCTAATCAACATCACACCATTAATCTGTTTAAAA
AAATAAAAAGAACCCGGTATGACACTTTTAAAGTGGATCCCGTAGAATTCGTAAAAAAGTTATC
GGATTTGTATCTATCTTGAACAAATATAAACCGGTTTATAGTTACGTCCTGTACGAGAACGTCCT
GTACGATGAGTTCAAATGTTTCATTGACTACGTGGAAACTAAGTATTTCTAAAATTAATGATGCCT
TTAATTTTTGTATTGATTCTCAATCCTAAAAACTAAAATGAATAAGTATTAAACATAGCGGTG
TACTAATTGATTTAACATAAAAAATAGTTGTTAACTAATCATGAGGACTCTACTTATTAGATATA
TTCTTTGGAGAAATGACAACGATCAAACCGGGCATGCAAGCTTGTCTCCCTATAGTGAGTCGTAT
TAGAGCTTGGCGTAATCATGGTCATAGCTGTTTCCTGTGTGAAATTGTTATCCGCTCACAATTCC
ACACAACATACGAGCCGGAAGCATAAAGTGTAAAGCCTGGGGTGCCTAATGAGTGAGCTAACTCA
CATTAATTGCGTTGCGCTCACTGCCCGCTTTCGAGTCGGGAAACCTGTCGTGCCAGCTGCATTAA
TGAATCGGCCAACGCGCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCGATAGGCTCCGCCCCCCTGACGAGCATCA
CAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGGCCTAA

-continued
```
CTACGGCTACACTAGAAGGACAGTATTTGGTATCTGCGCTCTGCTGAAGCCAGTTACCTTCGGAA
AAAGAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCT
TCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTGGTTC
ATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCAACGTTGTTGGCATTG
CTACAGGCATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGCACTGCATAATTCTC
TTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTT
ACTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCG
CGCACATTTCCCCGAAAAGTGCCACCTGACGTCTAAGAAACCATTATTATCATGACATTAACCTA
TAAAAATAGGCGTATCACGAGGCCCTTTCGTCTCGCGCGTTTCGGTGATGACGGTGAAAACCTCT
GACACATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACTATGCGGCATCAGAGCA
GATTGTACTGAGAGTGCACCATATGCGGTGTGAAATACCGCACAGATGCGTAAGGAGAAAATACC
GCATCAGGCGCCATTCGCCATTCAGGCTGCGCAACTGTTGGGAAGGGCGATCGGTGCGGGCCTCT
TCGCTATTACGCCAGCTGGCGAAAGGGGGATGTGCTGCAAGGCGATTAAGTTGGGTAACGCCAGG
GTTTTCCCAGTCACGACGTTGTAAAACGACGGCCAGTGAATTGGATTTAGGTGACACTATAGAAT
ACGAATTC
```

Appendix 3—DNA sequences of gagpol and env genes
from Kenyan HIV-1 clade A isolates:

```
KER2008 gagpol (SEQ ID NO: 58):
ATGGGTGCGAGAGCGTCAGTATTAAGTGGGGGAAAATTAGATGCATGGGAGAAAATTCGGTTAAG
GCCAGGGGGAAAGAAAAAATATAGACTGAAACACTTAGTATGGGCAAGCAGGGAGCTGGAAAAAT
TCGTACTTAACCCTAGCCTTTTAGAAACTTCAGAAGGATGTCAGCAAATAATGAACCAAATACAA
CCAGCTCTTCAGACAGGAACAGAAGAACTTAGATCATTATTTAATGCAGTAGCAACCCTCTATTG
TGTACATCAACGGATAGAGGTAAAAGACACCAAGGAAGCTTTAGATAAAGTAGAGGAAATACAAA
ACAAGAGCAAGCAAAAGACACAACAGGCAGCAGCTGATACAGGAAACAACAGCAAGGTCAGCCAT
AATTACCCTATAGTGCAAAATGCACAAGGGCAAATGATACATCAGTCCTTATCACCCAGGACTTT
GAATGCATGGGTAAAGGTAATAGAAGAAAGGGGTTTCAGCCCAGAAGTAATACCCATGTTCTCAG
CATTATCAGAAGGAGCCATCCCACAAGATTTAAATATGATGCTGAACATAGTGGGGGACACCAG
GCAGCTATGCAAATGTTAAAAGAAACTATCAATGAGGAAGCTGCAGAATGGGACAGGTTACATCC
AGCACAGGCAGGGCCTATTCCACCAGGCCAGATAAGAGACCCAAGGGGAAGTGACATAGCAGGAA
CTACTAGTACCCCTCAGGAACAAATAACATGGATGACAAACAACCCACCTATCCCAGTGGGAGAC
ATCTATAAAAGATGGATAATCCTAGGATTAAATAAAATAGTAAGAATGTATAGCCCTGTTAGCAT
TTTAGATATAAAACAGGGGCCAAAAGAACCCTTCAGAGACTATGTAGATAGGTTCTTTAAAGTTC
TCAGAGCCGAACAAGCTACACAGGAAGTAAAAGGCTGGATGACAGAGACCCTGCTGGTTCAAAAT
GCAAATCCAGATTGTAAGTCCATTTTAAGAGCATTAGGAACAGGGGCTACATTAGAAGAAATGAT
GACAGCATGTCAGGGAGTGGGAGGACCCGGCCATAAAGCAAGGGTTTTAGCTGAGGCAATGAGTC
AAGCACAACAGGCAAATGTAATGATGCAGAGGGGCAGCTTTAAGGGGCAGAAAAGAATTAAGTGC
TTCAACTGTGGCAAAGAGGGACACCTAGCCAGAAATTGCAGAGCCCCTAGGAAAAAAGGCTGTTG
GAAGTGTGGGAAAGAAGGACACCAAATGAAAGATTGCAATGAGAGACAGGCTAATTTTTTAGGGA
AAATTTGGCCTTCCAGCAAGGGGAGGCCAGGAAATTTTCCCCAGAGCAGACCGGAGCCAACAGCC
CCACCAGCAGAGATCTTTGGGATGGGGAAGAGATAACCTCCCCTCCGAAGCAGGAGCAGAAAGA
GAGGGAACAAACCCCACCCTTTGTTTCCCTCAAATCACTCTTTGGCAACGACCCCGTTGTCACAGT
AAAAGTAGGAGGAGAAATGAGAGAAGCTCTATTAGATACAGGAGCAGATGATACAGTATTAGAAG
ATATAAATTTGCCAGGAAAATGGAAACCAAAAATGATAGGGGGAATTGGAGGTTTTATCAAGGTA
AAACAATATGATCAGGTATCTATAGAAATTTGTGGAAAAAAGGCTATAGGTACGGTATTAGTAGG
ACCTACACCTGTCAACATAATTGGAAGAAATATGTTGACTCAGATTGGTTGTACCTTAAATTTTC
CAATTAGTCCTATTGAGACTGTACCAGTAACATTAAAGCCAGGAATGGATGGCCCAAGGGTTAAA
CAATGGCCATTGACAGAAGAGAAAATAAAAGCATTGACAGAAATTTGTAAAGAGATGGAAAAGGA
AGGAAAAATTTCAAAAATTGGGCCTGAAAATCCATACAATACTCCAATATTTGCAATAAAGAAAA
AAGATAGCACTAAATGGAGGAAATTAGTAGATTTCAGAGAGCTCAATAAAAGAACACAAGACTTT
TGGGAAGTTCAATTAGGAATACCGCATCCAGCGGGCCTAAAAAAGAAAAAATCAGTAACAGTACT
AGAGGTGGGGGATGCATATTTTTCAGTTCCCCTAGATAAAAACTTTAGAAAGTATACTGCATTTA
CCATACCTAGTTTAAATAATGAAACACCAGGAATCAGGTATCAGTACAATGTGCTTCCACAAGGA
TGGAAAGGATCACCAGCAATATTCCAGTGCAGTATGACAAAAATCTTAGAGCCCTTTAGATCAAA
AATCCAGAAATAATTATCTATCAATACATGCACGACTTGTATGTACAGATCAGATTTAGAAATAG
GGCAGCATAGAGCAAAAATAGAAGAATTAAGAGCTCATCTACTGAGCTGGGGATTTACTACACCA
GACAAAAAGCATCAGAAAGAACCTCCATTCCTTTGGATGGGATATGAGCTCCATCCTGACAAGTG
GACAGTCCAGCCTATAGAGCTGCCAGAAAAGAAAGCTGGACTGTCAATGATATACAGAAATTAG
TGGGAAAACTAAATTGGGCCAGTCAAATTTATCCAGGAATTAAAGTAAAGCAATTGTGTAAACTT
CTCAGGGGAGCCAAAGCCCTAACAGATATAGTAACACTGACTGAGGAAGCAGAATTAGAATTAGC
AGAGAACAGGGAGATTCTAAAAGACCCTGTGCATGGGGTATATTATGACCCATCAAAAGACTTAA
```

-continued

TAGCAGAAATACAGAAACAAGGGCAAGACCAATGGACATACCAAATTTATCAGGAGCCATTTAAA
AATCTAAAAACAGGAAAATATGCAAGAAAAAGGTCTGCTCACACTAATGATGTAAGACAATTAGC
AGAAGTAGTGCAGAAAGTGGTCATGGAAAGCATAGTAATATGGGGAAAGACTCCTAAATTTAAAC
TACCCATACAAAAAGAGACATGGGAGACATGGTGGATGGACTATTGGCAAGCTACCTGGATTCCT
GAGTGGGAGTTTGTCAATACCCCTCCCCTAGTAAAATTATGGTACCAGTTAGAGAAAGACCCCAT
AGCAGGGAGCAGAGACTTTCTAA

KNHh144 envelope (SEQ ID NO: 59):
ATGAGAGTGATGGGGATACAGATGAATTGTCAGCACTTATTGAGATGGGGAACTATGATCTTGGG
ATTGATAATAATCTGTAATGCTGTAAACAGCAACTTGTGGGTTACTGTCTATTATGGGGTACCTG
TGTGGAAAGATGCAGAGACCACCTTATTTTGTGCATCAGATGCTAAAGCATATAAAACAGAAAAG
CATAATGTCTGGGCTACAGATGCCTGTGTGCCCACAGACCCCAACCCACAAGAAATACCTTTGGA
AAATGTGACAGAAGAGTTTAACATGTGGAAAAATAAAATGGTAGAACAAATGCATACAGATATAA
TCAGTCTATGGGACCAAAGCCTACAGCCATGTGTAAAGTTAACCCCTCTCTGCATTACTTTAAAC
TGTACAGATGTTACTAATGTTACAGATGTTAGTGGTACGAGGGGCAACATCACCATCATGAAAGA
GATGGAGGGAGAAATAAAAAACTGTTCTTTCAATATGACCACAGAAATAAGGGATAAGAAACAGA
AAGTATATTCACTCTTTTATAGACTTGATGTAGTACCAATAAATCAGGGTAATAGTAGTAGTAAA
AACAGTAGTGAGTATAGATTAATAAGTTGTAATACCTCAGCCATTACACAAGCTTGCCGAAAGGT
AAGCTTTGAGGCAATTCCCATACATTATTGTGCCCCAGCTGGTTTTGGGATCCTGAAGTGTAGGG
ATAAGGAGTTCAATGGAACAGGGGAATGCAAGAATGTCAGCACAGTCCAATGCACACATGGAATC
AAGCCAGTAGTATCAACTCAACTACTGTTAAATGGCAGTCTAGCAGAGAAAAAGGTAAAAATCAG
AACTGAAAATATCACAAACAATGCCAAAACTATAGTAGTACAACTTGTCGAGCCTGTGAGAATTA
ATTGTACTAGACCTAATAACAATACAAGAGAGTGTGCGTATAGGGCCAGGACAAGCATTCTTT
GCAACAGGTGACATAATAGGGGATATAAGACAAGCACATTGTAATGTCAGTAGATCACAATGGAA
TAAGACTTTACAACAGGTAGCTGAACAATTAAGAGAACACTTTAAAAACAAACAATAATATTTA
ACAGTTCCTCAGGAGGGGATCTAGAAATCACAACACATAGTTTCAATTGTGGAGGAGAATTCTTC
TATTGTAATACATCAGGTCTGTTCAATAGCACCTGGAATACCAGCATGTCAGGGTCAAGTAACAC
GGAGAGAAATGACACTATAACTCTCCAATGCAGAATAAAGCAAATTATAAATATGTGGCAGAGAA
CAGGACAAGCAATATATGCCCCTCCCATCCAGGGAGTGATAAGGTGTGAATCAAACATCACAGGA
CTACTGTTAACAAGAGATGGTGGGAGGAGAAGAACAGTACAAATGAAATCTTCAGACCTGGAGG
AGGAGATATGAGGGACAACTGGAGAAGTGAATTATATAAGTATAAAGTAGTAAAAATTGAACCAC
TAGGAGTAGCACCCACCAGGGCAAGGAGAAGAGTGGTGGGAGAGAAAAAAGAGCAGTTGGAATA
GGAGCTGTTTTCCTTGGGTTCTTAGGAGCAGGAGGAAGCACTATGGGCGCGGCGTCAATAAGGCT
GACGGTACAGGCCAGGCAATTATTGTCTGGCATAGTGCAGCAGCAGAGCAATTTGCTGAGGGCTA
TAGAGGCTCAACAACATATGTTGAAACTCACGGTCTGGGGCATTAAACAGCTCCAGGCAAGAGTC
CTTGCTGTGGAAAGATACCTAAGGGATCAACAGCTCCTAGGAATTTGGGGCTGCTCTGGAAAACT
CATCTGCACCACTAATGTGCCCTGGAACTCTAGTTGGAGTAATAAATCTCAGGATGAAATATGGA
ACAACATGACCTGGCTGCAATGGGATAAAGAAATTAGCAATTACATAAACCTAATATATAGTCTA
ATTGAAGAATCGCAAAACCAGCAGGAAAAGAATGAACAAGACTTATTGGCATTGGGCAAGTGGGC
AAATCTGTGGACTTGGTTTGACATATCAAATTGGCTGTGGTATATAAGAATATTTATAATGATAG
TAGGAGGCTTAATAGGATTAAGAATAGTTTTTGCTGTGCTTGCTGTAATAAAGAGAGTTAGGCAG
GGATACTCACCTGTGTCATTTCAGATCCATGCCCCAAACCCAGGGGGTCTCGACAGGCCCGGAAG
AATCGAAGGAGAAGGTGGAGAGCAAGACTAA KNH1207 envelope (SEQ ID NO: 60)
ATGAGAGTGATGGGGATACAGATGAATTGTCAAAGCTTGTGGAGATGGGGAACTATGATCTTGGG
AATGTTAATGATTTGTAGTGTTGCAGGAAACTTGTGGGTTACTGTCTACTATGGGGTACCTGTGT
GGAAAGAGGCAGACACCACCTTATTTTGTGTATCAAATGCTAGAGCATATGATACAGAAGTGCAT
AATGTCTGGGCTACACATGCCTGTGTACCTACGGACCCCAACCCACAAGAAATAGATTTGGAGAA
TGTGACAGAAGAGTTTAACATGTGGAAAAATAACATGGTAGACAAATGCATACAGATATAATTA
GTCTATGGGACCAAAGCCTAAAACCATGTGTAAAGTTAACCCCTCTCTGCGTTACTTTAGATTGT
GGCTATAATGTAACCAACTTGAATTTCACCAGTAACATGAAAGGAGACATAACAAACTGCTCTTA
CAATATGACCACAGAAATAAGGGATAGGAAACAGAAAGTGTATTCACTTTTCTATAGGCTTGATA
TAGTACCAATTAATGAAGAAAGAATAATAGCAGGGAGACTAGTCCGATAGATTAATAAATTGT
AATACCTCAGCCATTACACAAGCTTGTCCTAAGGTATCTTTTGAACCAATTCCCATACATTATTG
TGCCCCAGCCGGTTTTGCGATTCTAAAATGTAAGGATGCAGAGTTCAATGGAACAGGGCCATGCA
AGAATGTCAGCACAGTACAATGTACACATGGAATCAGGCCAGTAATATCAACTCAACTGCTGTTA
AATGGCAGTTTAGCAGAGAATGGGACAAAGATTAGATCTGAAAATATCACAAACAATGCCAAAAC
CATAATAGTACAACTTAACGAGACCGTACAAATTAATTGTACCAGACTAGCAACAATACAAGAA
AAAGTGTACGTATAGGACCAGGACAAGCATTCTATCAACAGGTGATATAACAGGGGATATAAGA
CAAGCATATTGTAATGTCAGTAGACAAGAATGGGAACAAGCATTAAAGGGGTAGTTATACAATT
AAGAAAACACTTTAACAAAACAATAATCTTTAACAGTTCCTCAGGAGGGGATTTAGAAATTACAA
CACATAGTTTTAATTGTGGAGGAGAATTCTTCTATTGTGATACATCAGGCCTGTTTAATAGCACC
TGGAACACGAACACCACCGAGCCAAACAACACAACGTCAAATGGCACTATCATTCTCCAATGCAG
AATAAAGCAATTATAAATCTGTGGCAGAGAACCGGACAAGCAATGTATGCCCCTCCCATCCAAG
GGGTAATAAGGTGTGATTCCAACATTACAGGACTACTATTAACAAGAGATGGTGGAGTAGTTGAT
AGTATAAATGAAACCGAAATCTTCAGACCTGGAGGAGGAGATATGAGGGACAATTGGAAGTGA
ATTATATAAGTATAAAGTAGTAAAAATTGAACCACTAGGAGTAGCACCCACCGGGCAAAGAGAA
GAGTGGTGGAGAGAGAAAAAGAGCAGTTGGCATAGGAGCTGTATTCATTGGGTTCTTAGGAGCA
GCAGGAAGCACTATGGGCGCGGCGTCAATAACGCTGACGGTACAGGCCAGACAATTATTGTCTGG
CATAGTGCAACAGCAAAGCAATTTGCTGAGGGCTATAGAGGCTCAACAGCATATGTTGAGACTCA
CGGTCTGGGGCATTAAGCAGCTCCAGGCAAGAGTCCTGGCTGTGGAAAGATACCTAAGGGATCAA
CAGCTCCTAGGAATTTGGGGCTGCTCTGGAAAACTCATCTGCACCACTAATGTGCCCTGGAACTC
TAGTTGGAGTAATAAATCTCAGGAGGAATATGGGTAACATGACCTGGCTGCAATGGGATAAAG
AAATTAGCAATTACACACAACAATATATAACCTACTTGAAGAATCGCAGAACCAGCAGGAAAAG
AATGAACAAGACTTATTGGCATTGACAAGTGGGCAAATTTGCGGACTTGGTTTGACATAACAAA
TTGGCTGTGGTATATAAAAATGTTTATAATGATAGTAGGAGGCTTAATAGGATTAAGAATAGTTT
TTGCTGTGCTTTCTGTAATAAATAGAGTTAGGCAGGGATACTCACCTCTGTCGTTTCAGACCCAT
ATCCCGAGCCCAAGGGGTCTCGATAGGCCCGGAAGAATCGAAGGAGAAGGTGGAGAGCAAGACTA
A Appendix 4—DNA sequences of gagpol and env genes from Tanzanian HIV-1 clade C isolates:

```
TZA-246 gagpol (SEQ ID NO: 61):
ATGGGTGCGAGAGCGTCAATATTAAGAGGGGGAAAATTAGATCGATGGGAAAAAATTAGGTTAAG
GCCAGGGGGAAAGAAAAGCTATATGATAAAACACTTAGTATGGGCAAGCAGGGAGCTGGAAAGAT
TTGCACTTAACCCTAGCCTTTTAGAGACATCAGAAGGCTGTAAACAAATAATGAAACAGCTACAA
CGAGCTCTTCAGACAGGAACAGAAGAACTTAAATCATTATTCAATGCAATAGCAGTTCTCTATTG
TGTACATGAAGGGATAGATGTAAAAGACACCAAGGAAGCCTTAGACAAGATAGAGGAAGAACAGA
ACAAAAGTCAGCAAAAAACACAGCAGGCAGAAGCAGCTGGCGGAAAAGTCAGTCAAAATTATCCT
ATAGTGCAGAATCTCCAAGGACAAATGGTACACCAGTCCATATCACCTAGAACTTTGAATGCATG
GGTAAAAGTAATAGAGGAAAAGGCTTTTAGCCCAGAGGTAATACCCATGTTTACAGCATTATCAG
AAGGAGCCACCCCACAAGATTTAAACACCATGCTAAATACAGTGGGGGGACATCAAGCAGCCATG
CAAATGTTAAAAGATACCATCAATGAGGAGGCTGCAGAATGGGATAGGATACATCCAGTACATGC
AGGGCCTACTGCACCAGGCCAAATGAGAGAACCAAGGGGAAGTGACATAGCAGGAACTACTAGTA
CCCTTCAGGAACAAATAGCATGGATGACAGCTAACCCACCTGTTCCAGTGGGAGAAATCTACAAA
AGATGGATAATACTGGGTTTAAATAAAATAGTAAGAATGTATAGCCCTGTCAGCATTTTGGACAT
AAAACAAGGGCCAAAGGAACCCTTTAGAGACTATGTAGATCGGTTCTTTAAAACTTTAAGAGCTG
AACAGGCTACACAAGATGTAAAAAATTGGATGACAGACACCTTGTTGGTCCAAAATGCGAACCCA
GATTGTAAGACCATTTTAAGAGCATTAGGACCAGGGGCTACATTAGAAGAAATGATGACAGCATG
TCAAGGAGTGGGAGGACCTGGCCACAAAGCCAGAGTTTTGGCTGAGGCAATGAGCCAAGCAAACA
CACACATAATGATGCAGAGAAGCAATTTTAAAGGCTCTAAAAGAATTGTTAAATGTTTCAACTGT
GGCAAGGAAGGGCACATAGCCAGAAATTGCAGGGCCCCTAGGAAAAAGGGCTGTTGGAAATGTGG
AAAGGAAGGACACCAAATGAAAGACTGTACTGAGAGGCAGGCTAATTTTTTAGGGAAAATTTGGC
CTTCCCACAAGGGGAGGCCAGGGAATTTCCTTCAGAACAGGTCAGAGCCAACAGCCCCACCAACG
AACAGGCCAGAGCCAACAGCTCCACCAGCAGAGAGCTTCAGGTTCGAGGAAGCAACCCCTGCTCC
GAAGCAGGAGCTGAAAGACAGGGAACCTTTAATTTCCCTCAAATCACTCTTTGGCAGCGACCCCT
CGTCTCAATAAAAGTAGGGGGTCAAACAAAGGAGGCTCTTTTAGACACAGGAGCAGATGATACAG
TATTAGAAGAAATAAATTTGCCAGGAAAATGGAAACCCAAAATGATAGGAGGAATTGGAGGTTTT
ATCAAAGTAAGACAGTATGATCAGATAGTTATAGAAATTTGTGGAAAAAAGGCTATAGGTACAGT
ATTAGTAGGACCCACCCCTGTCAACATAATTGGAAGAAATATGTTGACTCAGCTTGGATGCACAC
TAAATTTTCCAATTAGTCCTATTGAAACTGTACCAGTAAAGTTAAAGCCAGGAATGGATGGCCCA
AAGGTTAAACAATGGCCATTGACAGAAGAAAAAATAAAGGCATTAACAGCAATTTGTGAAGAAAT
GGAGAAGGAAGGAAAAATTACAAAGATTGGGCCTGAAAATCCATATAACACTCCAGTATTTGCCA
TAAAAAAGAAGGACAGTACTAAGTGGAGAAATTAGTAGATTTCAGGGAACGCAATAAAAGAACT
CAAGATTTTTGGGAAGTTCAATTAGGCATACCACACCCAGCAGGGTTAAAAAAGAAAAAATCAGT
GACAGTACTGGAGGTGGGGGATGCATACTTCTCAGTTCCTTTAGATGAAGGCTTCAGGAAATATA
CTGCATTCACCATACCTAGTATAAACAATGAAACACCAGGAATTAGATATCAATACAATGTGCTT
CCACAGGGATGGAAAGGATCACCAGCAATATTCCAGAGTAGCATGACAAAAATCTTAGAGCCCTT
TAGAGCACAAAATCCAGAAATAGTCATCTATCAATATATGCACGACTTATATGTAGGATCTGACT
TAGAAATAGGGCAACATAGAGCAAAAATAGAGGAATTAAGAGAACATCTATTAAAGTGGGGATTT
ACCACACCAGACAAGAAACATCAGAAAGAACCCCCATTTCTTTGGATGGGGTATGAACTCCATCC
TGACAAATGGACAGTACAGCCTATAACGCTGCCAGAAAAGGAAAGCTGGACTGTCAATGATATAC
AGAAGTTAGTGGGAAAACTAAACTGGGCAAGTCAGATTTATGCAGGGATTAAAGTAAGGCAACTG
TATAAACTCCTTAGGGGAGCCAAAGCACTAACAGACATAGTACCACTAACTGAAGAGGCAGAATT
AGAATTGGCAGAGAACAGGGAAATTCTAAAAGAACCAGTACATGGGGTATATTATGACCCATCAA
AAGACTTGATAGCTGAAATACAGAAACAAGGGCATGACCAATGGACATATCAAATTTACCAAGAA
CCATTCAAAAATCTGAAAACAGGGAAGTATGCAAAAATGAGGAGTGCCCACACTAATGATGTAAA
ACAATTAACAGAGGCAGTGCAAAAAATAGCCATGGAAGGCATAGTAATATGGGGAAAGAGTCCTA
AATTTAGACTGCCCATTCAAAAGGAAACATGGGAAACATGGTGGACAGACTATTGGCAAGCCACC
TGGATTCCTGAGTGGGAGTTTGTTAATACCCCTCCCCTAGTAAAATTATGGTACCAGCTGGAGAA
AGAACCCATAGTAGGAGCAGAAACTTTC TZA-125 envelope (SEQ ID NO: 62):
ATGAGAGTGAAGGGGATATTGAGGAATTGGCAACACAGGTGGATATGGATCTGGATCATCTTAGG
CTTTTGGATGCTAATGATTTGTAATGGGAACTTGTGGGTCACTGTCTACTATGGGGTACCTGTGT
GGAAAGAAGCAAATGCTCCTCTATTTTGTGCATCAGATGCTAAAGCATATGAGAAAGAAGTGCAT
AATGTCTGGGCTACACATGCCTGTGTACCCACAGACCCCAACCCACAAGAACTAGACTTGGTAAA
TGTAACAGAAAATTTTAACATGTGGAAAAATGACATGGTAGATCAGATGCATGAGGATATAATCA
GTTTATGGGATGAAAGCCTAAAGCCATGTGTAAAGTTGACCCCACTCTGTGTCACTCTAAACTGT
ACTAATGCTAATATTAATAATGATACTGTTGCTAATAGTGGTACTTTTAAGGTTGATAATAGTAG
TAATGTAGTAAAAAATTGCTCTTTCAATATAACCACAGAAATAAGAGATAAGAAGAAAAAAGAAT
ATTCATTGTTTTATAGACTTGATATATTACCACTTGATAACTCTAGTGAGTCTAAGAACTATAGT
GAGTATGTATTAATAAATTGTAATGCCTCAACCGTAACACAAGCCTGTCCAAAGGTCTCTTTTGA
CGCAATTCCTATACATTATTGTGCTCCAGCTGGTTATGCGATTCTAAAGTGTAAAGATAAGACAT
TCAATGGAACAGGACCATGCAGTAATGTCAGCACAGTACTATGTACACATGGAATTAAGCCAGTG
GTATCAACTCAATTACTGTTAAATGGTAGCCTAGCAGAAGAAGGGATAGTAATTAGATCTGAAAA
TCTGACAAACAATGCCAAAACAACAATAGTACAGCTTAATGACCTGTAGAAATTATGTGTGTAA
GACCCGGCAATAATACAAGAAAAAGTGTGAGGATAGGACCAGGACAAACATTCTATGCAACAGGA
GGCATAATAGGAGATATAAGACAAGCACATTGTAACATTAGTAGAAGTGATTGGAATAAAACTTT
ACAAGAGGTAGGTAAAAAATTACGAGAATACTTCCACAATAAAACAATAAGATTTAAACCGGCGG
TCGTAGGAGGGGACCTGGAAATTACAACACATAGCTTTAATTGTAGAGGAGAATTCTTCTATTGC
AATACATCAGAACTGTTTACAGGTGAATATAATGGTACTGAGTATAAGAATACTTCAAATTCAAA
TCCTAACATCACACTCCCATGTAGAATAAAACAATTTGTAAACATGTGGCAGAGGGTAGGACGAG
CAATGTATGCCCCTCCTATTGAAGGAAACATAACATGTAACTCAAGTATCACAGGACTACTATTG
ACATGGGATGGAGGAAACAATACTAATGGCACAGAGACATTTAGACCTGGAGGAGGAGATATGAG
GGATAATTGGAGAAGTGAATTATATAAATATAAAGTGGTAGAAATTAAACCATTAGGAATAGCAC
CCACTAGTGCAAAAAGGAGAGTGGTGGAGAGAGAAAAGAGCAGTGGGAATAGGAGCTTTGTTC
CTTGGGTTCTTAGGAGCAGCAGGAAGCACTATGGGCGCAGCATCAATAACGCTGACGGTACAGGC
```

```
                                                 -continued
CAGACAATTATTGTCTGGTATAGTGCAACAGCAAAGCAATTTGCTGAGGGCCATAGAGGCGCAAC
AGCATATGTTGCAACTCACAGTCTGGGGCATTAAACAGCTCCAGACAAGAGTCCTGGCTATAGAA
AGATACCTAAAGGATCAACAGCTCCTAGGGATTTGGGGCTGCTCTGGAAAACTCATCTGCACCAC
TGCTGTGCCTTGGAACACTAGTTGGAGTAATAAAACTGAACAGGACATTTGGAATCTAACCTGGA
TGCAGTGGGATAGAGAAGTTAGTAATTACACAGACATAATATACAGGTTGCTTGAAGACTCACAA
ATCCAGCAGGAAAACAATGAAAAGGATTTACTAGCATTGGACAGTTGGAAAAATCTGTGGAATTG
GTTTGACATAACAAATTGGTTGTGGTATATAAGAACATTCATAATGATAGTAGGAGGCTTGATAG
GCTTAAGGATAATTTTTGCTGTAATTTCTATAGTGAATAGAGTTAGGCAGGGATACTCACCTTTG
TCATTTCAGACCCTTACCCCAACCCCGAGGGGACCAGAAAGGCTCGGAGGAATCGAAGAAGAAGG
TGGAGAGCAAGACTAA
```

While the present invention has been described in some detail for purposes of clarity and understanding, one skilled in the art will appreciate that various changes in form and detail can be made without departing from the true scope of the invention. All figures, tables, and appendices, as well as patents, applications, and publications, referenced to above, are hereby incorporated by reference.

What is claimed is:

1. An immunogenic composition comprising a recombinant MVA virus expressing modified HIV-1 gag, pol, and env genes from a Kenyan clade A isolate, wherein said gag and pol genes consist of SEQ ID NO:58 or a sequence having at least about 90%, 95% or 99.9% identity thereto, or said env gene is selected from the group consisting of SEQ ID NO:59, SEQ ID NO:60, and sequences having at least about 90%, 95% or 99.9% identity to SEQ ID NO:59 and SEQ ID NO:60.

2. The immunogenic composition of claim 1 expressing a modified gag-pol gene from a Kenyan clade A isolate consisting of SEQ ID NO:58, or a sequence having at least about 90%, 95% or 99.9% identity thereto.

3. The immunogenic composition of claim 1 expressing a modified env gene from a Kenyan clade A isolate consisting of SEQ ID NO:59, or a sequence having at least about 90%, 95% or 99.9% identity thereto.

4. The immunogenic composition of claim 1 expressing a modified env gene from a Kenyan clade A isolate consisting of SEQ ID NO:60, or a sequence having at least about 90%, 95% or 99.9% identity thereto.

5. The immunogenic composition of claim 1, wherein said recombinant MVA virus is MVA/KEA-1 expressing a modified HIV-1 gag-pol gene consisting of SEQ ID NO:58, or a sequence having at least about 90%, 95% or 99.9% identity thereto, and a modified HIV-1 env gene consisting of SEQ ID NO:59, or a sequence having at least about 90%, 95% or 99.9% identity thereto.

6. The immunogenic composition of claim 1, wherein said recombinant MVA virus is MVA/KEA-2 expressing a modified HIV-1 gag-pol gene consisting of SEQ ID NO:58, or a sequence having at least about 90%, 95% or 99.9% identity thereto, and a modified HIV-1 env gene consisting of SEQ ID NO:60, or a sequence having at least about 90%, 95% or 99.9% identity thereto.

7. The immunogenic composition of claim 1, wherein said recombinant MVA virus is MVA/KEA-3 expressing a modified HIV-1 gag-pol gene consisting of SEQ ID NO:58, or a sequence having at least about 90%, 95% or 99.9% identity thereto, and a modified HIV-1 env gene consisting of nucleotide 1 to 2064 of SEQ ID NO:59, or a sequence having at least about 90%, 95% or 99.9% identity thereto, and encoding for an Env protein truncated at the C-terminus just prior to the transmembrane domain yielding a soluble, secreted form of the protein.

8. The immunogenic composition of claim 1, wherein said recombinant MVA virus is MVA/KEA-4 expressing a modified HIV-1 gag-pol gene consisting of SEQ ID NO:58, or a sequence having at least about 90%, 95% or 99.9% identity thereto, and a modified HIV-1 env gene consisting of SEQ ID NO:59 with mutations at nucleotide positions 2149 to 2151, from TAG to GCG, which encodes for the Y717A amino acid mutation, or sequence containing said mutations and having at least about 90%, 95% or 99.9% identity thereto.

9. The immunogenic composition of claim 1, wherein said recombinant MVA virus is MVA/KEA-5 expressing a modified HIV-1 gag-pol gene consisting of SEQ ID NO:58, or a sequence having at least about 90%, 95% or 99.9% identity thereto, and a modified HIV-1 env gene consisting of SEQ ID NO:59 with mutations at nucleotide positions 2149 to 2151, from TAC to AGC, which encodes for the Y717S amino acid mutation, or sequence containing said mutations and having at least about 90%, 95% or 99.9% identity thereto.

10. The immunogenic composition of claim 1, wherein said recombinant MVA virus is MVA/KEA-1 expressing a modified HIV-1 gag-pol gene consisting of SEQ ID NO:58, and a modified HIV-1 env gene consisting of SEQ ID NO:59.

11. The immunogenic composition of claim 1, wherein said recombinant MVA virus is MVA/KEA-2 expressing a modified HIV-1 gag-pol gene consisting of SEQ ID NO:58, and a modified HIV-1 env gene consisting of SEQ ID NO:60.

12. The immunogenic composition of claim 1, wherein said recombinant MVA virus is MVA/KEA-3 expressing a modified HIV-1 gag-pol gene consisting of SEQ ID NO:58, and a modified HIV-1 env gene consisting of nucleotide 1 to 2064 of SEQ ID NO:59 and encoding for an Env protein truncated at the C-terminus just prior to the transmembrane domain yielding a soluble, secreted form of the protein.

13. The immunogenic composition of claim 1, wherein said recombinant MVA virus is MVA/KEA-4 expressing a modified HIV-1 gag-pol gene consisting of SEQ ID NO:58, and a modified HIV-1 env gene consisting of SEQ ID NO:59 with mutations at nucleotide positions 2149 to 2151, from TAC to GCG, which encodes for the Y717A amino acid mutation.

14. The immunogenic composition of claim 1, wherein said recombinant MVA virus is MVA/KEA-5 expressing a modified HIV-1 gag-pol gene consisting of SEQ ID NO:58, and a modified HIV-1 env gene consisting of SEQ ID NO:59 with mutations at nucleotide positions 2149 to 2151, from TAC to AGC, which encodes for the Y717S amino acid mutation.

* * * * *

SEQUENCE LISTING

<160> NUMBER OF SEQ ID NOS: 63

<210> SEQ ID NO 1
<211> LENGTH: 12225
<212> TYPE: DNA
<213> ORGANISM: Artificial Sequence
<220> FEATURE:
<223> OTHER INFORMATION: Plasmid pLW-48

<400> SEQUENCE: 1

```
gaattcgttg gtggtcgcca tggatggtgt tattgtatac tgtctaaacg cgttagtaaa      60
acatggcgag gaaataaatc atataaaaaa tgatttcatg attaaaccat gttgtgaaaa     120
agtcaagaac gttcacattg gcggacaatc taaaaacaat acagtgattg cagatttgcc     180
atatatggat aatgcggtat ccgatgtatg caattcactg tataaaaga atgtatcaag      240
aatatccaga tttgctaatt tgataaagat agatgacgat gacaagactc ctactggtgt     300
atataattat tttaaaccta aagatgccat tcctgttatt atatccatag gaaaggatag     360
agatgtttgt gaactattaa tctcatctga taaagcgtgt gcgtgtatag agttaaattc     420
ataaaagta gccattcttc ccatggatgt ttcctttttt accaaaggaa atgcatcatt      480
gattattctc ctgtttgatt tctctatcga tgcggcacct ctcttaagaa gtgtaaccga     540
taataatgtt attatatcta gacaccagcg tctacatgac gagcttccga gttccaattg     600
gttcaagttt tacataagta taaagtccga ctattgttct atattatata tggttgttga     660
tggatctgtg atgcatgcaa tagctgataa tagaacttac gcaaatatta gcaaaaatat     720
attagacaat actacaatta acgatgagtg tagatgctgt tattttgaac cacagattag     780
gattcttgat agagatgaga tgctcaatgg atcatcgtgt gatatgaaca gacattgtat     840
tatgatgaat ttacctgatg taggcgaatt tggatctagt atgttgggga aatatgaacc     900
tgacatgatt aagattgctc tttcggtggc tgggtaccag gcgcgccttt cattttgttt     960
tttttctatgc tataaatggt acgtcctgta gaaacccaa cccgtgaaat caaaaaactc    1020
gacggcctgt gggcattcag tctggatcgc gaaaactgtg gaattgatca gcgttggtgg    1080
gaaagcgcgt tacaagaaag ccgggcaatt gctgtgccag gcagttttaa cgatcagttc    1140
gccgatgcag atattcgtaa ttatgcgggc aacgtctggt atcagcgcga agtctttata    1200
ccgaaaggtt gggcaggcca gcgtatcgtg ctgcgtttcg atgcggtcac tcattacggc    1260
aaagtgtggg tcaataatca ggaagtgatg gagcatcagg gcggctatac gccatttgaa    1320
gccgatgtca cgccgtatgt tattgccggg aaaagtgtac gtatcaccgt tgtgtgaac    1380
```

-continued

```
aacgaactga actggcagac tatcccgccg ggaatggtga ttaccgacga aaacggcaag    1440
aaaaagcagt cttacttcca tgatttcttt aactatgccg gaatccatcg cagcgtaatg    1500
ctctacacca cgccgaacac ctgggtggac gatatcaccg tggtgacgca tgtcgcgcaa    1560
gactgtaacc acgcgtctgt tgactggcag gtggtggcca atggtgatgt cagcgttgaa    1620
ctgcgtgatg cggatcaaca ggtggttgca actggacaag gcactagcgg gactttgcaa    1680
gtggtgaatc cgcacctctg gcaaccgggt gaaggttatc tctatgaact gtgcgtcaca    1740
gccaaaagcc agacagagtg tgatatctac ccgcttcgcg tcggcatccg gtcagtggca    1800
gtgaagggcg aacagttcct gattaaccac aaaccgttct actttactgg ctttggtcgt    1860
catgaagatg cggacttgcg tggcaaagga ttcgataacg tgctgatggt gcacgaccac    1920
gcattaatgg actggattgg ggccaactcc taccgtacct cgcattaccc ttacgctgaa    1980
gagatgctcg actgggcaga tgaacatggc atcgtggtga ttgatgaaac tgctgctgtc    2040
ggctttaacc tctctttagg cattggtttc gaagcgggca caagccgaa  agaactgtac    2100 agcgaagagg cagtcaacgg ggaaactcag caagcgcact acaggcgat  taaagagctg    2160 atagcgcgtg acaaaaacca cccaagcgtg gtgatgtgga gtattgccaa cgaaccggat    2220
acccgtccgc aaggtgcacg ggaatatttc gcgccactgg cggaagcaac gcgtaaactc    2280
gacccgacgc gtccgatcac ctgcgtcaat gtaatgttct gcgacgctca caccgatacc    2340
atcagcgatc tctttgatgt gctgtgcctg aaccgttatt acggatggta tgtccaaagc    2400
ggcgatttgg aaacggcaga gaaggtactg gaaaagaac  ttctggcctg caggagaaa    2460 ctgcatcagc cgattatcat caccgaatac ggcgtggata cgttagccgg gctgcactca    2520
atgtacaccg acatgtggag tgaagagtat cagtgtgcat ggctgga tat gtatcaccgc    2580 gtctttgatc gcgtcagcgc cgtcgtcggt gaacaggtat ggaatttcgc cgattttgcg    2640
acctcgcaag gcatattgcg cgttggcggt aacaagaaag ggatcttcac tcgcgaccgc    2700
aaaccgaagt cggcggcttt tctgctgcaa aaacgctgga ctggcatgaa cttcggtgaa    2760
aaaccgcagc agggaggcaa acaatgagag ctcggttgtt gatggatctg tgatgcatgc    2820
aatagctgat aatagaactt acgcaaatat tagcaaaaat atattagaca atactacaat    2880
taacgatgag tgtagatgct gttattttga accacagatt aggattcttg atagagatga    2940
gatgctcaat ggatcatcgt gtgatatgaa cagacattgt attatgatga atttacctga    3000
tgtaggcgaa tttggatcta gtatgttggg gaaatatgaa cctgacatga ttaagattgc    3060
tctttcggtg gctggcggcc cgctcgagta aaaaatgaaa aaatattcta atttataggacggttttgat tttcttttttt tctatgctat aaataataaa tagcggccgc accatgaaag   3180
tgaaggggat caggaagaat tatcagcact tgtggaaatg gggcatcatg ctccttggga    3240
tgttgatgat ctgtagtgct gtagaaaatt tgtgggtcac agtttattat ggggtacctg    3300
tgtggaaaga agcaaccacc actctatttt gtgcatcaga tgctaaagca tatgatacag    3360
aggtacataa tgtttgggcc acacatgcct gtgtacccac agaccccaac ccacaagaag    3420
tagtattgga aaatgtgaca gaaaattta  acatgtggaa aaataacatg gtagaacaga    3480
tgcatgagga tataatcagt ttatgggatc aaagcctaaa gccatgtgta aaattaaccc    3540
cactctgtgt tactttaaat tgcactgatt tgaggaatgt tactaatatc aataatagta    3600
gtgagggaat gagaggagaa ataaaaaact gctctttcaa tatcaccaca agcataagag    3660
ataaggtgaa gaaagactat gcacttttct atagacttga tgtagtacca atagataatg    3720
```

| | |
|---|---|
| ataatactag ctataggttg ataaattgta atacctcaac cattacacag gcctgtccaa | 3780 |
| aggtatcctt tgagccaatt cccatacatt attgtacccc ggctggtttt gcgattctaa | 3840 |
| agtgtaaaga caagaagttc aatggaacag ggccatgtaa aaatgtcagc acagtacaat | 3900 |
| gtacacatgg aattaggcca gtagtgtcaa ctcaactgct gttaaatggc agtctagcag | 3960 |
| aagaagaggt agtaattaga tctagtaatt tcacagacaa tgcaaaaaac ataatagtac | 4020 |
| agttgaaaga atctgtagaa attaattgta caagacccaa caacaataca aggaaaagta | 4080 |
| tacatatagg accaggaaga gcattttata acacaggaga ataataggag atataagac | 4140 |
| aagcacattg caacattagt agaacaaaat ggaataacac tttaaatcaa atagctacaa | 4200 |
| aattaaaaga acaatttggg aataataaaa caatagtctt taatcaatcc tcaggagggg | 4260 |
| acccagaaat tgtaatgcac agttttaatt gtggagggga attcttctac tgtaattcaa | 4320 |
| cacaactgtt taatagtact tggaattttta atggtacttg gaatttaaca caatcgaatg | 4380 |
| gtactgaagg aaatgacact atcacactcc catgtagaat aaaacaaatt ataaatatgt | 4440 |
| ggcaggaagt aggaaaagca atgtatgccc ctcccatcag aggacaaatt agatgctcat | 4500 |
| caaatattac agggctaata ttaacaagag atggtggaac taacagtagt gggtccgaga | 4560 |
| tcttcagacc tgggggagga gatatgaggg acaattggag aagtgaatta tataaatata | 4620 |
| aagtagtaaa aattgaacca ttaggagtag cacccaccaa ggcaaaaaga agagtggtgc | 4680 |
| agagagaaaa aagagcagtg ggaacgatag gagctatgtt ccttgggttc ttgggagcag | 4740 |
| caggaagcac tatgggcgca gcgtcaataa cgctgacggt acaggccaga ctattattgt | 4800 |
| ctggtatagt gcaacagcag aacaatttgc tgagggctat tgaggcgcaa cagcatctgt | 4860 |
| tgcaactcac agtctggggc atcaagcagc tccaggcaag agtcctggct gtggaaagat | 4920 |
| acctaaggga tcaacagctc ctagggattt ggggttgctc tggaaaactc atctgcacca | 4980 |
| ctgctgtgcc ttggaatgct agttggagta ataaaactct ggatatgatt tgggataaca | 5040 |
| tgacctggat ggagtgggaa agagaaatcg aaaattacac aggcttaata tacaccttaa | 5100 |
| ttgaggaatc gcagaaccaa caagaaaaga atgaacaaga cttattagca ttagataagt | 5160 |
| gggcaagttt gtggaattgg tttgacatat caaattggct gtggtatgta aaaatcttca | 5220 |
| taatgatagt aggaggcttg ataggtttaa gaatagtttt tactgtactt tctatagtaa | 5280 |
| atagagttag gcagggatac tcaccattgt catttcagac ccacctccca gccccgaggg | 5340 |
| gacccgacag gcccgaagga atcgaagaag aaggtggaga cagagactaa ttttttatgcg | 5400 |
| gccgctggta cccaacctaa aaattgaaaa taaatacaaa ggttcttgag ggttgtgtta | 5460 |
| aattgaaagc gagaaataat cataaataag cccgggatc ctctagagtc gacaccatgg | 5520 |
| gtgcgagagc gtcagtatta gcggggggag aattagatcg atgggaaaaa attcggttaa | 5580 |
| ggccaggggg aaagaaaaaa tataaattaa aacatatagt atgggcaagc agggagctag | 5640 |
| aacgattcgc agttaatcct ggcctgttag aaacatcaga aggctgtaga caaatactgg | 5700 |
| gacagctaca accatcccctt cagacaggat cagaagaact tagatcatta tataatacag | 5760 |
| tagcaaccct ctattgtgtg catcaaagga tagagataaa agacaccaag gaagctttag | 5820 |
| acaagataga ggaagagcaa aacaaaagta agaaaaaagc acagcaagca gcagctgaca | 5880 |
| caggacacag caatcaggtc agccaaaatt accctatagt gcagaacatc caggggcaaa | 5940 |
| tggtacatca ggccatatca cctagaactt taaatgcatg ggtaaaagta gtagaagaga | 6000 |
| aggctttcag cccagaagtg atacccatgt tttcagcatt atcagaagga gccaccccac | 6060 |
| aagatttaaa caccatgcta aacacagtgg ggggacatca agcagccatg caaatgttaa | 6120 |

-continued

```
aagagaccat caatgaggaa gctgcagaat gggatagagt gcatccagtg catgcagggc    6180
ctattgcacc aggccagatg agagaaccaa ggggaagtga catagcagga actactagta    6240
cccttcagga acaaatagga tggatgacaa ataatccacc tatcccagta ggagaaattt    6300
ataaaagatg gataatcctg ggattaaata aaatagtaag aatgtatagc cctaccagca    6360
ttctggacat aagacaagga ccaaaagaac cctttagaga ctatgtagac cggttctata    6420
aaactctaag agccgagcaa gcttcacagg aggtaaaaaa ttggatgaca gaaaccttgt    6480
tggtccaaaa tgcgaaccca gattgtaaga ctatttttaaa agcattggga ccagcggcta    6540
cactagaaga aatgatgaca gcatgtcagg gagtaggagg acccggccat aaggcaagag    6600
ttttggctga agcaatgagc caagtaacaa attcagctac cataatgatg cagagaggca    6660
attttaggaa ccaaagaaag attgttaagt gtttcaattg tggcaaagaa gggcacacag    6720
ccagaaattg cagggcccct aggaaaaagg gctgttggaa atgtggaaag gaaggacacc    6780
aaatgaaaga ttgtactgag agacaggcta attttttagg gaagatctgg ccttcctaca    6840
agggaaggcc agggaatttt cttcagagca gaccagagcc aacagcccca ccagaagaga    6900
gcttcaggtc tggggtagag acaacaactc cccctcagaa gcaggagccg atagacaagg    6960
aactgtatcc tttaacttcc ctcagatcac tctttggcaa cgaccctcg tcacaataaa    7020 gatagggggg caactaaagg aagctctatt agatacagga gcagatgata cagtattaga    7080
agaaatgagt ttgccaggaa gatggaaacc aaaaatgata gggggaattg gaggttttat    7140
caaagtaaga cagtatgatc agatactcat agaaatctgt ggacataaag ctataggtac    7200
agtattagta ggacctacac ctgtcaacat aattggaaga aatctgttga ctcagattgg    7260
ttgcacttta aattttccca ttagccctat tgagactgta ccagtaaaat taaagccagg    7320
aatggatggc ccaaaagtta aacaatggcc attgacagaa gaaaaaataa agcattagt    7380 agaaatttgt acagaaatgg aaaaggaagg gaaaatttca aaaattgggc ctgagaatcc    7440
atacaatact ccagtatttg ccataaagaa aaaagacagt actaaatgga gaaaattagt    7500
agatttcaga gaacttaata agagaactca agacttctgg gaagttcaat taggaatacc    7560
acatcccgca gggttaaaaa agaaaaaatc agtaacagta ctggatgtgg gtgatgcata    7620
tttttcagtt cccttagatg aagacttcag gaagtatact gcatttacca tacctagtat    7680
aaacaatgag acaccaggga ttagatatca gtacaatgtg cttccacagg gatggaaagg    7740
atcaccagca atattccaaa gtagcatgac aaaaatctta gagccttta aaaaacaaaa    7800 tccagacata gttatctatc aatacatgaa cgatttgtat gtaggatctg acttagaaat    7860
agggcagcat agaacaaaaa tagaggagct gagacaacat ctgttgaggt ggggacttac    7920
cacaccagac aaaaaacatc agaaagaacc tccattcctt tggatgggtt atgaactcca    7980
tcctgataaa tggacagtac agcctatagt gctgccagaa aaagacagct ggactgtcaa    8040
tgacatacag aagttagtgg ggaaattgaa taccgcaagt cagatttacc cagggattaa    8100
agtaaggcaa ttatgtaaac tccttagagg aaccaaagca ctaacagaag taataccact    8160
aacagaagaa gcagagctag aactggcaga aaacagagag attctaaaag aaccagtaca    8220
tggagtgtat tatgacccat caaaagactt aatagcagaa atacagaagc aggggcaagg    8280
ccaatggaca tatcaaattt atcaagagcc atttaaaaat ctgaaaacag gaaaatatgc    8340
aagaatgagg ggtgcccaca ctaatgatgt aaaacaatta acagaggcag tgcaaaaaat    8400
aaccacagaa agcatagtaa tatgggggaaa gactcctaaa tttaaactac ccatacaaaa    8460
```

```
ggaaacatgg gaaacatggt ggacagagta ttggcaagcc acctggattc ctgagtggga   8520
gtttgttaat acccctcctt tagtgaaatt atggtaccag ttagagaaag aacccatagt   8580
aggagcagaa accttctatg tagatggggc agctaacagg gagactaaat taggaaaagc   8640
aggatatgtt actaacaaag gaagacaaaa ggttgtcccc ctaactaaca caacaaatca   8700
gaaaactcag ttacaagcaa tttatctagc tttgcaggat tcaggattag aagtaaacat   8760
agtaacagac tcacaatatg cattaggaat cattcaagca caaccagata aaagtgaatc   8820
agagttagtc aatcaaataa tagagcagtt aataaaaaag gaaaaggtct atctggcatg   8880
ggtaccagca cacaaaggaa ttggaggaaa tgaacaagta gataaattag tcagtgctgg   8940
aatcaggaaa atactatttt tagatggaat agataaggcc caagatgaac attagttttt   9000
atgtcgacct gcaggaaaag ttttataggt agttgataga acaaaataca aattttgta    9060
aaaataaatc acttttttata ctaatatgac acgattacca atacttttgt tactaatatc   9120
attagtatac gctacacctt ttcctcagac atctaaaaaa ataggtgatg atgcaacttt   9180
atcatgtaat cgaaataata caaatgacta cgttgttatg agtgcttggt ataaggagcc   9240
caattccatt attcttttag ctgctaaaag cgacgtcttg tattttgata attataccaa   9300
ggataaaata tcttacgact ctccatacga tgatctagtt acaactatca caattaaatc   9360
attgactgct agagatgccg gtacttatgt atgtgcattc tttatgacat cgcctacaaa   9420
tgacactgat aaagtagatt atgaagaata ctccacagag ttgattgtaa atacagatag   9480
tgaatcgact atagacataa tactatctgg atctacacat tcaccagaaa ctagttaagc   9540
ttgtctccct atagtgagtc gtattagagc ttggcgtaat catggtcata gctgtttcct   9600
gtgtgaaatt gttatccgct cacaattcca cacaacatac gagccggaag cataaagtgt   9660
aaagcctggg gtgcctaatg agtgagctaa ctcacattaa ttgcgttgcg ctcactgccc   9720
gctttcgagt cgggaaacct gtcgtgccag ctgcattaat gaatcggcca acgcgcgggg   9780
agaggcggtt tgcgtattgg gcgctcttcc gcttcctcgc tcactgactc gctgcgctcg   9840
gtcgttcggc tgcggcgagc ggtatcagct cactcaaagg cggtaatacg gttatccaca   9900
gaatcagggg ataacgcagg aaagaacatg tgagcaaaag gccagcaaaa ggccaggaac   9960
cgtaaaaagg ccgcgttgct ggcgtttttc cataggctcc gcccccctga cgagcatcac  10020
aaaaatcgac gctcaagtca gaggtggcga aacccgacag gactataaag ataccaggcg  10080
tttccccctg gaagctccct cgtgcgctct cctgttccga ccctgccgct taccggatac  10140
ctgtccgcct ttctcccttc gggaagcgtg gcgctttctc atagctcacg ctgtaggtat  10200
ctcagttcgg tgtaggtcgt tcgctccaag ctgggctgtg tgcacgaacc cccgttcag   10260
cccgaccgct gcgccttatc cggtaactat cgtcttgagt ccaacccggt aagacacgac  10320
ttatcgccac tggcagcagc cactggtaac aggattagca gagcgaggta tgtaggcggt  10380
gctacagagt tcttgaagtg gtggcctaac tacggctaca ctagaaggac agtatttggt  10440
atctgcgctc tgctgaagcc agttaccttc ggaaaaagag ttggtagctc ttgatccggc  10500
aaacaaacca ccgctggtag cggtggtttt tttgtttgca agcagcagat tacgcgcaga  10560
aaaaaaggat ctcaagaaga tcctttgatc ttttctacgg ggtctgacgc tcagtggaac  10620
gaaaactcac gttaagggat tttggtcatg agattatcaa aaaggatctt cacctagatc  10680
cttttaaatt aaaatgaag ttttaaatca atctaaagta tatatgagta aacttggtct   10740
gacagttacc aatgcttaat cagtgaggca cctatctcag cgatctgtct atttcgttca  10800
tccatagttg cctgactccc cgtcgtgtag ataactacga tacgggaggg cttaccatct  10860
```

```
ggccccagtg ctgcaatgat accgcgagac ccacgctcac cggctccaga tttatcagca   10920
ataaaccagc cagccggaag ggccgagcgc agaagtggtc ctgcaacttt atccgcctcc   10980
atccagtcta ttaattgttg ccgggaagct agagtaagta gttcgccagt taatagtttg   11040
cgcaacgttg ttggcattgc tacaggcatc gtggtgtcac gctcgtcgtt tggtatggct   11100
tcattcagct ccggttccca acgatcaagg cgagttacat gatcccccat gttgtgcaaa   11160
aaagcggtta gctccttcgg tcctccgatc gttgtcagaa gtaagttggc cgcagtgtta   11220
tcactcatgg ttatggcagc actgcataat tctcttactg tcatgccatc cgtaagatgc   11280
ttttctgtga ctggtgagta ctcaaccaag tcattctgag aatagtgtat gcggcgaccg   11340
agttgctctt gcccggcgtc aatacggat  ataccgcgc cacatagcag aactttaaaa   11400
gtgctcatca ttggaaaacg ttcttcgggg cgaaaactct caaggatctt accgctgttg   11460
agatccagtt cgatgtaacc cactcgtgca cccaactgat cttcagcatc ttttactttc   11520
accagcgttt ctgggtgagc aaaaacagga aggcaaaatg ccgcaaaaaa gggaataagg   11580
gcgacacgga aatgttgaat actcatactc ttccttttc  aatattattg aagcatttat   11640
cagggttatt gtctcatgag cggatacata tttgaatgta tttagaaaaa taaacaaata   11700
ggggttccgc gcacatttcc ccgaaaagtg ccacctgacg tctaagaaac cattattatc   11760
atgacattaa cctataaaaa taggcgtatc acgaggccct ttcgtctcgc gcgtttcggt   11820
gatgacggtg aaaacctctg acacatgcag ctcccggaga cggtcacagc ttgtctgtaa   11880
gcggatgccg ggagcagaca gcccgtcag  ggcgcgtcag cgggtgttgg cgggtgtcgg   11940
ggctggctta actatgcggc atcagagcag attgtactga gagtgcacca tatgcggtgt   12000
gaaataccgc acagatgcgt aaggagaaaa taccgcatca ggcgccattc gccattcagg   12060
ctgcgcaact gttgggaagg gcgatcggtg cgggcctctt cgctattacg ccagctggcg   12120
aaagggggat gtgctgcaag gcgattaagt tgggtaacgc cagggttttc ccagtcacga   12180
cgttgtaaaa cgacggccag tgaattggat ttaggtgaca ctata              12225
```

<210> SEQ ID NO 2
<211> LENGTH: 74
<212> TYPE: DNA
<213> ORGANISM: Artificial Sequence
<220> FEATURE:
<223> OTHER INFORMATION: Psyn II promoter

<400> SEQUENCE: 2

```
taaaaaatga aaaatatttc taatttatag gacggttttg attttctttt tttctatgct   60
ataaataata aata                                                    74
```

<210> SEQ ID NO 3
<211> LENGTH: 2214
<212> TYPE: DNA
<213> ORGANISM: Artificial Sequence
<220> FEATURE:
<223> OTHER INFORMATION: ADA envelope truncated

<400> SEQUENCE: 3

```
atgaaagtga agggatcag gaagaattat cagcacttgt ggaatggggg catcatgctc     60
cttgggatgt tgatgatctg tagtgctgta gaaaatttgt gggtcacagt ttattatggg    120
gtacctgtgt ggaaagaagc aaccaccact ctatttgtg  catcagatgc taaagcatat    180
gatacagagg tacataatgt ttgggccaca catgcctgtg tacccacaga ccccaaccca    240
```

```
caagaagtag tattggaaaa tgtgacagaa aattttaaca tgtggaaaaa taacatggta      300
gaacagatgc atgaggatat aatcagttta tgggatcaaa gcctaaagcc atgtgtaaaa      360
ttaaccccac tctgtgttac tttaaattgc actgatttga ggaatgttac taatatcaat      420
aatagtagtg agggaatgag aggagaaata aaaaactgct ctttcaatat caccacaagc      480
ataagagata aggtgaagaa agactatgca cttttctata gacttgatgt agtaccaata      540
gataatgata atactagcta taggttgata aattgtaata cctcaaccat tacacaggcc      600
tgtccaaagg tatcctttga gccaattccc atacattatt gtaccccggc tggttttgcg      660
attctaaagt gtaaagacaa gaagttcaat ggaacagggc catgtaaaaa tgtcagcaca      720
gtacaatgta cacatggaat taggccagta gtgtcaactc aactgctgtt aaatggcagt      780
ctagcagaag aagaggtagt aattagatct agtaatttca cagacaatgc aaaaaacata      840
atagtacagt tgaaagaatc tgtagaaatt aattgtacaa gacccaacaa caatacaagg      900
aaaagtatac atataggacc aggaagagca ttttatacaa caggagaaat aataggagat      960
ataagacaag cacattgcaa cattagtaga acaaaatgga ataacacttt aaatcaaata     1020
gctacaaaat taaagaaaca atttgggaat aataaaacaa tagtctttaa tcaatcctca     1080
ggaggggacc cagaaattgt aatgcacagt tttaattgtg gaggggaatt cttctactgt     1140
aattcaacac aactgtttaa tagtacttgg aattttaatg gtacttggaa tttaacacaa     1200
tcgaatggta ctgaaggaaa tgacactatc acactcccat gtagaataaa acaaattata     1260
aatatgtggc aggaagtagg aaaagcaatg tatgcccctc ccatcagagg acaaattaga     1320
tgctcatcaa atattacagg gctaatatta acaagagatg gtggaactaa cagtagtggg     1380
tccgagatct tcagacctgg gggaggagat atgagggaca attggagaag tgaattatat     1440
aaatataaag tagtaaaaat tgaaccatta ggagtagcac ccaccaaggc aaaaagaaga     1500
gtggtgcaga gagaaaaaag agcagtggga acgataggag ctatgttcct tgggttcttg     1560
ggagcagcag gaagcactat gggcgcagcg tcaataacgc tgacggtaca ggccagacta     1620
ttattgtctg gtatagtgca acagcagaac aatttgctga gggctattga ggcgcaacag     1680
catctgttgc aactcacagt ctggggcatc aagcagctcc aggcaagagt cctggctgtg     1740
gaaagatacc taagggatca acagctccta gggatttggg gttgctctgg aaaactcatc     1800
tgcaccactg ctgtgccttg gaatgctagt tggagtaata aaactctgga tatgatttgg     1860
gataacatga cctggatgga gtgggaaaga gaaatcgaaa attacacagg cttaatatac     1920
accttaattg aggaatcgca gaaccaacaa gaaaagaatg aacaagactt attagcatta     1980
gataagtggg caagtttgtg gaattggttt gacatatcaa attggctgtg gtatgtaaaa     2040
atcttcataa tgatagtagg aggcttgata ggtttaagaa tagtttttac tgtactttct     2100
atagtaaata gagttaggca gggatactca ccattgtcat ttcagaccca cctcccagcc     2160
ccgaggggac ccgacaggcc cgaaggaatc gaagaagaag tggagacaga agac           2214
```

<210> SEQ ID NO 4
<211> LENGTH: 70
<212> TYPE: DNA
<213> ORGANISM: Artificial Sequence
<220> FEATURE:
<223> OTHER INFORMATION: PmH5 promoter

<400> SEQUENCE: 4

```
aaaaattgaa ataaaataca aaggttcttg agggttgtgt taaattgaaa gcgagaaata       60
atcataaata                                                              70
```

-continued

<210> SEQ ID NO 5
<211> LENGTH: 3479
<212> TYPE: DNA
<213> ORGANISM: Artificial Sequence
<220> FEATURE:
<223> OTHER INFORMATION: HXB2 gag pol

<400> SEQUENCE: 5

| | |
|---|---|
| atgggtgcga gagcgtcagt attaagcggg ggagaattag atcgatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa aagcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaaa gaaccctttta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt cagggagtag gaggacccgg ccataaggca | 1080 |
| agagttttgg ctgaagcaat gagccaagta acaaattcag ctaccataat gatgcagaga | 1140 |
| ggcaattttta ggaaccaaag aaagattgtt aagtgtttca attgtggcaa agaagggcac | 1200 |
| acagccagaa attgcagggc ccctaggaaa aagggctgtt ggaaatgtgg aaaggaagga | 1260 |
| caccaaatga aagattgtac tgagagacag gctaatttttt tagggaagat ctggccttcc | 1320 |
| tacaagggaa ggccagggaa ttttcttcag agcagaccag agccaacagc cccaccagaa | 1380 |
| gagagcttca ggtctggggt agagacaaca actcccccctc agaagcagga gccgatagac | 1440 |
| aaggaactgt atcctttaac ttccctcaga tcactctttg gcaacgaccc ctcgtcacaa | 1500 |
| taaagatagg ggggcaacta aaggaagctc tattagatac aggagcagat gatacagtat | 1560 |
| tagaagaaat gagtttgcca ggaagatgga accaaaaaat gataggggga attggaggtt | 1620 |
| ttatcaaagt aagacagtat gatcagatac tcatagaaat ctgtggacat aaagctatag | 1680 |
| gtacagtatt agtaggacct acacctgtca acataattgg aagaaatctg ttgactcaga | 1740 |
| ttggttgcac tttaaatttt cccattagcc ctattgagac tgtaccagta aaattaaagc | 1800 |
| caggaatgga tggcccaaaa gttaaacaat ggccattgac agaagaaaaa ataaaagcat | 1860 |
| tagtagaaat ttgtacagaa atggaaaagg aagggaaaat ttcaaaaatt gggcctgaga | 1920 |
| atccatacaa tactccagta tttgccataa agaaaaaaga cagtactaaa tggaggaaat | 1980 |
| tagtagattt cagagaactt aataagagaa ctcaagactt ctgggaagtt caattaggaa | 2040 |

-continued

```
taccacatcc cgcagggtta aaaaagaaaa aatcagtaac agtactggat gtgggtgatg    2100
catatttttc agttccctta gatgaagact tcaggaagta tactgcattt accataccta    2160
gtataaacaa tgagacacca gggattagat atcagtacaa tgtgcttcca cagggatgga    2220
aaggatcacc agcaatattc caaagtagca tgacaaaaat cttagagcct tttaaaaaac    2280
aaaatccaga catagttatc tatcaataca tgaacgattt gtatgtagga tctgacttag    2340
aaatagggca gcatagaaca aaaatagagg agctgagaca acatctgttg aggtggggac    2400
ttaccacacc agacaaaaaa catcagaaag aacctccatt cctttggatg ggttatgaac    2460
tccatcctga taaatggaca gtacagccta tagtgctgcc agaaaaagac agctggactg    2520
tcaatgacat acagaagtta gtggggaaat tgaataccgc aagtcagatt tacccaggga    2580
ttaaagtaag gcaattatgt aaactcctta gaggaaccaa agcactaaca gaagtaatac    2640
cactaacaga agaagcagag ctagaactgg cagaaaacag agagattcta aaagaaccag    2700
tacatggagt gtattatgac ccatcaaaag acttaatagc agaaatacag aagcaggggc    2760
aaggccaatg gacatatcaa atttatcaag agccatttaa aaatctgaaa acaggaaaat    2820
atgcaagaat gagggggtgcc cacactaatg atgtaaaaca attaacagag gcagtgcaaa    2880
aaataaccac agaaagcata gtaatatggg gaaagactcc taaatttaaa ctacccatac    2940
aaaaggaaac atgggaaaca tggtggacag agtattggca agccacctgg attcctgagt    3000
gggagtttgt taatacccct cctttagtga aattatggta ccagttagag aaagaaccca    3060
tagtaggagc agaaaccttc tatgtagatg gggcagctaa cagggagact aaattaggaa    3120
aagcaggata tgttactaac aaaggaagac aaaaggttgt ccccctaact aacacaacaa    3180
atcagaaaac tcagttacaa gcaatttatc tagctttgca ggattcagga ttagaagtaa    3240
acatagtaac agactcacaa tatgcattag gaatcattca agcacaacca gataaaagtg    3300
aatcagagtt agtcaatcaa ataatagagc agttaataaa aaaggaaaag gtctatctgg    3360
catgggtacc agcacacaaa ggaattggag gaaatgaaca agtagataaa ttagtcagtg    3420
ctggaatcag gaaaatacta ttttagatg gaatagataa ggcccaagat gaacattag     3479
```

<210> SEQ ID NO 6
<211> LENGTH: 9
<212> TYPE: PRT
<213> ORGANISM: Artificial Sequence
<220> FEATURE:
<223> OTHER INFORMATION: Gag-CM9 peptide

<400> SEQUENCE: 6

Cys Thr Pro Tyr Asp Ile Asn Gln Met
1               5

<210> SEQ ID NO 7
<211> LENGTH: 8
<212> TYPE: PRT
<213> ORGANISM: Artificial Sequence
<220> FEATURE:
<223> OTHER INFORMATION: ovalbumin peptide

<400> SEQUENCE: 7

Ser Ile Ile Asn Phe Glu Lys Leu
1               5

<210> SEQ ID NO 8
<211> LENGTH: 20
<212> TYPE: DNA
<213> ORGANISM: Artificial Sequence

```
<220> FEATURE:
<223> OTHER INFORMATION: synthetic probe

<400> SEQUENCE: 8
ctgtctgcgt catttggtgc                                              20

<210> SEQ ID NO 9
<211> LENGTH: 4
<212> TYPE: PRT
<213> ORGANISM: Artificial Sequence
<220> FEATURE:
<223> OTHER INFORMATION: endocytosis motif
<220> FEATURE:
<221> NAME/KEY: VARIANT
<222> LOCATION: (1)...(4)
<223> OTHER INFORMATION: Xaa = Any Amino Acid
<220> FEATURE:
<221> NAME/KEY: VARIANT
<222> LOCATION: (1)...(4)
<223> OTHER INFORMATION: Xaa = Any Amino Acid

<400> SEQUENCE: 9

Tyr Xaa Xaa Leu
 1

<210> SEQ ID NO 10
<211> LENGTH: 93
<212> TYPE: DNA
<213> ORGANISM: Artificial Sequence
<220> FEATURE:
<223> OTHER INFORMATION: m7.5 promoter

<400> SEQUENCE: 10 cgcttttat agtaagtttt tcacccataa ataataaata caataattaa tttctcgtaa    60
aaattgaaaa actattctaa tttattgcac ggt                                93

<210> SEQ ID NO 11
<211> LENGTH: 74
<212> TYPE: DNA
<213> ORGANISM: Artificial Sequence
<220> FEATURE:
<223> OTHER INFORMATION: Psyn III  promoter

<400> SEQUENCE: 11
taaaaattga aaaatatattc taatttatag gacggttttg attttctttt tttctatact  60
ataaataata aata                                                    74

<210> SEQ ID NO 12
<211> LENGTH: 74
<212> TYPE: DNA
<213> ORGANISM: Artificial Sequence
<220> FEATURE:
<223> OTHER INFORMATION: Psyn IV promoter

<400> SEQUENCE: 12
taaaaattga aaactattc taatttatag gacggttttg attttctttt tttctatact   60
ataaataata aata                                                    74

<210> SEQ ID NO 13
<211> LENGTH: 75
<212> TYPE: DNA
<213> ORGANISM: Artificial Sequence
<220> FEATURE:
<223> OTHER INFORMATION: Psyn V promoter

<400> SEQUENCE: 13
```
aaaaaatgat aaagtaggtt cagtttatt gctggtttaa aatcacgctt tcgagtaaaa    60
actacgaata taaat                                                    75

<210> SEQ ID NO 14
<211> LENGTH: 7
<212> TYPE: DNA
<213> ORGANISM: Artificial Sequence
<220> FEATURE:
<223> OTHER INFORMATION: early transcription termination signal
<220> FEATURE:
<221> NAME/KEY: misc_feature
<222> LOCATION: (1)...(7)
<223> OTHER INFORMATION: n = A,T,C or G

<400> SEQUENCE: 14 tttttnt                                                              7

<210> SEQ ID NO 15
<211> LENGTH: 53
<212> TYPE: DNA
<213> ORGANISM: Artificial Sequence
<220> FEATURE:
<223> OTHER INFORMATION: 5' primer

<400> SEQUENCE: 15
gcgccccggg tcgacgcggc cgcgccatga gagtgagggg gatacagagg aac           53

<210> SEQ ID NO 16
<211> LENGTH: 57
<212> TYPE: DNA
<213> ORGANISM: Artificial Sequence
<220> FEATURE:
<223> OTHER INFORMATION: 3' primer

<400> SEQUENCE: 16
gcgccccggg cggccgcaga aaaattagcc ttgctctcca ccttcttctt ctattcc       57

<210> SEQ ID NO 17
<211> LENGTH: 56
<212> TYPE: DNA
<213> ORGANISM: Artificial Sequence
<220> FEATURE:
<223> OTHER INFORMATION: 5' primer

<400> SEQUENCE: 17
gcgccccggg tcgacgcggc cgcgccatga gagtgaggga gacagtgagg aattat        56

<210> SEQ ID NO 18
<211> LENGTH: 57
<212> TYPE: DNA
<213> ORGANISM: Artificial Sequence
<220> FEATURE:
<223> OTHER INFORMATION: 3' primer

<400> SEQUENCE: 18
gcgccccggg cggccgcaga aaaattagcc ttgctctcca ccttcttctt ctattcc       57

<210> SEQ ID NO 19
<211> LENGTH: 56
<212> TYPE: DNA
<213> ORGANISM: Artificial Sequence
<220> FEATURE:
<223> OTHER INFORMATION: 5' primer

<400> SEQUENCE: 19

```
gcgccccggg tcgacgcggc cgcgccatga gagtgagggg gatagagagg aattat        56
```

<210> SEQ ID NO 20
<211> LENGTH: 51
<212> TYPE: DNA
<213> ORGANISM: Artificial Sequence
<220> FEATURE:
<223> OTHER INFORMATION: 3' primer

<400> SEQUENCE: 20

```
gcgccccggg cggccgcaga aaaattagcc ttgctctcca ccttctcctt c             51
```

<210> SEQ ID NO 21
<211> LENGTH: 40
<212> TYPE: DNA
<213> ORGANISM: Artificial Sequence
<220> FEATURE:
<223> OTHER INFORMATION: 5' primer

<400> SEQUENCE: 21

```
gcgccccggg gccatgggtg cgagagcgtc agtattaagc                          40
```

<210> SEQ ID NO 22
<211> LENGTH: 49
<212> TYPE: DNA
<213> ORGANISM: Artificial Sequence
<220> FEATURE:
<223> OTHER INFORMATION: 3' primer

<400> SEQUENCE: 22

```
gcgccccggg agaaaaatta gaaggtttct gctcctacta tgggttcct                49
```

<210> SEQ ID NO 23
<211> LENGTH: 40
<212> TYPE: DNA
<213> ORGANISM: Artificial Sequence
<220> FEATURE:
<223> OTHER INFORMATION: 5' primer

<400> SEQUENCE: 23

```
gcgccccggg gccatgggtg cgagagcgtc agtgttaagt                          40
```

<210> SEQ ID NO 24
<211> LENGTH: 49
<212> TYPE: DNA
<213> ORGANISM: Artificial Sequence
<220> FEATURE:
<223> OTHER INFORMATION: 3' primer

<400> SEQUENCE: 24

```
gcgccccggg agaaaaatta gaaagtttct gctcctacta tgggttcct                49
```

<210> SEQ ID NO 25
<211> LENGTH: 30
<212> TYPE: DNA
<213> ORGANISM: Artificial Sequence
<220> FEATURE:
<223> OTHER INFORMATION: HIV env C-terminal truncation sequence

<400> SEQUENCE: 25

```
ggaatagaag aagaaggtgg agagcaaggc                                     30
```

<210> SEQ ID NO 26
<211> LENGTH: 10
<212> TYPE: PRT
<213> ORGANISM: Artificial Sequence

```
<220> FEATURE:
<223> OTHER INFORMATION: HIV env C-terminal truncation sequence

<400> SEQUENCE: 26

Gly Ile Glu Glu Glu Gly Gly Glu Gln Gly
 1               5                  10

<210> SEQ ID NO 27
<211> LENGTH: 30
<212> TYPE: DNA
<213> ORGANISM: Artificial Sequence
<220> FEATURE:
<223> OTHER INFORMATION: HIV env C-terminal truncation sequence

<400> SEQUENCE: 27
ggaatagaag aagaaggtgg agagcaaggc                                      30

<210> SEQ ID NO 28
<211> LENGTH: 10
<212> TYPE: PRT
<213> ORGANISM: Artificial Sequence
<220> FEATURE:
<223> OTHER INFORMATION: HIV env C-terminal truncation sequence

<400> SEQUENCE: 28

Gly Ile Glu Glu Glu Gly Gly Glu Gln Gly
 1               5                  10

<210> SEQ ID NO 29
<211> LENGTH: 30
<212> TYPE: DNA
<213> ORGANISM: Artificial Sequence
<220> FEATURE:
<223> OTHER INFORMATION: HIV env C-terminal truncation sequence

<400> SEQUENCE: 29
ggaacagaag gagaaggtgg agagcaaggc                                      30

<210> SEQ ID NO 30
<211> LENGTH: 10
<212> TYPE: PRT
<213> ORGANISM: Artificial Sequence
<220> FEATURE:
<223> OTHER INFORMATION: HIV env C-terminal truncation sequence

<400> SEQUENCE: 30

Gly Thr Glu Gly Glu Gly Gly Glu Gln Gly
 1               5                  10

<210> SEQ ID NO 31
<211> LENGTH: 30
<212> TYPE: DNA
<213> ORGANISM: Artificial Sequence
<220> FEATURE:
<223> OTHER INFORMATION: HIV gagpol C-terminal truncation sequence

<400> SEQUENCE: 31
aaggaaccca tagtaggagc agaaaccttc                                      30

<210> SEQ ID NO 32
<211> LENGTH: 10
<212> TYPE: PRT
<213> ORGANISM: Artificial Sequence
<220> FEATURE:
<223> OTHER INFORMATION: HIV gagpol C-terminal truncation sequence

<400> SEQUENCE: 32
```

Lys Glu Pro Ile Val Gly Ala Glu Thr Phe
 1               5                  10

<210> SEQ ID NO 33
<211> LENGTH: 30
<212> TYPE: DNA
<213> ORGANISM: Artificial Sequence
<220> FEATURE:
<223> OTHER INFORMATION: HIV gagpol C-terminal truncation sequence

<400> SEQUENCE: 33
aaggaaccca tagtaggagc agaaactttc                                    30

<210> SEQ ID NO 34
<211> LENGTH: 10
<212> TYPE: PRT
<213> ORGANISM: Artificial Sequence
<220> FEATURE:
<223> OTHER INFORMATION: HIV gagpol C-terminal truncation sequence

<400> SEQUENCE: 34

Lys Glu Pro Ile Val Gly Ala Glu Thr Phe
 1               5                  10

<210> SEQ ID NO 35
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 35
agaatcgaag gagaaggtgg agagcaagac                                    30

<210> SEQ ID NO 36
<211> LENGTH: 11
<212> TYPE: PRT
<213> ORGANISM: Artificial Sequence
<220> FEATURE:
<223> OTHER INFORMATION: HIV envelope C-terminal truncation sequence

<400> SEQUENCE: 36

Gly Arg Ile Glu Gly Glu Gly Gly Glu Gln Asp
 1               5                  10

<210> SEQ ID NO 37
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 37
agaatcgaag gagaaggtgg agagcaagac                                    30

<210> SEQ ID NO 38
<211> LENGTH: 11
<212> TYPE: PRT
<213> ORGANISM: Artificial Sequence
<220> FEATURE:
<223> OTHER INFORMATION: HIV envelope C-terminal truncation sequence

<400> SEQUENCE: 38

Gly Arg Ile Glu Gly Glu Gly Gly Glu Gln Asp
 1               5                  10

<210> SEQ ID NO 39
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 39
agaatcgaag gagaaggtgg agagcaagac                                    30

<210> SEQ ID NO 40
<211> LENGTH: 11
<212> TYPE: PRT
<213> ORGANISM: Artificial Sequence
<220> FEATURE:
<223> OTHER INFORMATION: HIV envelope C-terminal truncation sequence

<400> SEQUENCE: 40

Gly Arg Ile Glu Gly Glu Gly Gly Glu Gln Asp
 1               5                  10

<210> SEQ ID NO 41
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 41
agaatcgaag gagaaggtgg agagcaagac                                    30

<210> SEQ ID NO 42
<211> LENGTH: 11
<212> TYPE: PRT
<213> ORGANISM: Artificial Sequence
<220> FEATURE:
<223> OTHER INFORMATION: HIV envelope C-terminal truncation sequence

<400> SEQUENCE: 42

Gly Arg Ile Glu Gly Glu Gly Gly Glu Gln Asp
 1               5                  10

<210> SEQ ID NO 43
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 43
gacatatcaa attggctgtg gtatataaga                                    30

<210> SEQ ID NO 44
<211> LENGTH: 10
<212> TYPE: PRT
<213> ORGANISM: Artificial Sequence
<220> FEATURE:
<223> OTHER INFORMATION: HIV envelope C-terminal truncation sequence

<400> SEQUENCE: 44

Asp Ile Ser Asn Trp Leu Trp Tyr Ile Arg
 1               5                  10

<210> SEQ ID NO 45
<211> LENGTH: 27
<212> TYPE: DNA

```
<213> ORGANISM: Artificial Sequence
<220> FEATURE:
<223> OTHER INFORMATION: HIV gagpol C-terminal truncation sequence

<400> SEQUENCE: 45
gaccccatag caggagcaga gactttc                                        27

<210> SEQ ID NO 46
<211> LENGTH: 10
<212> TYPE: PRT
<213> ORGANISM: Artificial Sequence
<220> FEATURE:
<223> OTHER INFORMATION: HIV gagpol C-terminal truncation sequence

<400> SEQUENCE: 46

Lys Asp Pro Ile Ala Gly Ala Glu Thr Phe
 1               5                  10

<210> SEQ ID NO 47
<211> LENGTH: 30
<212> TYPE: DNA
<213> ORGANISM: Artificial Sequence
<220> FEATURE:
<223> OTHER INFORMATION: HIV envelope C-terminal truncation sequence

<400> SEQUENCE: 47
ggaatcgaag aagaaggtgg agagcaagac                                     30

<210> SEQ ID NO 48
<211> LENGTH: 10
<212> TYPE: PRT
<213> ORGANISM: Artificial Sequence
<220> FEATURE:
<223> OTHER INFORMATION: HIV envelope C-terminal truncation sequence

<400> SEQUENCE: 48

Gly Ile Glu Glu Glu Gly Gly Glu Gln Asp
 1               5                  10

<210> SEQ ID NO 49
<211> LENGTH: 31
<212> TYPE: DNA
<213> ORGANISM: Artificial Sequence
<220> FEATURE:
<223> OTHER INFORMATION: HIV gagpol C-terminal truncation sequence

<400> SEQUENCE: 49
aaagaaccca tagtaggagc agaaactttc t                                   31

<210> SEQ ID NO 50
<211> LENGTH: 10
<212> TYPE: PRT
<213> ORGANISM: Artificial Sequence
<220> FEATURE:
<223> OTHER INFORMATION: HIV gagpol C-terminal truncation sequence

<400> SEQUENCE: 50

Lys Glu Pro Ile Val Gly Ala Glu Thr Phe
 1               5                  10

<210> SEQ ID NO 51
<211> LENGTH: 3068
<212> TYPE: DNA
<213> ORGANISM: HIV-1

<400> SEQUENCE: 51
```

```
atgggtgcga gagcgtcagt attaagcggg ggaaaattag atgaatggga aaaaattcgg    60
ttacggccag ggggaaacaa aaatataga ttaaaacatt tagtatgggc aagcagggag    120
ctagaacgat ttgcacttaa tcctggtctt ttagaaacat cagaaggctg tagacaaata   180
atagaacagc tacaaccatc tattcagaca ggatcagagg aacttaaatc attacataat   240
acagtagtaa ccctctattg tgtacatgaa aggataaagg tagcagatac caaggaagct   300
ttagataaga taaaggaaga acaaaccaaa agtaagaaaa agcacagca agcaacagct    360
gacagcagcc aggtcagcca aaattatcct atagtacaaa acctacaggg gcaaatggta   420
caccagtcct tatcacctag gactttgaat gcatgggtaa aagtaataga gagaaggct    480
ttcagcccag aagtaatacc catgttttca gcattatcag aaggagccac cccaacagat   540
ttaaacacca tgctaaacac agtggggggga catcaagcag ccatgcaaat gttaaaagag   600
actatcaatg aggaagctgc agaatgggat aggctacatc cagtgcctgc agggcctgtt   660
gcaccaggcc aaatgagaga accaagggga agtgatatag caggaactac cagtacccctt  720
caggaacaaa taggatggat gacaagcaat ccacctatcc cagtaggaga atctataaa    780
agatggataa tcctaggatt aaataaaata gtaagaatgt atagccctgt cagcattttg   840
gacataagac aaggaccaaa ggaacccttt agagactatg tagatcggtt ctataaaact   900
ctacgagccg agcaagcttc acaggatgta aaaaattgga tgactgaaac cttgttagtc   960
caaaatgcga atccagattg taaaactatc ttaaaagcat tgggaccagc ggctacatta  1020
gaagaaatga tgacagcatg tcagggagtg ggggggaccca gtcataaagc aagagttttg  1080
gctgaggcaa tgagccaagc atcaaacaca aatgctgtta taatgatgca gagggcaat   1140
ttcaagggca agaaaatcat taagtgttc aactgtggca agaaggaca cctagcaaaa   1200
aattgtaggg ctcctaggaa aagaggctgt tggaaatgtg gaaaggaagg gcaccaaatg  1260
aaagattgta atgaaagaca ggctaatttt ttagggagaa tttggccttc ccacaagggg  1320
aggccaggga atttccttca gagcagacca gagccaacag ccccaccagc agagagcttc  1380
gggtttgggg aagagataac accctcccag aaacaggagg ggaaagagga gctgtatcct  1440
tcagcctccc tcaaatcact ctttggcaac gacccctagt cacaataaaa ataggggac   1500
agctaaagga agctctatta gatacaggag cagatgatac agtagtagaa gaatgaatt   1560
tgccaggaaa atggaaacca aaaatgatag ggggaattgg gggctttatc aaagtaagac  1620
agtatgatca atactcgta gaaatctatg gatataaggc tacaggtaca gtattagtag   1680
gacctacacc tgtcaacata attggaagaa atttgttgac tcagattggt tgcactttaa  1740
attttccaat tagtcctatt gaaactgtac cagtaaaatt aaagtcaggg atggatggtc  1800
caagagttaa acaatggcca ttgacagaag agaaaataaa agcactaata gaaatttgta  1860
cagaaatgga aaaggaagga aaactttcaa gaattggacc tgaaaatcca tacaatactc  1920
caatatttgc cataaagaaa aaagacagta ctaagtggag aaaattagta gatttcagag  1980
aacttaataa gagaactcaa gatttctggg aagttcaact aggaatacca catcctgcag  2040
ggctaaaaaa gaaaaaatca gtaacagtac tggaggtggg tgatgcatat ttttcagttc  2100
ccttatatga agactttaga aaatacactg cattcaccat acctagtata aacaatgaga  2160
caccaggaat tagatatcag tacaatgtgc ttccacaagg atggaaagga tcaccggcaa  2220
tattccaaag tagcatgaca aaaatttag aaccttttag aaaacaaaat ccagaagtgg   2280
ttatctacca atacatggac gatttgtatg taggatctga cttagaaata gggcagcata  2340
gaataaaaat agaggaatta agggacacc tattgaagtg ggatttacc acaccagaca   2400
```

-continued

```
aaaatcatca gaaggaacct ccatttcttt ggatgggtta tgaactccat cctgataaat    2460
ggacagtaca gcctataaaa ctgccagaaa agaaagctg gactgtcaat gatctgcaga     2520
agttagtggg gaaattaaat tgggcaagtc aaatttattc aggaattaaa gtaagacaat    2580
tatgcaaatg ccttagggga accaaagcac tgacagaagt agtaccactg acagaagaag    2640
cagaattaga actggcagaa acagggaac ttctaaaaga aacagtacat ggagtgtatt     2700
atgacccatc aaaagactta atagcagaaa tacagaaaca agggcaagac caatggacat    2760
atcaaattta tcaagaacaa tataaaaatt tgaaaacagg aaagtatgca agaggagga    2820 gtacccacac taatgatgta aacaattaa cagaggcagt gcaaaaaata gcccaagaat     2880
gtatagtgat atggggaaag actcctaaat tcagactacc catacaaaag gaaacatggg    2940
aaacatggtg gacagagtat tggcaggcca cctggattcc tgagtgggag tttgtcaata    3000
cccctccctt ggttaaatta tggtaccagt tagagaagga acccatagta ggagcagaaa    3060
ccttctaa                                                             3068
```

<210> SEQ ID NO 52
<211> LENGTH: 3080
<212> TYPE: DNA
<213> ORGANISM: HIV-1

<400> SEQUENCE: 52

```
atgggtgcga gagcgtcagt gttaagtggg ggaaaattag atgaatggga aagaattcgg      60
ttacggccag ggggaaacaa agatataaa ctaaaacata gtatgggc aagcagggag        120 ctagagcgat ttgcacttaa tcctggcctt ttagaaacat cagaaggctg taaacaaata    180
ttgggacagc tacaaccagc tattcagaca ggatcagaag aacttaaatc attatataat    240
acagtagcaa ccctctattg tgtacatgag aggctaaagg taacagacac caaggaagct    300
ttagacaaaa tagaggaaga acaaaccaaa agtaagaaaa agcacagca agcaacagct    360 gacacaaaaa acagcagcca ggtcagccaa aattatccta gtacaaaaa cctacagggg    420 caaatggtac accaggctat atcacctaga acgttaacg catgggtaaa agtaatagag    480
gagaaggctt tcagcccaga agtaataccc atgttttcag cattatcaga aggagccacc    540
ccacaagatt taaacaccat gctaaacaca gtggggggac atcaggcagc catgcagatg    600
ttaaaagaga ccatcaatga ggaagctgca gaatgggata ggttacatcc agtacatgca    660
gggcctattg caccaggaca aatgagagaa ccaacaggaa gtgatatagc aggaactact    720
agtacccttc aggaacaaat aggatggatg accagcaatc cacctatccc agtaggagaa    780
atctataaaa gatggataat cctaggatta aataaaatag taaggatgta tagccctgtc    840
agtattttgg acataaaaca agggccaaag gaacccttta gagactatgt agatcggttc    900
tataaaactc taagggccga gcaagcttca caggaggtaa aaggttggat gaccgaaacc    960
ttgttggtcc aaaatgcaaa cccagattgt aaaaccatct aaaagcatt gggaccagcg    1020 gctacattag aagaaatgat gacagcatgt caggagtgg ggggacccgg tcataaagca    1080
agagttttgg ctgaggcaat gagtcaagtc tcaacaaata ctgctataat gatgcagaga    1140
ggcaatttta agggcccaaa gaaaagcatt aagtgtttta actgtggcaa agaaggtcac    1200
acagcaaaaa actgtagagc tcctaggaaa agggctgtt ggaaatgtgg aagggaagga    1260
catcaaatga aagattgcac tgaaagacag gctaattttt tagggaaaat ttggccttcc    1320
cacaagggaa ggccagggaa tttccttcag aacagaccag agccaacagc cccaccagaa    1380
```

```
gaaagcttcg ggtttgggga agagataaca ccctctcaga aacaggagaa gaaggacaag    1440
gagctgtatc ctgtagcttc cctcaaatca ctctttggca acgaccctt gtcacaataa     1500 agatagggg acagctaaag gaagctctac tagatacagg agcagatgat acagtattag     1560
aagaaataaa tttgccagga aaatggaaac caaaaatgat agggggaatt ggaggcttta    1620
tcaaagtaag acagtatgag caaatacttg tagaaatctg tggacagaaa gctataggta    1680
cagtattagt agggcctaca cctgtcaaca taattggaag aaatttgttg actcagattg    1740
gttgcacttt aaattttcca attagcccta ttgaaactgt accagtaaaa ttaaagccag    1800
ggatggacgg tccaaaagtt aaacaatggc cattgacaga agaaaggta aaagcactaa     1860 tagaaatttg tacagaaatg gaaaggaag gaaaatttc aagaattgga cctgaaaatc      1920
catacaatac tccaatattt gccataaga aaaaggacag tactaagtgg agaaaattag      1980
tagatttcag ggaacttaat aagagaactc aagacttctg ggaagttcaa ctaggaatac    2040
cacatcctgc ggggctaaaa aagaaaaat cagtaacagt actggaggtg ggtgatgcat     2100 attttttcagt tcccttatat gaagatttta gaaaatatac tgcattcacc atacctagta    2160
taaacaatga acaccagga attagatatc agtacaatgt gcttccacaa gggtggaaag     2220
gatcaccagc aatattccaa agtagcatga caaaaatctt agaaccttt agaaaacaaa      2280 atccagaaat ggttatctat caatacatgg acgatttgta tgtaggatct gacttagaaa    2340
tagggcagca tagaataaaa atagaagaat taagggggaca cctgttgaag tggggattta    2400
ccacaccaga caaaaagcat cagaaagaac ctccatttct ttggatgggt tatgaactcc    2460
atcctgataa atggacagta cagtctataa aactgccaga acaagaaagc tggactgtca    2520
atgatataca gaagttagtg ggaaaattaa attgggcaag ccagatttat ccaggaatta    2580
aggtaagaca attatgcaaa tgcattaggg gtaccaaagc actgacagaa gtagtaccac    2640
tgacagaaga agcagaatta gaactggcag aaaacaggga aattctaaga gaaccagtac    2700
atggagtgta ttatgaccca tcaaaagact taatagcaga gatacagaaa caagggcaag    2760
accagtggac ataccaaatt tatcaagaac aatataaaaa tctgaaaaca ggaaagtatg    2820
caaaagtgag gggtacccac actaatgatg taaaacaatt aacagaggca gtacaaaaaa    2880
taacccaaga atgtatagtg atatgggaa agcctcctaa atttagacta cccatacaaa     2940
aagaaacatg gaaatatgg tggacagagt attggcaggc cacctggatt cctgagtggg     3000
agtttgtcaa tacccctcct ttagttaaat tatggtacca attagagaag gaacccatag    3060
taggagcaga aactttctaa                                               3080
```

<210> SEQ ID NO 53
<211> LENGTH: 2181
<212> TYPE: DNA
<213> ORGANISM: HIV-1

<400> SEQUENCE: 53

```
atgagagtga gggggataca gaggaactat caaaacttgt ggagatgggg caccttgctc      60
cttgggatgt tgatgatatg taaggctaca gaacagttgt gggtcacagt ttactatggg     120
gtacctgtgt ggaaagaagc aaccactact ctattttgtg catcagatgc taaatcatat    180
aaagaagaag cacataatat ctgggctaca catgcctgtg taccaacaga ccccaaccca     240
cgagaattaa aatagaaaa tgtcacagaa actttaaca tgtggaaaaa taacatggtg       300
gagcagatgc atgaggatat aatcagttta tgggatcaaa gcctaaaacc atgtgtaaaa    360
ttaaccccca ctctgtgtca ctttaaactgc actgaatgga ggaagaataa cactatcaat    420
```

-continued

```
gccaccagaa tagaaatgaa aaactgctct ttcaatctaa ccacagaaat aagagatagg    480
aaaaagcaag tgcatgcact tttctataaa cttgatgtgg taccaataga tgataataat    540
agtactaata ccagctatag gttaataaat tgtaatacct cagccattac acaggcgtgt    600
ccaaaggtaa cctttgagcc aattcccata cattattgtg ccccagctgg atatgcgatt    660
ctaaaatgta acaataagaa gttcaatggg acaggtccat gcgataatgt cagtacagta    720
cagtgtacac atggaattag gccagtagta tccactcaat tgttgttgaa tggcagtcta    780
gcagaagaag acataataat tagatctgag aatctcacaa ataatgctaa aatcataata    840
gtacagctta atgagtctgt aacaattaat tgcacaaggc cctacaacaa tacaagaaga    900
ggtgtacata taggaccagg gcgagcatac tatacaacag acataatagg agatataaga    960
caagcacatt gtaacattag tggagcagaa tggaataaga ctttacatcg ggtagctaaa   1020
aaattaagag acctatttaa aaagacaaca ataattttta accgtcctc cggaggggac   1080 ccagaaatta caacacacag ctttaattgt agaggggaat tcttctactg caatacaaca   1140
agactgttta atagcatatg gggaaataat agtacaggag ttgatgagag tataacactc   1200
ccatgcagaa taaaacaaat tataaacatg tggcagggag taggaaaagc aatgtatgcc   1260
cctcccattg aaggactaat cagctgctca tcaaatatta caggattact gttgacaaga   1320
gatggtggtg aagtaacag tagtcagaat gagaccttca gacctggagg gggagatatg   1380
agagacaatt ggagaagtga attatataaa tataaagtag taagaattga accattaggt   1440
ctagcaccct ccaaggcaaa aagaagagta gtagaaagag agaaaagagc aataggacta   1500
ggagctatgt tccttgggtt cttgggagca gcaggaagca cgatgggcgc agcgtcactg   1560
acgctgacgg tacaggccag acagctattg tctggtatag tgcaacagca aaacaatttg   1620
ctgaaggcta tagaggcgca acagcacctg ttgcaactca cagtctgggg cgttaaacag   1680
ctccaggcaa gagtcctggc tgtggaaagc tacctaaggg atcaacagct cctaggaatt   1740
tggggttgct ctggaaaaca catttgcacc accaatgtgc cctggaactc tagctggagt   1800
aataaaactc taaatcaat ttgggataac atgacctgga tggagtggga agagaaaatt   1860
gacaattaca cagggataat atacaattta cttgaagaat cgcaaaccca gcaagaaaga   1920
aatgaacaag accttattga attggaccaa tgggcaagtt tgtggaattg gtttagcata   1980
acaaaatggc tgtggtatat aaaaatattt ataatgatag taggaggctt gataggctta   2040
aggatagttt ttgctgtgct ttctatagta aatagagtta ggcagggata ttcacctctg   2100
tcgtttcaga ccctcctccc agccccgcgg ggacccgaca ggcccgaagg aatagaagaa   2160
gaaggtggag agcaaggcta a                                            2181
```

<210> SEQ ID NO 54
<211> LENGTH: 2214
<212> TYPE: DNA
<213> ORGANISM: HIV-1

<400> SEQUENCE: 54

```
atgagagtga gggagacagt gaggaattat cagcacttgt ggagatgggg catcatgctc    60
cttgggatgt taatgatatg tagtgctgca gaccagctgt gggtcacagt gtattatggg   120
gtacctgtgt ggaaagaagc aaccactact ctattttgtg catcagatgc taaagcacat   180
aaagcagagg cacataatat ctgggctaca catgcctgtg taccaacaga ccccaatcca   240
cgagaaataa tactaggaaa tgtcacagaa aactttaaca tgtggaagaa taacatggta   300
```

```
gagcagatgc atgaggatat aatcagttta tgggatcaaa gtctaaaacc atgtgtaaaa      360
ttaaccccac tctgtgttac tttaaactgc actacatatt ggaatggaac tttacagggg      420
aatgaaacta aagggaagaa tagaagtgac ataatgacat gctctttcaa tataaccaca      480
gaaataagag gtagaaagaa gcaagaaact gcacttttct ataaacttga tgtggtacca      540
ctagaggata aggatagtaa taagactacc aactatagca gctatagatt aataaattgc      600
aatacctcag tcgtgacaca ggcgtgtcca aaagtaacct ttgagccaat tcccatacat      660
tattgtgccc cagctggatt tgcgattctg aaatgtaata ataagacgtt caatggaacg      720
ggtccatgca aaatgtcag cacagtacag tgtacacatg gaattaggcc agtagtgtca      780
actcaactgt tgttgaatgg cagtctagca gaagaagaga taataattag atctgaaaat      840
atcacaaata atgcaaaaac cataatagta cagcttaatg agtctgtaac aattgattgc      900
ataaggccca caacaatac aagaaaaagt atacgcatag gaccagggca agcactctat      960
acaacagaca taatagggaa tataagacaa gcacattgta atgttagtaa agtaaaatgg     1020
ggaagaatgt taaaaggggt agctgaaaaa ttaaaagacc ttcttaacca gacaaagaac     1080
ataacttttg aaccatcctc aggaggggac ccagaaatta caacacacag ctttaattgt     1140
ggaggggaat tcttctactg caatacatca ggactattta tgggagtct gcttaatgag      1200 cagtttaatg agacatcaaa tgatactctc acactccaat gcagaataaa acaaattata     1260
aacatgtggc aaggagtagg aaaagcaatg tatgcccctc ccattgcagg accaatcagc     1320
tgttcatcaa atattacagg actattgttg acaagagatg gtggtaatac tggtaatgat     1380
tcagagatct tcagacctgg agggggagat atgagagaca attggagaag tgaattatac     1440
aaatataaag tagtaagaat tgaaccaatg ggtctagcac ccaccagggc aaaaagaaga     1500
gtggtggaaa gagaaaaaag agcaatagga ctgggagcta tgttccttgg gttcttggga     1560
gcggcaggaa gcacgatggg cgcagcgtca ctgacgctga cggtacaggc cagacagtta     1620
ttgtctggta tagtgcaaca gcaaaacaat ttgctgagag ctatagaggc gcaacagcat     1680
ctgttgcaac tcacagtctg ggcattaaa cagctccagg caagagtcct ggctatggaa     1740
agctacctaa aggatcaaca gctcctagga atttggggtt gctctggaaa acacatttgc     1800
accactactg tgccctggaa ctctacctgg agtaatagat ctgtagagga gatttggaat     1860
aatatgacct ggatgcagtg ggaaagagaa attgagaatt acacaggttt aatatacacc     1920
ttaattgaag aatcgcaaac ccagcaagaa aagaatgaac aagaactatt gcaattggat     1980
aaatgggcaa gtttgtggaa ttggtttagt ataacaaaat ggctgtggta tataaaaata     2040
ttcataatga tagtaggagg cttaataggt ttaagaatag ttttgctgt gctttcttta     2100 gtaaatagag ttaggcaggg atattcacct ctgtcttttc agaccctcct cccagccccg     2160
aggggacccg acaggcccga aggaatagaa gaagaaggtg gagagcaagg ctaa           2214
```

<210> SEQ ID NO 55
<211> LENGTH: 2265
<212> TYPE: DNA
<213> ORGANISM: HIV-1

<400> SEQUENCE: 55

```
atgagagtga gggggataga gaggaattat cagcacttat ggtggagatg ggcaccatg       60 ctccttggga tattgatgat atgtagtgct gcagaacaat gtgggtcac agtttattat      120 ggggtacctg tgtggaaaga agcaaccact actctatttt gtgcatcaga tgctaaagca      180
tataaagcag aggcacacaa tatctgggct acacatgcct gtgtaccaac agaccccaac      240
```

```
ccacaagaaa tagtactaga aaatgtcaca gaaaacttta acatgtggaa aaatagcatg      300
gtggagcaga tgcatgagga tgtaatcagt ttatgggatc aaagcctaaa accatgtgta      360
aaattaaccc cactctgtgt cactttaaac tgcactaatg ccactgccac taatgccact      420
gccactagtc aaaatagcac tgatggtagt aataaaactg ttaacacaga cacaggaatg      480
aaaaactgct ctttcaatgt aaccacagat ctaaaagata agaagaggca agactatgca      540
cttttctata aacttgatgt ggtacgaata gatgataaga ataccaatgg tactaatacc      600
aactatagat taataaattg taatacctca gccattacac aagcgtgtcc aaagataacc      660
tttgagccaa ttcccataca ttattgtgcc ccagctggat atgcgattct aaaatgtaat      720
aataagacat tcaatgggac gggtccatgc aaaaacgtca gcacagtaca gtgtacacat      780
gggattaggc cagtagtgtc aactcaactg ttgttgaatg gcagtctagc agaggaagag      840
atagtaatta gatctgaaaa cctcacaaat aatgctaaaa ttataatagt acagcttaat      900
gaagctgtaa caattaattg cacaagaccc tccaacaata caagacgaag tgtacatata      960
ggaccagggc aagcaatcta ttcaacagga caaataatag gagatataag aaaagcacat     1020
tgtaatatta gtagaaaaga atggaatagc accttacaac aggtaactaa aaaattagga     1080
agcctgttta acacaacaaa aataattttt aatgcatcct cgggagggga cccagaaatt     1140
acaacacaca gctttaattg taacggggaa ttcttctact gcaatacagc aggactgttt     1200
aatagtacat ggaacaggac aaatagtgaa tggataaata gtaaatgac aaataagaca     1260 gaagatgtaa atatcacact tcaatgcaga ataaaacaaa ttataaacat gtggcaggga     1320
gtaggaaaag caatgtatgc ccctcccgtt agtggaataa tccgatgttc atcaaatatt     1380
acaggactgt tgctgacaag agatggtggt ggtgcagata ataataggca gaatgagacc     1440
ttcagacctg ggggaggaga tatgagagac aattggagaa gtgaattata caaatataaa     1500
gtagtaagaa ttgaaccact aggtatagca cccaccaagg caaggagaag agtggtggaa     1560
agagaaaaaa gagcaatagg actgggagcc ttgttccttg ggttcttggg aacagcagga     1620
agcacgatgg gcgcagtgtc aatgacgctg acggtacagg ccagacaagt attgtctggt     1680
atagtgcaac agcaaaacaa tctgctgagg gctatagagg cgcaacagca tctgttgcaa     1740
ctcacagtct ggggcattaa acagctccag gcaagaatcc tggctgtgga agctacccta     1800
aaggatcaac agctcctagg aatttggggt tgctctggaa aacacatttg caccactaat     1860
gtgccctgga actctagctg gagtaataaa tctctaaatt atatttggaa taacatgacc     1920
tggatggagt gggaaaagga aattgacaat tacacagaat aatatacag cttaattgaa     1980 gtatcgcaaa tccagcaaga aaagaatgaa caagaactat tgaaattgga cagttgggca     2040
agtttgtgga attggtttag cataacaaaa tggctgtggt atataaaaat attcataatg     2100
atagtaggag gcttgatagg cttaagaata gtttttgctg tgctttcttt agtaaataga     2160
gttaggcagg gatactcacc tctgtcgttt cagacccttat cccagcctc gaggggaccc     2220 gacaggcccg aaggaacaga aggagaaggt ggagagcaag gctaa                     2265
```

<210> SEQ ID NO 56
<211> LENGTH: 5326
<212> TYPE: DNA
<213> ORGANISM: Artificial Sequence
<220> FEATURE:
<223> OTHER INFORMATION: MVA shuttle plasmid pLAS-1

<400> SEQUENCE: 56

| | |
|---|---|
| gaattcgttg gtggtcgcca tggatggtgt tattgtatac tgtctaaacg cgttagtaaa | 60 |
| acatggcgag gaaataaatc atataaaaaa tgatttcatg attaaaccat gttgtgaaaa | 120 |
| agtcaagaac gttcacattg gcggacaatc taaaaacaat acagtgattg cagatttgcc | 180 |
| atatatggat aatgcggtat ccgatgtatg caattcactg tataaaaga atgtatcaag | 240 |
| aatatccaga tttgctaatt tgataaagat agatgacgat gacaagactc ctactggtgt | 300 |
| atataattat tttaaaccta agatgccat tcctgttatt atatccatag gaaggatag | 360 |
| agatgtttgt gaactattaa tctcatctga taaagcgtgt gcgtgtatag agttaaattc | 420 |
| atataaagta gccattcttc ccatggatgt ttcctttttt accaaaggaa atgcatcatt | 480 |
| gattattctc ctgtttgatt tctctatcga tgcggcacct ctcttaagaa gtgtaaccga | 540 |
| taataatgtt attatatcta gacaccagcg tctacatgac gagcttccga gttccaattg | 600 |
| gttcaagttt tacataagta taaagtccga ctattgttct atattatata tggttgttga | 660 |
| tggatctgtg atgcatgcaa tagctgataa tagaacttac gcaaatatta gcaaaaatat | 720 |
| attagacaat actacaatta acgatgagtg tagatgctgt tattttgaac cacagattag | 780 |
| gattcttgat agagatgaga tgctcaatgg atcatcgtgt gatatgaaca gacattgtat | 840 |
| tatgatgaat ttacctgatg taggcgaatt tggatctagt atgttgggga aatatgaacc | 900 |
| tgacatgatt aagattgctc tttcggtggc tgggtaccag gcgcgccttt cattttgttt | 960 |
| ttttctatgc tataaatggt gagcaagggc gaggagctgt tcaccggggt ggtgcccatc | 1020 |
| ctggtcgagc tggacggcga cgtaaacggc cacaagttca gcgtgtccgg cgagggcgag | 1080 |
| ggcgatgcca cctacggcaa gctgaccctg aagttcatct gcaccaccgg caagctgccc | 1140 |
| gtgccctggc ccacccttcgt gaccaccctg acctacggcg tgcagtgctt cagccgctac | 1200 |
| cccgaccaca tgaagcagca cgacttcttc aagtccgcca tgcccgaagg ctacgtccag | 1260 |
| gagcgcacca tcttcttcaa ggacgacggc aactacaaga cccgcgccga ggtgaagttc | 1320 |
| gagggcgaca ccctggtgaa ccgcatcgag ctgaagggca tcgacttcaa ggaggacggc | 1380 |
| aacatcctgg ggcacaagct ggagtacaac tacaacagcc acaacgtcta tatcatggcc | 1440 |
| gacaagcaga agaacggcat caaggtgaac ttcaagatcc gccacaacat cgaggacggc | 1500 |
| agcgtgcagc tcgccgacca ctaccagcag aacacccca tcggcgacgg ccccgtgctg | 1560 |
| ctgcccgaca ccactacct gagcacccag tccgccctga gcaaagaccc caacgagaag | 1620 |
| cgcgatcaca tggtcctgct ggagttcgtg accgccgccg ggatcactct cggcatgcac | 1680 |
| gagctgtaca agtaagagct cggttgttga tggatctgtg atgcatgcaa tagctgataa | 1740 |
| tagaacttac gcaaatatta gcaaaaatat attagacaat actacaatta acgatgagtg | 1800 |
| tagatgctgt tattttgaac cacagattag gattcttgat agagatgaga tgctcaatgg | 1860 |
| atcatcgtgt gatatgaaca gacattgtat tatgatgaat ttacctgatg taggcgaatt | 1920 |
| tggatctagt atgttgggga aatatgaacc tgacatgatt aagattgctc tttcggtggc | 1980 |
| tggcggcccg ctcgaggccg ctggtaccca acctaaaaat tgaaataaa tacaaaggtt | 2040 |
| cttgagggtt gtgttaaatt gaaagcgaga aataatcata aataagcccg gggatcctct | 2100 |
| agagtcgacc tgcagggaaa gttttatagg tagttgatag aacaaaatac ataattttgt | 2160 |
| aaaaataaat cacttttat actaatatga cacgattacc aatactttg ttactaatat | 2220 |
| cattagtata cgctacacct tttcctcaga catctaaaaa aataggtgat gatgcaactt | 2280 |
| tatcatgtaa tcgaaataat acaaatgact acgttgttat gagtgcttgg tataaggagc | 2340 |
| ccaattccat tattctttta gctgctaaaa gcgacgtctt gtattttgat aattataca | 2400 |

```
aggataaaat atcttacgac tctccatacg atgatctagt tacaactatc acaattaaat    2460
cattgactgc tagagatgcc ggtacttatg tatgtgcatt ctttatgaca tcgcctacaa    2520
atgacactga taaagtagat tatgaagaat actccacaga gttgattgta aatacagata    2580
gtgaatcgac tatagacata atactatctg gatctacaca ttcaccagaa actagttaag    2640
cttgtctccc tatagtgagt cgtattagag cttggcgtaa tcatggtcat agctgtttcc    2700
tgtgtgaaat tgttatccgc tcacaattcc acacaacata cgagccggaa gcataaagtg    2760
taaagcctgg ggtgcctaat gagtgagcta actcacatta attgcgttgc gctcactgcc    2820
cgctttcgag tcgggaaacc tgtcgtgcca gctgcattaa tgaatcggcc aacgcgcggg    2880
gagaggcggt ttgcgtattg ggcgctcttc cgcttcctcg ctcactgact cgctgcgctc    2940
ggtcgttcgg ctgcggcgag cggtatcagc tcactcaaag gcggtaatac ggttatccac    3000
agaatcaggg gataacgcag gaaagaacat gtgagcaaaa ggccagcaaa aggccaggaa    3060
ccgtaaaaag gccgcgttgc tggcgttttt cgataggctc cgcccccctg acgagcatca    3120
caaaaatcga cgctcaagtc agaggtggcg aaacccgaca ggactataaa gataccaggc    3180
gtttccccct ggaagctccc tcgtgcgctc tcctgttccg accctgccgc ttaccggata    3240
cctgtccgcc tttctccctt cgggaagcgt ggcgctttct catagctcac gctgtaggta    3300
tctcagttcg gtgtaggtcg ttcgctccaa gctgggctgt gtgcacgaac cccccgttca    3360
gcccgaccgc tgcgccttat ccggtaacta tcgtcttgag tccaacccgg taagacacga    3420
cttatcgcca ctggcagcag ccactggtaa caggattagc agagcgaggt atgtaggcgg    3480
tgctacagag ttcttgaagt ggtggcctaa ctacggctac actagaagga cagtatttgg    3540
tatctgcgct ctgctgaagc cagttacctt cggaaaaaga gttggtagct cttgatccgg    3600
caaacaaacc accgctggta gcggtggttt ttttgtttgc aagcagcaga ttacgcgcag    3660
aaaaaaagga tctcaagaag atcctttgat cttttctacg gggtctgacg ctcagtggaa    3720
cgaaaactca cgttaaggga ttttggtcat gagattatca aaaggatctt cacctagat     3780 ccttttaaat taaaaatgaa gttttaaatc aatctaaagt atatatgagt aaacttggtc    3840
tgacagttac caatgcttaa tcagtgaggc acctatctca gcgatctgtc tatttcgttc    3900
atccatagtt gcctgactcc ccgtcgtgta gataactacg atacgggagg gcttaccatc    3960
tggccccagt gctgcaatga taccgcgaga cccacgctca ccggctccag atttatcagc    4020
aataaaccag ccagccggaa gggccgagcg cagaagtggt cctgcaactt tatccgcctc    4080
catccagtct attaattgtt gccgggaagc tagagtaagt agttcgccag ttaatagttt    4140
gcgcaacgtt gttggcattg ctacaggcat cgtggtgtca cgctcgtcgt ttggtatggc    4200
ttcattcagc tccggttccc aacgatcaag gcgagttaca tgatccccca tgttgtgcaa    4260
aaaagcggtt agctccttcg gtcctccgat cgttgtcaga agtaagttgg ccgcagtgtt    4320
atcactcatg gttatggcag cactgcataa ttctcttact gtcatgccat ccgtaagatg    4380
cttttctgtg actggtgagt actcaaccaa gtcattctga atagtgta tgcggcgacc      4440 gagttgctct tgcccggcgt caatacggga taataccgcg ccacatagca gaactttaaa    4500
agtgctcatc attggaaaac gttcttcggg gcgaaaactc tcaaggatct taccgctgtt    4560
gagatccagt tcgatgtaac ccactcgtgc acccaactga tcttcagcat cttttacttt    4620
caccagcgtt tctgggtgag caaaaacagg aaggcaaaat gccgcaaaaa agggaataag    4680
ggcgacacgg aaatgttgaa tactcatact cttcctttt caatattatt gaagcattta     4740
```

-continued

```
tcagggttat tgtctcatga gcggatacat atttgaatgt atttagaaaa ataaacaaat    4800
aggggttccg cgcacatttc cccgaaaagt gccacctgac gtctaagaaa ccattattat    4860
catgacatta acctataaaa ataggcgtat cacgaggccc tttcgtctcg cgcgtttcgg    4920
tgatgacggt gaaaacctct gacacatgca gctcccggag acggtcacag cttgtctgta    4980
agcggatgcc gggagcagac aagcccgtca gggcgcgtca gcgggtgttg gcgggtgtcg    5040
gggctggctt aactatgcgg catcagagca gattgtactg agagtgcacc atatgcggtg    5100
tgaaataccg cacagatgcg taaggagaaa ataccgcatc aggcgccatt cgccattcag    5160
gctgcgcaac tgttgggaag ggcgatcggt gcgggcctct tcgctattac gccagctggc    5220
gaaaggggga tgtgctgcaa ggcgattaag ttgggtaacg ccagggtttt cccagtcacg    5280
acgttgtaaa acgacggcca gtgaattgga tttaggtgac actata                  5326

<210> SEQ ID NO 57
<211> LENGTH: 5143
<212> TYPE: DNA
<213> ORGANISM: MVA shuttle plasmid pLAS-2

<400> SEQUENCE: 57
cctcctgaaa aactggaatt taatacacca tttgtgttca tcatcagaca tgatattact      60
ggatttatat tgtttatggg taaggtagaa tctccttaat atgggtacgg tgtaaggaat     120
cattatttta tttatattga tgggtacgtg aaatctgaat tttcttaata atatattttt     180
ttattaaatg tgtatatgtt gttttgcgat agccatgtat ctactaatca gatctattag     240
agatattatt aattctggtg caatatgaca aaaattatac actaattagc gtctcgtttc     300
agacatggat ctgtcacgaa ttaatacttg gaagtctaag cagctgaaaa gctttctctc     360
tagcaaagat gcatttaagg cggatgtcca tggacatagt gccttgtatt atgcaatagc     420
tgataataac gtgcgtctag tatgtacgtt gttgaacgct ggagcattga aaaatcttct     480
agagaatgaa tttccattac atcaggcagc cacattggaa gataccaaaa tagtaaagat     540
tttgctattc agtggactgg atgattcgag gtaccaggcg cgccctttca ttttgttttt     600
ttctatgcta taaatggtga gcaagggcga ggagctgttc accggggtgg tgcccatcct     660
ggtcgagctg gacggcgacg taaacggcca caagttcagc gtgtccggcg agggcgaggg     720
cgatgccacc tacggcaagc tgaccctgaa gttcatctgc accaccggca agctgcccgt     780
gccctggccc accctcgtga ccaccctgac ctacggcgtg cagtgcttca gccgctaccc     840
cgaccacatg aagcagcacg acttcttcaa gtccgccatg cccgaaggct acgtccagga     900
gcgcaccatc ttcttcaagg acgacggcaa ctacaagacc cgcgccgagg tgaagttcga     960
gggcgacacc ctggtgaacc gcatcgagct gaagggcatc gacttcaagg aggacggcaa    1020
catcctgggg cacaagctgg agtacaacta caacagccac aacgtctata tcatggccga    1080
caagcagaag aacggcatca aggtgaactt caagatccgc cacaacatcg aggacggcag    1140
cgtgcagctc gccgaccact accagcagaa caccccatc ggcgacggcc ccgtgctgct    1200
gcccgacaac cactacctga gcacccagtc cgccctgagc aaagacccca acgagaagcg    1260
cgatcacatg gtcctgctgg agttcgtgac cgccgccggg atcactctcg gcatgcacga    1320
gctgtacaag taagagctcg ctttctctct agcaaagatg catttaaggc ggatgtccat    1380
ggacatagtg ccttgtatta tgcaatagct gataataacg tgcgtctagt atgtacgttg    1440
ttgaacgctg gagcattgaa aaatcttcta gagaatgaat ttccattaca tcaggcagcc    1500
acattggaag ataccaaaat agtaaagatt ttgctattca gtggactgga tgattctccg    1560
```

-continued

```
gatggtaccc aacctaaaaa ttgaaaataa atacaaaggt tcttgagggt tgtgttaaat      1620
tgaaagcgag aaataatcat aaataagccc ggggatcctc tagagtcgac ctgcaggcat      1680
gctcgagcgg ccgccagtgt gatggatatc tgcagaattc ggcttggggg gctgcaggtg      1740
gatgcgatca tgacgtcctc tgcaatggat aacaatgaac ctaaagtact agaaatggta      1800
tatgatgcta caattttacc cgaaggtagt agcatggatt gtataaacag acacatcaat      1860
atgtgtatac aacgcaccta tagttctagt ataattgcca tattggatag attcctaatg      1920
atgaacaagg atgaactaaa taatacacag tgtcatataa ttaaagaatt tatgacatac      1980
gaacaaatgg cgattgacca ttatggagaa tatgtaaacg ctattctata tcaaattcgt      2040
aaaagaccta atcaacatca caccattaat ctgtttaaaa aaataaaaag aacccggtat      2100
gacactttta aagtggatcc cgtagaattc gtaaaaaaag ttatcggatt tgtatctatc      2160
ttgaacaaat ataaaccggt ttatagttac gtcctgtacg agaacgtcct gtacgatgag      2220
ttcaaatgtt tcattgacta cgtggaaact aagtatttct aaaattaatg atgcattaat      2280
ttttgtattg attctcaatc ctaaaaacta aaatatgaat aagtattaaa catagcggtg      2340
tactaattga tttaacataa aaaatagttg ttaactaatc atgaggactc tacttattag      2400
atatattctt tggagaaatg acaacgatca aaccgggcat gcaagcttgt ctccctatag      2460
tgagtcgtat tagagcttgg cgtaatcatg gtcatagctg tttcctgtgt gaaattgtta      2520
tccgctcaca attccacaca catacgagc cggaagcata agtgtaaag cctggggtgc        2580 ctaatgagtg agctaactca cattaattgc gttgcgctca ctgcccgctt tcgagtcggg      2640
aaacctgtcg tgccagctgc attaatgaat cggccaacgc gcgggagag gcggtttgcg       2700 tattgggcgc tcttccgctt cctcgctcac tgactcgctg cgctcggtcg ttcggctgcg      2760
gcgagcggta tcagctcact caaaggcggt aatacggtta ccacagaat cagggataa        2820 cgcaggaaag aacatgtgag caaaaggcca gcaaaaggcc aggaaccgta aaaaggccgc      2880
gttgctggcg ttttttcgata ggctccgccc cctgacgag catcacaaaa atcgacgctc      2940
aagtcagagg tggcgaaacc cgacaggact ataaagatac caggcgtttc ccctggaag       3000 ctccctcgtg cgctctcctg ttccgaccct gccgcttacc ggatacctgt ccgcctttct      3060
cccttcggga agcgtggcgc tttctcatag ctcacgctgt aggtatctca gttcggtgta      3120
ggtcgttcgc tccaagctgg gctgtgtgca cgaaccccc gttcagcccg accgctgcgc       3180
cttatccggt aactatcgtc ttgagtccaa cccggtaaga cacgacttat cgccactggc      3240
agcagccact ggtaacagga ttagcagagc gaggtatgta ggcggtgcta cagagttctt     3300
gaagtggtgg cctaactacg gctacactag aaggacagta tttggtatct gcgctctgct     3360
gaagccagtt accttcggaa aaagagttgg tagctcttga tccggcaaac aaaccaccgc      3420
tggtagcggt ggtttttttg tttgcaagca gcagattacg cgcagaaaaa aaggatctca      3480
agaagatcct ttgatctttt ctacggggtc tgacgctcag tggaacgaaa actcacgtta      3540
agggattttg gtcatgagat tatcaaaaag gatcttcacc tagatccttt taaattaaaa      3600
atgaagtttt aaatcaatct aaagtatata tgagtaaact tggtctgaca gttaccaatg      3660
cttaatcagt gaggcaccta tctcagcgat ctgtctattt cgttcatcca tagttgcctg      3720
actccccgtc gtgtagataa ctacgatacg ggagggctta ccatctggcc ccagtgctgc      3780
aatgataccg cgagacccac gctcaccggc tccagattta tcagcaataa accagccagc      3840
cggaagggcc gagcgcagaa gtggtcctgc aactttatcc gcctccatcc agtctattaa      3900
```

```
ttgttgccgg gaagctagag taagtagttc gccagttaat agtttgcgca acgttgttgg   3960
cattgctaca ggcatcgtgg tgtcacgctc gtcgtttggt atggcttcat tcagctccgg   4020
ttcccaacga tcaaggcgag ttacatgatc ccccatgttg tgcaaaaaag cggttagctc   4080
cttcggtcct ccgatcgttg tcagaagtaa gttggccgca gtgttatcac tcatggttat   4140
ggcagcactg cataattctc ttactgtcat gccatccgta agatgctttt ctgtgactgg   4200
tgagtactca accaagtcat tctgagaata gtgtatgcgg cgaccgagtt gctcttgccc   4260
ggcgtcaata cgggataata ccgcgccaca tagcagaact ttaaaagtgc tcatcattgg   4320
aaaacgttct cggggcgaa  aactctcaag gatcttaccg ctgttgagat ccagttcgat   4380
gtaacccact cgtgcaccca actgatcttc agcatctttt actttcacca gcgtttctgg   4440
gtgagcaaaa acaggaaggc aaaatgccgc aaaaaaggga ataagggcga cacgaaatg    4500
ttgaatactc atactcttcc ttttcaata  ttattgaagc atttatcagg gttattgtct   4560
catgagcgga tacatatttg aatgtattta gaaaaataaa caataggggg ttccgcgcac   4620
atttccccga aaagtgccac ctgacgtcta agaaaccatt attatcatga cattaaccta   4680
taaaaatagg cgtatcacga ggccctttcg tctcgcgcgt ttcggtgatg acggtgaaaa   4740
cctctgacac atgcagctcc cggagacggt cacagcttgt ctgtaagcgg atgccgggag   4800
cagacaagcc cgtcagggcg cgtcagcggg tgttggcggg tgtcggggct ggcttaacta   4860
tgcggcatca gagcagattg tactgagagt gcaccatatg cggtgtgaaa taccgcacag   4920
atgcgtaagg agaaaatacc gcatcaggcg ccattcgcca ttcaggctgc gcaactgttg   4980
ggaagggcga tcggtgcggg cctcttcgct attacgccag ctggcgaaag ggggatgtgc   5040
tgcaaggcga ttaagttggg taacgccagg gttttcccag tcacgacgtt gtaaaacgac   5100
ggccagtgaa ttggatttag gtgacactat agaatacgaa ttc                     5143
```

<210> SEQ ID NO 58
<211> LENGTH: 3077
<212> TYPE: DNA
<213> ORGANISM: HIV-1 clade A

<400> SEQUENCE: 58

```
atgggtgcga gagcgtcagt attaagtggg ggaaaattag atgcatggga gaaaattcgg    60
ttaaggccag ggggaaagaa aaaatataga ctgaaacact tagtatgggc aagcagggag   120
ctggaaaaat tcgtacttaa ccctagcctt ttagaaactt cagaaggatg tcagcaaata   180
atgaaccaaa tacaaccagc tcttcagaca ggaacagaag aacttagatc attatttaat   240
gcagtagcaa ccctctattg tgtacatcaa cggatagagg taaaagacac caaggaagct   300
ttagataaag tagaggaaat acaaaacaag agcaagcaaa agacacaaca ggcagcagct   360
gatacaggaa acaacagcaa ggtcagccat aattacccta tagtgcaaaa tgcacaaggg   420
caaatgatac atcagtcctt atcaccaagg actttgaatg catgggtaaa ggtaatagaa   480
gaaaggggtt tcagcccaga agtaataccc atgttctcag cattatcaga aggagccatc   540
ccacaagatt taaatatgat gctgaacata gtggggggac accaggcagc tatgcaaatg   600
ttaaaagaaa ctatcaatga ggaagctgca gaatgggaca ggttacatcc agcacaggca   660
gggcctattc caccaggcca gataagagac caaggggga gtgacatagc aggaactact   720
agtacccctc aggaacaaat aacatggatg acaaacaacc cacctatccc agtgggagac   780
atctataaaa gatggataat cctaggatta aataaaatag taagaatgta tagccctgtt   840
agcattttag atataaaaca ggggccaaaa gaacccttca gagactatgt agataggttc   900
```

```
tttaaagttc tcagagccga acaagctaca caggaagtaa aaggctggat gacagagacc    960
ctgctggttc aaaatgcaaa tccagattgt aagtccattt taagagcatt aggaacaggg   1020
gctacattag aagaaatgat gacagcatgt cagggagtgg gaggacccgg ccataaagca   1080
agggttttag ctgaggcaat gagtcaagca aacaggcaa atgtaatgat gcagaggggc    1140
agctttaagg ggcagaaaag aattaagtgc ttcaactgtg gcaaagaggg acacctagcc   1200
agaaattgca gagcccctag gaaaaaggc tgttggaagt gtgggaaaga aggacaccaa    1260
atgaaagatt gcaatgagag acaggctaat ttttagggaa aaatttggcc ttccagcaag   1320
ggaggccag gaaattttcc ccagagcaga ccggagccaa cagccccacc agcagagatc    1380
tttgggatgg gggaagagat aacctcccct ccgaagcagg agcagaaaga gagggaacaa   1440
accccacct ttgtttccct caaatcactc tttggcaacg acccgttgtc acagtaaaag    1500
taggaggaga aatgagagaa gctctattag atacaggagc agatgataca gtattagaag   1560
atataaattt gccaggaaaa tggaaaccaa aaatgatagg gggaattgga ggttttatca   1620
aggtaaaaca atatgatcag gtatctatag aaatttgtgg aaaaaaggct ataggtacgg   1680
tattagtagg acctacacct gtcaacataa ttggaagaaa tatgttgact cagattggtt   1740
gtaccttaaa ttttccaatt agtcctattg agactgtacc agtaacatta aagccaggaa   1800
tggatggccc aagggttaaa caatggccat tgacagaaga gaaaataaaa gcattgacag   1860
aaatttgtaa agagatggaa aaggaaggaa aaatttcaaa aattgggcct gaaaatccat   1920
acaatactcc aatatttgca ataaagaaaa agatagcac taaatggagg aaattagtag   1980
atttcagaga gctcaataaa agaacacaag acttttggga agttcaatta gggataccgc   2040
atccagcggg cctaaaaaag aaaaaatcag taacagtact agaggtgggg gatgcatatt   2100
tttcagttcc cctagataaa aactttagaa gtatactgc atttaccata cctagtttaa    2160
ataatgaaac accaggaatc aggtatcagt acaatgtgct tccacaagga tggaaaggat   2220
caccagcaat attccagtgc agtatgacaa aaatcttaga gccctttaga tcaaaaaatc   2280
cagaaataat tatctatcaa tacatgcacg acttgtatgt aggatcagat ttagaaatag   2340
ggcagcatag agcaaaaata gaagaattaa gagctcatct actgagctgg ggatttacta   2400
caccagacaa aaagcatcag aaagaacctc cattcctttg gatgggatat gagctccatc   2460
ctgacaagtg gacagtccag cctatagagc tgccagaaaa agaaagctgg actgtcaatg   2520
atatacagaa attagtggga aaactaaatt gggccagtca aatttatcca ggaattaaag   2580
taaagcaatt gtgtaaactt ctcaggggag ccaaagccct aacagatata gtaacactga   2640
ctgaggaagc agaattagaa ttagcagaga cagggagat tctaaaagac cctgtgcatg   2700
gggtatatta tgacccatca aaagacttaa tagcagaaat acagaaacaa gggcaagacc   2760
aatggacata ccaaatttat caggagccat ttaaaaatct aaaaacagga aaatatgcaa   2820
gaaaaggtc tgctcacact aatgatgtaa gacaattagc agaagtagtg cagaaagtgg   2880
tcatggaaag catagtaata tggggaaaga ctcctaaatt taaactaccc atacaaaaag   2940
agacatggga gacatggtgg atggactatt ggcaagctac ctggattcct gagtgggagt   3000
ttgtcaatac ccctcccta gtaaaattat ggtaccagtt agagaaagac cccatagcag    3060
gagcagagac tttctaa                                                  3077

<210> SEQ ID NO 59
<211> LENGTH: 2241
<212> TYPE: DNA
```

<213> ORGANISM: HIV-1 Clade A

<400> SEQUENCE: 59

```
atgagagtga tgggdataca gatgaattgt cagcacttat tgagatgggg aactatgatc    60
ttgggattga taataatctg taatgctgta acagcaact tgtgggttac tgtctattat    120
ggggtacctg tgtggaaaga tgcagagacc accttatttt gtgcatcaga tgctaaagca    180
tataaaacag aaaagcataa tgtctgggct acacatgcct gtgtgcccac agaccccaac    240
ccacaagaaa tacctttgga aaatgtgaca gaagagttta acatgtggaa aataaaatg     300
gtagaacaaa tgcatacaga tataatcagt ctatgggacc aaagcctaca gccatgtgta    360
aagttaaccc ctctctgcat tactttaaac tgtacagatg ttactaatgt tacagatgtt    420
agtggtacga ggggcaacat caccatcatg aagagatgg agggagaaat aaaaaactgt    480
tctttcaata tgaccacaga ataagggat aagaaacaga agtatattc actctttat       540
agacttgatg tagtaccaat aaatcaggggt aatagtagta gtaaaaacag tagtgagtat    600
agattaataa gttgtaatac ctcagccatt acacaagctt gcccaaaggt aagctttgag    660
ccaattccca tacattattg tgcccagct ggttttgcga tcctgaagtg tagggataag     720
gagttcaatg gaacagggga atgcaagaat gtcagcacag tccaatgcac acatggaatc    780
aagccagtag tatcaactca actactgtta aatggcagtc tagcagaaga aaaggtaaaa    840
atcagaactg aaaatatcac aaacaatgcc aaaactatag tagtacaact tgtcgagcct    900
gtgagaatta attgtactag acctaataac aatacaagag agagtgtgcg tatagggcca    960
ggacaagcat tctttgcaac aggtgacata ataggggata agacaagca acattgtaat   1020
gtcagtagat cacaatggaa taagacttta caacaggtag ctgaacaatt aagagaacac   1080
tttaaaaaca aaacaataat atttaacagt tcctcaggag gggatctaga aatcacaaca   1140
catagttttca attgtggagg agaattcttc tattgtaata catcaggtct gttcaatagc   1200
acctggaata ccagcatgtc aggtcaagt aacacggaga caaatgacac tataactctc     1260
caatgcagaa taaagcaaat tataaatatg tggcagagaa caggacaagc aatatatgcc   1320
cctcccatcc agggagtgat aaggtgtgaa tcaaacatca caggactact gttaacaaga   1380
gatggtgggg aggagaagaa cagtacaaat gaaatcttca gacctggagg aggagatatg   1440
agggacaact ggagaagtga attatataag tataaagtag taaaaattga accactagga   1500
gtagcaccca ccagggcaag gagaagagtg gtgggaagag aaaaaagagc agttggaata   1560
ggagctgttt tccttgggtt cttaggagca gcaggaagca ctatgggcgc ggcgtcaata   1620
acgctgacgg tacaggccag gcaattattg tctggcatag tgcagcagca gagcaatttg   1680
ctgagggcta tagaggctca acaacatatg ttgaaactca cggtctgggg cattaaacag   1740
ctccaggcaa gagtccttgc tgtggaaaga tacctaaggg atcaacagct cctaggaatt   1800
tggggctgct ctggaaaact catctgcacc actaatgtgc cctggaactc tagttggagt   1860
aataaatctc aggatgaaat atggaacaac atgacctggc tgcaatggga taagaaatt    1920
agcaattaca taaacctaat atatagtcta attgaagaat cgcaaaacca gcaggaaaag   1980
aatgaacaag acttattggc attgggcaag tgggcaaatc tgtggacttg gtttgacata   2040
tcaaattggc tgtggtatat aagaatattt ataatgatag taggaggctt aataggatta   2100
agaatagttt ttgctgtgct tgctgtaata aagagagtta ggcagggata ctcacctgtg   2160
tcatttcaga tccatgcccc aaacccaggg ggtctcgaca ggcccggaag aatcgaagga   2220
gaaggtggag agcaagacta a                                             2241
```

<210> SEQ ID NO 60
<211> LENGTH: 2211
<212> TYPE: DNA
<213> ORGANISM: HIV-1 Clade A

<400> SEQUENCE: 60

```
atgagagtga tggggataca gatgaattgt caaagcttgt ggagatgggg aactatgatc      60
ttgggaatgt taatgatttg tagtgttgca ggaaacttgt gggttactgt ctactatggg     120
gtacctgtgt ggaaagaggc agacaccacc ttattttgtg tatcaaatgc tagagcatat     180
gatacagaag tgcataatgt ctgggctaca catgcctgtg tacctacgga ccccaaccca     240
caagaaatag atttggagaa tgtgacagaa gagtttaaca tgtggaaaaa taacatggta     300
gagcaaatgc atacagatat aattagtcta tgggaccaaa gcctaaaacc atgtgtaaag     360
ttaacccctc tctgcgttac tttagattgt ggctataatg taaccaactt gaatttcacc     420
agtaacatga aggagacat aacaaactgc tcttacaata tgaccacaga ataagggat      480
aggaaacaga agtgtattc acttttctat aggcttgata tagtaccaat taatgaagaa     540
aagaataata gcagggagac tagtccgtat agattaataa attgtaatac ctcagccatt     600
acacaagctt gtcctaaggt atctttttgaa ccaattccca tacattattg tgccccagcc     660
ggttttgcga ttctaaaatg taaggatgca gagttcaatg gaacagggcc atgcaagaat     720
gtcagcacag tacaatgtac acatggaatc aggccagtaa tatcaactca actgctgtta     780
aatggcagtt tagcagagaa tgggacaaag attagatctg aaaatatcac aaacaatgcc     840
aaaaccataa tagtacaact taacgagacc gtacaaatta ttgtaccag acctagcaac     900
aatacaagaa aaagtgtacg tataggacca ggacaagcat tctatacaac aggtgatata     960
acaggggata taagacaagc atattgtaat gtcagtagac aagaatggga caagcatta     1020
aaggggtag ttatacaatt aagaaaacac tttaacaaaa caataatctt taacagttcc     1080
tcaggagggg atttagaaat tacaacacat agttttaatt gtggaggaga attcttctat     1140
tgtgatacat caggcctgtt taatagcacc tggaacacga acaccaccga gccaaacaac     1200
acaacgtcaa atggcactat cattctccaa tgcagaataa agcaaattat aaatctgtgg     1260
cagagaaccg gacaagcaat gtatgcccct cccatccaag gggtaataag gtgtgattcc     1320
aacattacag gactactatt aacaagagat ggtggagtag ttgatagtat aaatgaaacc     1380
gaaatcttca gacctggagg aggagatatg agggacaatt ggagaagtga attatataag     1440
tataaagtag taaaaattga accactagga gtagcaccca ccggggcaaa gagaagagtg     1500
gtggagagag aaaaaagagc agttggcata ggagctgtat tcattgggtt cttaggagca     1560
gcaggaagca ctatgggcgc ggcgtcaata acgctgacgg tacaggccag acaattattg     1620
tctggcatag tgcaacagca aagcaatttg ctgagggcta tagaggctca acagcatatg     1680
ttgagactca cggtctgggg cattaagcag ctccaggcaa gagtcctggc tgtggaaaga     1740
tacctaaggg atcaacagct cctaggaatt tggggctgct ctggaaaact catctgcacc     1800
actaatgtgc cctggaactc tagttggagt aataaatctc aggaggaaat atgggtaac      1860
atgacctggc tgcaatggga taagaaaatt agcaattaca cacaaacaat atataaccta     1920
cttgaagaat cgcagaacca gcaggaaaag aatgaacaag acttattggc attggacaag     1980
tgggcaaatt tgcggacttg gtttgacata caaaattggc tgtggtatat aaaaatgttt     2040
ataatgatag taggaggctt aataggatta agaatagttt ttgctgtgct ttctgtaata     2100
```

-continued

| | |
|---|---|
| aatagagtta ggcagggata ctcacctctg tcgtttcaga cccatatccc gagcccaagg | 2160 |
| ggtctcgata ggcccggaag aatcgaagga gaaggtggag agcaagacta a | 2211 |

<210> SEQ ID NO 61
<211> LENGTH: 3083
<212> TYPE: DNA
<213> ORGANISM: HIV-1 Clade C

<400> SEQUENCE: 61

| | |
|---|---|
| atgggtgcga gagcgtcaat attaagaggg ggaaaattag atcgatggga aaaaattagg | 60 |
| ttaaggccag ggggaaagaa aagctatatg ataaaacact tagtatgggc aagcagggag | 120 |
| ctggaaagat ttgcacttaa ccctagcctt ttagagacat cagaaggctg taaacaaata | 180 |
| atgaaacagc tacaaccagc tcttcagaca ggaacagaag aacttaaatc attattcaat | 240 |
| gcaatagcag ttctctattg tgtacatgaa gggatagatg taaaagacac caaggaagcc | 300 |
| ttagacaaga tagaggaaga acagaacaaa agtcagcaaa aaacacagca ggcagaagca | 360 |
| gctggcggaa aagtcagtca aaattatcct atagtgcaga atctccaagg acaaatggta | 420 |
| caccagtcca tatcacctag aactttgaat gcatgggtaa agtaataga ggaaaaggct | 480 |
| tttagcccag aggtaatacc catgtttaca gcattatcag aaggagccac cccacaagat | 540 |
| ttaaacacca tgctaaatac agtggggggga catcaagcag ccatgcaaat gttaaaagat | 600 |
| accatcaatg aggaggctgc agaatgggat aggatacatc cagtacatgc agggcctact | 660 |
| gcaccaggcc aaatgagaga accaagggga agtgacatag caggaactac tagtacccctt | 720 |
| caggaacaaa tagcatggat gacagctaac ccacctgttc cagtgggaga aatctacaaa | 780 |
| agatggataa tactgggttt aaataaaata gtaagaatgt atagccctgt cagcattttg | 840 |
| gacataaaac aagggccaaa ggaacccttt agagactatg tagatcggtt ctttaaaact | 900 |
| ttaagagctg aacaggctac acaagatgta aaaaattgga tgacagacac cttgttggtc | 960 |
| caaaatgcga acccagattg taagaccatt ttaagagcat taggaccagg ggctacatta | 1020 |
| gaagaaatga tgacagcatg tcaaggagtg ggaggacctg ccacaaaagc cagagttttg | 1080 |
| gctgaggcaa tgagccaagc aaacacacac ataatgatgc agagaagcaa ttttaaaggc | 1140 |
| tctaaaagaa ttgttaaatg tttcaactgt ggcaaggaag gcacatagc cagaaattgc | 1200 |
| agggccccta ggaaaaaggg ctgttggaaa tgtggaaagg aaggacacca aatgaaagac | 1260 |
| tgtactgaga gcaggctaa ttttttaggg aaaatttggc cttcccacaa ggggaggcca | 1320 |
| gggaatttcc ttcagaacag gtcagagcca acagccccac caacgaacag gccagagcca | 1380 |
| acagctccac cagcagagag cttcaggttc gaggaagcaa cccctgctcc gaagcaggag | 1440 |
| ctgaaagaca gggaaccttt aatttccctc aaatcactct ttggcagcga ccctcgtct | 1500 |
| caataaaagt aggggggtcaa acaaaggagg ctcttttaga cacaggagca gatgatacag | 1560 |
| tattagaaga aataaatttg ccaggaaaat ggaaacccaa aatgatagga ggaattggag | 1620 |
| gttttatcaa agtaagacag tatgatcaga tagttataga aatttgtgga aaaaaggcta | 1680 |
| taggtacagt attagtagga cccacccctg tcaacataat tggaagaaat atgttgactc | 1740 |
| agcttggatg cacactaaat tttccaatta gtcctattga aactgtacca gtaaagttaa | 1800 |
| agccaggaat ggatggccca aaggttaaac aatggccatt gacagaagaa aaaataaagg | 1860 |
| cattaacagc aatttgtgaa gaaatggaga aggaagaaaa attacaaag attgggcctg | 1920 |
| aaaatccata taacactcca gtatttgcca taaaaaagaa ggacagtact aagtggagaa | 1980 |
| aattagtaga tttcagggaa cgcaataaaa gaactcaaga ttttgggaa gttcaattag | 2040 |

```
gcataccaca cccagcaggg ttaaaaaaga aaaaatcagt gacagtactg gaggtggggg    2100
atgcatactt ctcagttcct ttagatgaag gcttcaggaa atatactgca ttcaccatac    2160
ctagtataaa caatgaaaca ccaggaatta gatatcaata caatgtgctt ccacagggat    2220
ggaaaggatc accagcaata ttccagagta gcatgacaaa aatcttagag ccctttagag    2280
cacaaaatcc agaaatagtc atctatcaat atatgcacga cttatatgta ggatctgact    2340
tagaaatagg gcaacataga gcaaaaatag aggaattaag agaacatcta ttaaagtggg    2400
gatttaccac accagacaag aaacatcaga agaaccccc atttctttgg atggggtatg     2460
aactccatcc tgacaaatgg acagtacagc ctataacgct gccagaaaag aaagctgga    2520 ctgtcaatga tatacagaag ttagtgggaa aactaaactg gcaagtcag atttatgcag     2580 ggattaaagt aaggcaactg tataaactcc ttaggggagc caaagcacta acagacatag    2640
taccactaac tgaagaggca gaattagaat tggcagagaa cagggaaatt ctaaaagaac    2700
cagtacatgg ggtatattat gacccatcaa aagacttgat agctgaaata cagaaacaag    2760
ggcatgacca atggacatat caaatttacc aagaaccatt caaaaatctg aaaacaggga    2820
agtatgcaaa aatgaggagt gcccacacta atgatgtaaa acaattaaca gaggcagtgc    2880
aaaaaatagc catggaaggc atagtaatat ggggaaagac tcctaaattt agactgccca    2940
ttcaaaagga aacatgggaa acatggtgga cagactattg gcaagccacc tggattcctg    3000
agtgggagtt tgttaatacc cctcccctag taaaattatg gtaccagctg gagaaagaac    3060
ccatagtagg agcagaaact ttc                                            3083

<210> SEQ ID NO 62
<211> LENGTH: 2226
<212> TYPE: DNA
<213> ORGANISM: HIV-1 Clade C

<400> SEQUENCE: 62
atgagagtga agggatatt gaggaattgg caacacaggt ggatatggat ctggatcatc      60
ttaggctttt ggatgctaat gatttgtaat gggaacttgt gggtcactgt ctactatggg    120
gtacctgtgt ggaaagaagc aaatgctcct ctattttgtg catcagatgc taaagcatat    180
gagaaagaag tgcataatgt ctgggctaca catgcctgtg tacccacaga ccccaaccca    240
caagaactag acttggtaaa tgtaacagaa aattttaaca tgtggaaaaa tgacatggta    300
gatcagatgc atgaggatat aatcagttta tgggatgaaa gcctaaagcc atgtgtaaag    360
ttgaccccac tctgtgtcac tctaaactgt actaatgcta atattaataa tgatactgtt    420
gctaatagtg gtactttta ggttgataat agtagtaatg tagtaaaaaa ttgctctttc     480
aatataacca cagaaataag agataagaag aaaaagaat attcattgtt ttatagactt     540
gatatattac cacttgataa ctctagtgag tctaagaact atagtgagta tgtattaata    600
aattgtaatg cctcaaccgt aacacaagcc tgtccaaagg tctcttttga cccaattcct    660
atacattatt gtgctccagc tggttatgcg attctaaagt gtaaagataa gacattcaat    720
ggaacaggac catgcagtaa tgtcagcaca gtactatgta cacatggaat taagccagtg    780
gtatcaactc aattactgtt aaatggtagc ctagcagaag aagggatagt aattagatct    840
gaaaatctga caaacaatgc caaaacaaca atagtacagc ttaatgaacc tgtagaaatt    900
atgtgtgtaa gacccggcaa taatacaaga aaaagtgtga ggataggacc aggacaaaca    960
ttctatgcaa caggaggcat aataggagat ataagacaag cacattgtaa cattagtaga   1020
```

```
                                        -continued
agtgattgga ataaaacttt acaagaggta ggtaaaaaat tacgagaata cttccacaat    1080
aaaacaataa gatttaaacc ggcggtcgta ggaggggacc tggaaattac aacacatagc    1140
tttaattgta gaggagaatt cttctattgc aatacatcag aactgtttac aggtgaatat    1200
aatggtactg agtataagaa tacttcaaat tcaaatccta acatcacact cccatgtaga    1260
ataaaacaat ttgtaaacat gtggcagagg gtaggacgag caatgtatgc ccctcctatt    1320
gaaggaaaca taacatgtaa ctcaagtatc acaggactac tattgacatg ggatggagga    1380
aacaatacta atggcacaga gacatttaga cctggaggag gagatatgag ggataattgg    1440
agaagtgaat tatataaata taaagtggta gaaattaaac cattaggaat agcacccact    1500
agtgcaaaaa ggagagtggt ggagagagag aaaagagcag tgggaatagg agctttgttc    1560
cttgggttct taggagcagc aggaagcact atgggcgcag catcaataac gctgacggta    1620
caggccagac aattattgtc tggtatagtg caacagcaaa gcaatttgct gagggccata    1680
gaggcgcaac agcatatgtt gcaactcaca gtctggggca ttaaacagct ccagacaaga    1740
gtcctggcta tagaaagata cctaaaggat caacagctcc tagggatttg gggctgctct    1800
ggaaaactca tctgcaccac tgctgtgcct tggaacacta gttggagtaa taaaactgaa    1860
caggacattt ggaatctaac ctggatgcag tgggatagag aagttagtaa ttacacagac    1920
ataatataca ggttgcttga agactcacaa atccagcagg aaaacaatga aaaggattta    1980
ctagcattgg acagttggaa aaatctgtgg aattggtttg acataacaaa ttggttgtgg    2040
tatataagaa cattcataat gatagtagga ggcttgatag gcttaaggat aattttgct    2100 gtaatttcta tagtgaatag agttaggcag ggatactcac ctttgtcatt tcagacccct    2160
accccaaccc cgaggggacc agaaaggctc ggaggaatcg aagaagaagg tggagagcaa    2220
gactaa                                                              2226

<210> SEQ ID NO 63
<211> LENGTH: 9
<212> TYPE: PRT
<213> ORGANISM: Artificial Sequence
<220> FEATURE:
<223> OTHER INFORMATION: synthetic peptide

<400> SEQUENCE: 63

Ala Met Gln Met Leu Lys Glu Thr Ile
 1               5
```